United States Patent
Miller

(10) Patent No.: US 11,384,068 B2
(45) Date of Patent: Jul. 12, 2022

(54) ESTROGEN RECEPTOR-MODULATING COMPOUNDS

(71) Applicant: Radius Pharmaceuticals, Inc., Waltham, MA (US)

(72) Inventor: Chris Miller, San Mateo, CA (US)

(73) Assignee: Radius Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/963,794

(22) PCT Filed: Jan. 22, 2019

(86) PCT No.: PCT/US2019/014581
§ 371 (c)(1),
(2) Date: Jul. 21, 2020

(87) PCT Pub. No.: WO2019/144132
PCT Pub. Date: Jul. 25, 2019

(65) Prior Publication Data
US 2020/0347032 A1 Nov. 5, 2020

Related U.S. Application Data

(60) Provisional application No. 62/620,441, filed on Jan. 22, 2018.

(51) Int. Cl.
| | |
|---|---|
| *C07D 313/08* | (2006.01) |
| *C07D 333/64* | (2006.01) |
| *C07D 409/12* | (2006.01) |
| *C07D 487/04* | (2006.01) |
| *C07D 209/12* | (2006.01) |
| *C07D 209/30* | (2006.01) |
| *A61K 31/404* | (2006.01) |
| *A61P 35/00* | (2006.01) |
| *C07D 403/10* | (2006.01) |
| *A61P 35/04* | (2006.01) |
| *C07D 495/04* | (2006.01) |

(52) U.S. Cl.
CPC ............ *C07D 403/10* (2013.01); *A61P 35/04* (2018.01); *C07D 209/30* (2013.01); *C07D 333/64* (2013.01); *C07D 409/12* (2013.01); *C07D 487/04* (2013.01); *C07D 495/04* (2013.01)

(58) Field of Classification Search
CPC .. C07D 313/08; C07D 333/64; C07D 409/12; C07D 487/04; C07D 209/12; C07D 209/30; A61K 31/404; A61P 35/00
See application file for complete search history.

(56) References Cited

FOREIGN PATENT DOCUMENTS

| | | |
|---|---|---|
| EP | 0835867 A1 | 4/1998 |
| EP | 1226823 A2 | 7/2002 |
| WO | 2001068634 A1 | 9/2001 |
| WO | 2003091239 A1 | 11/2003 |
| WO | 2013090829 A1 | 6/2013 |

OTHER PUBLICATIONS

PCT/US2019/014581 International Search Report dated Mar. 19, 2019.

*Primary Examiner* — Bruck Kifle
(74) *Attorney, Agent, or Firm* — Honigman LLP

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

19 Claims, No Drawings

ESTROGEN RECEPTOR-MODULATING COMPOUNDS

CROSS-REFERENCE TO RELATED APPLICATIONS

This application is a National Stage Application and claims priority under 35 U.S.C. § 371 to Patent Cooperation Treaty application PCT/US2019/014581, filed Jan. 22, 2019, which claims the benefit of and priority under 35 U.S.C. § 119(e) to U.S. Provisional Application No. 62/620,441, filed Jan. 22, 2018. Priority is claimed to both of these applications and the disclosures of these prior applications are considered part of the disclosure of this application, and to the extent allowed, the entire contents of the aforementioned applications are incorporated herein.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrone. The estrogen receptor has been found to have two isoforms, ER-α (ESR1) and ER-β (ESR2). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions, such as infertility, osteoporosis, vaginal atrophy, dyspareunia, contraception, male hypogonadism, gynecomastia, breast pain, and accordingly find use in the treatment of these and other conditions and diseases that are at least in part attributable to regulation of the estrogen receptor.

Selective estrogen receptor modulators (SERMs) are a class of drugs that act on the estrogen receptor. They tend to be competitive ligands of the estrogen receptor. A characteristic that distinguishes these substances from pure ER agonists and antagonists (that is, full agonists and silent antagonists) is that their action is different in various tissues, thereby granting the possibility to selectively inhibit or stimulate estrogen-like action in various tissues. For example, ER-α is typically found as the predominant form in the female reproductive tract and mammary glands, while ER-β is found in higher levels in vascular endothelial cells, bone, and male prostate tissue. Different tissues have different degrees of sensitivity to and activity of endogenous estrogens, so SERMs produce estrogenic or antiestrogenic effects depending on the specific tissue in question as well as the percentage of intrinsic activity (IA) of the SERM. Moreover, their levels in various tissues may change in response to physical development, aging or disease state. Antagonizing at the ER can either occur through competitive inhibition, wherein one ligand displaces a more agonistic ligand (eg 17β-estradiol) and signals to a lesser degree or not at all relative to the agonist ligand. There is a second mode of inhibiting ER-agonist signaling and this comprises the binding of a ligand to ER and inducing a conformation or conformations that trigger the degradation of the ER in the proteasome. Often, the degradation is triggered by ubiquination and/or palmoylation of ER subsequent to a binding event of the degradation-triggering compound. Compounds that bind ER and accelerate its degradation are often referred to as selective estrogen receptor degraders ("SERDs"). Referring to a compound as a SERM or SERD is a general way to focus on that aspect of its pharmacology. As it turns out, many compounds that function as SERMs, meaning they have at least some agonist activity in some (but not all) ER-expressing tissues, can also trigger at least some receptor degradation. Accordingly, it should be appreciated that many if not most of the compounds falling under the embodiments of this invention represent a spectrum of SERM/SERD activity. Whether SERMs, SERDs and SERM/SERDs, the compounds of the present disclosure are able to achieve the methods disclosed herein.

SUMMARY OF THE INVENTION

In one aspect, presented herein are compounds of Formulas I to VII, I' to X', or a pharmaceutically acceptable salt, solvate or prodrug thereof, that modify the effects of endogeneous estrogens acting through ER and/or trigger ER degradation, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are selective estrogen receptor degrader compounds.

In one aspect, compounds of Formulas I to VII, I' to X', or a pharmaceutically acceptable salt, solvate or prodrug thereof, are useful for the treatment of ER-related diseases or conditions including, but not limited to, ER-α dysfunction associated with cancer such as, breast cancer, lung cancer, colorectal cancer, endometrial cancer, prostate cancer, ovarian and uterine cancer, including metastatic cancers.

In one aspect, described herein are compounds of Formulas I to VII, I' to X', and pharmaceutically acceptable salts, solvates, metabolites and prodrugs thereof. Compounds described herein are estrogen receptor modulators. In some embodiments, the compound of Formulas I to VII or I' to X' is an estrogen receptor antagonist. In some embodiments, the compound of Formulas I to VII or I' to X' displays minimal estrogen receptor agonist activity. In some embodiments, in the context of treating cancers, the compound of Formulas I to VII or I' to X' may offer improved therapeutic activity characterized by complete or longer-lasting tumor regression, a lower incidence or rate of development of resistance to treatment, and/or a reduction in tumor invasiveness.

In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from the group consisting of active metabolites, tautomers, pharmaceutically acceptable solvates, pharmaceutically acceptable salts, and prodrugs of a compound of Formulas I to VII or I' to X'.

In certain embodiments, the present invention describes a compound of Formula I:

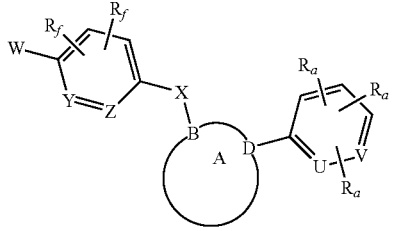

I wherein:

B is nitrogen or carbon;

D is carbon;

A is a fused ring system selected from the group consisting of:

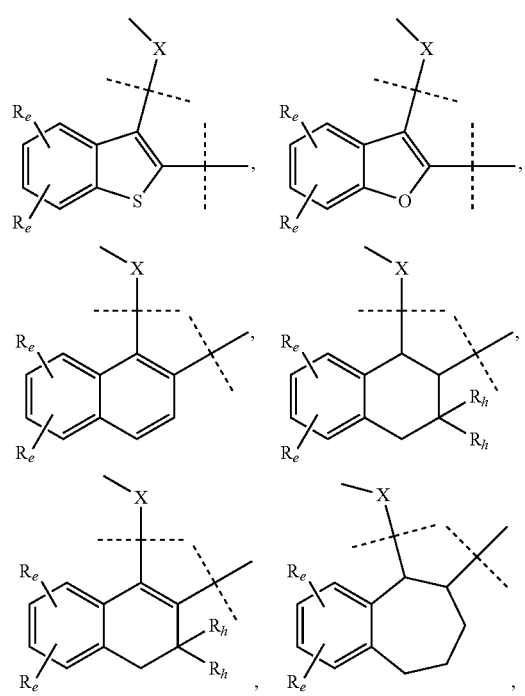

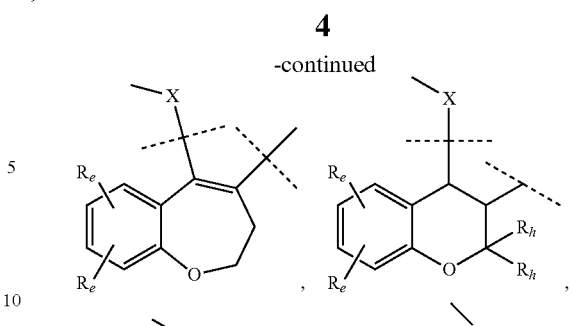

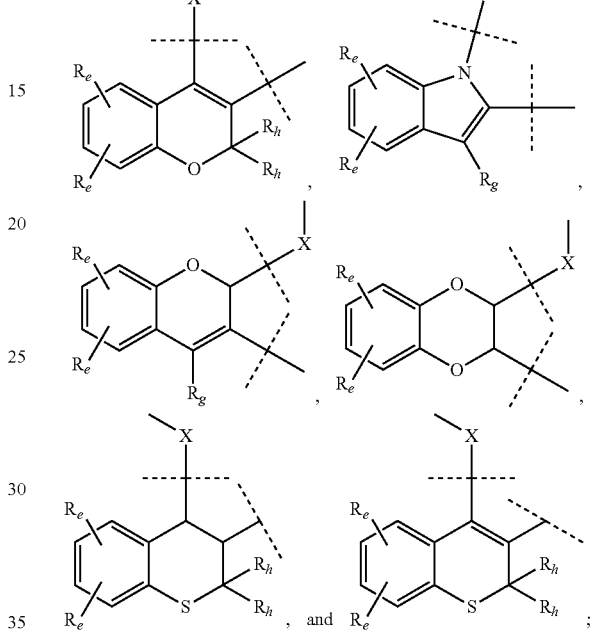

each $R_e$ is independently selected from the group consisting of hydrogen, halogen, OH, O(CO)R, O(CO)NR$_1$R$_2$, OPO$_3$, OSO$_3$, O(SO$_2$)NR$_1$R$_2$, or wherein two adjacent $R_e$ together form:

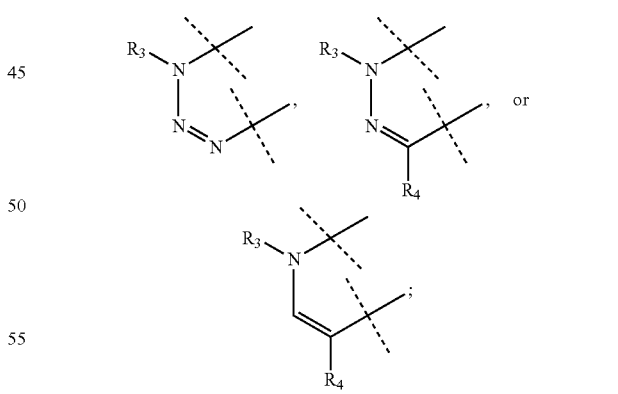

each R is independently $C_1$-$C_6$ alkyl or aryl;
each $R_1$ and $R_2$ are each independently hydrogen or $C_1$-$C_6$ alkyl;
each $R_3$ is hydrogen, $C_1$-$C_{12}$ acyl, or $C_1$-$C_{12}$ acyloxy;
each $R_4$ is independently hydrogen, $C_1$-$C_3$ alkyl, fluorine or chlorine;
each $R_h$ is independently hydrogen or CH$_3$;
$R_g$ is hydrogen, $C_1$-$C_3$ alkyl, $C_1$-$C_3$ fluoroalkyl, CN, fluorine, chlorine or bromine;

each $R_a$ is independently H, $C_1$-$C_3$ alkyl, $C_1$-$C_3$ fluoroalkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, bromine, O(CO)R, O(CO)$NR_1R_2$, $OPO_3$, $OSO_3$, $O(SO_2)NR_1R_2$, or two adjacent $R_a$ together form:

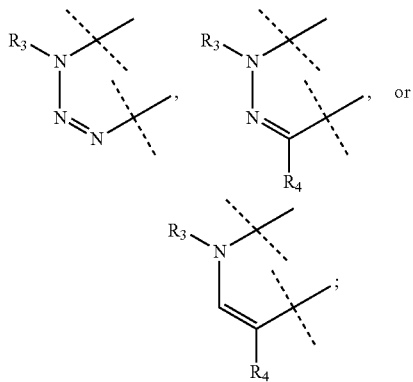

X is O, S, $CH_2$, NH or a bond when B is carbon, or $CH_2$ or a bond when B is nitrogen;

Y and Z are each independently selected from $CR_f$ or N;

U and V are each independently selected from $CR_a$ or N;

each $R_f$ is independently H, $C_1$-$C_3$ alkyl, $OC_1$-$C_3$ alkyl, fluorine or chlorine; and W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl,

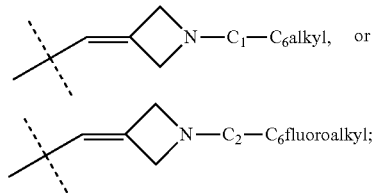

wherein each R' is independently H or $C_1$-$C_3$alkyl;
or a pharmaceutically acceptable salt thereof.

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

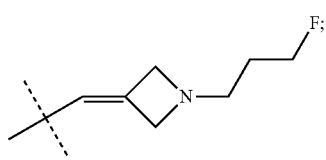

in certain embodiments, W is

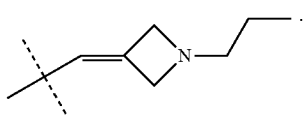

In certain embodiments, provided herein are pharmaceutical compositions comprising a compound selected from the group consisting of formulas I-VII, I' to X', and all structural embodiments described herein and at least one pharmaceutically acceptable excipient.

In certain embodiments, provided herein is a method of modulating an estrogen receptor in a cell, comprising the administration of a compound to said cell wherein said compound is selected from the group consisting of formulas I-VII, I' to X', and all the structural embodiments described herein, or a pharmaceutically acceptable salt thereof.

In certain embodiments, provided herein is a method of identifying a compound capable of modulating an estrogen receptor comprising contacting a cell expressing an estrogen receptor with a compound according to formula I, and monitoring the effect of the compound on the cell.

Also described herein is a prodrug of a compound selected from the group consisting of formulas I-VII, I' to X', and all structural embodiments described herein. Also described herein is a pharmaceutically acceptable salt of a prodrug of a compound selected from the group consisting of formulas I-VII, I' to X', and all structural embodiments described herein. In some embodiments, the pharmaceutically acceptable salt of the prodrug of a compound of Formulas I-VII, I' to X', is a hydrochloride salt.

In some embodiments, described herein is a pharmaceutical composition comprising a compound selected from the group consisting of formulas I-VII, I' to X', and all structural embodiments described herein or a pharmaceutically acceptable salt or prodrug of a compound selected from the group consisting of formulas I-VII, I' to X', and all structural embodiments described herein. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient or overabundant estrogen levels in a mammal in need thereof, wherein said method comprises the administration to said mammal of an effective amount of a compound selected from the group consisting of formulas I-VII, I' to X', and all structural embodiments described herein or a pharmaceutically acceptable salt thereof, or a pharmaceutical composition comprising a compound of formulas I-VII, I' to X', or one of the structural embodiments described herein, or a pharmaceutically acceptable salt thereof and a pharmaceutically acceptable excipient. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, lung cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound selected from the group consisting of formulas I-VII, I' to X', and all structural embodiments described herein, or a pharmaceutically acceptable salt thereof, or a pharmaceutical composition comprising a compound selected from the group consisting of formulas I-VII, I' to X', and all structural embodiments described herein including pharmaceutically acceptable salts thereof and a pharmaceutically acceptable excipient. In an embodiment, the mammal is a human. In some embodiments, the cancer is positive for the expression of ESR1. In certain embodiments, the cancers are resistant to prior lines of treatment (e.g., prior endocrinological therapy). In certain embodiments, the cancer progresses after exposure to one or more agents selected from the group consisting of tamoxifen, toremifene, letrozole, aromasin, anastrazole, and faslodex. In some embodiments, the treatment is in adjuvant setting and in some embodiments the treatment is in the metastatic setting. In certain embodiments, SERD and/or SERMS compounds disclosed herein are combined with other active compounds including, cdk4/6 inhibitors, PI3k inhibitors, mTOR inhibitors, taxanes, and Her2 inhibitors.

DETAILED DESCRIPTION OF THE INVENTION

As employed above and throughout the disclosure, the following terms, unless otherwise indicated, shall be understood to have the following meanings.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

In some situations, compounds may exist as tautomers. All tautomers are included within the scope of the compounds presented herein.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonism" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%. In some embodiments, a degrader as described herein lowers steady state estrogen receptor levels by at least 65%. In some embodiments, a degrader as described herein lowers steady state estrogen receptor levels by at least 85%.

The term "selective estrogen receptor degrader" or "SERD" as used herein, refers to a small molecule agent that preferentially binds to estrogen receptors versus other receptors and subsequently lowers the steady state estrogen receptor levels. In addition, SERD can mean a compound that degrades in one cell or tissue type more than in another, thus expressing possibly SERM type activity while effecting degradation differentially depending on the cellular or tissue context.

The term "Estrogen Receptor-dependent", as used herein, refers to diseases or conditions that would not occur, or would not occur to the same extent, in the absence of estrogen receptors.

The term "Estrogen Receptor-mediated", as used herein, refers to diseases or conditions that are at least in part dependent on estrogen signaling for their status.

The term "Estrogen Receptor-sensitive", as used herein, refers to diseases or conditions that would not occur, or would not occur to the same extent, in the absence of estrogens. Estrogen receptor sensitive also refers to cells or tissues that respond to the presence of estrogen receptor agonists, antagonists, SERMs and/or SERDs.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, or skin (melanoma or basal cell cancer)) or hematological tumors (such as the leukemias and lymphomas) at any stage of the disease with or without metastases.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula I through VII, I' to X', or a pharmaceutically acceptable salt thereof, and a co-agent, are both administered to a patient simultaneously in the form of a single entity or dosage. The term "non-fixed combination" means that the active ingredients, e.g. a compound of Formula I through VII, I' to X', or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In some embodiments, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

In the context of this disclosure, the phrase "formula I through VII," "formula I to VII" or "formula I-VII" is meant to, in each instance, include compounds of formula I, II, IIa, IIb, IIc, IId, IIe, IIf, IIg, IIh, IIj, III, IIIa, IIIb, IIIc, IIId, IIIe, IIIf, IV, IVa, IVb, IVc, IVd, IVe, IVf, IVg, IVh, IVj, V, Va, Vb, Vc, Vd, Ve, Vf, Vg, Vh, VI, VIa, VIb, VIc, VId, VIe, VIf, VIg, VIh, VII.

The term "alkyl" as used herein refers to both straight and branch chain hydrocarbon radicals, having the number of carbon atoms falling within the specified range. For example, $C_{1-4}$ alkyl means that a hydrocarbon radical is attached that may contain anywhere from 1 to 4 carbon atoms with the remaining valence filled in by hydrogen atoms. The definition also includes separately each permutation as though it were separately listed. Thus, $C_{1-2}$ alkyl includes methyl and ethyl. The term $C_{1-3}$ alkyl includes methyl, ethyl, propyl and 2-propyl. The term $C_{1-4}$ alkyl includes methyl, ethyl, n-propyl, 2-propyl, n-butyl, 2-butyl, iso-butyl and tert-butyl. The term $C_{1-5}$ alkyl includes methyl, ethyl, 2-propyl, n-butyl, 2-methylbutyl, tert-butyl, n-pentyl, pentan-2-yl, pentan-3-yl, and tert-pentyl, iso-pentyl.

The term "halogen" as used herein refers to a fluorine, chlorine, bromine or iodine radical.

The term "haloalkyl" refers to an alkyl radical wherein said alkyl radical is the same as defined for the term "alkyl" except that the alkyl radical additionally has from 1 to 5 halogen atoms attached to the alkyl chain. For example, $C_1$ haloalkyl includes —$CH_2F$, —$CHF_2$, —$CF_3$ and the like, $C_{1-2}$ haloalkyl includes —$CH_2F$, $CHF_2$, $CF_3$, —$CH_2CH_2F$, —$CH_2CHF_2$, —$CH_2CF_3$, —$CF_2CHF_2$, —$CF_2CF_3$ and the like. $C_{1-3}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CH_2F$, —$CH_2CH_2CF_3$, and the like. $C_{1-4}$ haloalkyl is defined to include —$CH_2F$, —$CHF_2$, —$CF_3$, —$CH_2CF_3$, —$CHFCF_3$, —$CF_2CF_3$, —$CHClCH_3$, —$CH_2CH_2Cl$, —$CH_2CH_2CF_3$, —$CH_2CH_2CH_2CF_3$, $CHClCF_2CH_2CH_3$, $CF_2CH_2CH_2CHF_2$, $CH_2CH_2CH_2CH_2F$, $CH_2CH_2CH_2CH_2Cl$, and the like. The term "fluoroalkyl" as in "$C_1$-$C_4$fluoroalkyl" includes $C_1$, $C_2$, $C_3$ and $C_4$ alkyl chains, straight or branched, with from 1-4 fluorine atoms such as —$CH_2CH_2F$, —$CH_2CHF_2$, —$CH_2CF_3$, —$CF_2CHF_2$, —$CH_2F$, —$CHF_2$, —$CF_3$, —$CH_2CF_3$, —$CHFCF_3$, —$CF_2CF_3$, —$CH_2CH_2CF_3$, $CH_2CH_2CH_2F$, —$CH_2CH_2CH_2CF_3$, $CF_2CH_2CH_2CHF_2$, $CH_2CH_2CH_2CH_2F$, $CH(CH_3)CH_2F$, $CH_2(CH)(CH_3)CH_2F$, $CH_2(CH)(CH_2F)(CH_2F)$.

The term "aryl" means a monovalent six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Representative examples include phenyl, naphthyl, and indanyl, and the like.

The term "acyl" refers to a group having the general formula —(CO)-alkyl wherein said alkyl radical is the same as defined for the term "alkyl" and wherein the alkyl portion of the acyl group has the number of carbon atoms falling within the specified range.

The term "acyloxy" refers to a group having the general formula —O(CO)-alkyl wherein said alkyl radical is the same as defined for the term "alkyl" and wherein the alkyl portion of the acyloxy group has the number of carbon atoms falling within the specified range.

The compounds of this invention may contain at least one stereocenter and therefore, exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. Thus, "R" and "S" denote the relative configurations of substituents around one or more chiral carbon atoms. When the stereochemistry of a disclosed compound is named or depicted by structure, the named or depicted stereoisomer is at least 50%, 60%, 70%, 80%, 90%, 95%, 98%, 99% or 99.9% by weight pure relative to the other stereoisomers. When a single enantiomer is named or depicted by structure, the depicted or named enantiomer is at least 50%, 60%, 70%, 80%, 90%, 95%, 98%, 99% or 99.9% by weight optically pure. Percent optical purity by weight is the ratio of the weight of the enantiomer over the weight of the enantiomer plus the weight of its optical isomer.

The compounds of the invention may be prepared as individual isomers by incorporating or starting with a specific isomer, isomer-specific synthesis, separation of diastereomers or resolution from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Reference to a use of a compound of Formula I through VII or I' to X' or a composition that includes a compound of Formula I through VII or I' to X', wherein the compound contains at least one stereomeric center, refers to the racemate or in any optical purity of the compound of Formula I through VII or I' to X' in the composition, including but not limited to an optically pure compound.

In some embodiments, the enantiomeric ratio of the compound of Formula I through VII or I' to X' having a stereomeric center is greater than 90:10. In some embodiments, the enantiomeric ratio of the compound of Formula I through VII or I' to X' is greater than 95:5. In some embodiments, the enantiomeric ratio of the compound of Formula I through VII or I' to X' is greater than 99:1. In some embodiments, the compound of Formula I through VII or I' to X' is optically pure.

Where compounds of of Formula I through VII or I' to X' include one or more basic sites such as amines, acid addition salts can be made and this invention includes such acid addition salts. Some representative (non-limiting) acid addition salts include hydrochloride, hydrobromide, hydroiodide, acetate, benzenesulfonate, mesylate, besylate, benzoate, tosylate, citrate, tartrate, sulfate, bisulfate, lactate, maleate, mandelate, valerate, laurate, caprylate, propionate, succinate, phosphate, salicylate, napsylate, nitrate, tannate, resorcinate and the like, including multiprotic salts as well as mixtures of the acid addition salts. In cases where an amine is present, this invention also embraces quaternized ammonium salts of those amines. Likewise, where compounds of this invention include one or more acid sites such as carboxylic acids, phenols and the like, basic addition salts can be made and this invention includes such basic addition salts. For example, some representative (non-limiting) acidic compounds of this invention may be present as their lithium, sodium, potassium, ammonium, trialkyammonium, calcium, magnesium, barium and the like.

The compounds of this invention can also be present as solvates and such solvates are embraced within the scope of this invention even where not explicitly described. Such solvates are preferably hydrates but can be solvates comprised of other solvents, preferably where those solvents are considered to be non-toxic or at least acceptable for administration to mammals, preferably humans. The solvates can be stoichiometric or non-stoichiometric, singular or in combination. Some exemplary solvates include water, ethanol, acetic acid and the like.

The compounds of this invention, when used as therapeutics can be administered by any method known to one of skill in the art such as orally, bucally, intravenously, subcutaneously, intramuscularly, transdermally, intradermally, intravascularly, intranasally, sublingually, intracranially, rectally, intratumorally, intravaginally, intraperitonealy, pulmonary, ocularly and intratumorally.

When administered, the compounds and compositions of this invention may be given once daily or with multiple daily doses such as twice per day, three times per day and four times per day.

In one embodiment of this invention, the compound is administered orally where it can be formulated for solid dosage administration or liquid dosage administration. Solid dosage administration can be in the form of a tablet, granule, capsule, pill, pellet, powder and the like. Liquid dosage formulations include syrups, solutions, gels, suspensions, elixirs, emulsions, colloids, oils, and the like.

As mentioned previously, the compounds of this invention may be solids and when present as solids, they may be of defined particle size. Where the compound of this invention is not particularly water soluble, it is sometimes preferable to administer the compound with a certain particle size—a particle size with a preferred range where the average mean particle size diameter is under 100 microns, or 75 microns, or 50 microns, or 35 microns, or 10 microns or 5 microns.

Solid dosage formulations will comprise at least one compound of this invention together with one or more pharmaceutical excipients.

The solid dosage forms of this invention also include capsules wherein the drug is enclosed inside the capsule either as a powder together with optional excipients or as granules containing usually including one or more excipients together with the drug and wherein the granule in turn can be optionally coated, for example, enterically or non-enterically.

The compounds of this invention may be employed alone or in combination with other therapeutic agents. By way of non-limiting example, the compounds of this invention can be used in combination with one or more of a cdk4/6 inhibitor, PI3K inhibitor, mTOR inhibitor, and a taxane.

The compounds of this invention may be administered according to different dosage scheduling and the dosage may be adjusted as deemed necessary by the subject or preferably by the subject in consultation with a qualified practitioner of medicine. Dosing of the compounds of this invention can take place by multiple routes and consequently, the dosing schedule and amounts are dependent not only on the particular subject's weight, sex, age, therapy contemplated, etc but also by the route of the drug chosen.

By way of non-limiting example, the compounds of this invention may be considered for dosing by the oral route with optimal efficacy and/or safety being the goal.

It is understood that the amount of compound dosed per day can be administered every day, every other day, every 2 days, every 3 days, every 4 days, every 5 days, etc. For example, with every other day administration, a 5 mg per day dose can be initiated on Monday with a first subsequent 5 mg per day dose administered on Wednesday, a second subsequent 5 mg per day dose administered on Friday, etc. In one embodiment, a compound is dosed once every seven days.

This invention also provides a method of treating (e.g., preventing, or ameliorating the symptoms associated with, or reducing the incidence of, reducing the pathogenesis of, facilitating the recovery from or delaying the onset of) a disease, syndrome, illness, or symptom associated with insufficient or overabundant estrogen levels in a mammal in need thereof, wherein said method comprises the administration to said mammal of an effective amount of a compound selected from the group consisting of formulas I-VII, I' to X', and all structural embodiments described herein or a pharmaceutically acceptable salt thereof, or a pharmaceutical composition comprising a compound of formulas I-VII, I' to X', or one of the structural embodiments described herein, or a pharmaceutically acceptable salt thereof and a pharmaceutically acceptable excipient. In a particular embodiment, the mammal is a human.

In certain aspects, this invention describes a method of treating (e.g., preventing, or ameliorating the symptoms associated with, or reducing the incidence of, reducing the pathogenesis of, facilitating the recovery from or delaying the onset of) prostate cancer, breast cancer, endometrial cancer, lung cancer, hepatocellular cancer, lymphoma, multiple endocrine neoplasia, vaginal cancer, renal cancer, thyroid cancer, testicular cancer, leukemia, and ovarian cancer in a mammal in need thereof comprising the administration to said mammal of a compound selected from the group consisting of formulas I-VII, I' to X', and all structural embodiments described herein, or a pharmaceutically acceptable salt thereof, or a pharmaceutical composition comprising a compound selected from the group consisting of formulas I-VII, I' to X', and all structural embodiments described herein including pharmaceutically acceptable salts thereof and a pharmaceutically acceptable excipient. In an embodiment, the mammal is a human. In some embodiments, the cancer is positive for the expression of ESR1. In certain embodiments, the cancers are resistant to prior lines of treatment (e.g., prior endocrinological therapy). In certain embodiments, the cancer progresses after exposure to one or more agents selected from the group consisting of tamoxifen, toremifene, letrozole, aromasin, anastrazole, and faslodex. In some embodiments, the treatment is in adjuvant setting and in some embodiments the treatment is in the metastatic setting. In certain embodiments, SERD and/or SERMS compounds disclosed herein are combined with other active compounds including, cdk4/6 inhibitors, PI3k inhibitors, mTOR inhibitors, taxanes, and Her2 inhibitors.

Also provided herein is a method of inhibiting tumor growth or producing tumor regression in a subject having an estrogen receptor alpha-positive cancer comprising administering to said subject a therapeutically effective amount of a compound of Formulas I to VII or I' to X' or a pharmaceutically acceptable salt, solvate or prodrug thereof. In some embodiments, the estrogen receptor alpha-positive cancer is a drug-resistant estrogen receptor alpha-positive cancer. In some embodiments, the cancer is selected from breast cancer, uterine cancer, ovarian cancer, and pituitary cancer. In some embodiments, the cancer is breast cancer. In some embodiments, the cancer is metastatic. In some embodiments, the cancer is positive for the mutant estrogen receptor alpha comprising one or more mutations selected from the group consisting of $Y537X_1$ (wherein $X_1$ is S, N, or C), $L536X_2$ (wherein $X_2$ is R or Q), P535H, V534E, S463P, V392I, E380Q, D538G, and combinations thereof. In some embodiments, the mutation is Y537S. In some embodiments, the subject has osteoporosis or a high risk of osteoporosis. In some embodiments, the subject is a pre-menopausal woman. In some embodiments, the subject is a post-menopausal woman who had relapsed or progressed after previous treatment with SERMs, CDK inhibitors, and/or AIs. In some embodiments, the tumor is resistant to a drug selected from the group consisting of anti-estrogens (e.g., tamoxifen or fulvestrant), aromatase inhibitors (e.g., aromasin), CDK inhibitors (e.g., abemaciclib, ribociclib, or palbociclib), and combinations thereof. In some embodiments, the therapeutically effective amount of a compound of Formulas I to VII or I' to X' or a pharmaceutically acceptable salt, solvate or prodrug thereof is employed in combination with one or more of an anti-estrogen, an aromatase inhibitor, a CDK inhibitor, a PI3K inhibitor, an mTOR inhibitor, and a taxane.

Also provided herein is a method of inhibiting tumor growth or producing tumor regression in a subject having a mutant estrogen receptor alpha positive-cancer comprising administering to said subject a therapeutically effective amount of a compound of Formulas I to VII or I' to X' or a pharmaceutically acceptable salt, solvate or prodrug thereof. In some embodiments, the cancer is selected from breast cancer, uterine cancer, ovarian cancer, and pituitary cancer. In some embodiments, the cancer is breast cancer. In some embodiments, the cancer is metastatic. In some embodiments, the cancer is positive for the mutant estrogen receptor alpha comprising one or more mutations selected from the group consisting of $Y537X_1$ (wherein $X_1$ is S, N, or C), $L536X_2$ (wherein $X_2$ is R or Q), P535H, V534E, S463P, V392I, E380Q, D538G, and combinations thereof. In some embodiments, the mutation is Y537S. In some embodiments, the subject has osteoporosis or a high risk of osteoporosis. In some embodiments, the subject is a pre-menopausal woman. In some embodiments, the subject is a post-menopausal woman who had relapsed or progressed after previous treatment with SERMs, CDK inhibitors, and/or AIs. In some embodiments, the tumor is resistant to a drug selected from the group consisting of anti-estrogens (e.g., tamoxifen or fulvestrant), aromatase inhibitors (e.g., aromasin), CDK inhibitors (e.g., abemaciclib, ribociclib, or palbociclib), and combinations thereof. In some embodiments, the therapeutically effective amount of a compound of Formulas I to VII or I' to X' or a pharmaceutically acceptable salt, solvate or prodrug thereof is employed in combination with one or more of an anti-estrogen, an aromatase inhibitor, a CDK inhibitor, a PI3K inhibitor, an mTOR inhibitor, and a taxane.

Also provided herein is a method of treating breast cancer in a subject having a drug-resistant estrogen receptor alpha-positive cancer comprising administering to said subject a therapeutically effective amount of a compound of Formulas I to VII or I' to X' or a pharmaceutically acceptable salt, solvate or prodrug thereof. In some embodiments, the drug resistant breast cancer is resistant to one or more antiestrogens (e.g., tamoxifen, toremifene, fulvestrant), CDK inhibitors (e.g., abemaciclib, ribociclib, or palbociclib), and/or aromatase inhibitors (e.g., aromasin, letrozole, anastrozole).

In some embodiments, the therapeutically effective amount of a compound of Formulas I to VII or I' to X' or a pharmaceutically acceptable salt, solvate or prodrug thereof is employed in combination with one or more of an anti-estrogen, an aromatase inhibitor, a CDK inhibitor, a PI3K inhibitor, an mTOR inhibitor, and a taxane. In some embodiments, the subject expresses at least one mutant estrogen receptor alpha selected from D538G, Y537S, Y537N, Y537C, E380Q, S463P, L536R, L536Q, P535H, V392I and V534E. In some embodiments, the mutant estrogen receptor alpha is selected from Y537S, Y537N, Y537C, D538G, L536R, S463P and E380Q. In some embodiments, the mutant receptor alpha is Y537S. In some embodiments, the subject is a post-menopausal woman. In some embodiments, the subject is first identified for treatment through measuring for increased expression of one or more genes selected from ABL1, AKT1, AKT2, ALK, APC, AR, ARID1A, ASXL1, ATM, AURKA, BAP, BAP1, BCL2L11, BCR, BRAF, BRCA1, BRCA2, CCND1, CCND2, CCND3, CCNE1, CDH1, CDK4, CDK6, CDK8, CDKN1A, CDKN1B, CDKN2A, CDKN2B, CEBPA, CTNNB1, DDR2, DNMT3A, E2F3, EGFR, EML4, EPHB2, ERBB2, ERBB3, ESR1, EWSR1, FBXW7, FGF4, FGFR1, FGFR2, FGFR3, FLT3, FRS2, HIF1A, HRAS, IDH1, IDH2, IGF1R, JAK2, KDM6A, KDR, KIF5B, KIT, KRAS, LRP1B, MAP2K1, MAP2K4, MCL1, MDM2, MDM4, MET, MGMT, MLL, MPL, MSH6, MTOR, MYC, NF1, NF2, NKX2-1, NOTCH1, NPM, NRAS, PDGFRA, PIK3CA, PIK3R1, PML, PTEN, PTPRD, RARA, RB1, RET, RICTOR, ROS1, RPTOR, RUNX1, SMAD4, SMARCA4, SOX2, STK11, TET2, TP53, TSC1, TSC2, and VHL. In some embodiments, the one or more genes are selected from AKT1, AKT2, BRAF, CDK4, CDK6, PIK3CA, PIK3R1 and MTOR.

The compounds of this invention can be prepared by a variety of synthetic routes and techniques known to those of skill in the art. The processes disclosed herein should not be construed as limiting the examples or scope of the invention in any way but rather are provided as just some of the representative ways that the compounds of this invention can be or were prepared.

In some cases, protective groups are employed in the synthesis of the compounds of this invention and it should be appreciated that there are a diverse array of protective groups and strategies that can be employed in organic synthesis (T. W. Green and P. G. M. Wuts (2006) Greene's Protective Groups in Organic Synthesis, herein incorporated by reference in its entirety) and that where a protective group is referred to generically, any appropriate protective group should be considered.

In some instances, leaving groups are employed in the synthesis of compounds of this invention. Where a specific leaving group is referred to, it should be appreciated that other leaving groups might also be used. Leaving groups typically include those groups that can stabilize an anion. In the case of nucleophilic aromatic substitutions, the leaving group may be an anion or a neutrally charged group. In some cases, the leaving group for nucleophilic aromatic substitution may be a group that is not typically considered to be a stabilized anion (e.g. fluoride or hydride). While not intending to be bound by theory or the examples, some typical nucleophilic leaving groups include halogens, sulfonates (O-mesylates, O-tosylates, etc.), hydrides, quaternized amines, nitro, and the like. Additional discussion and examples can be found in leading textbooks on organic chemistry including, for example, March's Advanced Organic Chemistry: Reactions, Mechanisms, and Structure, 5$^{th}$ Edition, which is herein incorporated by reference in its entirety.

When any variable occurs more than one time in any constituent or in any formula, its definition in each occurrence is independent of its definition at every other occurrence. Combinations of substituents and/or variables are permissible only if such combinations result in stable compounds.

Accordingly, in one embodiment, the present invention provides novel pharmaceutically active compounds or pharmaceutical salts thereof of formula I

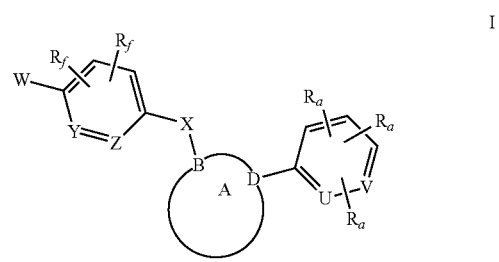

wherein:

B is nitrogen or carbon;

D is carbon;

A is a fused ring system selected from the group consisting of:

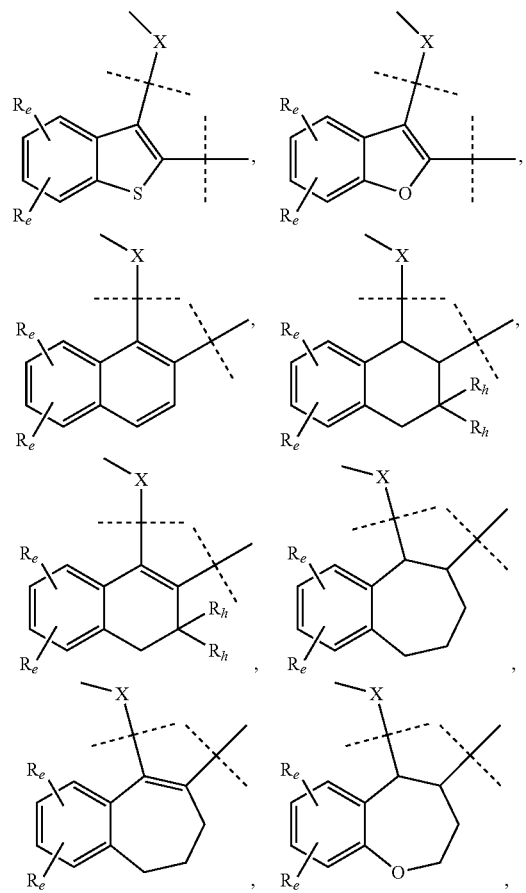

-continued

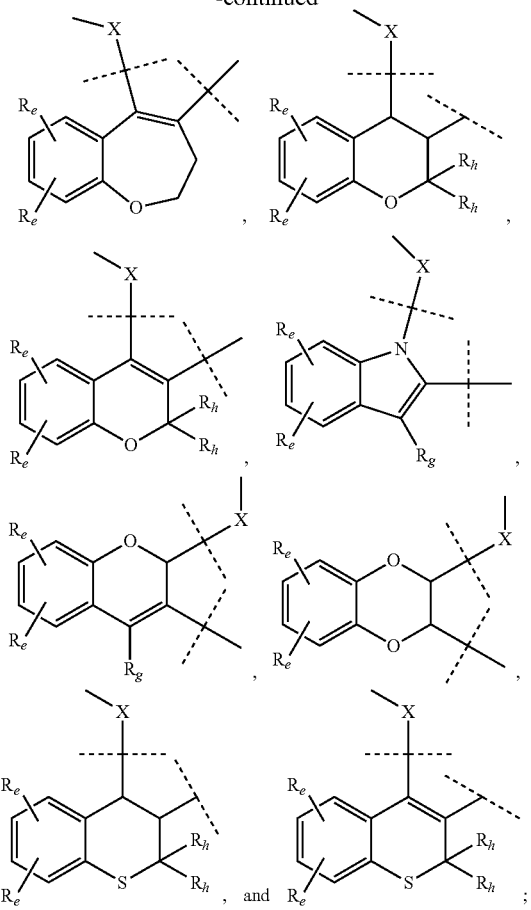

, and

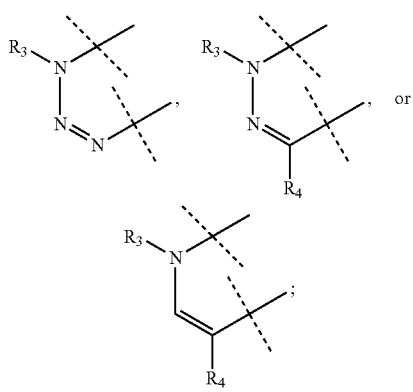

;

each $R_e$ is independently hydrogen, halogen, OH, O(CO)R, O(CO)NR$_1$R$_2$, OPO$_3$, OSO$_3$, O(SO$_2$)NR$_1$R$_2$, or wherein two adjacent $R_e$ together form:

R is C$_1$-C$_6$ alkyl or aryl;
R$_1$ and R$_2$ are each independently hydrogen or C$_1$-C$_6$ alkyl;
each R$_3$ is hydrogen, C$_1$-C$_{12}$ acyl; C$_1$-C$_{12}$ acyloxy;
each R$_4$ is independently hydrogen, C$_1$-C$_3$ alkyl, fluorine or chlorine;
each R$_h$ is independently hydrogen or CH$_3$;
R$_g$ is hydrogen, C$_1$-C$_3$ alkyl, C$_1$-C$_3$ fluoroalkyl, CN, fluorine, chlorine or bromine;

each R$_a$ is independently selected from: H, C$_1$-C$_3$ alkyl, C$_1$-C$_3$ fluoroalkyl, phenyl (optionally substituted with 1-3 groups that are fluorine, chlorine, C$_1$-C$_3$ alkyl, CN, OC$_1$-C$_3$ alkyl, OH), OH, OC$_{1-3}$alkyl, CN, fluorine, chlorine, O(CO)R, O(CO)NR$_1$R$_2$, OPO$_3$, OSO$_3$, O(SO$_2$)NR$_1$R$_2$, or two adjacent Ra together form:

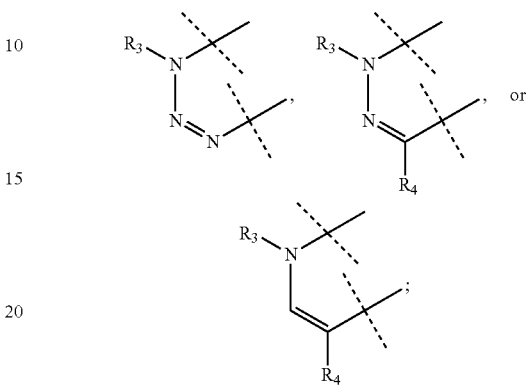

X is O, S, CH$_2$, NH or a bond when B is carbon, or CH$_2$ or a bond when B is nitrogen;
Y and Z are each independently CR$_f$ or N;
U and V are each independently CR$_a$ or N;
each R$_f$ is independently H, C$_1$-C$_3$ alkyl, OC$_1$-C$_3$ alkyl, fluorine or chlorine; and
W is —CHR'—CHR'—NH—C$_1$-C$_4$alkyl, —CHR'—CHR'—NH—C$_1$-C$_4$fluoroalkyl, —CHR'—CHR'—NH—C$_3$-C$_6$cycloalkyl, —CHR'—CHR'—NH—C$_1$-C$_4$alky-C$_3$-C$_6$cycloalkyl,

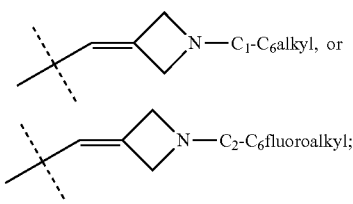

wherein each R' is independently H or C$_1$-C$_3$alkyl;
or a pharmaceutically acceptable salt, solvate or prodrug thereof.

In some embodiments, the compound of formula I is the compound. In other embodiments, it is a pharmaceutically acceptable salt thereof.

In certain embodiments, the compound of formula I is a pharmaceutically acceptable salt, solvate or prodrug thereof.

In some embodiments, the pharmaceutically acceptable salt of the compound is an acid addition salt.

In other embodiments, the compound of formula I is a prodrug. In yet other embodiments, the compound of formula I is the pharmaceutically acceptable salt of the prodrug. In some aspects the pharmaceutically acceptable salt of the prodrug of a compound of Formula I is a hydrochloride salt.

In some embodiments, a pharmaceutical composition comprising a compound or a pharmaceutically acceptable salt or prodrug of a compound of Formula I is described. In other embodiments, the pharmaceutical composition is formulated for intravenous injection, subcutaneous injection, oral administration, or topical administration. In certain embodiments, the pharmaceutical composition is a tablet, a pill, a capsule, a liquid, a suspension, a gel, a dispersion, a solution, an emulsion, an ointment, or a lotion.

In some embodiments of formula I compounds, W is —$CH_2$—$CH_2$—NH—$CH_2$—$CH_2$—$CH_3$; in other embodiments W is —$CH_2$—$CH_2$—NH—$CH_2$—$CH_2$—$CH_2F$.

In certain embodiments of formula I compounds, B is carbon. When B is carbon, X is O, S, $CH_2$, NH or a bond. In some embodiments when B is carbon, X is O, $CH_2$, or a bond. In other embodiments, B is nitrogen. When B is nitrogen X is $CH_2$ or a bond. In certain embodiments, when B is nitrogen, X is $CH_2$.

In some embodiments of formula I compounds, A is selected from the group consisting of:

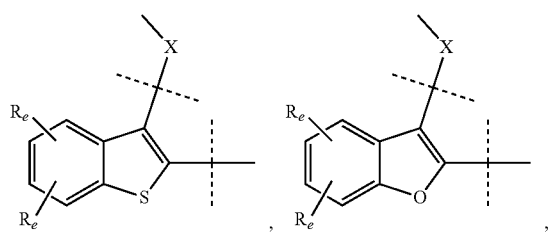

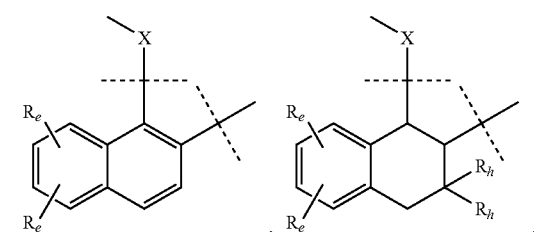

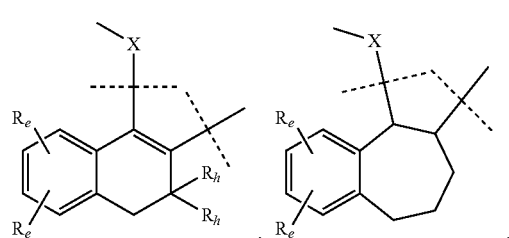

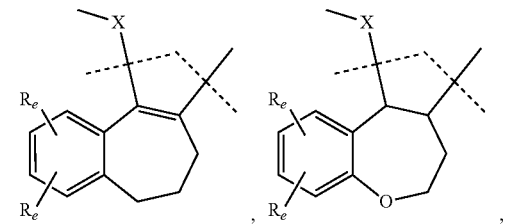

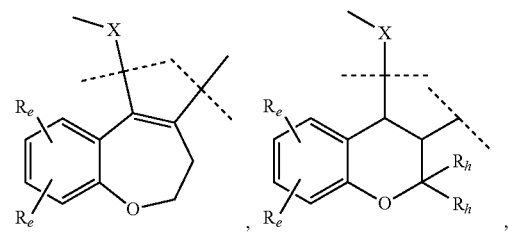

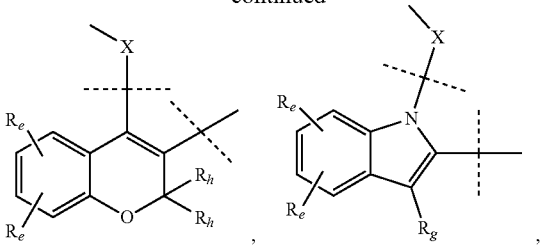

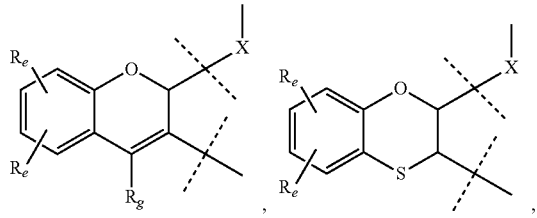

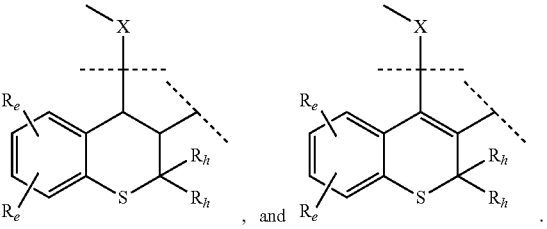

, and

In other embodiments of formula I compounds, A is:

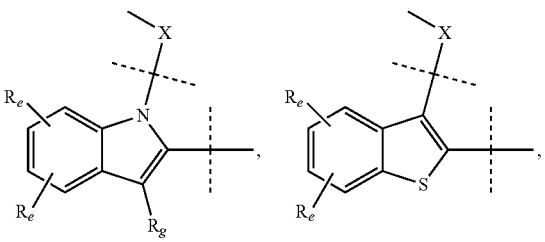

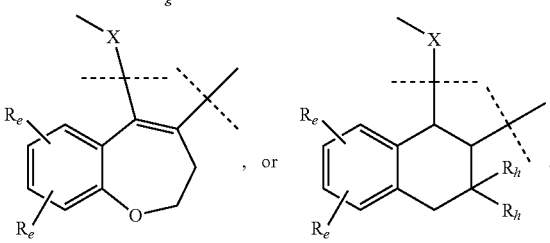

, or .

In certain embodiments of formula I compounds, B and D are adjacent ring atoms on the A ring.

In some other embodiments of formula I compounds, each $R_e$ is independently hydrogen, halogen, OH, O(CO)R, O(CO)$NR_1R_2$, $OPO_3$, and $OSO_3$, O($SO_2$)$NR_1R_2$, or wherein two adjacent $R_e$ together form:

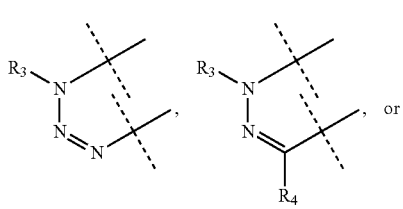

, or

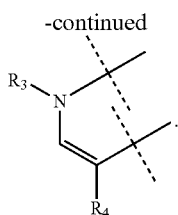

In certain embodiments of formula I compounds, each $R_e$ is independently selected from the group consisting of hydrogen, halogen, OH, O(CO)R, O(CO)$NR_1R_2$, $OPO_3$, and $OSO_3$, O($SO_2$)$NR_1R_2$. In other embodiments of formula I compounds, each $R_e$ is independently hydrogen or OH.

In certain other embodiments of formula I compounds, two adjacent $R_a$ together form:

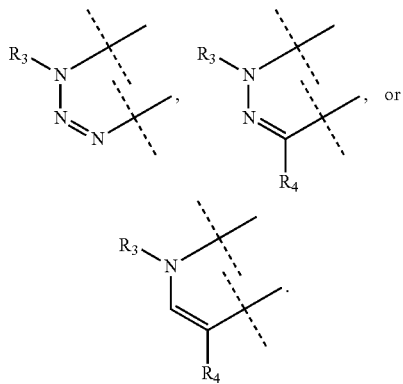

In embodiments of formula I compounds where two adjacent $R_a$ together form:

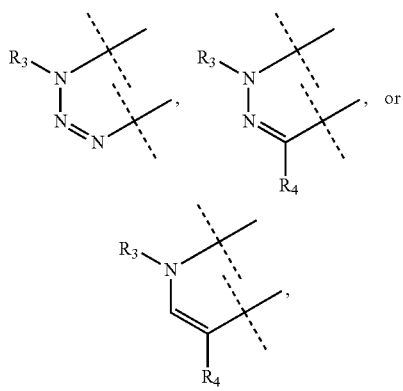

any other $R_a$ are each independently hydrogen, halogen, OH, O(CO)R, O(CO)$NR_1R_2$, $OPO_3$, $OSO_3$, and O($SO_2$)$NR_1R_2$. In other embodiments of formula I compounds, at least one $R_a$ is H, or at least two $R_a$ are H.

In some embodiments of formula I compounds, each $R_h$ is independently hydrogen or $CH_3$. In certain embodiments of formula I compounds, at least one $R_h$ is hydrogen; in other embodiments of formula I compounds, both are hydrogen.

In still other embodiments of formula I compounds, R is $C_1$-$C_6$ alkyl; in others, R is aryl.

In certain embodiments of formula I compounds, $R_1$ and $R_2$ are each independently hydrogen or $C_1$-$C_6$ alkyl. In some embodiments of formula I compounds, at least one of $R_1$ and $R_2$ is hydrogen.

In other embodiments of formula I compounds, each $R_3$ is hydrogen, $C_1$-$C_{12}$ acyl; or $C_1$-$C_{12}$ acyloxy.

In other embodiments of formula I compounds, each $R_4$ is independently hydrogen, $C_1$-$C_3$alkyl, fluorine or chlorine. When $R_4$ is $C_1$-$C_3$ alkyl, it is methyl, ethyl, or $C_3$ alkyl, or any combination or subcombination thereof. In some embodiments of formula I compounds, $R_4$ is hydrogen. In some embodiments of formula I compounds, $R_4$ is fluorine.

In yet other embodiments of formula I compounds, $R_g$ is hydrogen, $C_1$-$C_3$ alkyl, $C_1$-$C_3$ fluoroalkyl, CN, fluorine, chlorine or bromine. In certain embodiments of formula I compounds, $R_g$ is hydrogen, $C_1$-$C_3$ alkyl or fluorine. In other embodiments of formula I compounds, $R_g$ is $C_1$-$C_3$ alkyl or fluorine. When $R_g$ is $C_1$-$C_3$ alkyl, it is methyl, ethyl, or $C_3$ alkyl, or any combination or subcombination thereof.

In certain embodiments of formula I compounds, each $R_a$ is independently selected from the group consisting of H, $C_1$-$C_3$ alkyl, $C_1$-$C_3$ fluoroalkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, O(CO)R, O(CO)$NR_1R_2$, $OPO_3$, $OSO_3$, and O($SO_2$)$NR_1R_2$, or two adjacent $R_a$ together form:

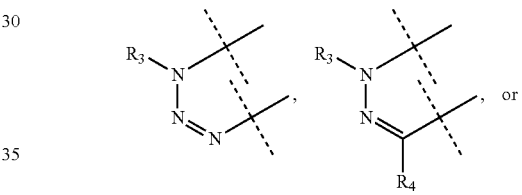

In certain embodiments of formula I compounds, each $R_a$ is independently selected from H, $C_1$-$C_3$ alkyl, $C_1$-$C_3$ fluoroalkyl, or phenyl (optionally substituted with 1-3 groups selected from fluorine, chlorine, $C_1$-$C_3$ alkyl, $OC_1$-$C_3$ alkyl, OH), OH, $OC_{1-3}$alkyl, fluorine, chlorine. In other embodiments of formula I compounds, an $R_a$ is positioned ortho or para to the bond attached to D. In some embodiments of formula I compounds, $R_a$ is —$OCH_3$ attached para to the bond attached to D. In some embodiments of formula I compounds, $R_a$ is methyl attached ortho to the bond attached to D. In certain other embodiments of formula I compounds, two adjacent $R_a$ together form:

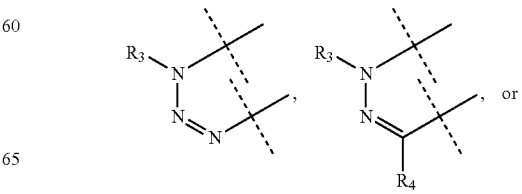

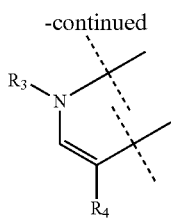

In embodiments where two adjacent $R_a$ together form:

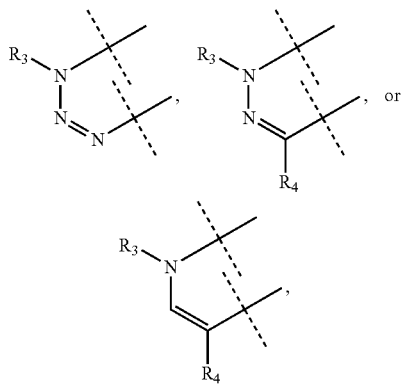

any other $R_a$ are each independently selected from hydrogen, halogen, OH, O(CO)R, O(CO)NR$_1$R$_2$, OPO$_3$, OSO$_3$, and O(SO$_2$)NR$_1$R$_2$.

In certain other embodiments of formula I compounds, X is O, S, CH$_2$, NH or a bond when B is carbon, or CH$_2$ or a bond when B is nitrogen. In other embodiments of formula I compounds, B is carbon and X is O, CH$_2$, or a bond. In some embodiments when B is carbon, X is O or CH$_2$.

In some embodiments of formula I compounds, Y and Z are each independently selected from CR$_f$ or N, and U and V are each independently selected from CR$_a$ or N. In certain embodiments of formula I compounds, Y is CR$_f$. In other embodiments of formula I compounds, Y is N. In some embodiments of formula I compounds, U is CR$_a$. In some embodiments of formula I compounds, Z is CR$_f$. In some embodiments of formula I compounds, V is CR$_a$. In certain embodiments of formula I compounds, Y and Z are each CR$_f$ and U and V are each CR$_a$.

In certain embodiments of formula I compounds, each R$_f$ is independently H, C$_1$-C$_3$ alkyl, fluorine or chlorine. In some embodiments of formula I compounds, each R$_f$ is H.

In yet other embodiments of formula I compounds, W is —CHR'—CHR'—NH—C$_1$-C$_4$alkyl, —CHR'—CHR'—NH—C$_1$-C$_4$fluoroalkyl, —CHR'—CHR'—NH—C$_3$-C$_6$cycloalkyl, —CHR'—CHR'—NH—C$_1$-C$_4$alkyl-C$_3$-C$_6$cycloalkyl,

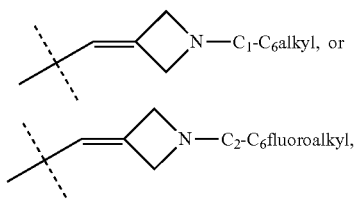

wherein each R' is independently H or C$_1$-C$_3$alkyl, or any combination or subcombination thereof. When W is —CHR'—CHR'—NH—C$_1$-C$_4$alkyl, each R' is independently methyl, ethyl, C$_3$ alkyl or hydrogen, or any combination or subcombination thereof. In certain embodiments of formula I compounds when W is —CHR'—CHR'—NH—C$_1$-C$_4$fluoroalkyl, each R' is independently methyl, ethyl, C$_3$ alkyl, or any combination or subcombination thereof wherein 1 to 3 fluoro atoms are attached to the alkyl group. In other embodiments of formula I compounds when W is —CHR'—CHR'—NH—C$_3$-C$_6$cycloalkyl, the C$_3$-C$_6$cycloalkyl is cyclopropyl or cyclobutyl. In still other embodiments of formula I compounds when W is —CHR'—CHR'—NH—C$_1$-C$_4$alkyl-C$_3$-C$_6$cycloalkyl, each R' is independently methyl, ethyl, C$_3$ alkyl or C$_4$ alkyl, or any combination or subcombination thereof, and the C$_3$-C$_6$cycloalkyl is cyclopropyl or cyclobutyl. In certain embodiments the C$_1$-C$_4$ alkyl is C$_1$ alkyl. In some other embodiments of formula I compounds, when W is

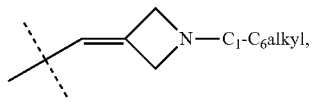

C$_1$-C$_6$alkyl is methyl, ethyl or C$_3$ alkyl. In yet other embodiments of formula I compounds, when W is

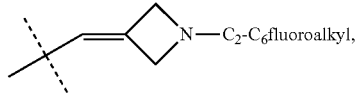

C$_1$-C$_6$ alkyl is methyl, ethyl or C$_3$ alkyl wherein 1 to 3 fluoro atoms are attached to the alkyl group. In some embodiments, W is —CH$_2$—CH$_2$—NH—CH$_2$—CH$_2$—CH$_3$; in some embodiments W is —CH$_2$—CH$_2$—NH—CH$_2$—CH$_2$—CH$_2$F; in some embodiments W is

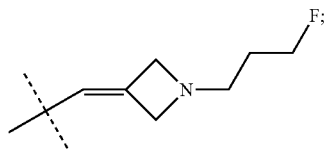

in certain embodiments, W is

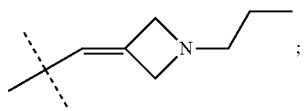

in some embodiments, W is —CH$_2$—CH$_2$—NH—CH$_2$—CH$_3$; in some embodiments, W is —CH$_2$—CH$_2$—NH-cyclopropyl; in some embodiments, W is —CH$_2$—CH$_2$—NH—CH$_2$-cyclopropyl.

In some embodiments, the present invention describes compounds or pharmaceutical salts thereof of formula I having the structure of formula II:

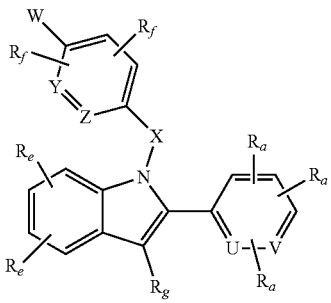

II wherein
each $R_a$ is independently selected from H, $C_1$-$C_3$ alkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, O(CO)R, O(CO)NR$_1$R$_2$, OPO$_3$, OSO$_3$, O(SO$_2$)NR$_1$R$_2$, or two adjacent $R_a$ together form:

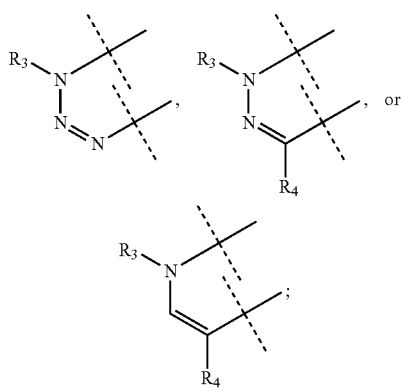

R is $C_1$-$C_6$ alkyl or aryl;
$R_1$ and $R_2$ are each independently hydrogen or $C_1$-$C_6$ alkyl;
each $R_3$ is independently hydrogen; $C_1$-$C_{12}$ acyl or $C_1$-$C_{12}$ acyloxy;
each $R_4$ is independently hydrogen, $C_1$-$C_3$ alkyl, fluorine or chlorine;
each $R_e$ is independently selected from hydrogen, halogen, OH, O(CO)R, O(CO)NR$_1$R$_2$, OPO$_3$, OSO$_3$, O(SO$_2$)NR$_1$R$_2$, or wherein two adjacent $R_e$ together form:

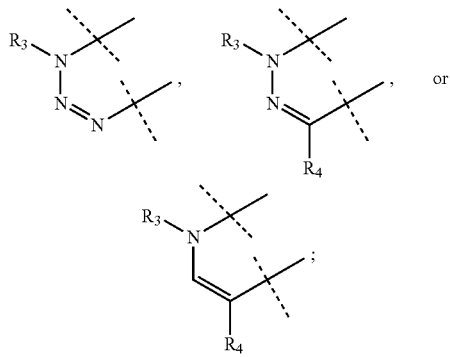

each $R_f$ is independently H, $C_1$-$C_3$ alkyl, $OC_1$-$C_3$ alkyl, fluorine or chlorine;
$R_g$ is hydrogen, $C_1$-$C_3$ alkyl, $C_1$-$C_3$ fluoroalkyl, CN, fluorine, chlorine or bromine;
X is CH$_2$ or a bond;
Y and Z are each independently selected from CR$_f$ or N;
U and V are each independently selected from CR$_a$ or N; and
W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alky-$C_3$-$C_6$cycloalkyl,

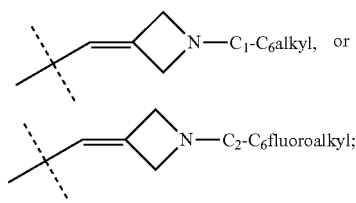

wherein each R' is independently H or $C_1$-$C_3$alkyl.
In some embodiments of formula II compounds, W is —CH$_2$—CH$_2$—NH—CH$_2$—CH$_2$—CH$_3$; in some embodiments of formula II compounds W is —CH$_2$—CH$_2$—NH—CH$_2$—CH$_2$—CH$_2$F; in some embodiments of formula II compounds W is

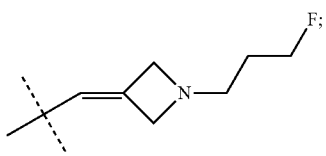

in certain embodiments of formula II compounds, W is

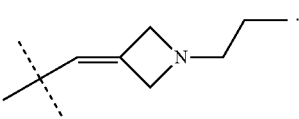

In certain embodiments of formula II compounds, X is CH$_2$.
In still other embodiments of formula II compounds, Y and Z are each CR$_f$ and U and V are each CR$_a$.
In some embodiments of formula II compounds, each $R_a$ is independently selected from H, $C_1$-$C_3$ alkyl, $C_1$-$C_3$ fluoroalkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$ alkyl, CN, fluorine, and chlorine.
In some other embodiments of formula II compounds, two adjacent $R_e$ together form:

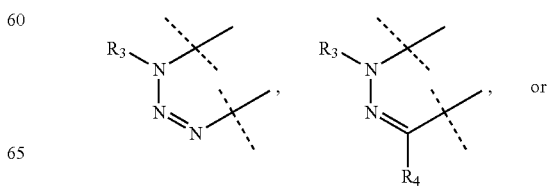

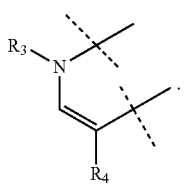

In certain embodiments of formula II compounds, two adjacent $R_e$ together form:

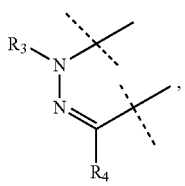

wherein $R_4$ is H.

In certain other embodiments of formula II compounds, two adjacent $R_e$ together form:

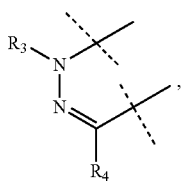

wherein $R_4$ is fluorine.

In certain embodiments of formula II compounds, two adjacent $R_e$ together form:

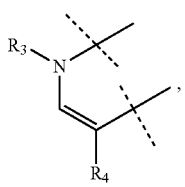

wherein $R_4$ is H.

In certain other embodiments of formula II compounds, two adjacent Re together form:

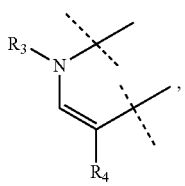

wherein $R_4$ is fluorine.

In certain embodiments of formula II compounds, two adjacent Re together form:

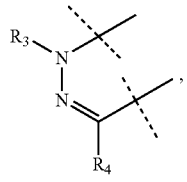

wherein $R_3$ is hydrogen.

In certain embodiments of formula II compounds, two adjacent Re together form:

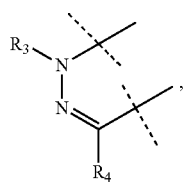

wherein $R_3$ is hydrogen and R4 is hydrogen.

In certain embodiments of formula II compounds, two adjacent $R_e$ together form:

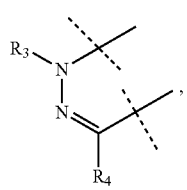

wherein $R_3$ is hydrogen and $R_4$ is fluorine.

In some embodiments of formula II compounds, each $R_e$ is independently selected from H and OH.

In other embodiments of formula II compounds, $R_f$ is H or fluorine.

In other embodiments of formula II compounds, $R_f$ is H.

In yet other embodiments of formula II compounds, W is —CHR'—CHR'—NH—$C_1$-$C_4$alkyl, —CHR'—CHR'—NH—$C_1$-$C_4$fluoroalkyl, wherein each R' is independently H or $C_1$-$C_3$alkyl. In certain embodiments, one or more R' are H.

In some embodiments of formula II compounds, W is —CHR'—CHR'—NH—$C_3$-$C_6$ cycloalkyl, or —CHR'—CHR'—NH—$C_1$-$C_4$ alkyl-$C_3$-$C_6$ cycloalkyl, wherein each R' is independently H or $C_1$-$C_3$alkyl. In certain embodiments of formula II compounds, one or more R' are H. In other embodiments of formula II compounds wherein W contains a $C_3$-$C_6$ cycloalkyl moiety, the cycloalkyl group is $C_3$-$C_4$ cycloalkyl.

In still other embodiments of formula II compounds, W is

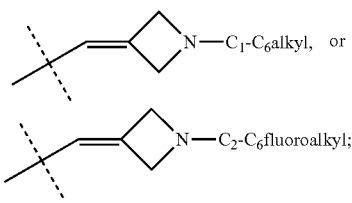

In some embodiments, W is —CH₂—CH₂—NH—CH₂—CH₂—CH₃; in some embodiments W is —CH₂—CH₂—NH—CH₂—CH₂—CH₂F; in some embodiments W is

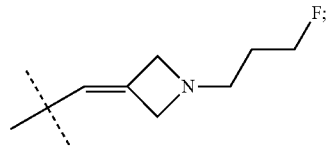

in certain embodiments, W is

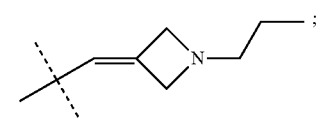

in some embodiments, W is —CH₂—CH₂—NH—CH₂—CH₃; in some embodiments, W is —CH₂—CH₂—NH-cyclopropyl; and in some embodiments, W is —CH₂—CH₂—NH—CH₂-cyclopropyl.

In other embodiments of formula II compounds, $R_g$ is hydrogen, $C_1$-$C_3$ alkyl, or fluorine. In yet other embodiments, $R_g$ is methyl; in other embodiments, $R_g$ is fluorine.

In some embodiments of formula II compounds, each $R_f$ is H. In other embodiments of formula II compounds, when $R_f$ is H, each $R_e$ is independently selected from H and OH.

In certain other embodiments of formula II compounds, at least one of $R_a$ is OCH₃, fluorine, —OH, —CH₃, or chlorine.

Some embodiments of formula II compounds have the formula IIa, IIb, or IIc:

IIa
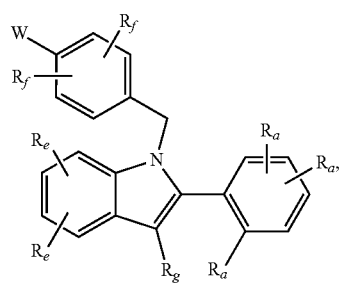

IIb
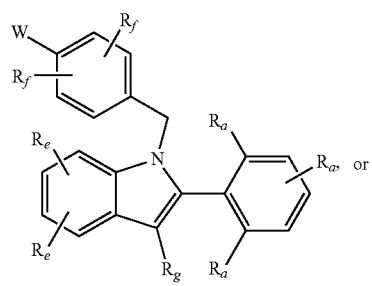

IIc
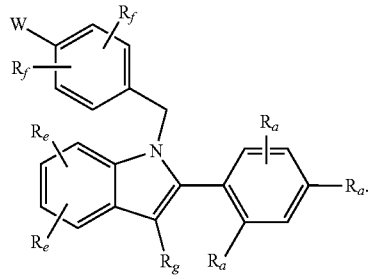

In certain embodiments, formula II compounds have the formula IId, IIe, or IIf:

IId
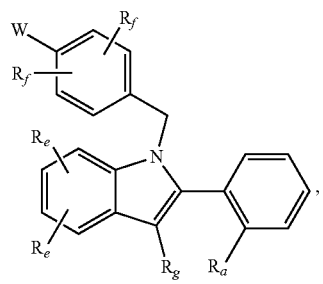

IIe
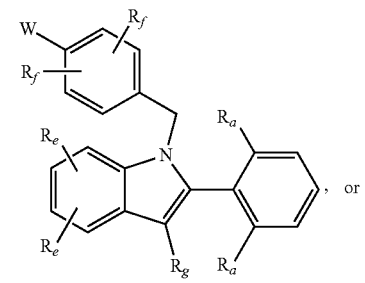

, or

IIf
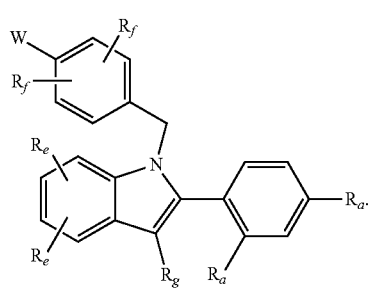

In other embodiments, formula II compounds have the formula IIg, IIh, or IIj:

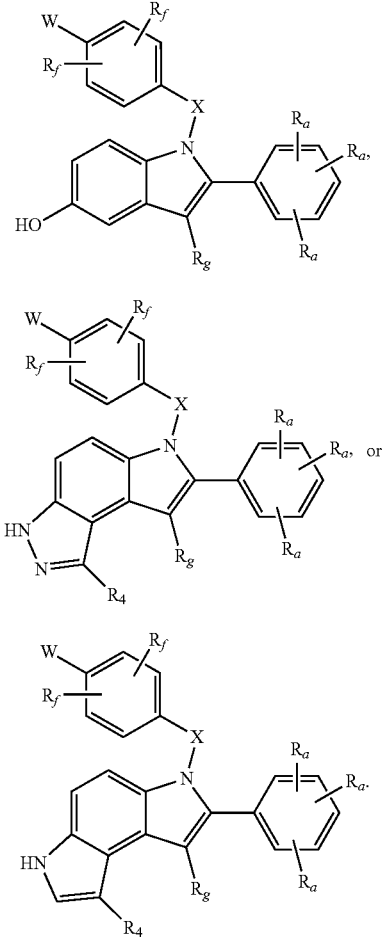

In certain embodiments, the compound of formula II, IIa, IIb, IIc, IId, IIe, IIf, IIg, IIh, or IIj is a pharmaceutically acceptable salt, solvate or prodrug thereof.

In some embodiments, the pharmaceutically acceptable salt of the compound is an acid addition salt.

In other embodiments, the compound of formula II, IIa, IIb, IIc, IId, IIe, IIf, IIg, IIh, or IIj is a prodrug. In yet other embodiments, the compound of formula II is the pharmaceutically acceptable salt of the prodrug. In some aspects the pharmaceutically acceptable salt of the prodrug of a compound of Formula II, IIa, IIb, IIc, IId, IIe, IIf, IIg, IIh, or IIj is a hydrochloride salt.

In some embodiments a pharmaceutical composition comprising a compound or a pharmaceutically acceptable salt or prodrug of a compound of Formula II, IIa, IIb, IIc, IId, IIe, IIf, IIg, IIh, or IIj is described. In other embodiments, the pharmaceutical composition is formulated for intravenous injection, subcutaneous injection, oral administration, or topical administration. In certain embodiments, the pharmaceutical composition is a tablet, a pill, a capsule, a liquid, a suspension, a gel, a dispersion, a solution, an emulsion, an ointment, or a lotion.

In some embodiments, the present invention describes compounds or pharmaceutical salts thereof of formula I having the structure of formula III:

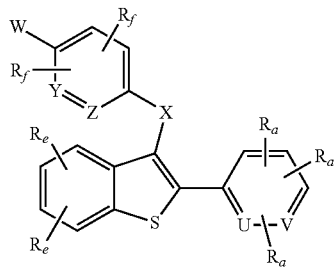

wherein each $R_a$ is independently selected from H, $C_1$-$C_3$ alkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, O(CO)R, O(CO)$NR_1R_2$, $OPO_3$, $OSO_3$, $O(SO_2)NR_1R_2$, or two adjacent $R_a$ together form:

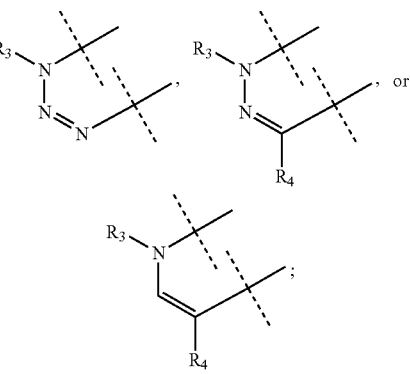

R is $C_1$-$C_6$ alkyl or aryl;

$R_1$ and $R_2$ are each independently hydrogen or $C_1$-$C_6$ alkyl;

each $R_3$ is independently hydrogen or $C_1$-$C_3$ alkyl;

each $R_4$ is independently hydrogen, $C_1$-$C_3$ alkyl, fluorine or chlorine;

each $R_e$ is independently selected from hydrogen, halogen, OH, O(CO)R, O(CO)$NR_1R_2$, $PO_3$, $OSO_3$, $O(SO_2)NR_1R_2$, or wherein two adjacent $R_e$ together form:

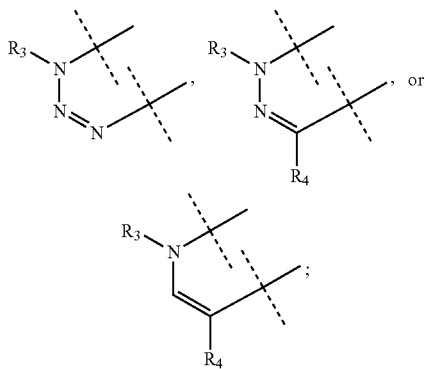

each $R_f$ is independently H, $C_1$-$C_3$ alkyl, fluorine or chlorine;

X is O, $CH_2$, N, S or a bond;

Y and Z are each independently selected from $CR_f$ or N;

U and V are each independently selected from $CR_a$ or N; and

W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl,

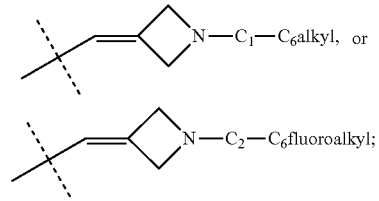

wherein each R' is independently H or $C_1$-$C_3$alkyl.

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2F$; in some embodiments W is

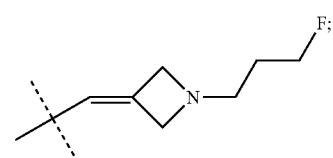

in certain embodiments, W is

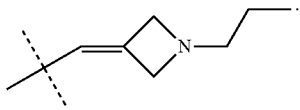

In some embodiments, W is —$CH_2$—$CH_2$—NH—$CH_2$—$CH_3$; in some embodiments, W is —$CH_2$—$CH_2$—NH-cyclopropyl; in some embodiments, W is —$CH_2$—$CH_2$—NH—$CH_2$-cyclopropyl.

In certain embodiments of formula III compounds, X is O.

In still other embodiments of formula III compounds, Y and Z are each $CR_f$ and U and V are each $CR_a$.

In some embodiments of formula III compounds, each $R_a$ is independently selected from H, phenyl, OH, $OC_{1-3}$ alkyl, fluorine, and chlorine. In yet other embodiments of formula III compounds, each $R_a$ is independently selected from H, phenyl, OH, $OCH_3$, fluorine, and chlorine. In certain embodiments of formula III compounds, $R_a$ is independently selected from H, $OCH_3$, fluorine, and chlorine. In certain other embodiments of formula III compounds, at least one of $R_a$ is $OCH_3$, fluorine, or chlorine. In some embodiments $R_a$ can be $C_{1-3}$ alkyl.

In some other embodiments of formula III compounds, two adjacent $R_e$ together form:

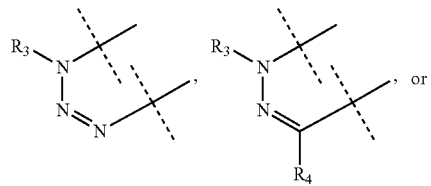

In certain embodiments of formula III compounds, two adjacent $R_e$ together form:

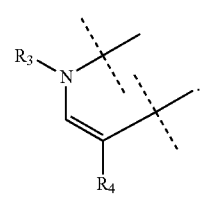

wherein $R_4$ is H.

In certain other embodiments of formula III compounds, two adjacent $R_e$ together form:

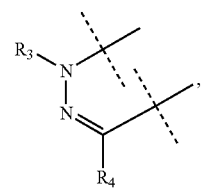

wherein $R_4$ is fluorine.

In certain embodiments of formula III compounds, two adjacent $R_e$ together form:

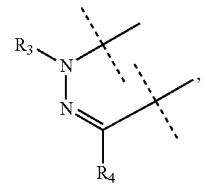

wherein $R_4$ is H.

In certain other embodiments of formula III compounds, two adjacent $R_e$ together form:

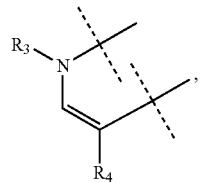

wherein $R_4$ is fluorine.

In some embodiments of formula III compounds, each $R_e$ is independently selected from H and OH. In other embodiments, $R_f$ is H. In certain embodiments, one or more R' are H.

In yet other embodiments of formula III compounds, W is —CHR'—CHR'—NH—$C_1$-$C_4$alkyl, —CHR'—CHR'—NH—$C_1$-$C_4$fluoroalkyl, wherein one or more R' are H or $C_1$-$C_3$alkyl. In certain embodiments, one or more R' are H.

In some embodiments of formula III compounds, W is —CHR'—CHR'—NH—$C_3$-$C_6$ cycloalkyl, or —CHR'—CHR'—NH—$C_1$-$C_4$ alkyl-$C_3$-$C_6$ cycloalkyl, wherein each R' is independently H or $C_1$-$C_3$alkyl. In certain embodiments, one or more R' are H. In other embodiments wherein W contains a $C_3$-$C_6$ cycloalkyl moiety, the cycloalkyl group is $C_3$-$C_4$ cycloalkyl.

In still other embodiments of formula III compounds, W is

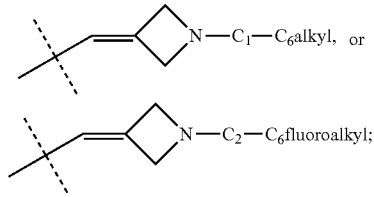

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

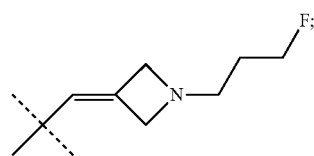

in certain embodiments, W is

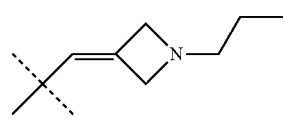

In certain other embodiments of formula III compounds, at least one of $R_a$ is $OCH_3$, fluorine, or chlorine.

In some embodiments, at least one of $R_a$ is —$CH_3$.

In some embodiments of formula III compounds, each $R_f$ is H. In other embodiments of formula III compounds, when $R_f$ is H, each $R_e$ is independently selected from H and OH.

Some embodiments of formula III compounds have the formula IIIa, IIIb, or IIIc:

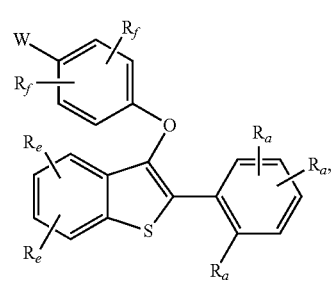

IIIa

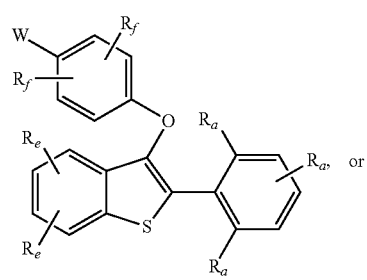

IIIb

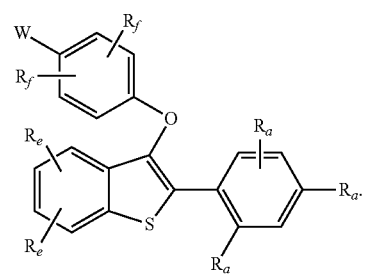

IIIc

In certain embodiments, formula III compounds have the formula IIId, IIIe, or IIIf:

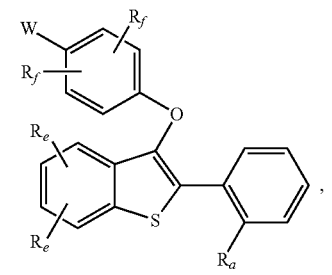

IIId

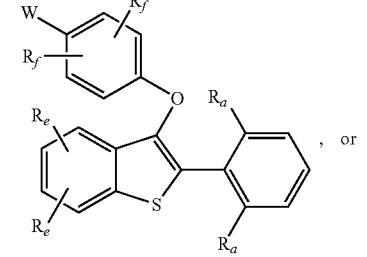

IIIe

IIIf

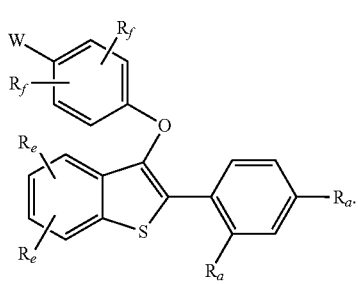

In certain other embodiments, formula III compounds have the formula IIIg, IIIh, or IIIj:

IIIg

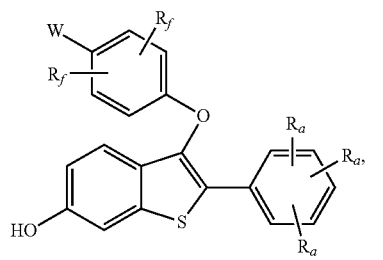

IIIh

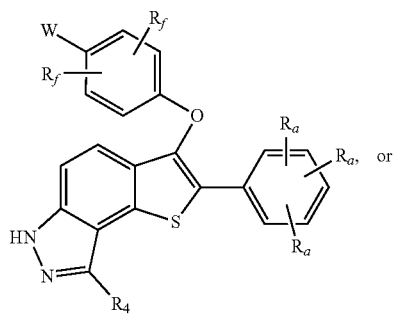

IIIj

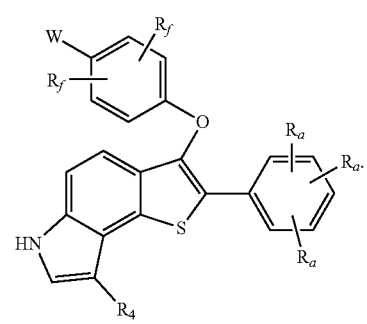

In certain embodiments, the compound of formula III, IIIa, IIIb, IIc, IId, IIIe, or IIIf is a pharmaceutically acceptable salt, solvate or prodrug thereof.

In some embodiments, the pharmaceutically acceptable salt of the compound is an acid addition salt.

In other embodiments, the compound of formula III is a prodrug. In yet other embodiments, the compound of formula III, IIa, IIIb, IIc, IId, IIIe, or IIIf is the pharmaceutically acceptable salt of the prodrug. In some aspects the pharmaceutically acceptable salt of the prodrug of a compound of Formula III, IIIa, IIIb, IIc, IId, IIIe, or IIf is a hydrochloride salt.

In some embodiments a pharmaceutical composition comprising a compound or a pharmaceutically acceptable salt or prodrug of a compound of Formula III, IIIa, IIIb, IIIc, IIId, IIIe, or IIIf is described. In other embodiments, the pharmaceutical composition is formulated for intravenous injection, subcutaneous injection, oral administration, or topical administration. In certain embodiments, the pharmaceutical composition is a tablet, a pill, a capsule, a liquid, a suspension, a gel, a dispersion, a solution, an emulsion, an ointment, or a lotion.

In some embodiments, the present invention describes compounds or pharmaceutical salts thereof of formula I having the structure of formula IV:

IV

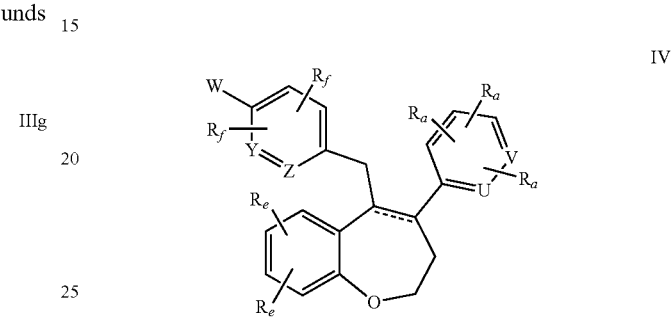

wherein each $R_a$ is independently selected from H, $C_1$-$C_3$ alkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, O(CO)R, O(CO)NR$_1$R$_2$, OPO$_3$, OSO$_3$, O(SO$_2$)NR$_1$R$_2$, or two adjacent $R_a$ together form:

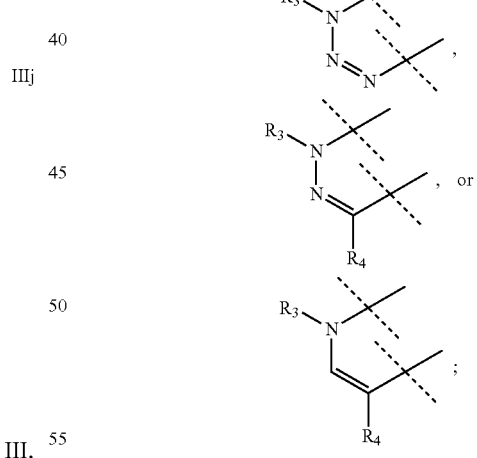

R is $C_1$-$C_6$ alkyl or aryl;

$R_1$ and $R_2$ are each independently hydrogen or $C_1$-$C_6$ alkyl;

each $R_3$ is independently hydrogen or $C_1$-$C_3$ alkyl;

each $R_4$ is independently hydrogen, $C_1$-$C_3$ alkyl, fluorine or chlorine;

each $R_e$ is independently selected from hydrogen, halogen, OH, O(CO)R, O(CO)NR$_1$R$_2$, OPO$_3$, OSO$_3$, O(SO$_2$)NR$_1$R$_2$, or wherein two adjacent $R_e$ together form:

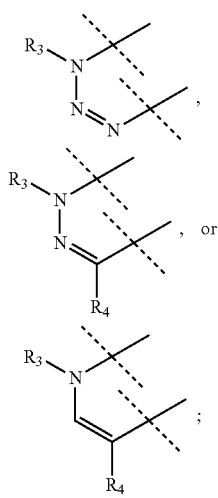

each $R_f$ is independently H, $C_1$-$C_3$ alkyl, fluorine or chlorine;

Y and Z are each independently selected from $CR_f$ or N;

U and V are each independently selected from $CR_a$ or N; and

W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl,

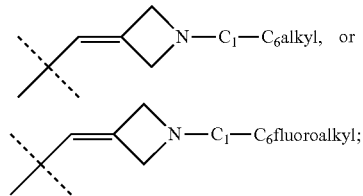

wherein each R' is independently H or $C_1$-$C_3$alkyl.

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

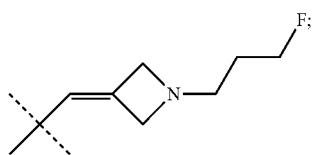

in certain embodiments, W is

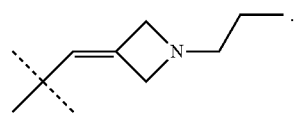

In some embodiments, W is —$CH_2$—$CH_2$—NH—$CH_2$—$CH_3$; in some embodiments, W is —$CH_2$—$CH_2$—NH-cyclopropyl; in some embodiments, W is —$CH_2$—$CH_2$—NH—$CH_2$-cyclopropyl.

In certain embodiments of formula IV compounds, X is $CH_2$.

In still other embodiments of formula IV compounds, Y and Z are each $CR_f$ and U and V are each $CR_a$.

In some embodiments of formula IV compounds, each $R_a$ is independently selected from H, phenyl, OH, $OC_{1-3}$ alkyl, fluorine, and chlorine. In yet other embodiments, each $R_a$ is independently selected from H, phenyl, OH, $OCH_3$, fluorine, and chlorine. In certain embodiments, $R_a$ is independently selected from H, $OCH_3$, fluorine, and chlorine. In certain other embodiments of formula IV compounds, at least one of $R_a$ is methyl, $OCH_3$, fluorine, or chlorine.

In some other embodiments of formula IV compounds, two adjacent $R_e$ together form:

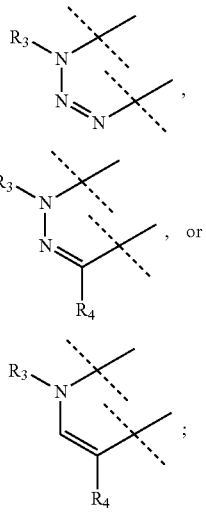

In certain embodiments of formula IV compounds, two adjacent $R_e$ together form:

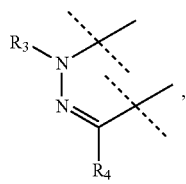

wherein $R_4$ is H.

In certain other embodiments of formula IV compounds, two adjacent $R_e$ together form:

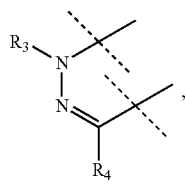

wherein $R_4$ is fluorine.

In certain embodiments of formula IV compounds, two adjacent $R_e$ together form:

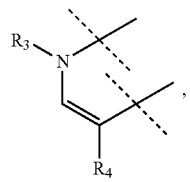

wherein $R_4$ is H.

In certain other embodiments of formula IV compounds, two adjacent $R_e$ together form:

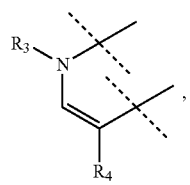

wherein $R_4$ is fluorine.

In some embodiments of formula IV compounds, each $R_e$ is independently selected from H and OH. In other embodiments of formula IV compounds, $R_f$ is H. In certain embodiments of formula IV compounds, one or more R' are H.

In yet other embodiments of formula IV compounds, W is —CHR'—CHR'—NH—$C_1$-$C_4$alkyl, —CHR'—CHR'—NH—$C_1$-$C_4$fluoroalkyl, wherein each R' is independently H or $C_1$-$C_3$alkyl. In certain embodiments of formula IV compounds, each R' is independently H.

In some embodiments of formula IV compounds, W is —CHR'—CHR'—NH—$C_3$-$C_6$ cycloalkyl, or —CHR'—CHR'—NH—$C_1$-$C_4$ alkyl-$C_3$-$C_6$ cycloalkyl, wherein each R' is independently H or $C_1$-$C_3$alkyl. In certain embodiments of formula IV compounds, one or more R' are H. In other embodiments of formula IV compounds wherein W contains a $C_3$-$C_6$ cycloalkyl moiety, the cycloalkyl group is $C_3$-$C_4$ cycloalkyl.

In still other embodiments of formula IV compounds, W is

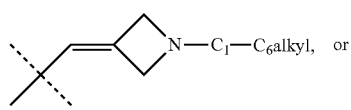

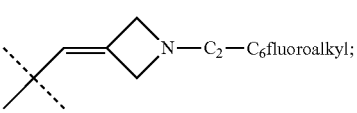

in some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

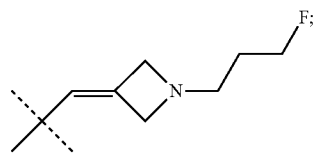

in certain embodiments, W is

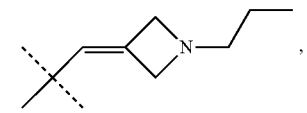

wherein each R' is independently H or $C_1$-$C_3$alkyl. In certain embodiments of formula IV compounds, one or more R' are H. In some embodiments of formula IV compounds, each $R_f$ is H. In other embodiments of formula IV compounds, when $R_f$ is H, each $R_e$ is independently selected from H and OH.

Some embodiments of formula IV compounds have the formula IVa or IVb:

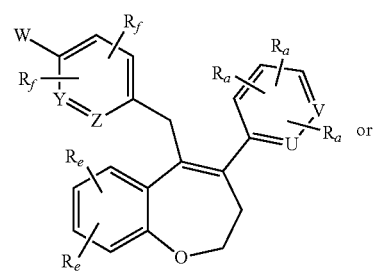

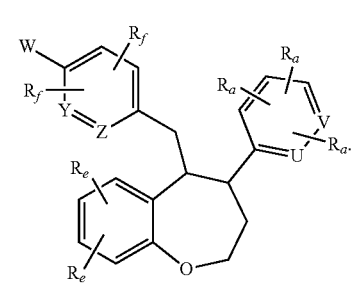

In certain embodiments of formula IV compounds, formula IV compounds have the formula IVc, IVd, IVe, or IVf:

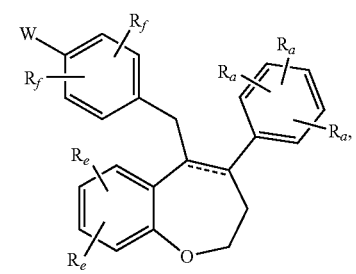

-continued

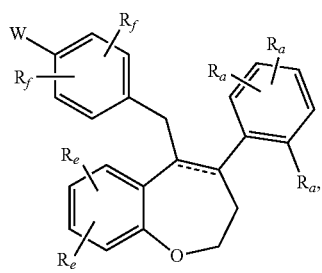
IVd

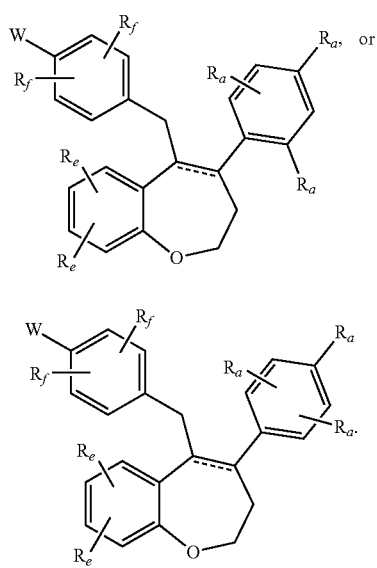
IVe

IVf

In other embodiments of formula IV compounds, formula IV compounds have the formula IVg, IVh or IVj.

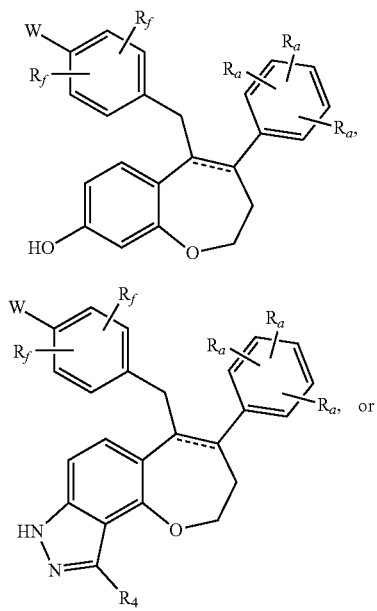
IVg

IVh

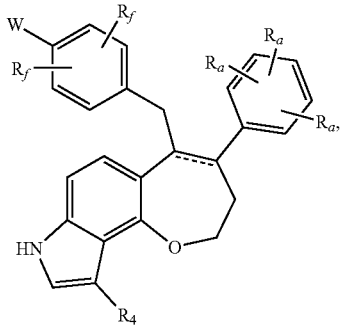
IVj

In certain embodiments, the compound of formula IV, IVa, IVb, IVc, IVd, IVe, IVf, IVg, IVh, or IVj is a pharmaceutically acceptable salt, solvate or prodrug thereof.

In some embodiments, the pharmaceutically acceptable salt of the compound is an acid addition salt.

In other embodiments, the compound of formula IV, IVa, IVb, IVc, IVd, IVe, IVf, IVg, IVh, or IVj is a prodrug. In yet other embodiments, the compound of formula IV, IVa, IVb, IVc, IVd, IVe, IVf, IVg, IVh, or IVj is the pharmaceutically acceptable salt of the prodrug. In some aspects the pharmaceutically acceptable salt of the prodrug of a compound of Formula IV, IVa, IVb, IVc, IVd, IVe, IVf, IVg, IVh, or IVj is a hydrochloride salt.

In some embodiments, a pharmaceutical composition comprising a compound or a pharmaceutically acceptable salt or prodrug of a compound of Formula IV, IVa, IVb, IVc, IVd, IVe, IVf, IVg, IVh, or IVj is described. In other embodiments, the pharmaceutical composition is formulated for intravenous injection, subcutaneous injection, oral administration, or topical administration. In certain embodiments, the pharmaceutical composition is a tablet, a pill, a capsule, a liquid, a suspension, a gel, a dispersion, a solution, an emulsion, an ointment, or a lotion.

In some embodiments, the present invention describes compounds or pharmaceutical salts thereof of formula I having the structure of formula V:

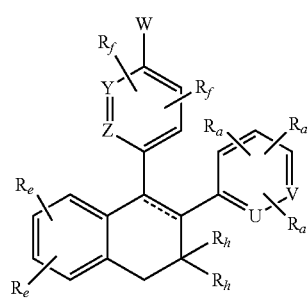
V wherein each $R_a$ is independently selected from H, $C_1$-$C_3$ alkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, O(CO)R, O(CO)$NR_1R_2$, $OPO_3$, $OSO_3$, $O(SO_2)NR_1R_2$, or two adjacent $R_a$ together form:

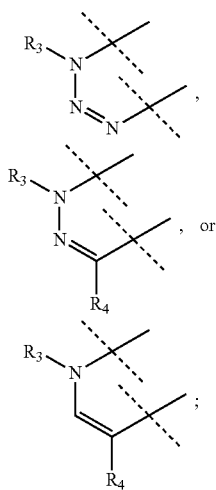

R is $C_1$-$C_6$ alkyl or aryl;

$R_1$ and $R_2$ are each independently hydrogen or $C_1$-$C_6$ alkyl;

each $R_3$ is independently hydrogen or $C_1$-$C_3$ alkyl;

each $R_4$ is independently hydrogen, $C_1$-$C_3$ alkyl, fluorine or chlorine;

each $R_e$ is independently selected from hydrogen, halogen, OH, O(CO)R, O(CO)$NR_1R_2$, $OPO_3$, $OSO_3$, $O(SO_2)NR_1R_2$, or wherein two adjacent $R_e$ together form:

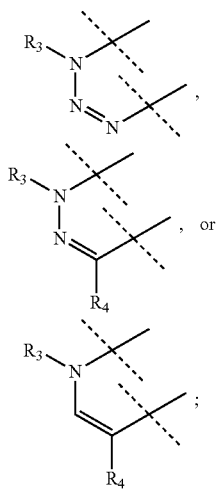

each $R_f$ is independently H, $C_1$-$C_3$ alkyl, fluorine or chlorine;

each $R_h$ is independently selected from hydrogen or $CH_3$;

X is O, $CH_2$, N, S or a bond;

Y and Z are each independently selected from $CR_f$ or N;

U and V are each independently selected from $CR_a$ or N; and

W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl;

wherein each R' is independently H or $C_1$-$C_3$ alkyl.

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

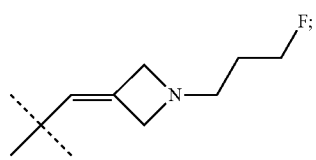

in certain embodiments, W is

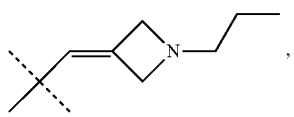

In some embodiments, W is —$CH_2$—$CH_2$—NH—$CH_2$—$CH_3$; in some embodiments, W is —$CH_2$—$CH_2$—NH-cyclopropyl; in some embodiments, W is —$CH_2$—$CH_2$—NH—$CH_2$-cyclopropyl.

In certain embodiments of formula V compounds, X is a bond.

In still other embodiments of formula V compounds, Y and Z are each $CR_f$ and U and V are each $CR_a$.

In some embodiments of formula V compounds, each $R_a$ is independently selected from H, phenyl, OH, $OC_{1-3}$ alkyl, fluorine, and chlorine. In yet other embodiments of formula V compounds, each $R_a$ is independently selected from H, phenyl, OH, $OCH_3$, fluorine, and chlorine. In certain embodiments of formula V compounds, $R_a$ is independently selected from H, $OCH_3$, fluorine, and chlorine. In certain other embodiments of formula V compounds, at least one of $R_a$ is methyl, $OCH_3$, fluorine, or chlorine.

In some other embodiments of formula V compounds, two adjacent $R_e$ together form:

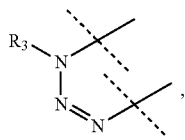

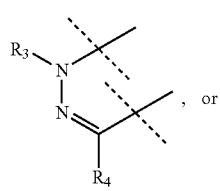

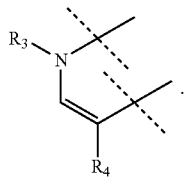

In certain embodiments of formula V compounds, two adjacent $R_e$ together form:

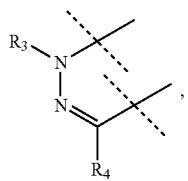

wherein $R_4$ is H.

In certain other embodiments of formula V compounds, two adjacent $R_e$ together form:

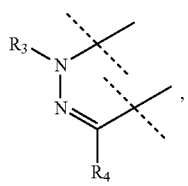

wherein $R_4$ is fluorine.

In certain embodiments of formula V compounds, two adjacent $R_e$ together form:

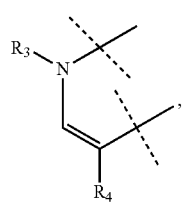

wherein $R_4$ is H.

In certain other embodiments of formula V compounds, two adjacent $R_e$ together form:

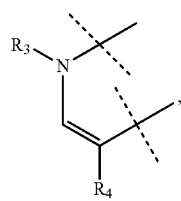

wherein $R_4$ is fluorine.

In some embodiments of formula V compounds, each $R_e$ is independently selected from H and OH. In other embodiments of formula V compounds, $R_f$ is H. In certain embodiments of formula V compounds, one or more R' are H.

In yet other embodiments of formula V compounds, W is —CHR'—CHR'—NH—$C_1$-$C_4$alkyl, —CHR'—CHR'—NH—$C_1$-$C_4$fluoroalkyl, wherein each R' is independently H or $C_1$-$C_3$alkyl. In certain embodiments of formula V compounds, one or more R' are H.

In some embodiments of formula V compounds, W is —CHR'—CHR'—NH—$C_3$-$C_6$ cycloalkyl, or —CHR'—CHR'—NH—$C_1$-$C_4$ alkyl-$C_3$-$C_6$ cycloalkyl, wherein each R' is independently H or $C_1$-$C_3$alkyl. In certain embodiments of formula V compounds, one or more R' are H. In other embodiments of formula V compounds wherein W contains a $C_3$-$C_6$ cycloalkyl moiety, the cycloalkyl group is $C_3$-$C_4$ cycloalkyl.

In still other embodiments of formula V compounds, W is

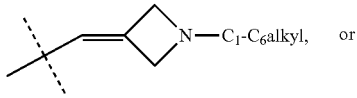

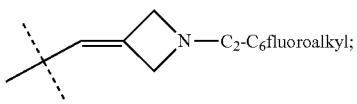

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

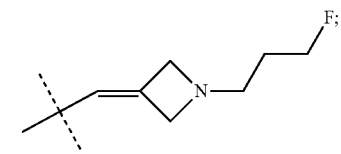

in certain embodiments, W is

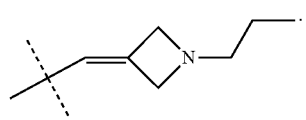

wherein each R' is independently H or $C_1$-$C_3$alkyl. In certain embodiments of formula V compounds, one or more R' are H.

In some embodiments of formula V compounds, each $R_f$ is H. In other embodiments of formula V compounds, when $R_f$ is H, each $R_e$ is independently selected from H and OH.

Some embodiments of formula V compounds have the formula Va or Vb:

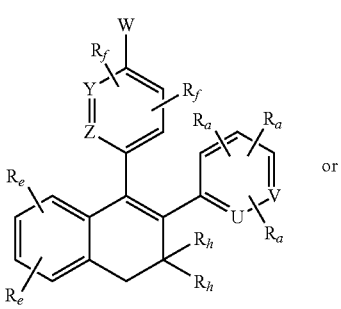

Va or

-continued

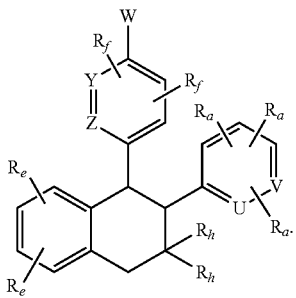
Vb

In certain embodiments, formula V compounds have the formula Vc, Vd, Ve, or Vf:

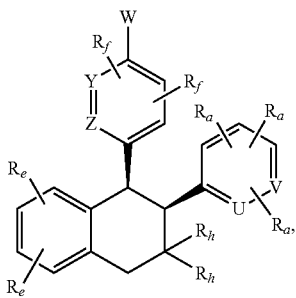
Vc

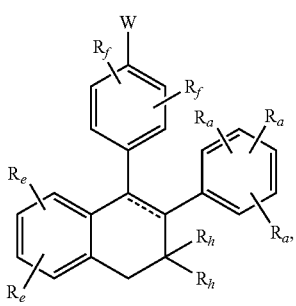
Vd

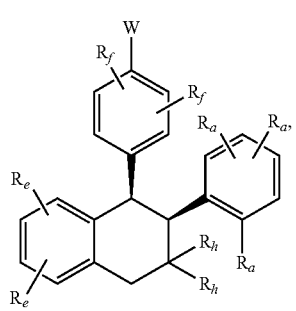
Ve

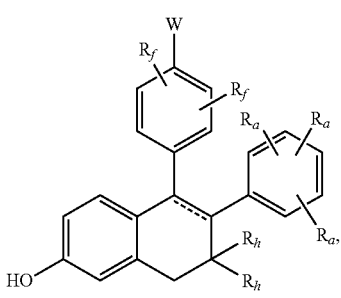
Vf

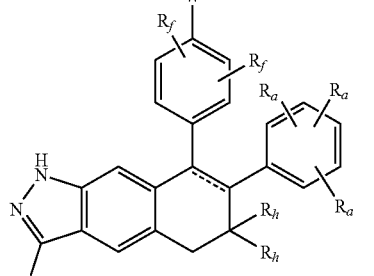
Vg or

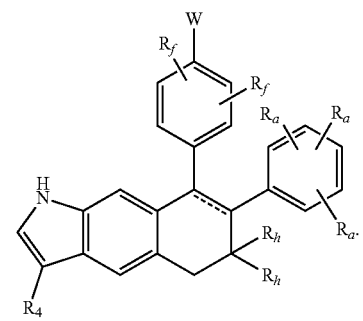
Vh

In certain embodiments, the compound of formula V, Va, Vb, Vc, Vd, Ve, Vf, Vg, or Vh is a pharmaceutically acceptable salt, solvate or prodrug thereof.

In certain embodiments, for the compound of formulas V, Va, Vb, Vc, Vd, Ve, Vf, Vg, or Vh, at least one $R_f$ is fluoro and in some embodiments, said fluoro is in the 2-position and if both $R_f$ are fluoro, they are in the 2,6 positions.

In some embodiments, the pharmaceutically acceptable salt of the compound is an acid addition salt.

In other embodiments, the compound of formula V, Va, Vb, Vc, Vd, Ve, Vf, Vg, or Vh is a prodrug. In yet other embodiments, the compound of formula V, Va, Vb, Vc, Vd, Ve, Vf, Vg, or Vh is the pharmaceutically acceptable salt of the prodrug. In some aspects the pharmaceutically acceptable salt of the prodrug of a compound of Formula V, Va, Vb, Vc, Vd, Ve, Vf, Vg, or Vh is a hydrochloride salt.

In some embodiments, a pharmaceutical composition comprising a compound or a pharmaceutically acceptable salt or prodrug of a compound of Formula V, Va, Vb, Vc, Vd, Ve, Vf, Vg, or Vh is described. In other embodiments, the pharmaceutical composition is formulated for intravenous injection, subcutaneous injection, oral administration, or topical administration. In certain embodiments, the pharmaceutical composition is a tablet, a pill, a capsule, a liquid, a suspension, a gel, a dispersion, a solution, an emulsion, an ointment, or a lotion.

In some embodiments, the present invention describes compounds or pharmaceutical salts thereof of formula I having the structure of formula VI:

VI

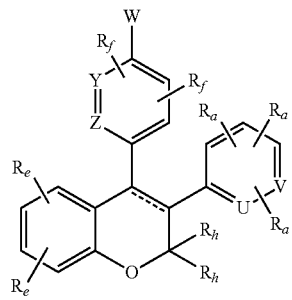

wherein each $R_a$ is independently selected from H, $C_1$-$C_3$ alkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine O(CO)R, O(CO)$NR_1R_2$, $OPO_3$, $OSO_3$, $O(SO_2)NR_1R_2$, or two adjacent $R_a$ together form:

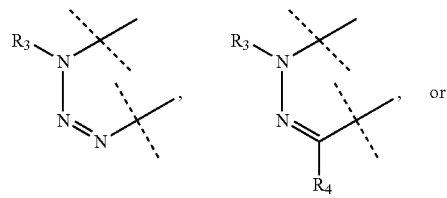

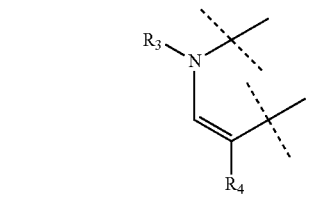

R is $C_1$-$C_6$ alkyl or aryl;

$R_1$ and $R_2$ are each independently hydrogen or $C_1$-$C_6$ alkyl;

each $R_3$ is independently hydrogen or $C_1$-$C_3$ alkyl;

each $R_4$ is independently hydrogen, $C_1$-$C_3$ alkyl, fluorine or chlorine;

each $R_e$ is independently selected from hydrogen, halogen, OH, O(CO)R, O(CO)$NR_1R_2$, $OPO_3$, $OSO_3$, $O(SO_2)NR_1R_2$, or wherein two adjacent $R_e$ together form:

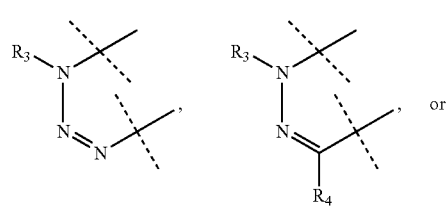

-continued

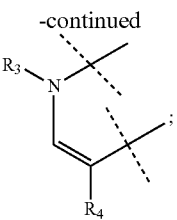

each $R_f$ is independently H, $C_1$-$C_3$ alkyl, fluorine or chlorine;

each $R_h$ is independently selected from hydrogen or $CH_3$;

Y and Z are each independently selected from $CR_f$ or N;

U and V are each independently selected from $CR_a$ or N; and

W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—N—$C_1$-$C_4$alkyl-$C_3$-$C_6$cycloalkyl,

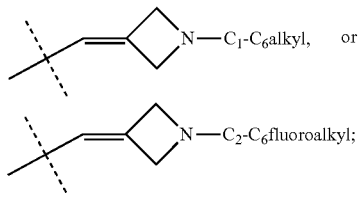

wherein each R' is independently H or $C_1$-$C_3$alkyl.

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

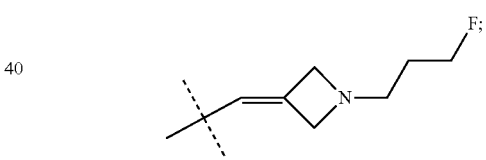

in certain embodiments, W is

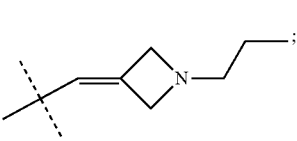

In certain embodiments of formula VI compounds, X is a bond.

In still other embodiments of formula VI compounds, Y and Z are each $CR_f$ and U and V are each $CR_a$.

In some embodiments of formula VI compounds, each $R_a$ is independently selected from H, phenyl, OH, $OC_{1-3}$ alkyl, fluorine, and chlorine. In yet other embodiments of formula VI compounds, each $R_a$ is independently selected from H, phenyl, OH, $OCH_3$, fluorine, and chlorine. In certain embodiments of formula VI compounds, $R_a$ is independently selected from H, $OCH_3$, fluorine, and chlorine. In certain other embodiments of formula VI compounds, at least one of $R_a$ is methyl, $OCH_3$, fluorine, or chlorine.

In some other embodiments of formula VI compounds, two adjacent $R_e$ together form:

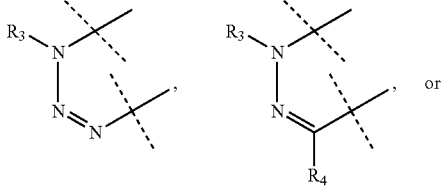

In certain embodiments of formula VI compounds, two adjacent $R_e$ together form:

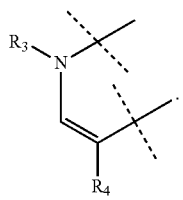

wherein $R_4$ is H.

In certain other embodiments of formula VI compounds, two adjacent $R_e$ together form:

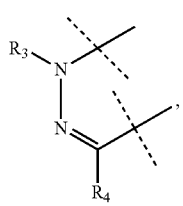

wherein $R_4$ is fluorine.

In certain embodiments of formula VI compounds, two adjacent $R_e$ together form:

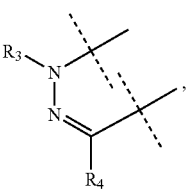

wherein $R_4$ is H.

In certain other embodiments of formula VI compounds, two adjacent $R_e$ together form:

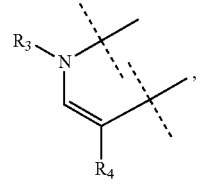

wherein $R_4$ is fluorine.

In some embodiments of formula VI compounds, each $R_e$ is independently selected from H and OH. In other embodiments of formula VI compounds, $R_f$ is H. In certain embodiments of formula VI compounds, one or more R' are H.

In yet other embodiments of formula VI compounds, W is —CHR'—CHR'—NH—$C_1$-$C_4$alkyl, —CHR'—CHR'—NH—$C_1$-$C_4$fluoroalkyl, wherein each R' is independently H or $C_1$-$C_3$alkyl. In certain embodiments of formula VI compounds, one or more R' are H.

In some embodiments of formula VI compounds, W is —CHR'—CHR'—NH—$C_3$-$C_6$ cycloalkyl, or —CHR'—CHR'—NH—$C_1$-$C_4$ alkyl-$C_3$-$C_6$ cycloalkyl, wherein each R' is independently H or $C_1$-$C_3$alkyl. In certain embodiments of formula VI compounds, one or more R' are H. In other embodiments of formula VI compounds wherein W contains a $C_3$-$C_6$ cycloalkyl moiety, the cycloalkyl group is $C_3$-$C_4$ cycloalkyl.

In still other embodiments of formula VI compounds, W is

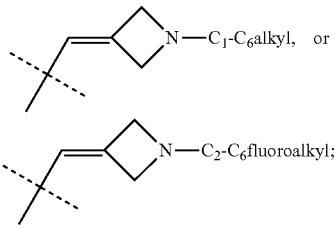

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

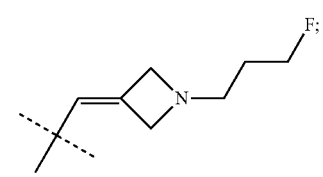

in certain embodiments, W is

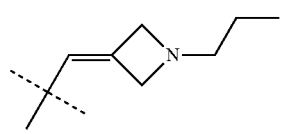

wherein each R' is independently H or $C_1$-$C_3$alkyl. In certain embodiments of formula VI compounds, one or more R' are H.

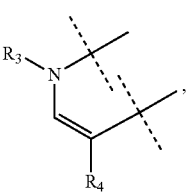

In some embodiments of formula VI compounds, each $R_f$ is H. In other embodiments of formula VI compounds, when $R_f$ is H, each $R_e$ is independently selected from H and OH.

Some embodiments of formula VI compounds have the formula VIa or VIb:

VIa

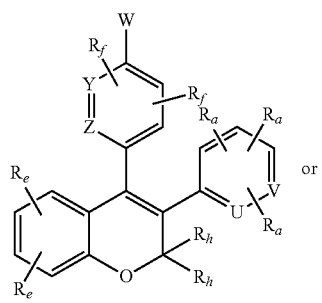

or

VIb

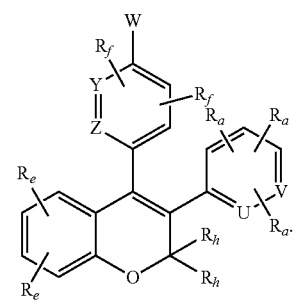

In certain embodiments, formula VI compounds have the formula VIc, VId, VIe, VIf, VIg or VIh:

VIc

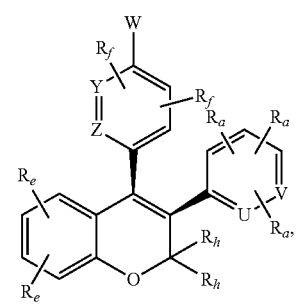

VId

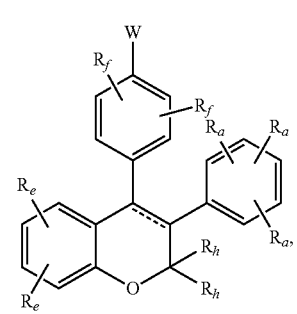

VIe

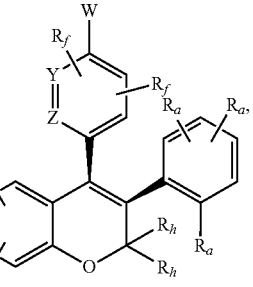

VIf

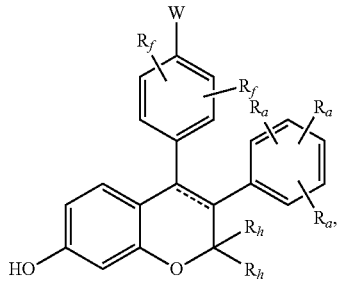

VIg

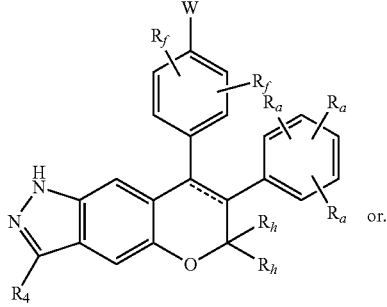

or.

VIh

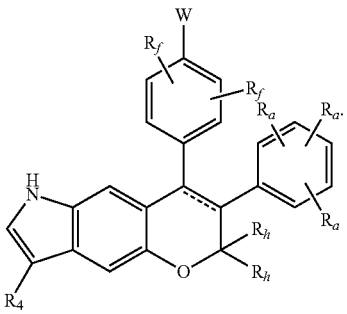

In certain embodiments, the compound of formula VI, VIa, VIb, VIc, VId, VIe, VIf, VIg, or VIh is a pharmaceutically acceptable salt, solvate or prodrug thereof.

In some embodiments, the pharmaceutically acceptable salt of the compound is an acid addition salt. In other embodiments, the compound of formula VI, VIa, VIb, VIc, VId, VIe, VIf, VIg, or VIh is a prodrug. In yet other embodiments, the compound of formula VI, VIa, VIb, VIc, VId, VIe, VIf, VIg, or VIh is the pharmaceutically acceptable salt of the prodrug. In some aspects the pharmaceutically acceptable salt of the prodrug of a compound of Formula VI, VIa, VIb, VIc, VId, VIe, VIf, VIg, or VIh is a hydrochloride salt.

In some embodiments, a pharmaceutical composition comprising a compound or a pharmaceutically acceptable salt or prodrug of a compound of Formula VI, VIa, VIb, VIc, VId, VIe, VIf, VIg, or VIh is described. In other embodiments, the pharmaceutical composition is formulated for intravenous injection, subcutaneous injection, oral administration, or topical administration. In certain embodiments, the pharmaceutical composition is a tablet, a pill, a capsule, a liquid, a suspension, a gel, a dispersion, a solution, an emulsion, an ointment, or a lotion.

In some embodiments, a compound comprising a structure of formula VII is disclosed

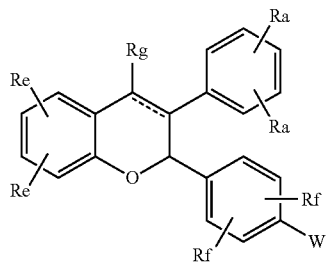

VII wherein
each $R_a$ is independently selected from H, $C_1$-$C_3$ alkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, O(CO)R, O(CO)$NR_1R_2$, $OPO_3$, $OSO_3$, $O(SO_2)NR_1R_2$, or two adjacent $R_a$ together form:

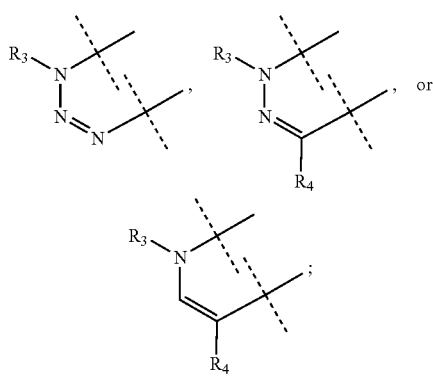

R is $C_1$-$C_6$ alkyl or aryl;
$R_1$ and $R_2$ are each independently hydrogen or $C_1$-$C_6$ alkyl;
each $R_3$ is independently hydrogen or $C_1$-$C_3$ alkyl;
each $R_4$ is independently hydrogen, $C_1$-$C_3$ alkyl, fluorine or chlorine;
each $R_e$ is independently selected from hydrogen, halogen, OH, O(CO)R, O(CO)$NR_1R_2$, $OPO_3$, $OSO_3$, $O(SO_2)NR_1R_2$, or wherein two adjacent $R_e$ together form:

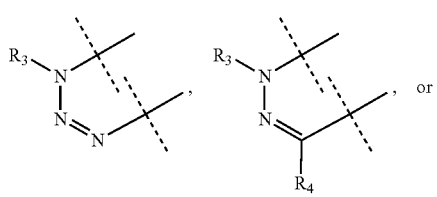

-continued

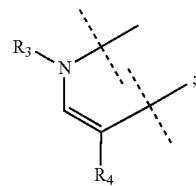

each $R_f$ is independently H, $C_1$-$C_3$ alkyl, fluorine or chlorine;
$R_g$ is hydrogen, $CH_3$, F, Cl or CN;
W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl,

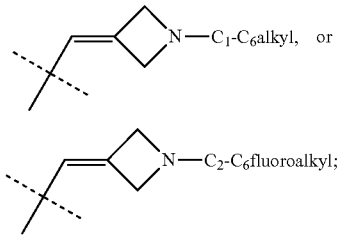

wherein each R' is independently H or $C_1$-$C_3$alkyl.

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

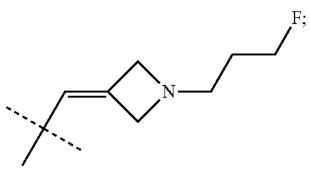

in certain embodiments, W is

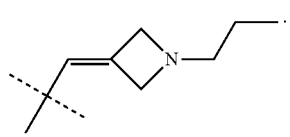

In some embodiments of formula VII compounds, each $R_a$ is independently selected from H, phenyl, OH, $OC_{1-3}$ alkyl, fluorine, and chlorine. In yet other embodiments of formula VII compounds, each $R_a$ is independently selected from H, phenyl, OH, $OCH_3$, fluorine, and chlorine. In certain embodiments of formula VII compounds, $R_a$ is independently selected from H, $OCH_3$, fluorine, and chlorine. In certain other embodiments of formula VII compounds, at least one of $R_a$ is methyl, $OCH_3$, fluorine, or chlorine.

In some other embodiments of formula VII compounds, two adjacent $R_e$ together form:

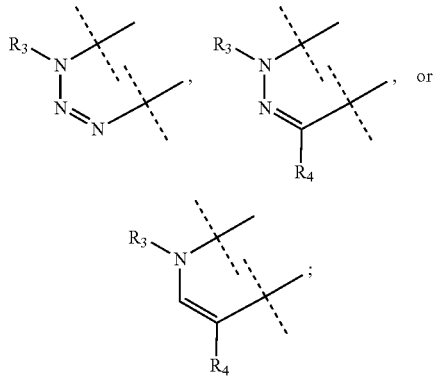

In certain embodiments of formula VII compounds, two adjacent $R_e$ together form:

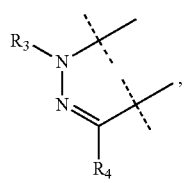

wherein $R_4$ is H.

In certain other embodiments of formula VII compounds, two adjacent $R_e$ together form:

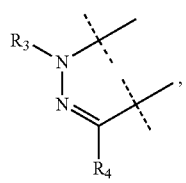

wherein $R_4$ is fluorine.

In certain embodiments of formula VII compounds, two adjacent $R_e$ together form:

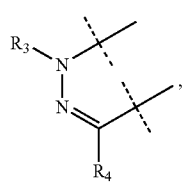

wherein $R_4$ is H.

In certain other embodiments of formula VII compounds, two adjacent $R_e$ together form:

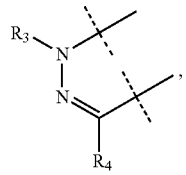

wherein $R_4$ is fluorine.

In some embodiments of formula VII compounds, each $R_e$ is independently selected from H and OH. In other embodiments of formula VII compounds, $R_f$ is H. In certain embodiments of formula VII compounds, one or more R' are H.

In yet other embodiments of formula VII compounds, W is —CHR'—CHR'—NH—$C_1$-$C_4$alkyl, —CHR'—CHR'—NH—$C_1$-$C_4$fluoroalkyl, wherein each R' is independently H or $C_1$-$C_3$alkyl. In certain embodiments of formula VII compounds, one or more R' are H.

In some embodiments of formula VII compounds, W is —CHR'—CHR'—NH—$C_3$-$C_6$ cycloalkyl, or —CHR'—CHR'—NH—$C_1$-$C_4$ alkyl-$C_3$-$C_6$ cycloalkyl, wherein each R' is independently H or $C_1$-$C_3$alkyl. In certain embodiments of formula VI compounds, one or more R' are H. In other embodiments of formula VII compounds wherein W contains a $C_3$-$C_6$ cycloalkyl moiety, the cycloalkyl group is $C_3$-$C_4$ cycloalkyl.

In still other embodiments of formula VII compounds, W is

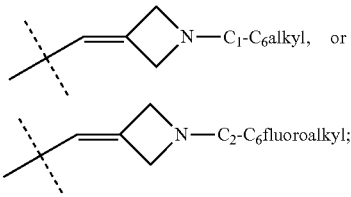

In some embodiments, W is —$CH_2$—$CH_2$—NH—$CH_2$—$CH_2$—$CH_3$; in some embodiments W is —$CH_2$—$CH_2$—NH—$CH_2$—$CH_2$—$CH_2$F; in some embodiments W is

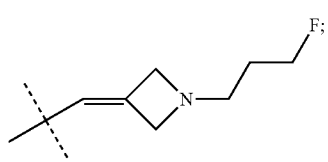

in certain embodiments, W is

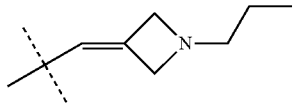

wherein each R' is independently H or $C_1$-$C_3$alkyl. In certain embodiments of formula VII compounds, one or more R' are H.

In some embodiments of formula VII compounds, each $R_f$ is H. In other embodiments of formula VII compounds, when $R_f$ is H, each $R_e$ is independently selected from H and OH.

In certain embodiments, a compound according to formula I' is described

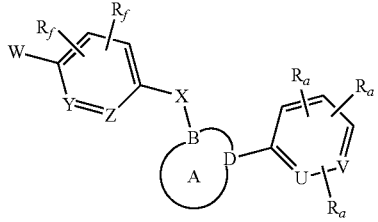

wherein:

B is nitrogen or carbon;

D is carbon;

A is a fused ring system selected from:

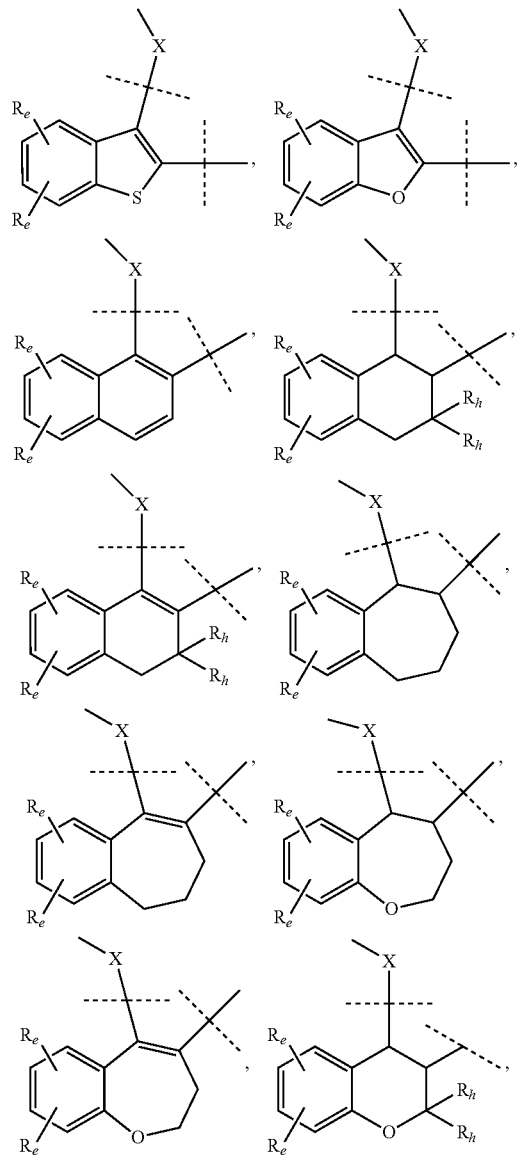

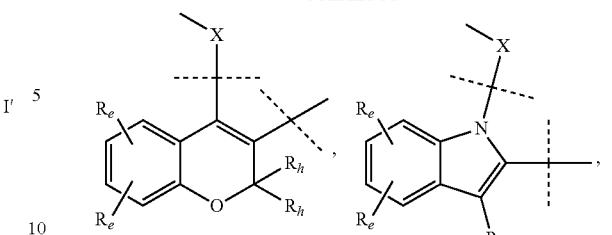

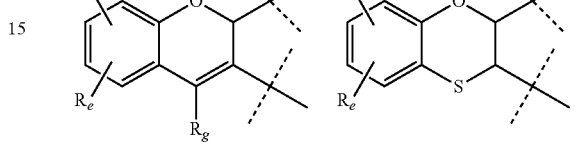

each $R_e$ is independently selected from hydrogen, halogen, OH, O(CO)R, O(CO)NR$_1$R$_2$, OPO$_3$, OSO$_3$, O(SO$_2$)NR$_1$R$_2$, or wherein two adjacent $R_e$ together form:

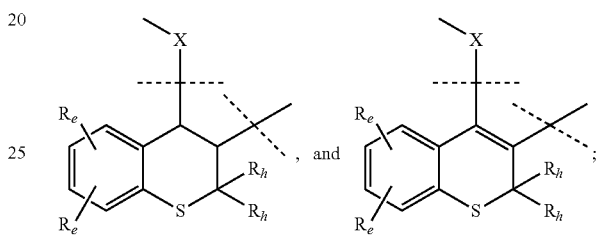

R is $C_1$-$C_6$ alkyl or aryl;

$R_1$ and $R_2$ are each independently hydrogen or $C_1$-$C_6$ alkyl;

each $R_3$ is hydrogen, $C_1$-$C_{12}$ acyl; $C_1$-$C_{12}$ acyloxy;

each $R_4$ is independently hydrogen, $C_1$-$C_3$ alkyl, fluorine or chlorine;

each $R_h$ is independently selected from hydrogen or CH$_3$;

$R_g$ is hydrogen, $C_1$-$C_3$ alkyl, $C_1$-$C_3$ fluoroalkyl, CN, fluorine, chlorine or bromine;

each $R_a$ is independently selected from: H, $C_1$-$C_3$ alkyl, $C_1$-$C_3$ fluoroalkyl, phenyl (optionally substituted with 1-3 groups selected from fluorine, chlorine, $C_1$-$C_3$ alkyl, CN, OC$_1$-$C_3$ alkyl, OH), OH, OC$_{1-3}$alkyl, CN, fluorine, chlorine, O(CO)R, O(CO)NR$_1$R$_2$, OPO$_3$, OSO$_3$, O(SO$_2$)NR$_1$R$_2$, or two adjacent $R_a$ together form:

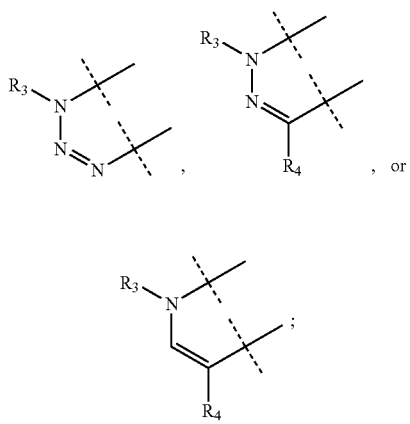

X is O, S, CH₂, NH or a bond when B is carbon, or CH₂ or a bond when B is nitrogen;

Y and Z are each independently selected from CR$_f$ or N;

U and V are each independently selected from CR$_a$ or N;

each R$_f$ is independently H, C₁-C₃ alkyl, OC₁-C₃ alkyl, fluorine or chlorine; and W is —CHR'—CHR'—NH—C₁-C₄alkyl, —CHR'—CHR'—NH—C₁-C₄fluoroalkyl, —CHR'—CHR'—NH—C₃-C₆cycloalkyl, —CHR'—CHR'—NH—C₁-C₄alky-C₃-C₆cycloalkyl,

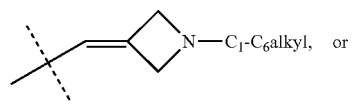

wherein each R' is independently H or C₁-C₃alkyl;

or a pharmaceutically acceptable salt thereof.

In some embodiments of formula I', W is —CH₂—CH₂—NH—CH₂—CH₂—CH₃; —CH₂—CH₂—NH—CH₂—CH₂—CH₂F;

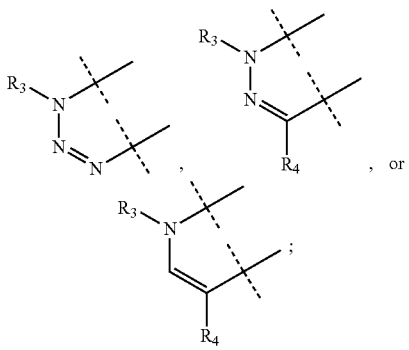

or a pharmaceutically acceptable salt thereof.

In some embodiments, a compound according to formula II' is described:

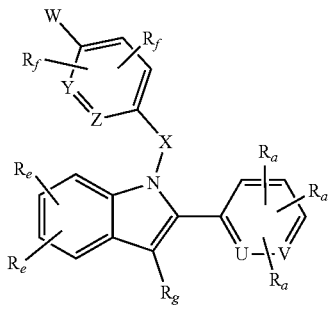

each R$_a$ is independently selected from H, C₁-C₃ alkyl, phenyl (optionally substituted with 1-3 groups selected from fluorine, chlorine, C₁-C₃ alkyl, CN, OC₁-C₃ alkyl, OH), OH, OC₁₋₃alkyl, CN, fluorine, chlorine, O(CO)R, O(CO)NR₁R₂, OPO₃, OSO₃, O(SO₂)NR₁R₂, or two adjacent R$_a$ together form:

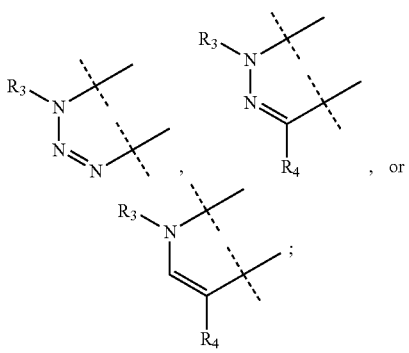

R is C₁-C₆ alkyl or aryl;

R₁ and R₂ are each independently hydrogen or C₁-C₆ alkyl;

each R₃ is independently hydrogen; C₁-C₁₂ acyl or C₁-C₁₂ acyloxy;

each R₄ is independently hydrogen, C₁-C₃ alkyl, fluorine or chlorine;

each R$_e$ is independently selected from hydrogen, halogen, OH, O(CO)R, O(CO)NR₁R₂, OPO₃, OSO₃, O(SO₂)NR₁R₂, or wherein two adjacent R$_e$ together form:

each $R_f$ is independently H, $C_1$-$C_3$ alkyl, $OC_1$-$C_3$ alkyl, fluorine or chlorine;

$R_g$ is hydrogen, $C_1$-$C_3$ alkyl, $C_1$-$C_3$ fluoroalkyl, CN, fluorine, chlorine or bromine;

X is $CH_2$ or a bond;

Y and Z are each independently selected from $CR_f$ or N;

U and V are each independently selected from $CR_a$ or N; and

W is —CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alky-$C_3$-$C_6$cycloalkyl,

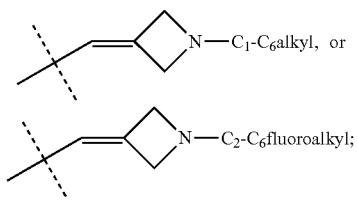

wherein each R' is independently H or $C_1$-$C_3$alkyl;

or a pharmaceutically acceptable salt thereof.

In some embodiments formula II', X is $CH_2$; Y and Z are each $CR_f$; U and V are each $CR_a$; $R_g$ is F, Cl or $CH_3$; each $R_a$ is independently selected from H, OH, $CH_3$ and Cl; each $R_f$ is H; and W is —$CH_2$—$CH_2$—NH—$CH_2$—$CH_2$—$CH_3$, —$CH_2$—$CH_2$—NH—$CH_2$—$CH_2$—$CH_2$F,

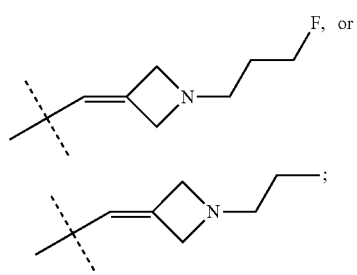

or a pharmaceutically acceptable salt thereof.

In some embodiments of II', each $R_e$ is independently selected from hydrogen, OH, or wherein two adjacent $R_e$ together form:

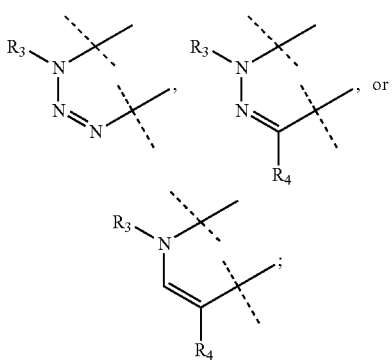

and wherein $R_3$ is H and $R_4$ is H.

In certain embodiments, a compound having the structure of formula III' is disclosed:

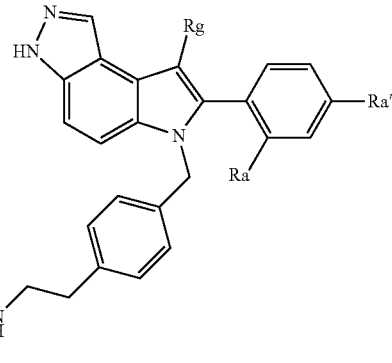

wherein: Q is H or F; Rg is F, Cl, or $CH_3$; Ra is $CH_3$, Cl or OMe; and Ra' is H, F or OH; or a pharmaceutically acceptable salt thereof.

In some embodiments of III', Rg is F.

In some embodiments of III', Rg is F; Ra is $CH_3$; and Ra' is H.

In certain embodiments, a compound having the structure IV' is disclosed:

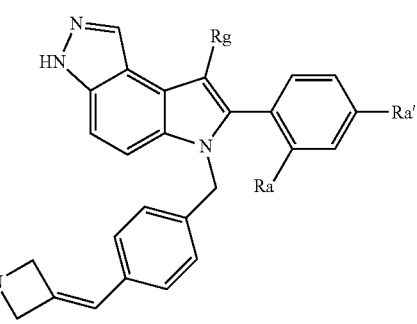

wherein: Q is H or F; Rg is F, Cl, or $CH_3$; Ra is $CH_3$, Cl or OMe; and Ra' is H, F or OH; or a pharmaceutically acceptable salt thereof.

In some embodiments of IV', Rg is F.

In certain embodiments of IV', Rg is F; Ra is $CH_3$; and Ra' is H.

In some embodiments, a compound of formula V' is described:

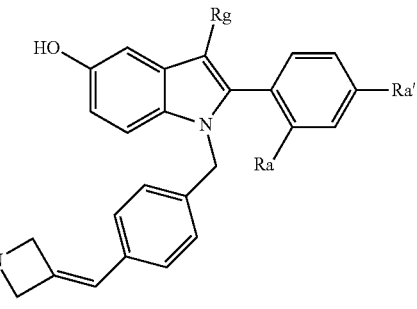

wherein: Q is H or F; Rg is F, Cl, or CH$_3$; Ra is CH$_3$, Cl or OMe; and Ra' is H, F or OH; or a pharmaceutically acceptable salt thereof.

In some embodiments of V', Rg is F.

In some embodiments of V', Rg is F; Ra is CH$_3$; and Ra' is H.

In certain embodiments, a structure of formula VI' is disclosed:

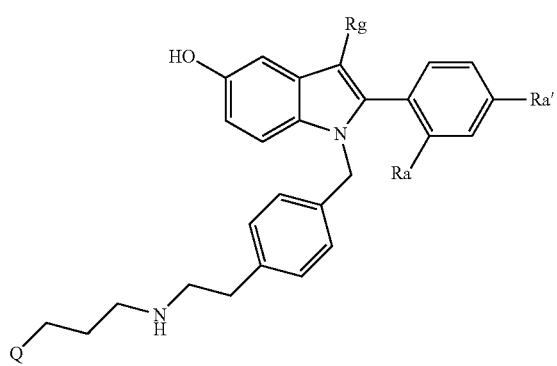

VI' wherein: Q is H or F; Rg is F, Cl, or CH$_3$; Ra is CH$_3$, Cl or OMe; and Ra' is H, F or OH; or a pharmaceutically acceptable salt thereof.

In some embodiments, the compound of VI' has Rg is F.

In certain embodiments of VI', Rg is F and Ra is CH$_3$.

In some embodiments of VI', Rg is F; Ra is CH$_3$; and Ra' is H.

In some embodiments of a compound of formula VII' is disclosed:

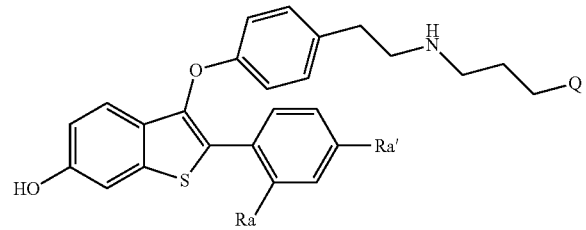

VII' wherein: Q is H or F; Ra is CH$_3$, Cl or OMe; and Ra' is H, F or OH; or a pharmaceutically acceptable salt thereof.

In some embodiments of structure VII', Ra is CH$_3$ and Ra' is H.

In certain embodiments, a structure of formula VIII' is disclosed:

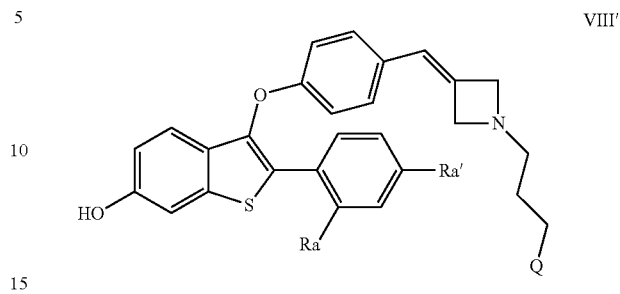

VIII' wherein: Q is H or F; Ra is CH$_3$, Cl or OMe; and Ra' is H, F or OH; or a pharmaceutically acceptable salt thereof.

In some embodiments, formula VIII', Ra is CH$_3$ and Ra' is H.

In certain embodiments, a compound of formula IX' is described

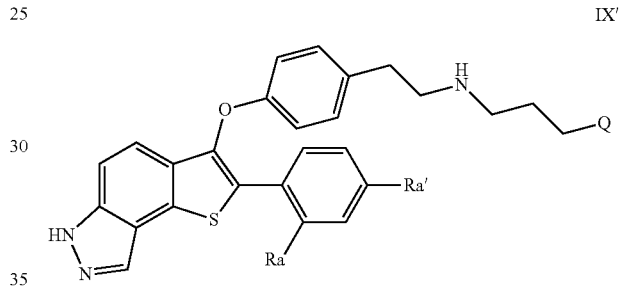

IX' wherein: Q is H or F; Ra is CH$_3$, Cl or OMe; and Ra' is H, F or OH; or a pharmaceutically acceptable salt thereof.

In certain embodiments of IX', Ra is CH$_3$ and Ra' is H.

In certain embodiments, a compound of formula X' is described:

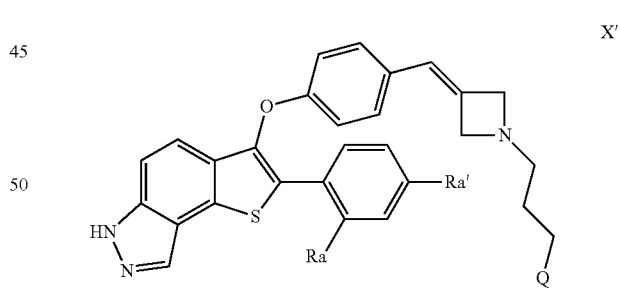

X' wherein: Q is H or F; Ra is CH$_3$, Cl or OMe; Ra' is H, F or OH; or a pharmaceutically acceptable salt thereof.

In some embodiments of X', R$_a$ is CH$_3$ and Ra' is H.

In some embodiments of compounds of Formulas I through VII and I' through X', the enantiomeric ratio of the compound is greater than 95:5. In some embodiments, the enantiomeric ratio of the compound is greater than 99:1.

Articles of manufacture, which include: packaging material; a compound of Formula I through VII, I' through X', or a pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Compounds described herein are synthesized using standard synthetic techniques or using methods known in the art in combination with methods described herein. In additions, solvents, temperatures and other reaction conditions presented herein may vary.

The starting material used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In some embodiments, the compounds described herein are prepared as outlined in the following Schemes.

SCHEME I

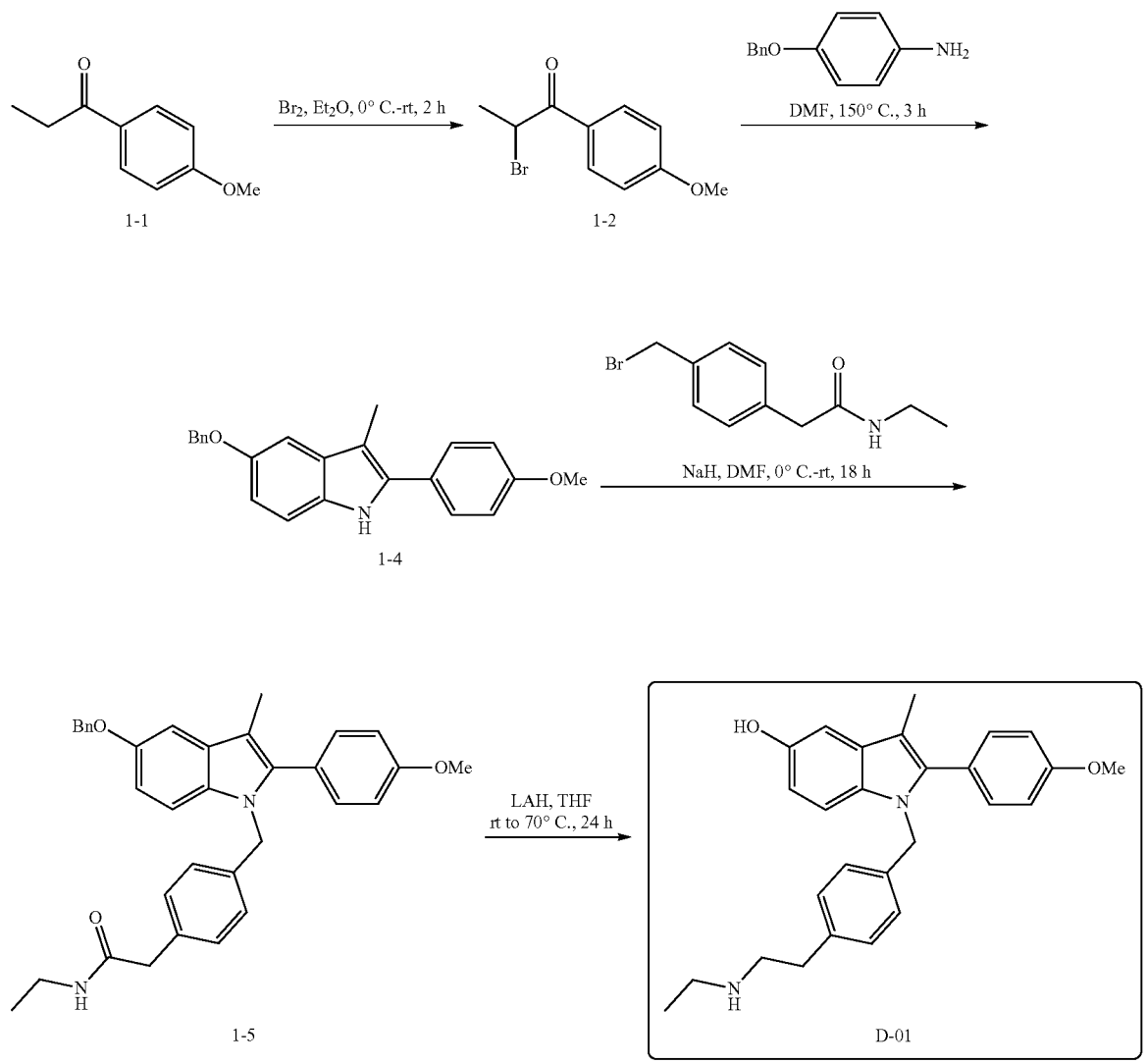

Treatment of 1-1 with bromine followed by reaction with para-benzyloxyaniline provided 1-4. Subsequent N-alkylation with the benzylic bromide under basic conditions provided intermediate 1-5. Reduction with LAH gave D-01 (Scheme I).
SCHEME II
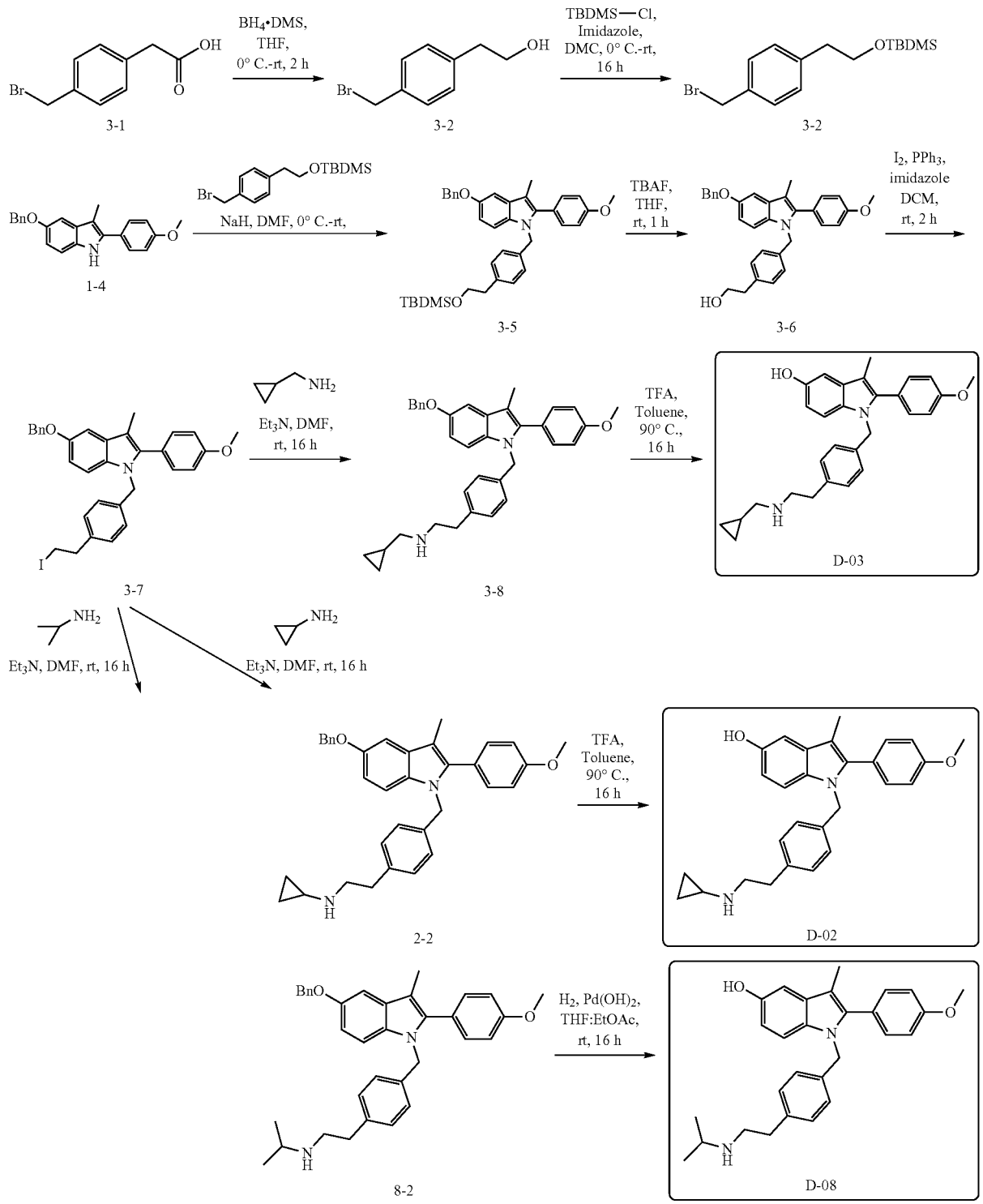

Reduction of acid 3-1 provided alcohol 3-2, which was protected with TBDMS chloride to provide 3-3.3-3 was reacted with 1-4 (Scheme I) under basic conditions to yield 3-5, which was deprotected with TBAF and converted to the corresponding primary iodide 3-7 with iodine and triphenylphosphine (Scheme II). Iodide 3-7 was reacted with a variety of amines, which after debenzylation, resulted in compounds D-02, D-03, and D-08.

SCHEME III

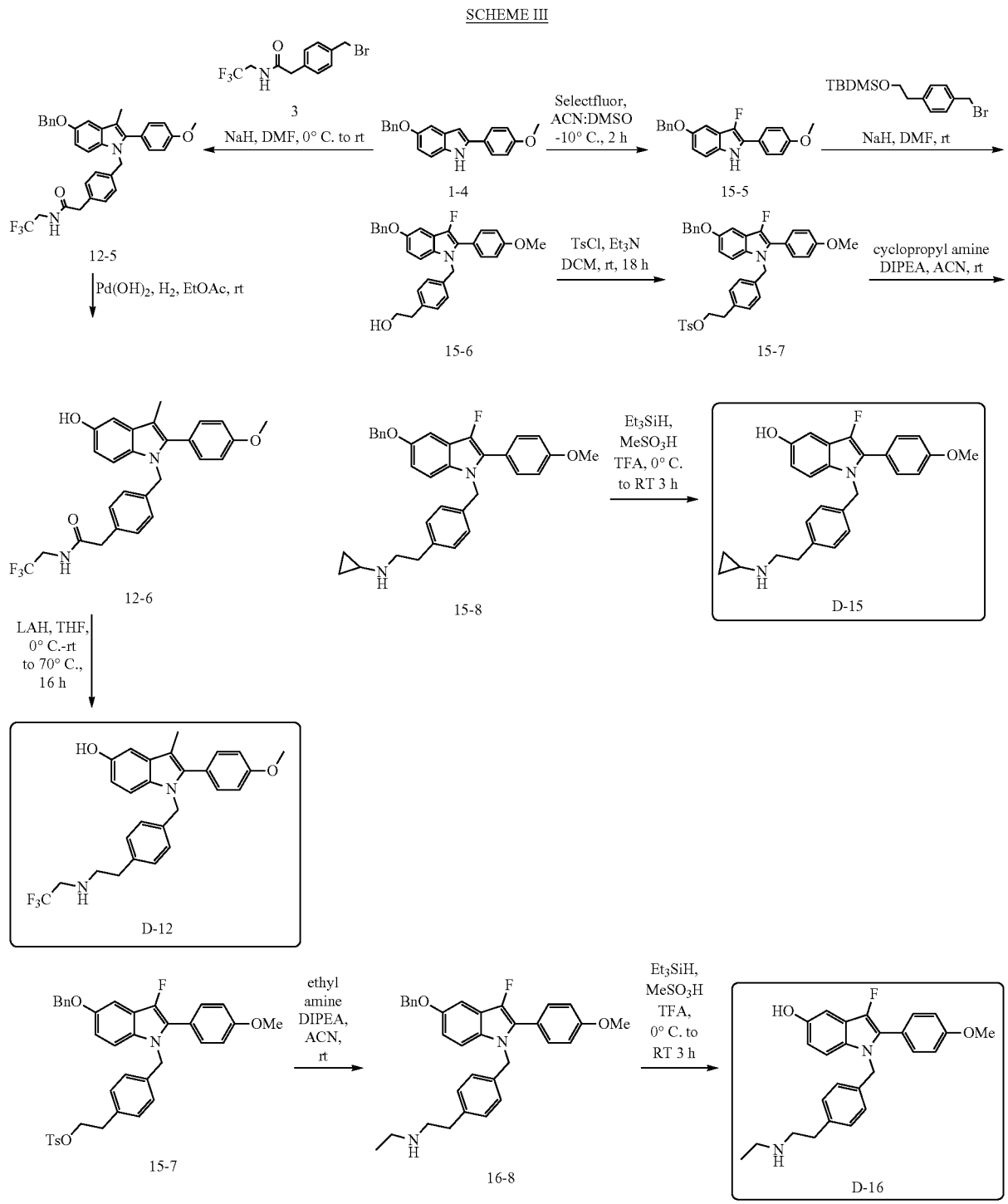

Indole 1-4 was reacted with benzyl bromide 3 under basic conditions, resultant 12-5 catalytically deprotected to give 12-6, which was reduced with LAH to yield D-12 (Scheme III). Alternatively, 1-4 was fluorinated (15-5), and N-benzylated and deprotected (15-6), tosylated (15-7), reacted with cyclopropyamine (15-8) and debenzylatedto give D-15. Tosylate 15-7 was also converted with ethylamine and deprotected to yield D-16.

SCHEME IV

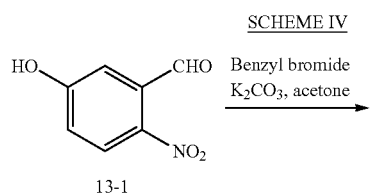

13-1

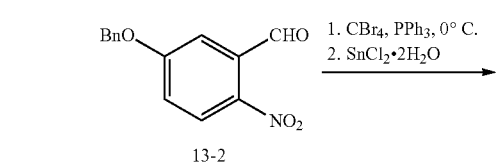

13-2

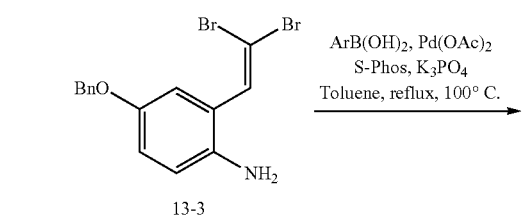

13-3

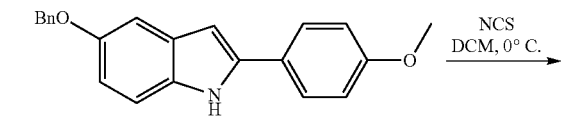

13-4

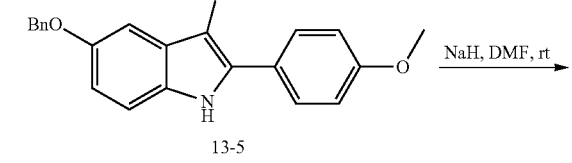

13-5

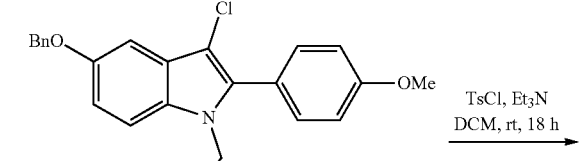

13-7

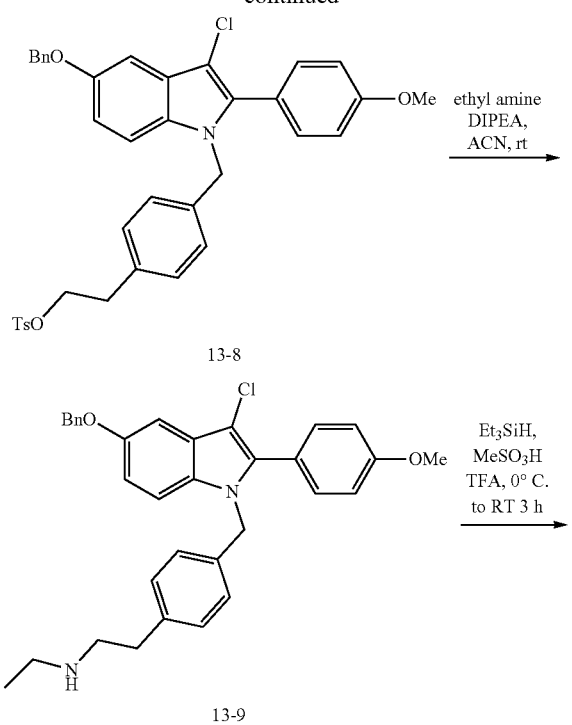

13-8

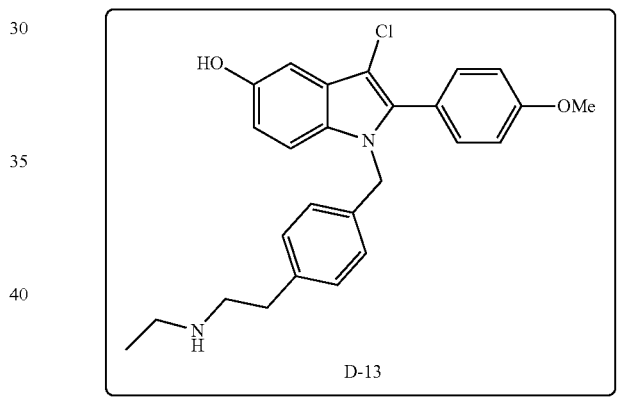

13-9

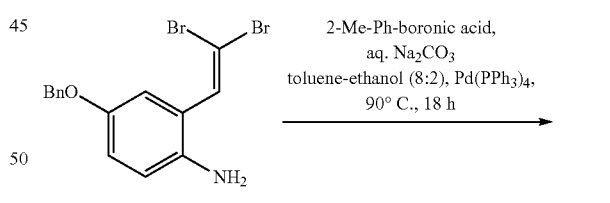

D-13

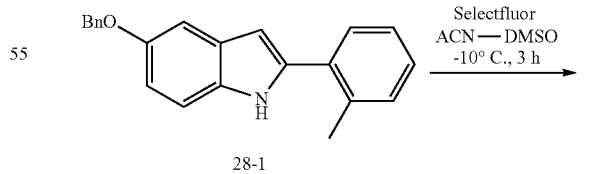

13-3

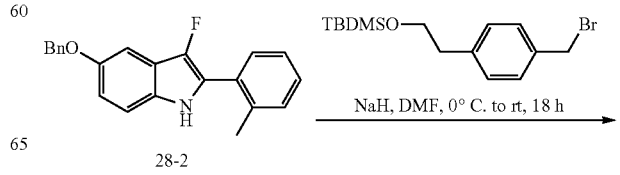

28-1

28-2

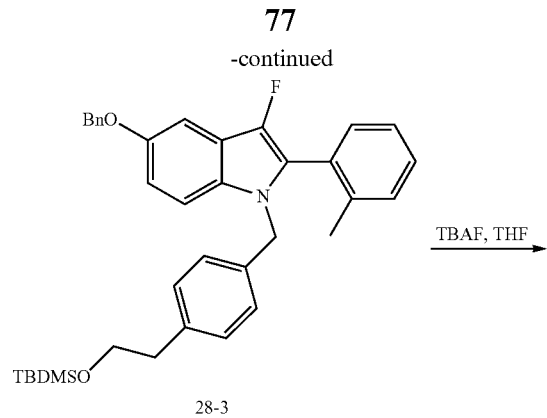

28-3

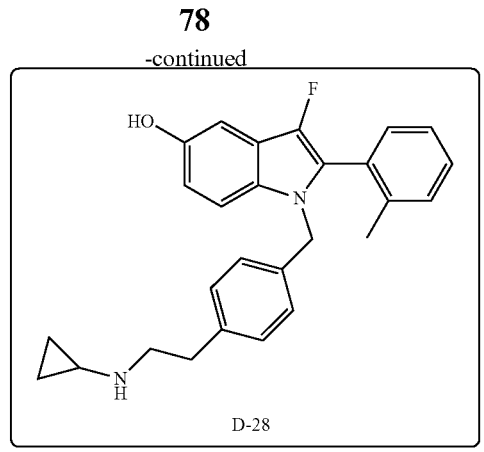

D-28

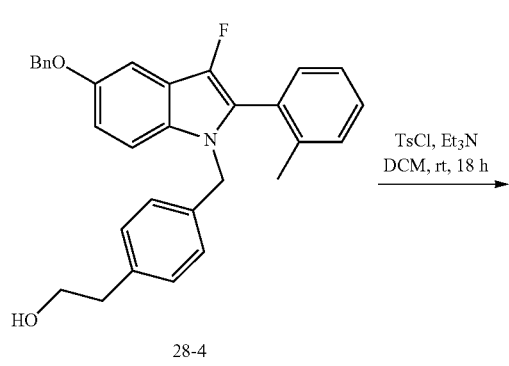

28-4

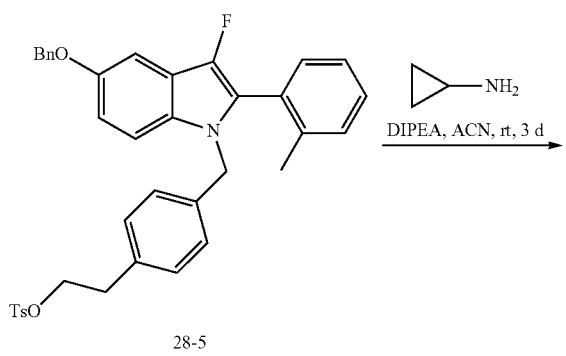

28-5

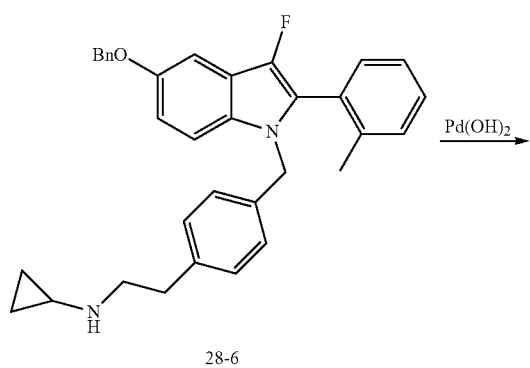

28-6

Hydroxybenzaldehyde 13-1 was benzylated to yield 13-2, which was olefinated to 13-3 with carbon tetrabromide and triphenyl phosphine. 13-3 was treated with (4-methoxyphenyl)boronic acid in the presence of palladium acetate to yield 13-4, which was chlorinated with N-chlorosuccinimide and subsequently reacted with (4-(bromomethyl) phenethoxy)(tert-butyl)dimethylsilane under basic conditions to provide 13-7. Tosylation to 13-8 followed by reaction with ethyl amine to 13-9 and debenzylation resulted in D-13. (Scheme IV). 1,1-Dibromo alkene 13-3 was treated with (4-methylphenyl)boronic acid in the presence of palladium acetate to yield 28-1, which was fluorinated with selectfluor and subsequently N-benzylated to give the TBDMS-protected 28-3. After removal of the TBDMS protecting group, 28-4 was tosylated to 28-5, reacted with cyclopropylamine to 28-6 and debenzylated to give D-28. (Scheme IV)

SCHEME IVb

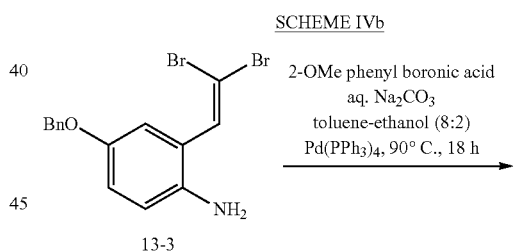

13-3

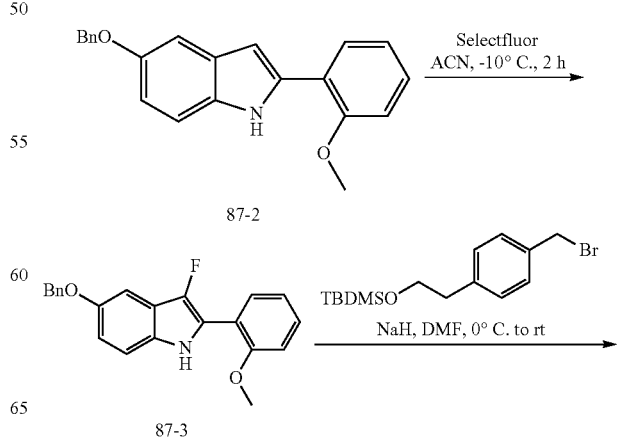

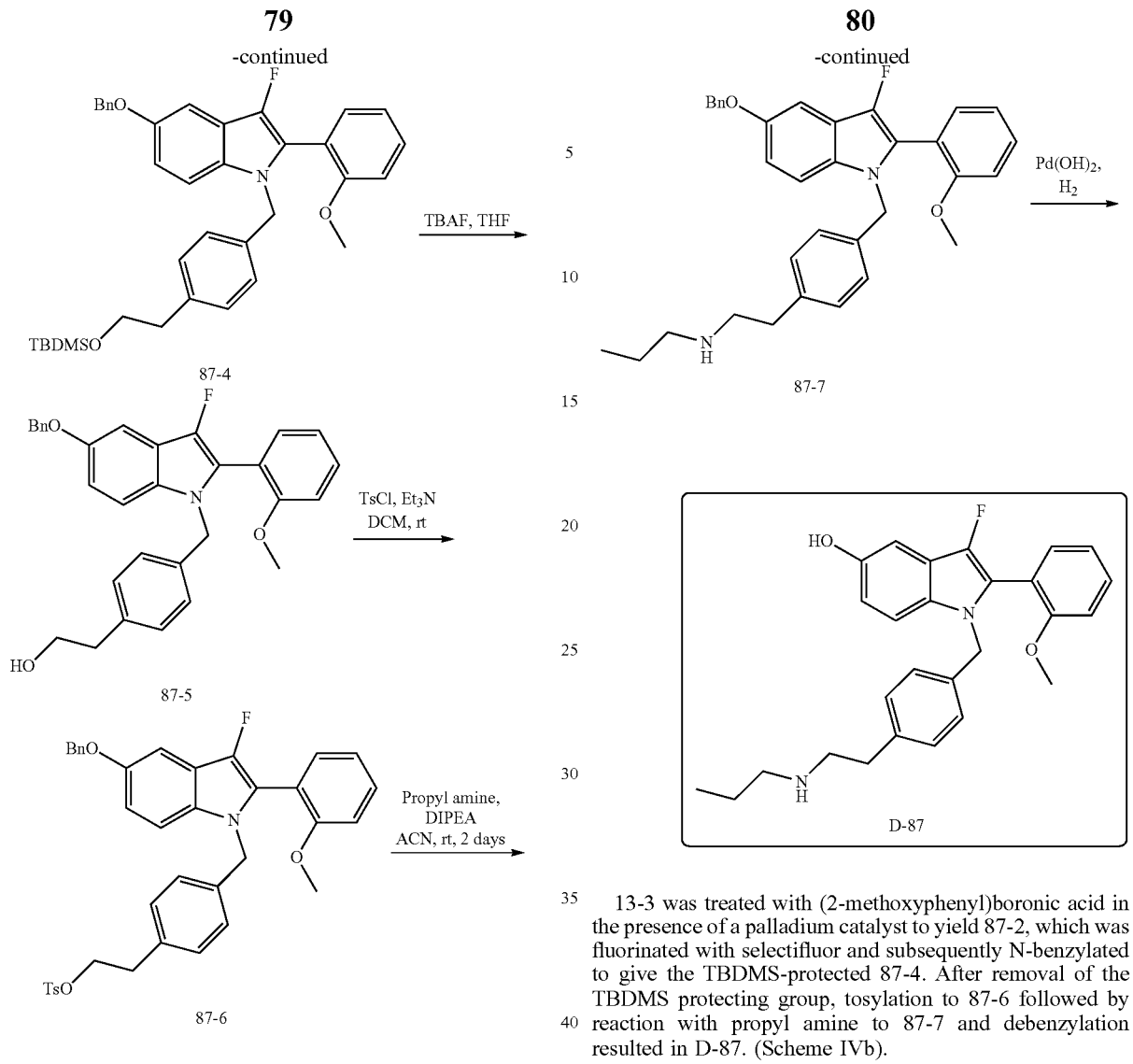
13-3 was treated with (2-methoxyphenyl)boronic acid in the presence of a palladium catalyst to yield 87-2, which was fluorinated with selectifluor and subsequently N-benzylated to give the TBDMS-protected 87-4. After removal of the TBDMS protecting group, tosylation to 87-6 followed by reaction with propyl amine to 87-7 and debenzylation resulted in D-87. (Scheme IVb).
SCHEME IVc.
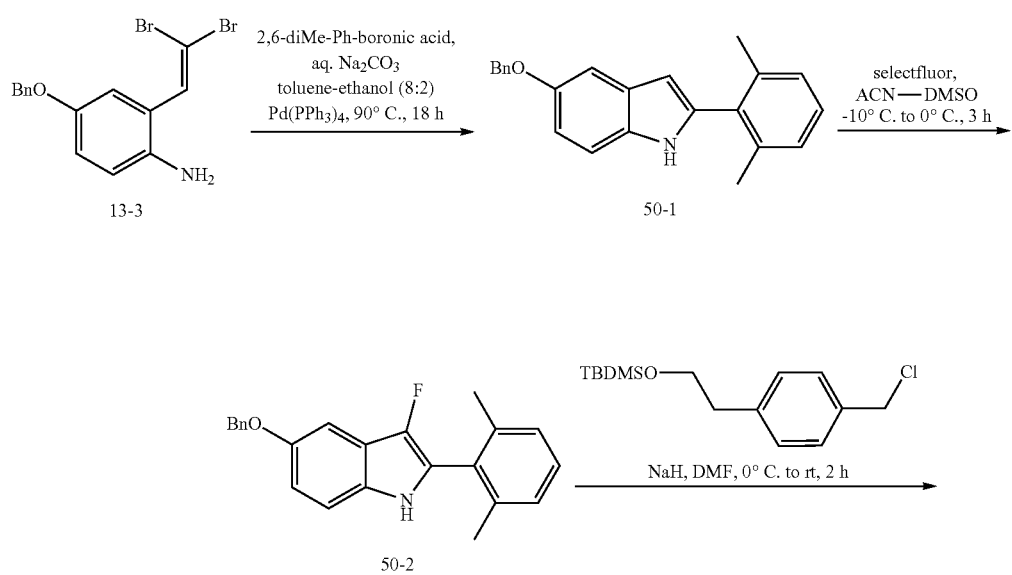

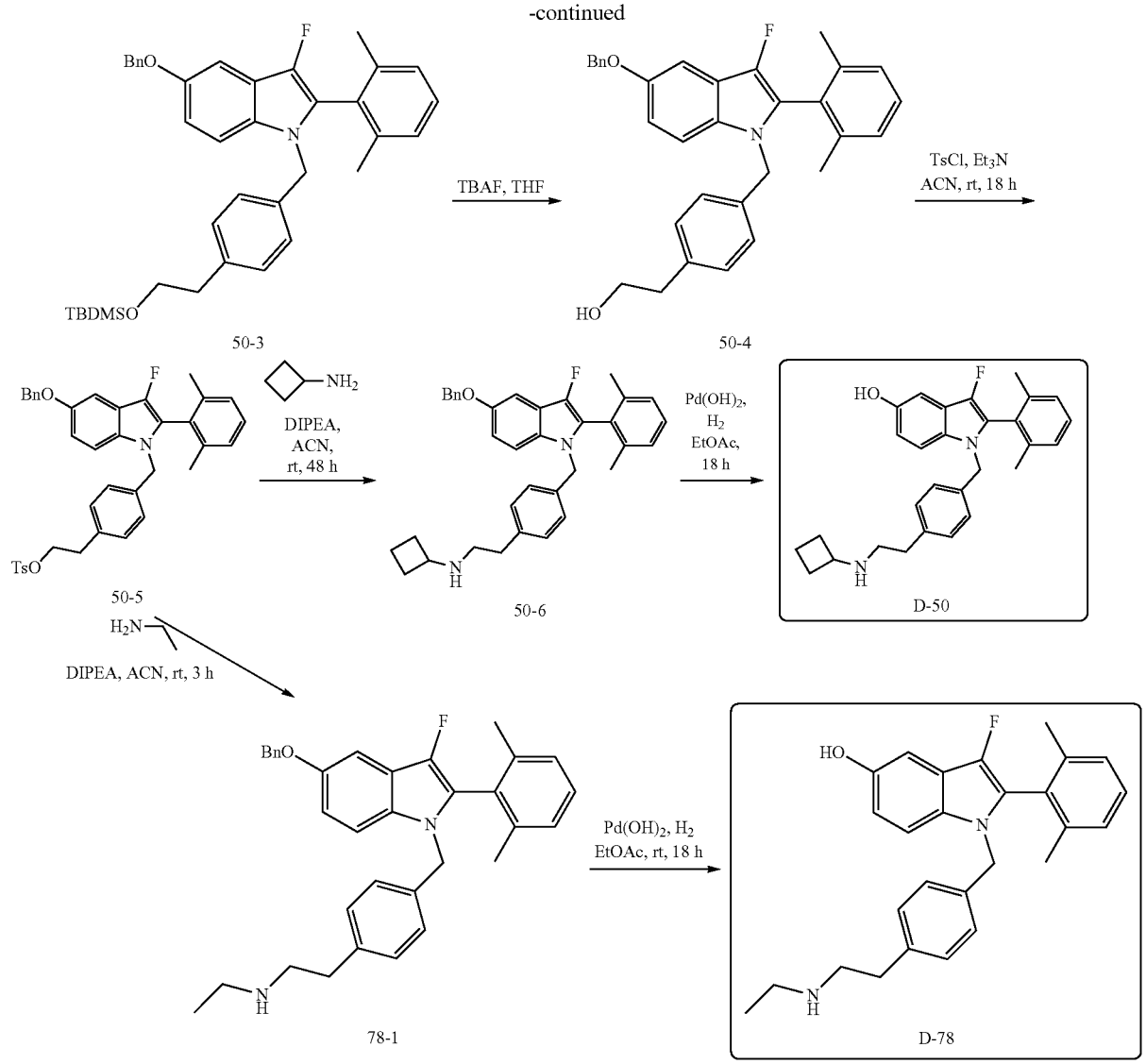

13-3 was treated with (2,6-dimethylphenyl)boronic acid in the presence of catalytic palladium to yield 50-1, which was fluorinated with selectfluor and subsequently N-benzylated to give the TBDMS-protected 50-3. After removal of the TBDMS protecting group, tosylation to 50-5 followed by reaction with cyclobutyl amine to 50-6 and debenzylation resulted in D-50. (Scheme IVc). Intermediate 50-5 was also reacted with ethyl amine to 78-1 and subsequent debenzylation resulted in D-78.

SCHEME IVd

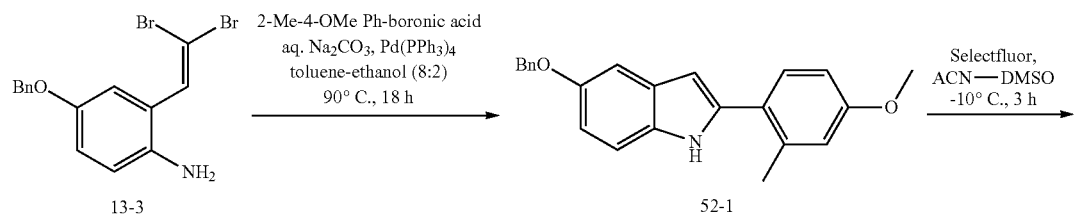

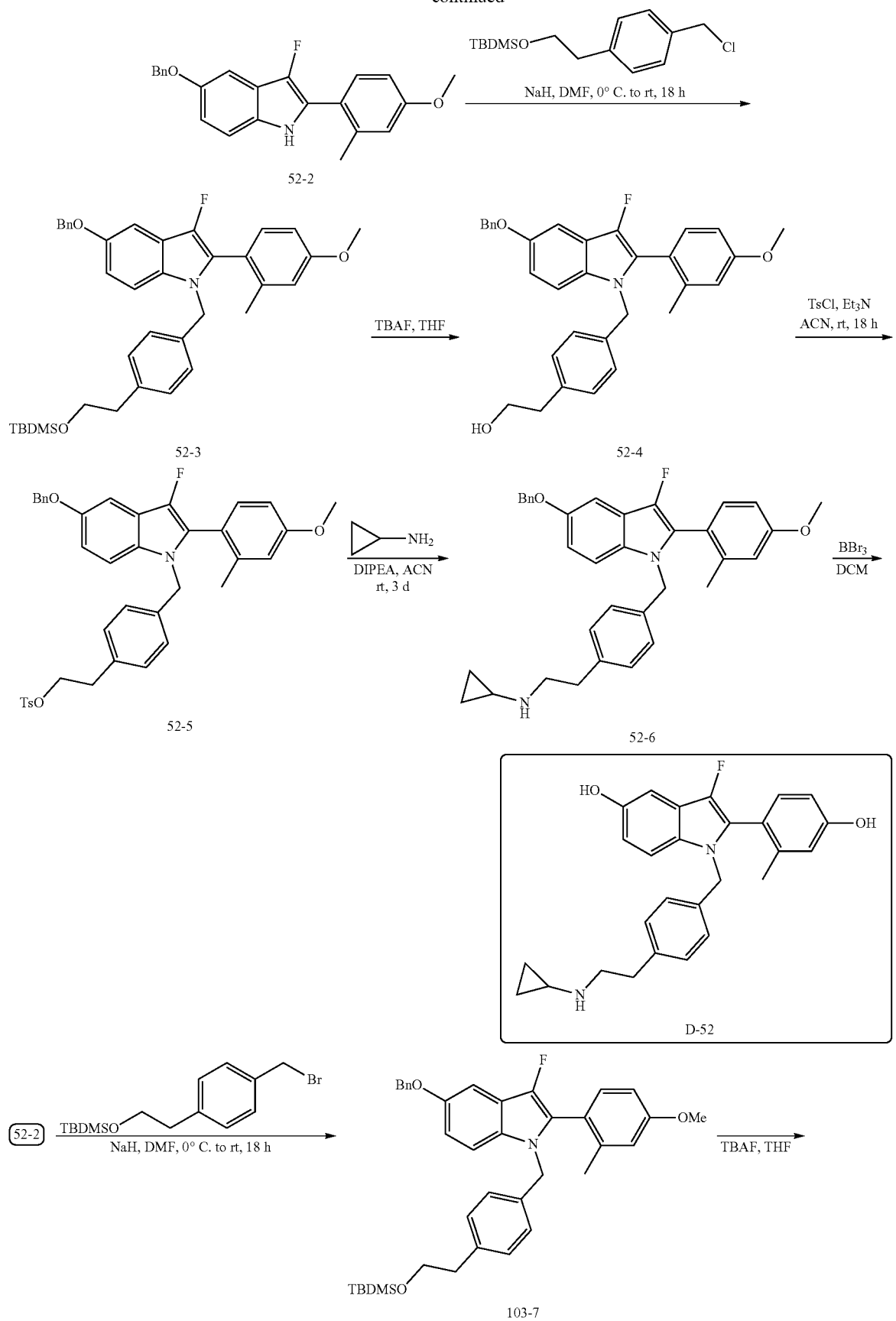

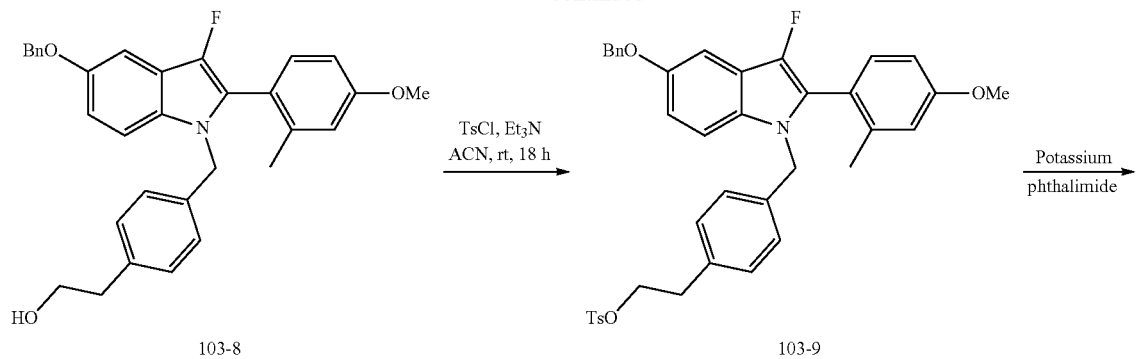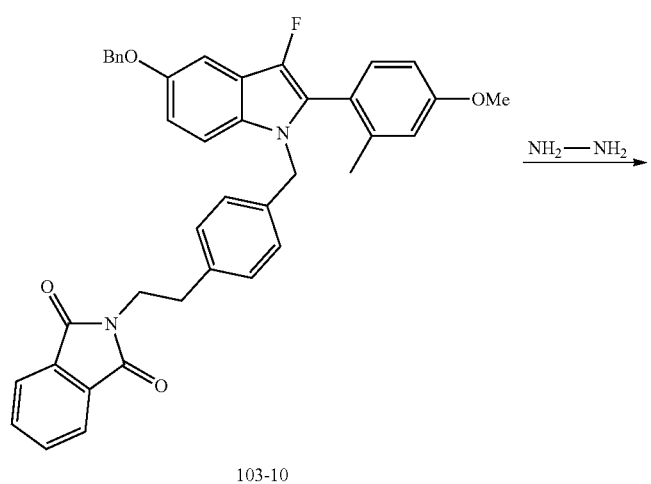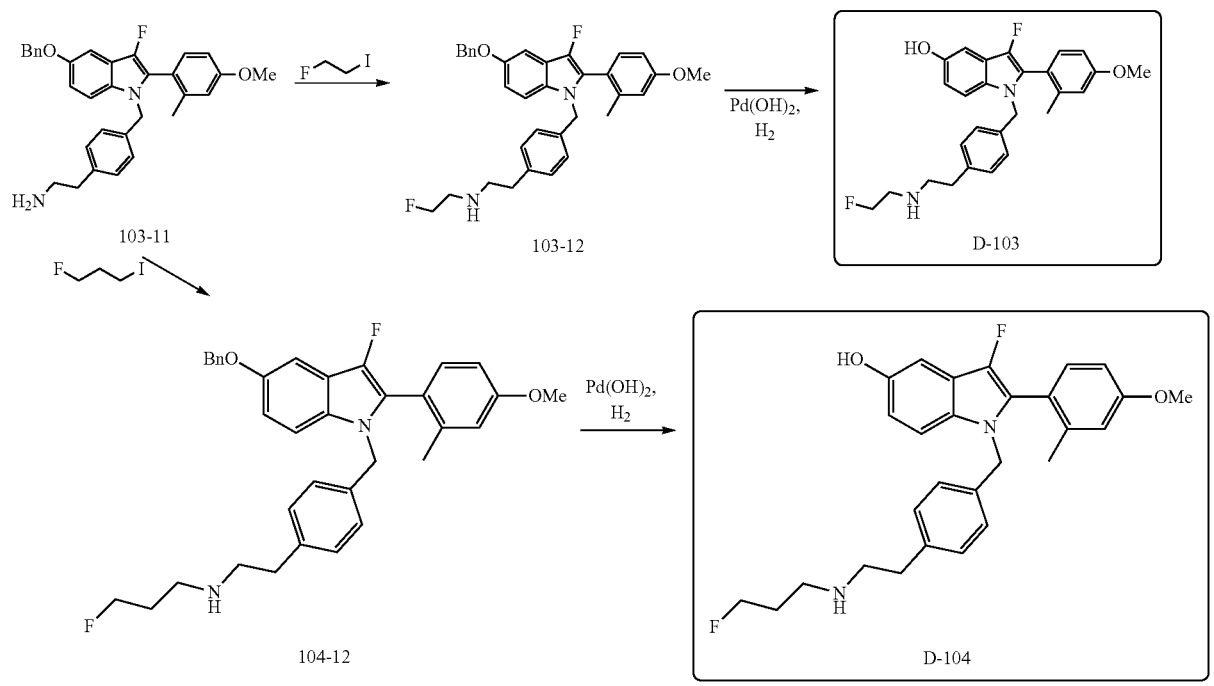

13-3 was treated with (2-methyl-4-methoxyphenyl)boronic acid in the presence of catalytic palladium to yield 52-1, which was fluorinated with selectifluor and subsequently N-benzylated to give the TBDMS-protected 52-3. After removal of the TBDMS protecting group, tosylation to 52-5 followed by reaction with cyclopropyl amine to 52-6 and debenzylation/demethylation with BBr₃ resulted in D-52. (Scheme IVd). Intermediate 52-2 was N-benzylated to give the TBDMS-protected 103-7. After removal of the TBDMS protecting group, tosylation to 103-9 followed by reactions with potassium phthalimide and with hydrazine gave 103-11. Primary amine 103-11 was reacted with fluoroiodo propane and debenzylated to yield D-103. Primary amine 103-11 was similarly reacted with fluoroiodo propane and debenzylated to yield D-104.

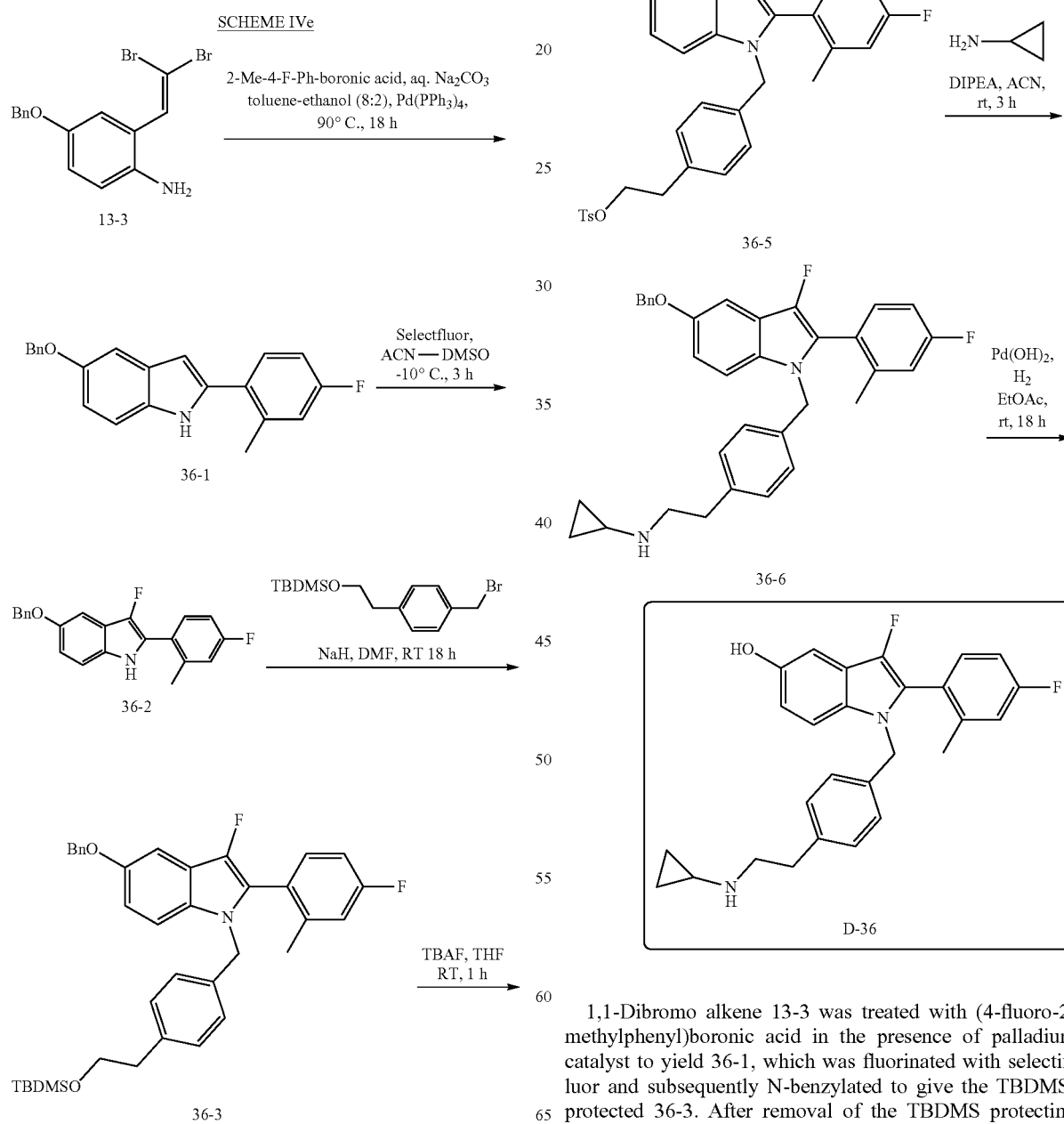

1,1-Dibromo alkene 13-3 was treated with (4-fluoro-2-methylphenyl)boronic acid in the presence of palladium catalyst to yield 36-1, which was fluorinated with selectifluor and subsequently N-benzylated to give the TBDMS-protected 36-3. After removal of the TBDMS protecting group, 36-4 was tosylated to 36-5, reacted with cyclopropylamine to 36-6 and debenzylated to give D-36.

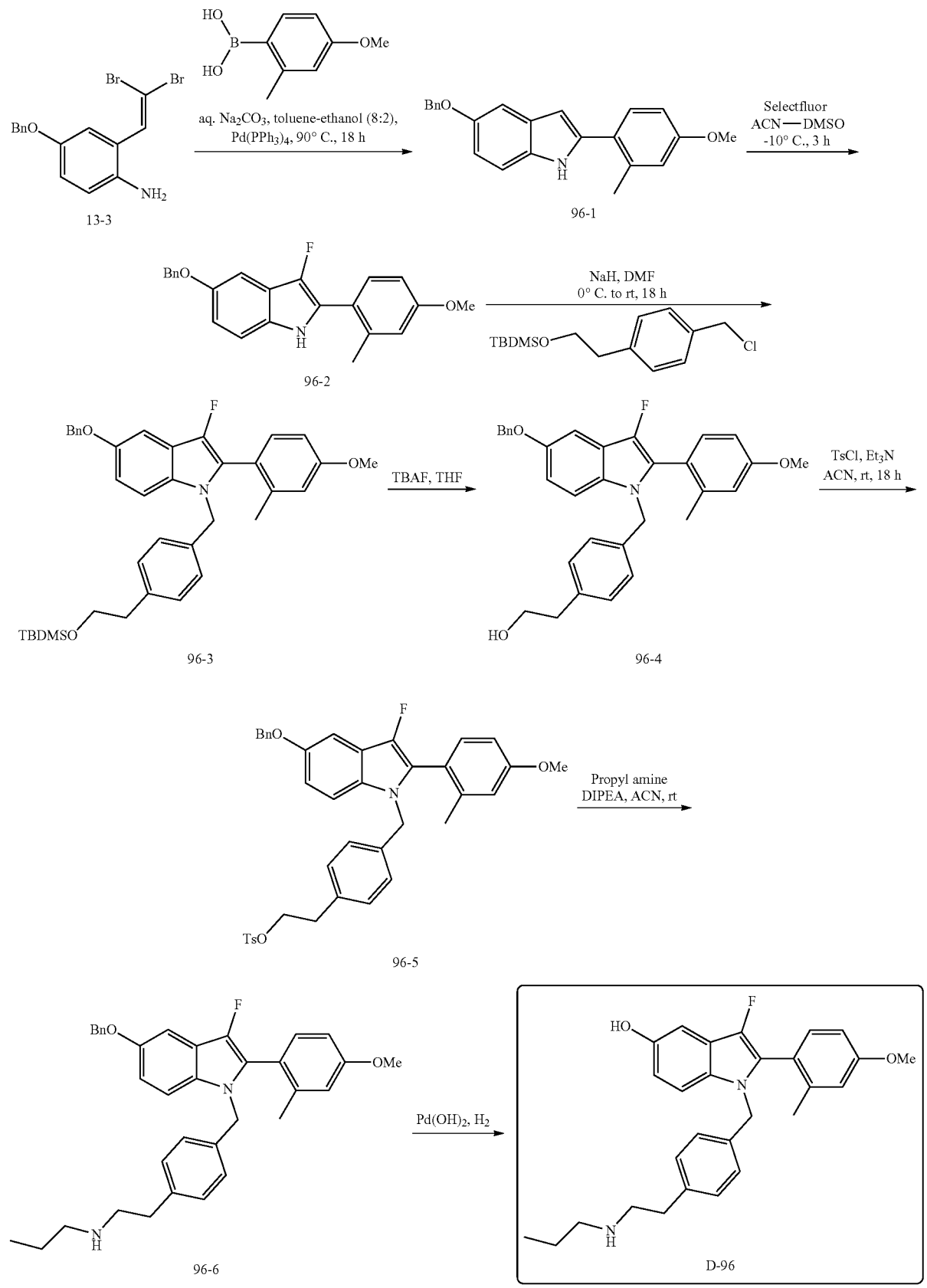

-continued
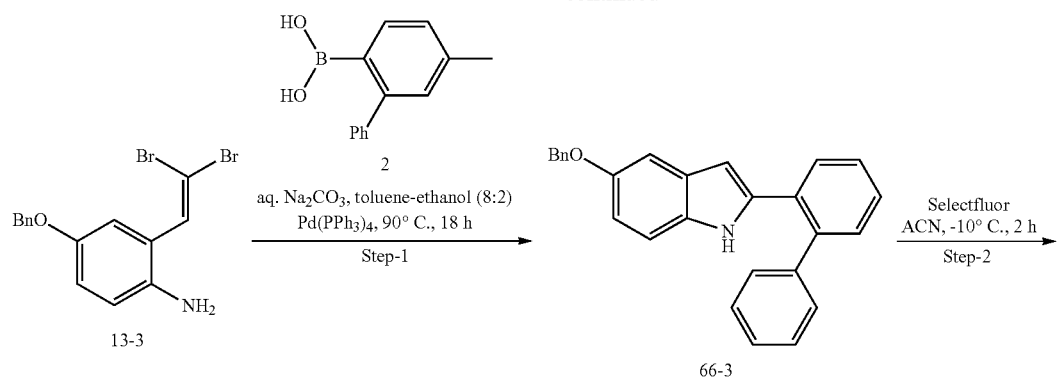
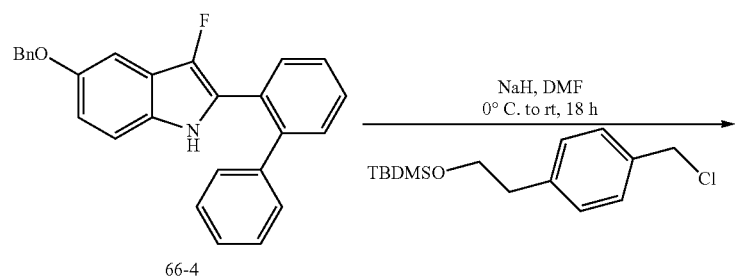
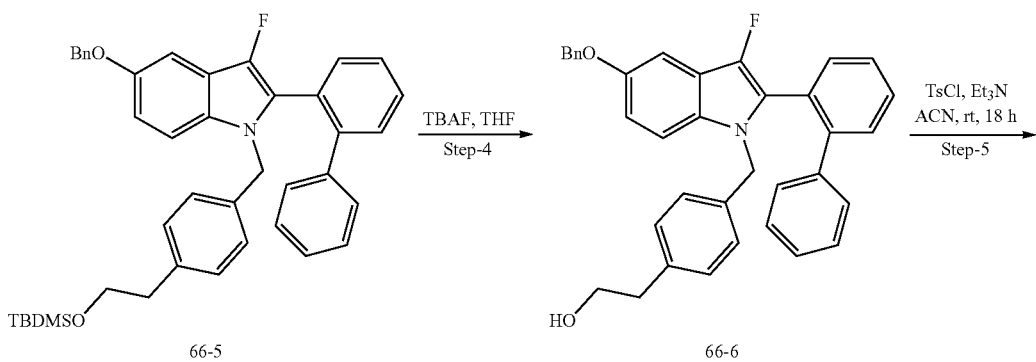
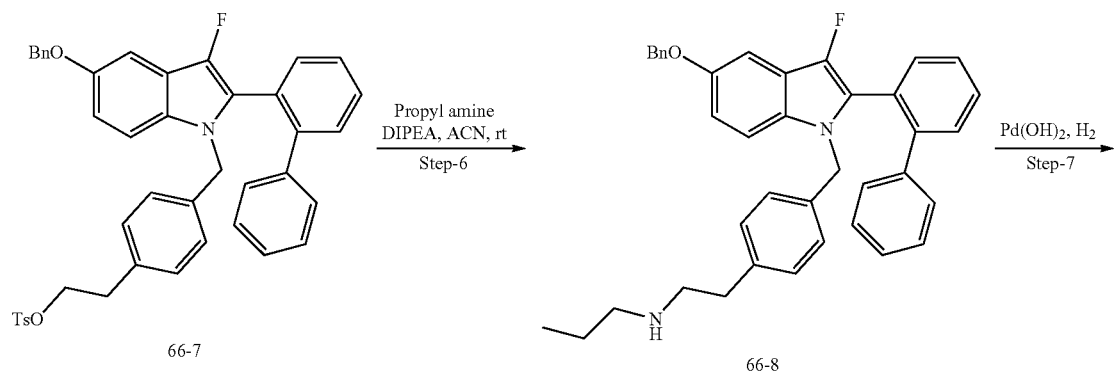

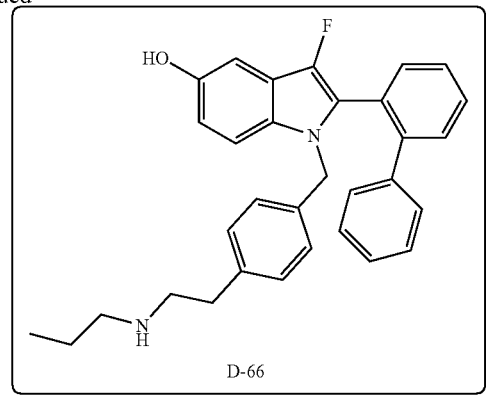

D-66

Intermediate 96-5 was provided in a sequence similar to that preparing 52-5 from 13-3 (see also Scheme IVd). Thereafter, 96-5 was reacted with propylamine to 96-6 and debenzylated to give D-96 (Scheme IVf). Intermediate 13-3 was treated with (2-phenylphenyl)boronic acid in the presence of catalytic palladium to yield 66-3, which was fluorinated with selectifluor and subsequently N-benzylated to give the TBDMS-protected 66-5. After removal of the TBDMS protecting group, tosylation to 66-7 was followed by reaction with propyl amine to 66-8 and debenzylated to yield D-66. (Scheme IVf).

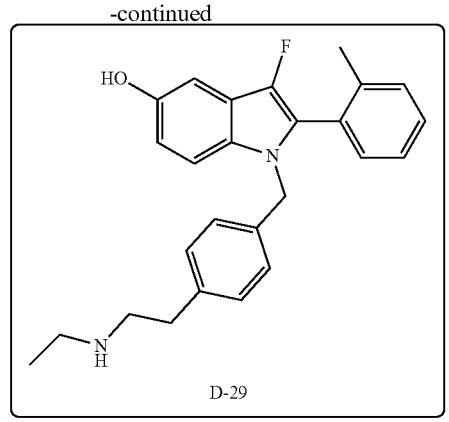

D-29

SCHEME V

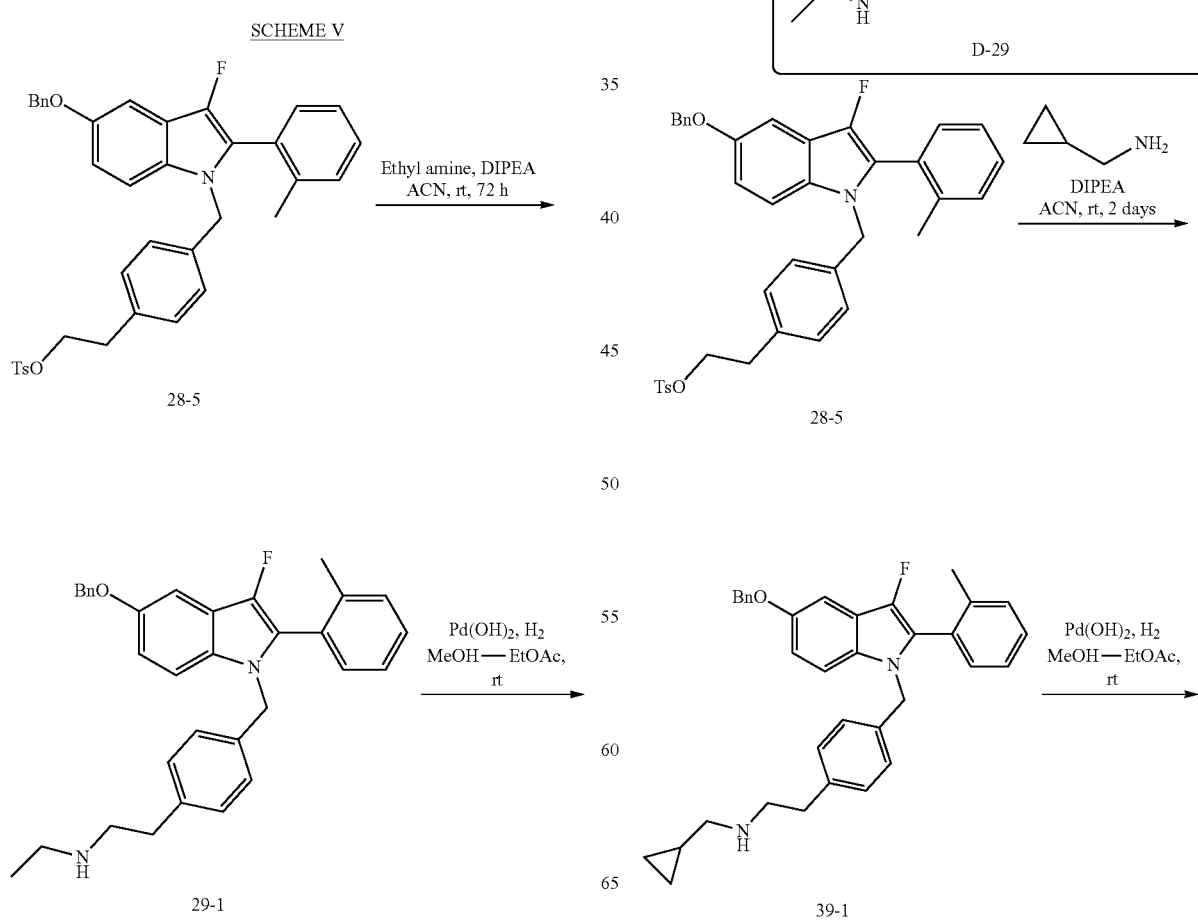

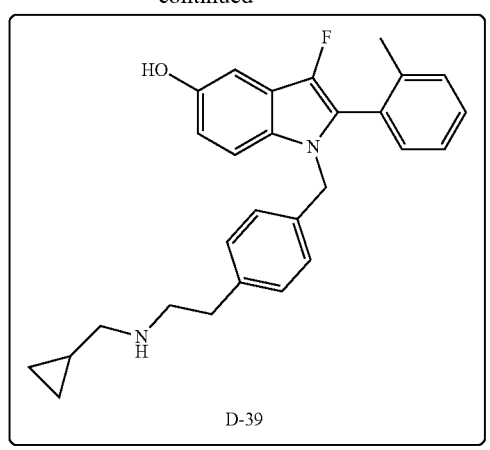
D-39
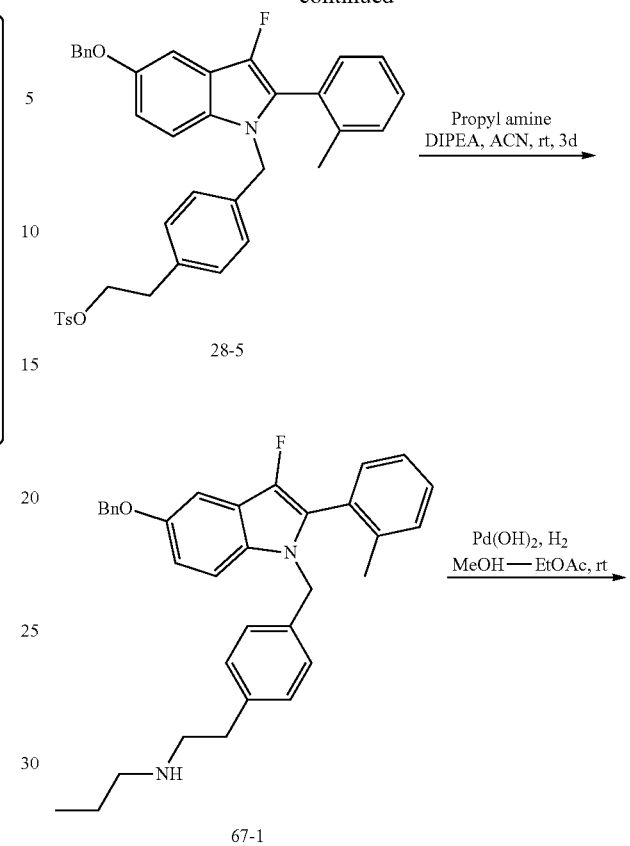
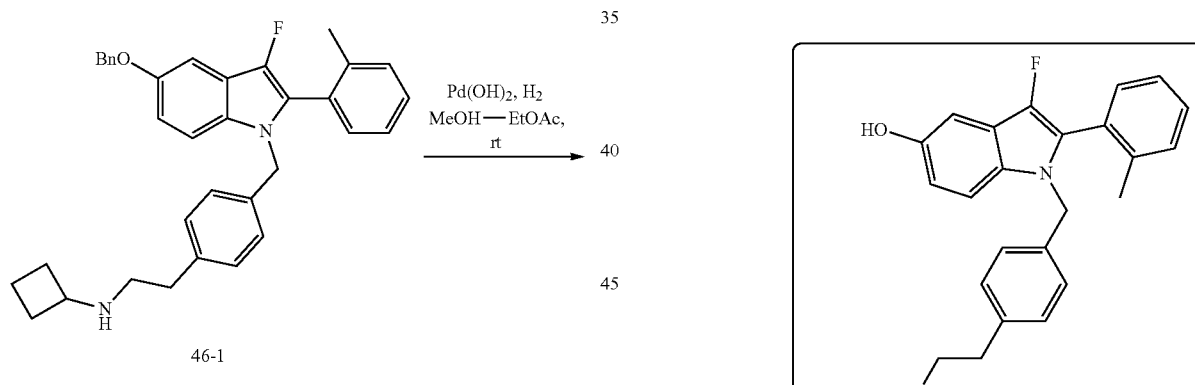
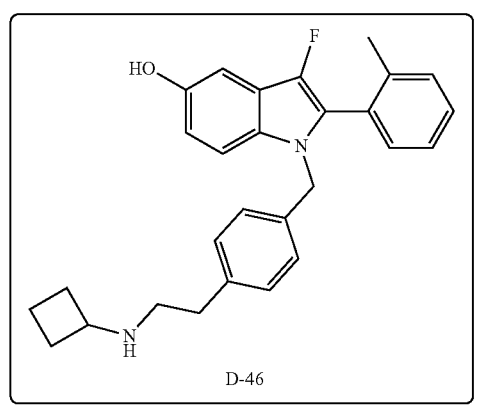
D-46
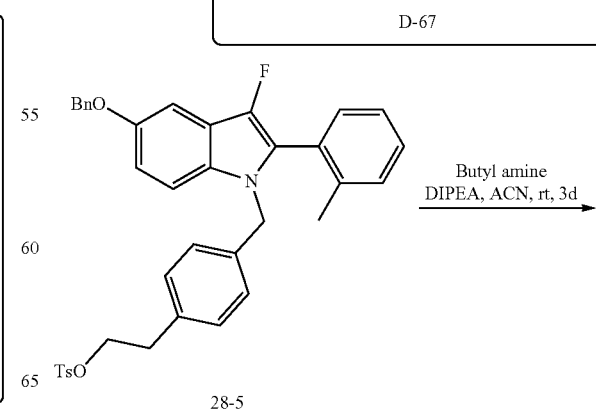

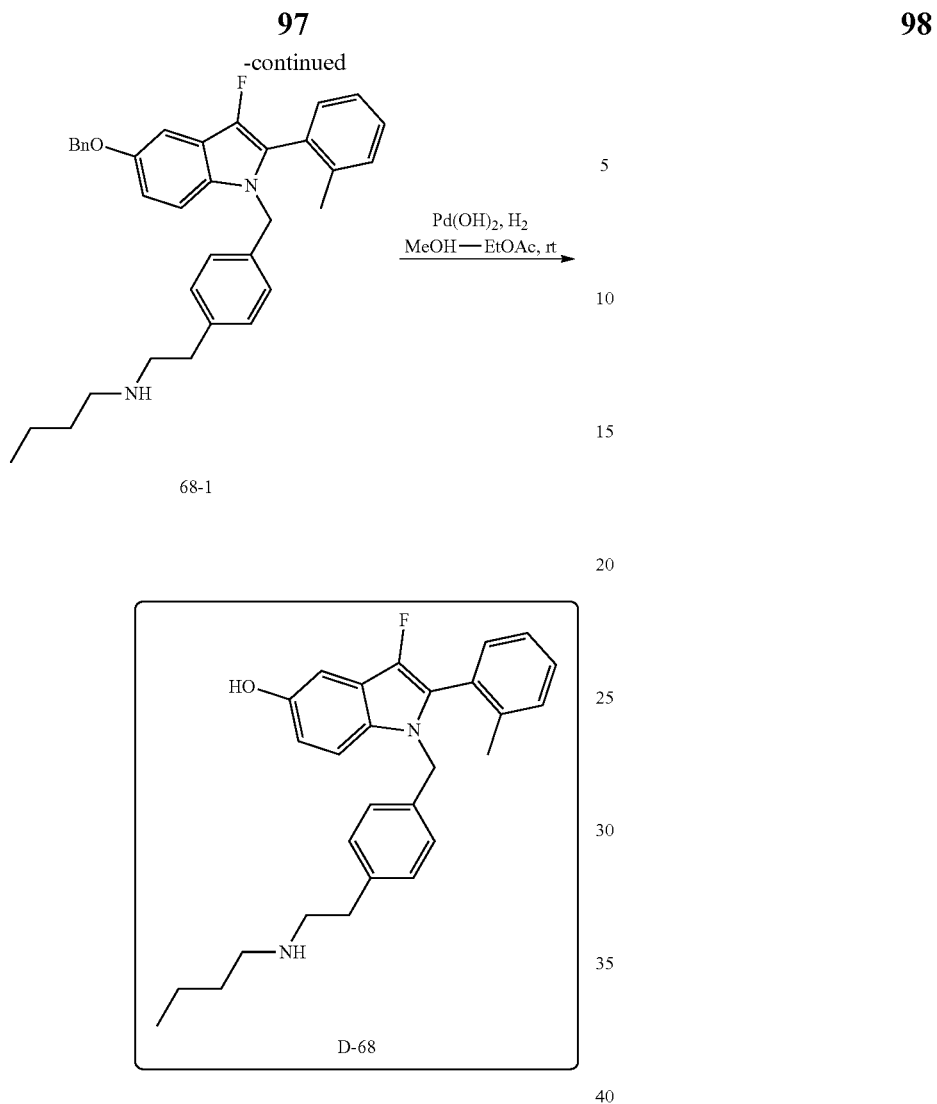
Tosylate 28-5 (see Scheme IV) was treated with ethyl amine to give 29-1, which was catalytically debenzylated to yield D-29. (Scheme V). Similarly, 28-5 was treated with cyclopropylmethylamine, cyclobutyl amine, propyl amine or butyl amine, followed by catalytic debenzylation to provide D-39, D-46, D-67, and D-68, respectively.
SCHEME Vb
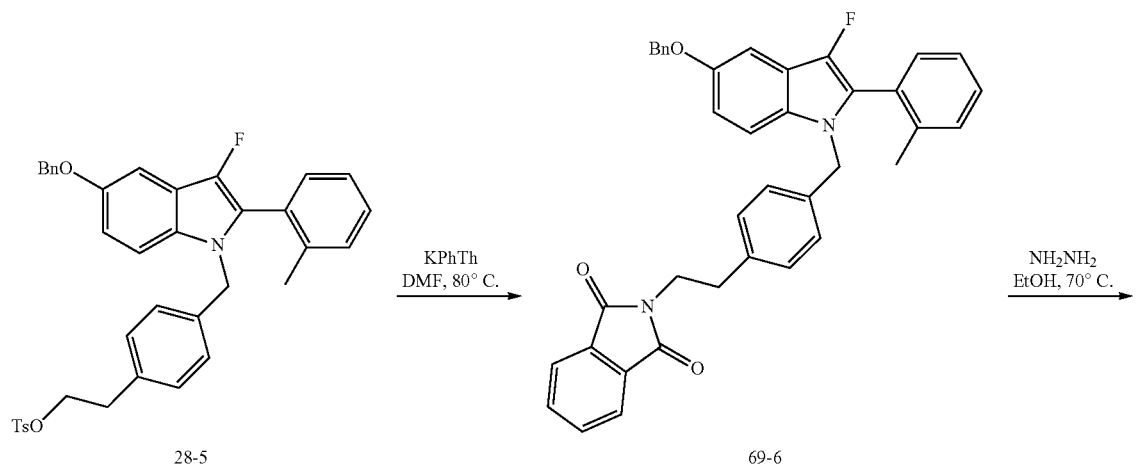

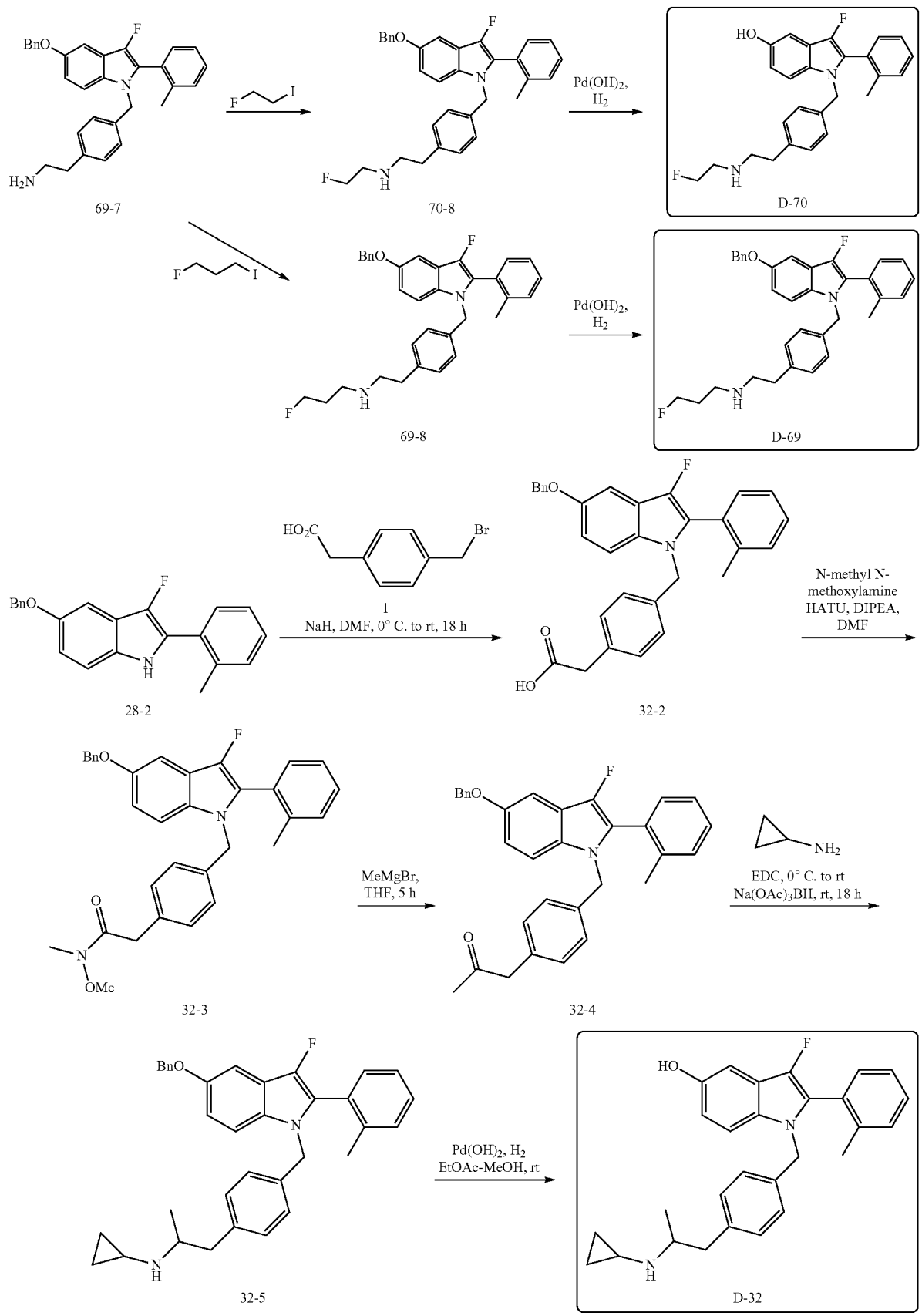

Tosylate 28-5 (see Scheme IV) was reacted with potassium phthalimide and subsequently with hydrazine to give 69-7. Primary amine 69-7 was reacted with fluoroiodo propane and debenzylated to yield D-69. Primary amine 69-7 was similarly reacted with fluoroiodo ethane and debenzylated to yield D-70. Intermediate 28-2 was N-alkylated with para-bromomethylphenylacetic acid 32-2 followed by reaction with N-methyl-N-methoxyamine to prepare 32-3. Compound 32-3 was treated with methyl magnesium bromide and the resultant ketone 32-4 reacted with cyclopropylamine and debenzylated to D-32.

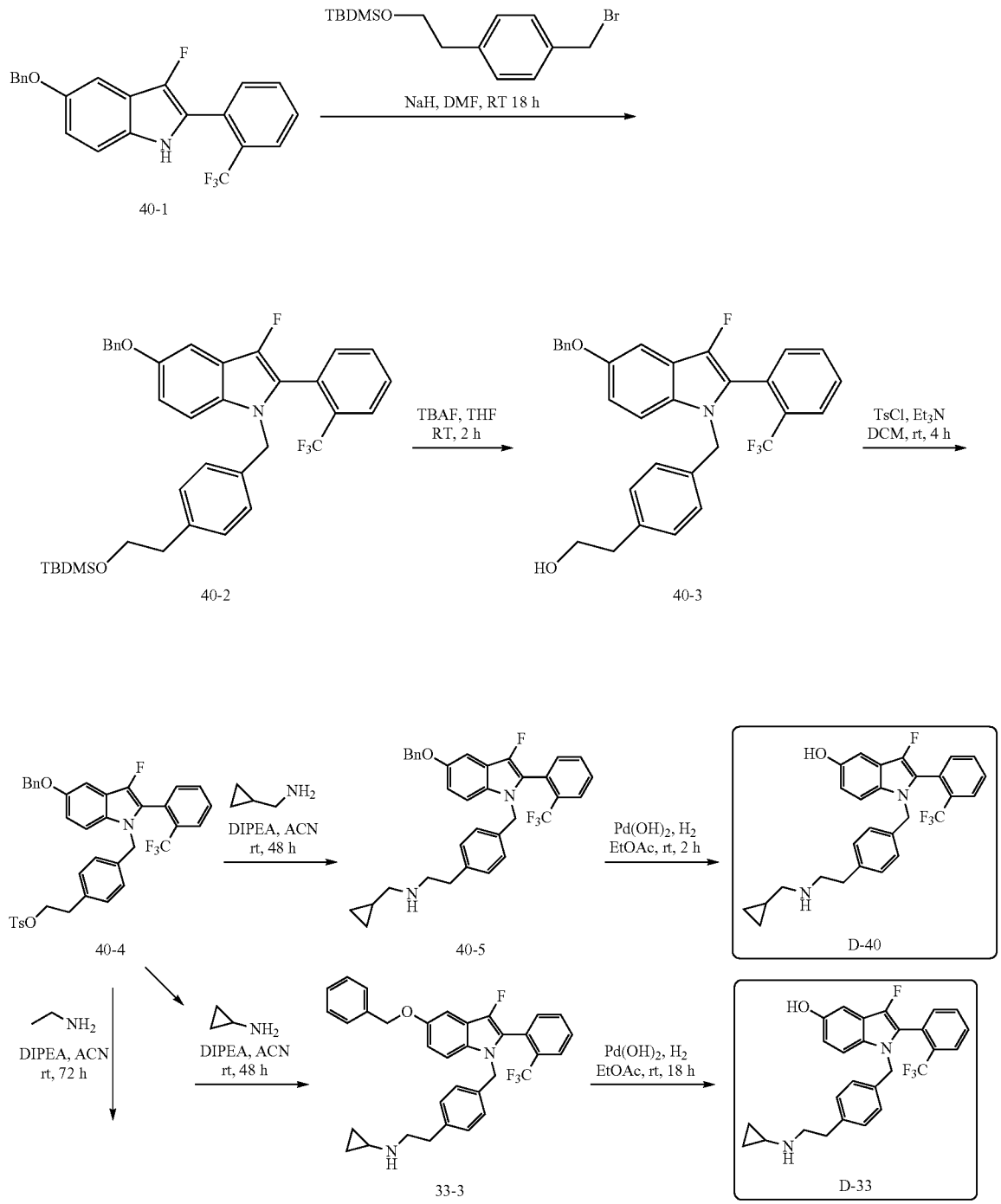

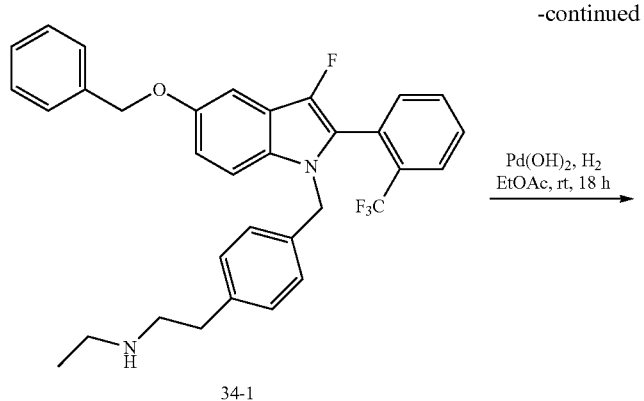
34-1
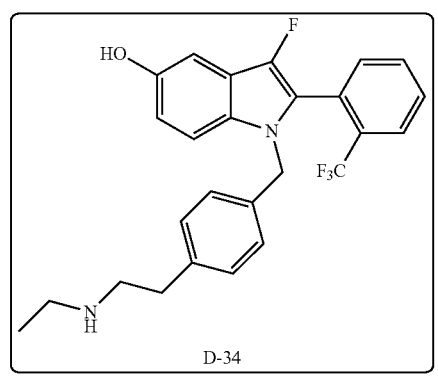
D-34
Compound 40-1 was N-benzylated to give the TBDMS-protected 40-2. After removal of the TBDMS protecting group, tosylation to 40-4 followed by reaction with cyclopropylmethyl amine, cyclopropyl amine or ethyl amine followed by catalytic removal of the benzyl protecting group led to D-40, D-33, and D-34, respectively. (Scheme VI).
SCHEME VII
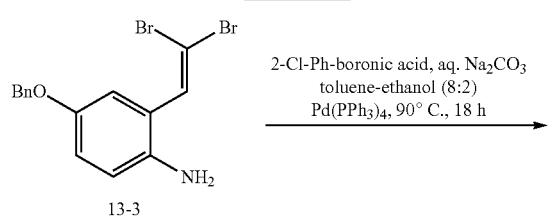
37-1
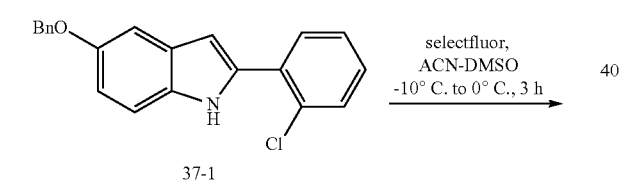
37-1
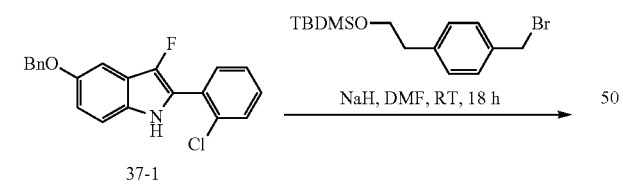
37-3
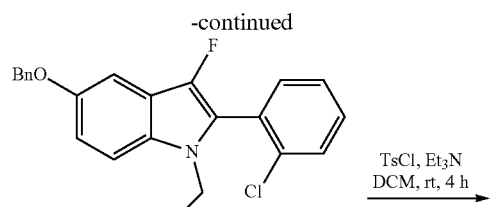
37-4
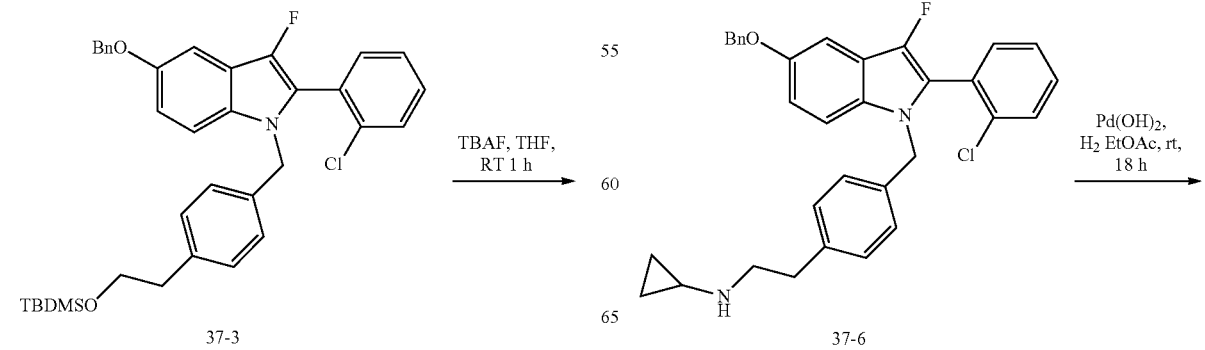

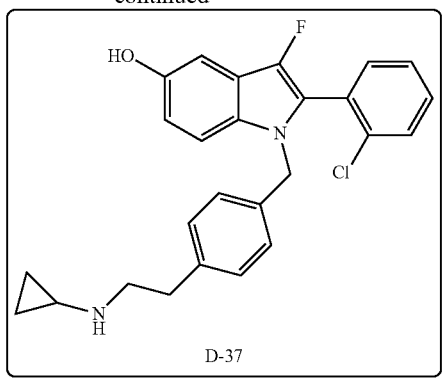
D-37
1,1-Dibromo alkene 13-3 was treated with (2-chlorophenyl)boronic acid in the presence of palladium catalyst to yield 37-1, which was fluorinated with selectfluor and subsequently N-benzylated to give the TBDMS-protected 37-3. After removal of the TBDMS protecting group, 37-4 was tosylated to 37-5, reacted with cyclopropylamine to 37-6 and debenzylated to give D-37.
SCHEME VIII
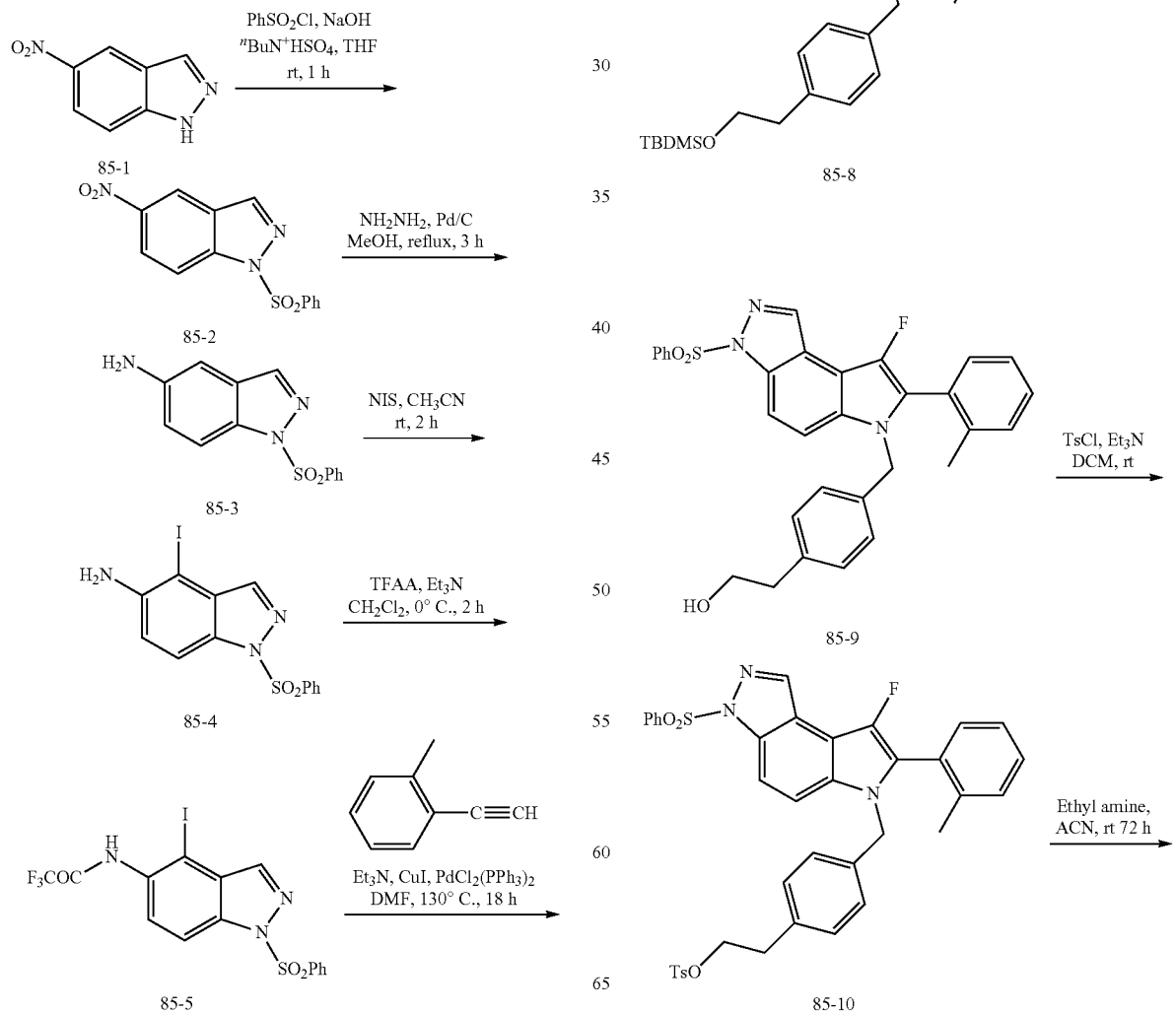
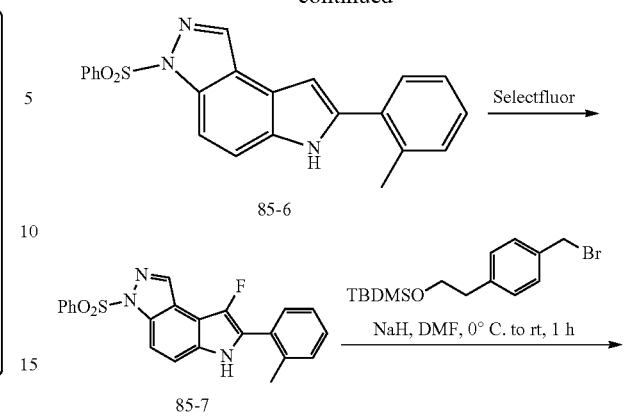

107

-continued

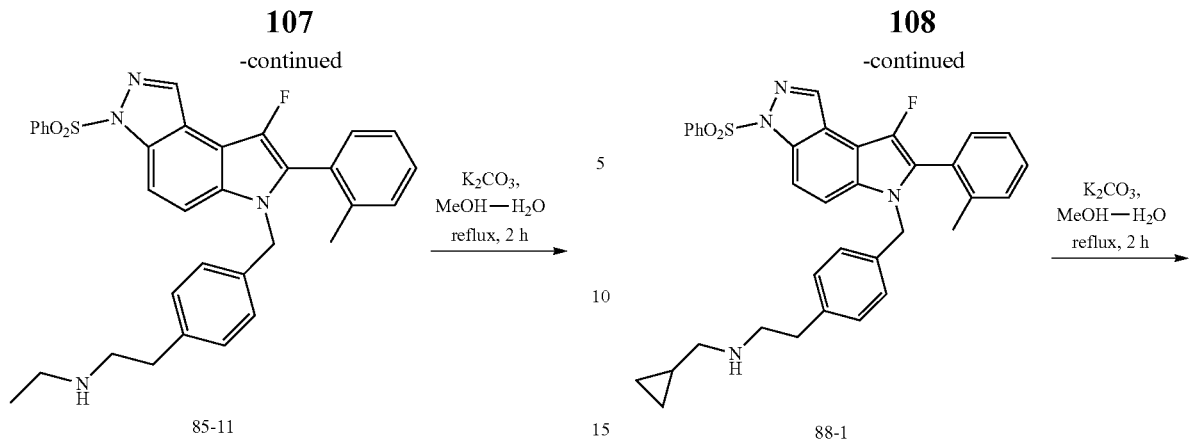

Compound 85-1 was N-sulfonylated and subsequently reduced with hydrazine to yield indazolamine 85-3. After aromatic iodination with N-iodosuccinimide, compound 85-4 was acetylated with trifluoroacetic anhydride, giving rise to 85-5. Arylation/cyclization of 85-5 gave 85-6, which was fluorinated with selectifluor and subsequently N-benzylated to give the TBDMS-protected 85-8. After removal of the TBDMS protecting group, 85-9 was tosylated to 85-10, reacted with ethylamine to 85-11 and debenzylated to give D-85.

SCHEME VIII b

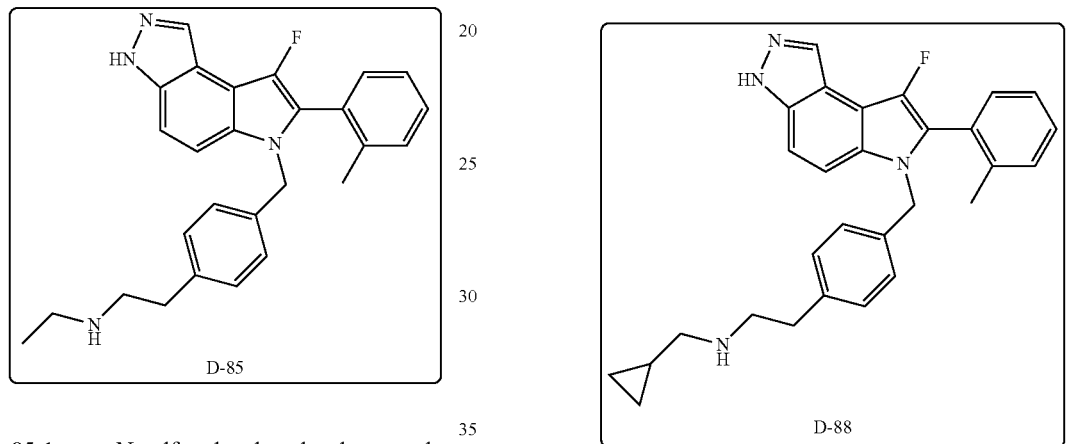

108

-continued

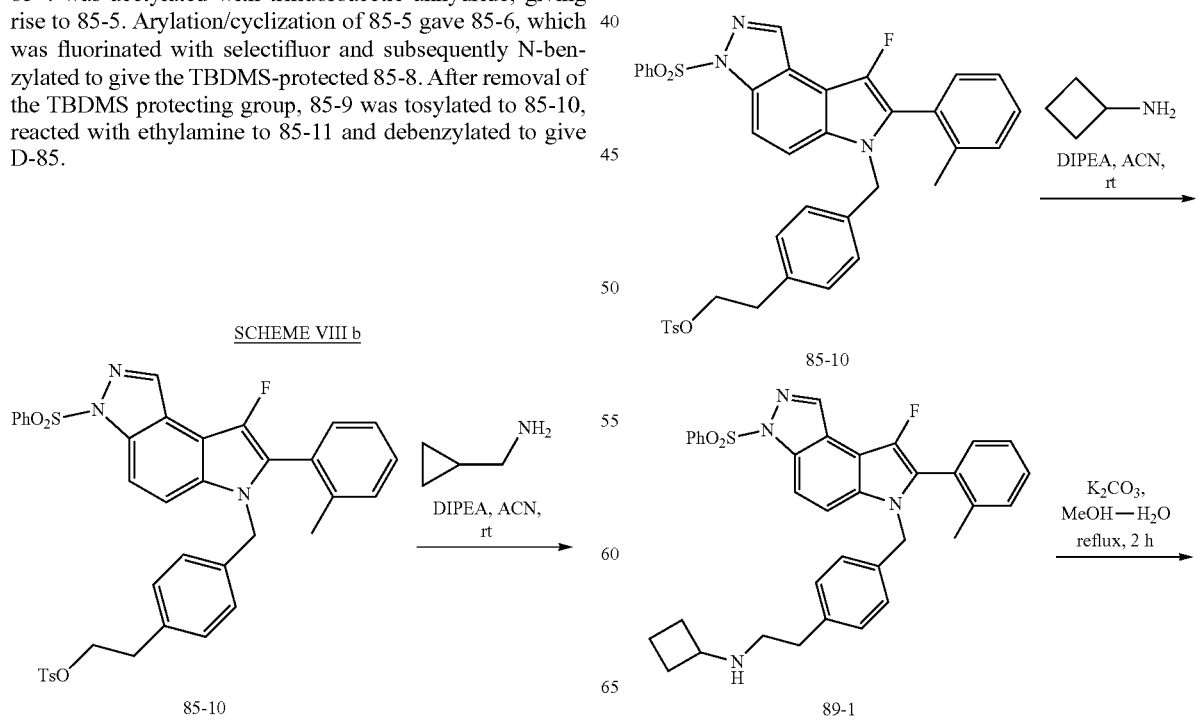

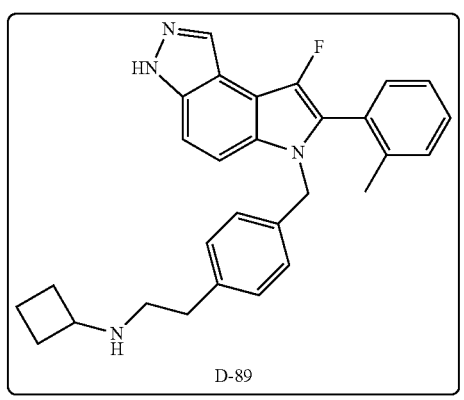
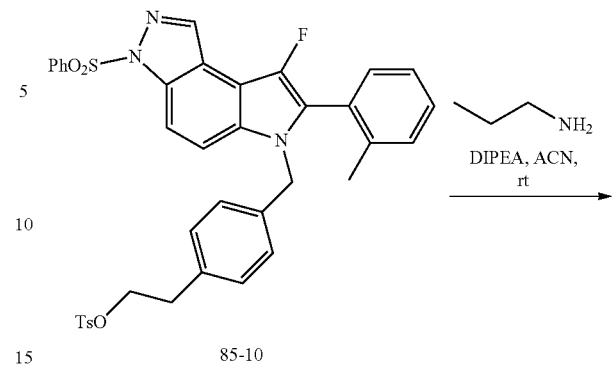
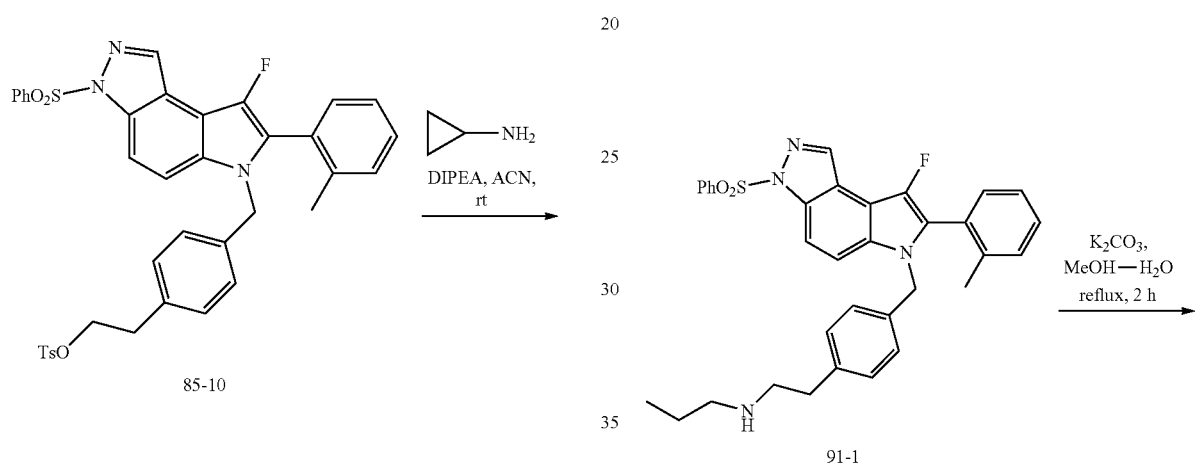
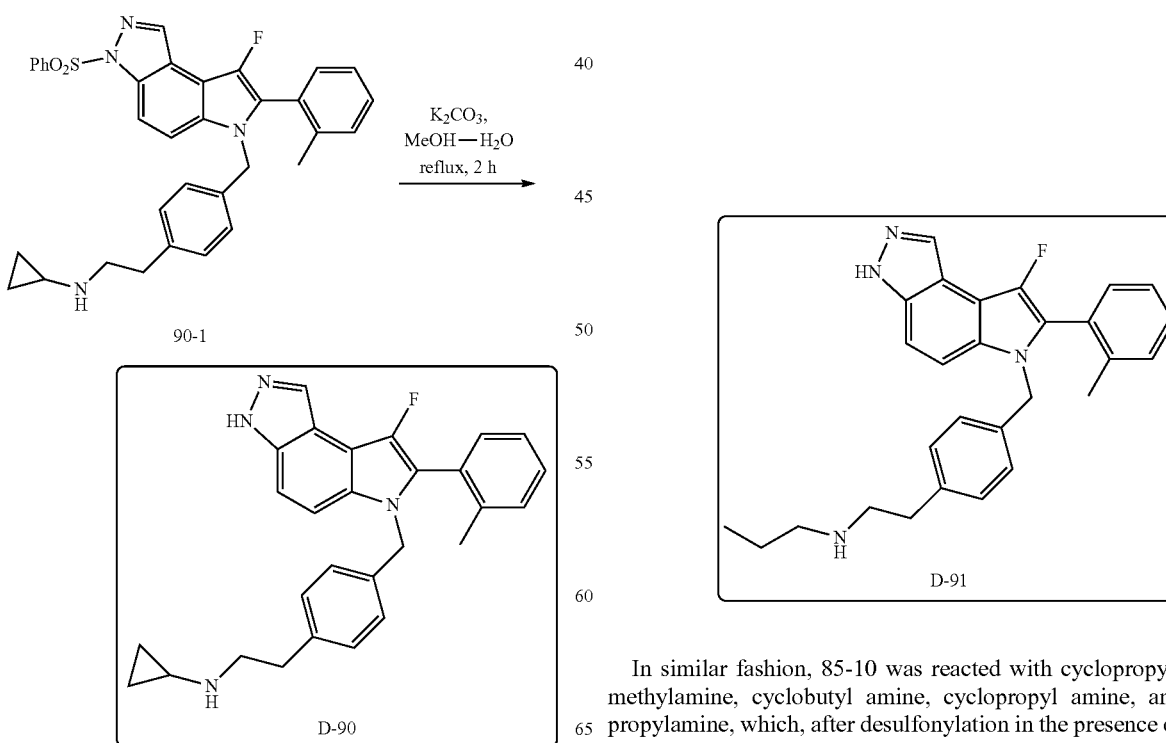
In similar fashion, 85-10 was reacted with cyclopropylmethylamine, cyclobutyl amine, cyclopropyl amine, and propylamine, which, after desulfonylation in the presence of basic methanol/water, gave to D-88, D-89, D-90, and D-91 respectively.

SCHEME VIIIc
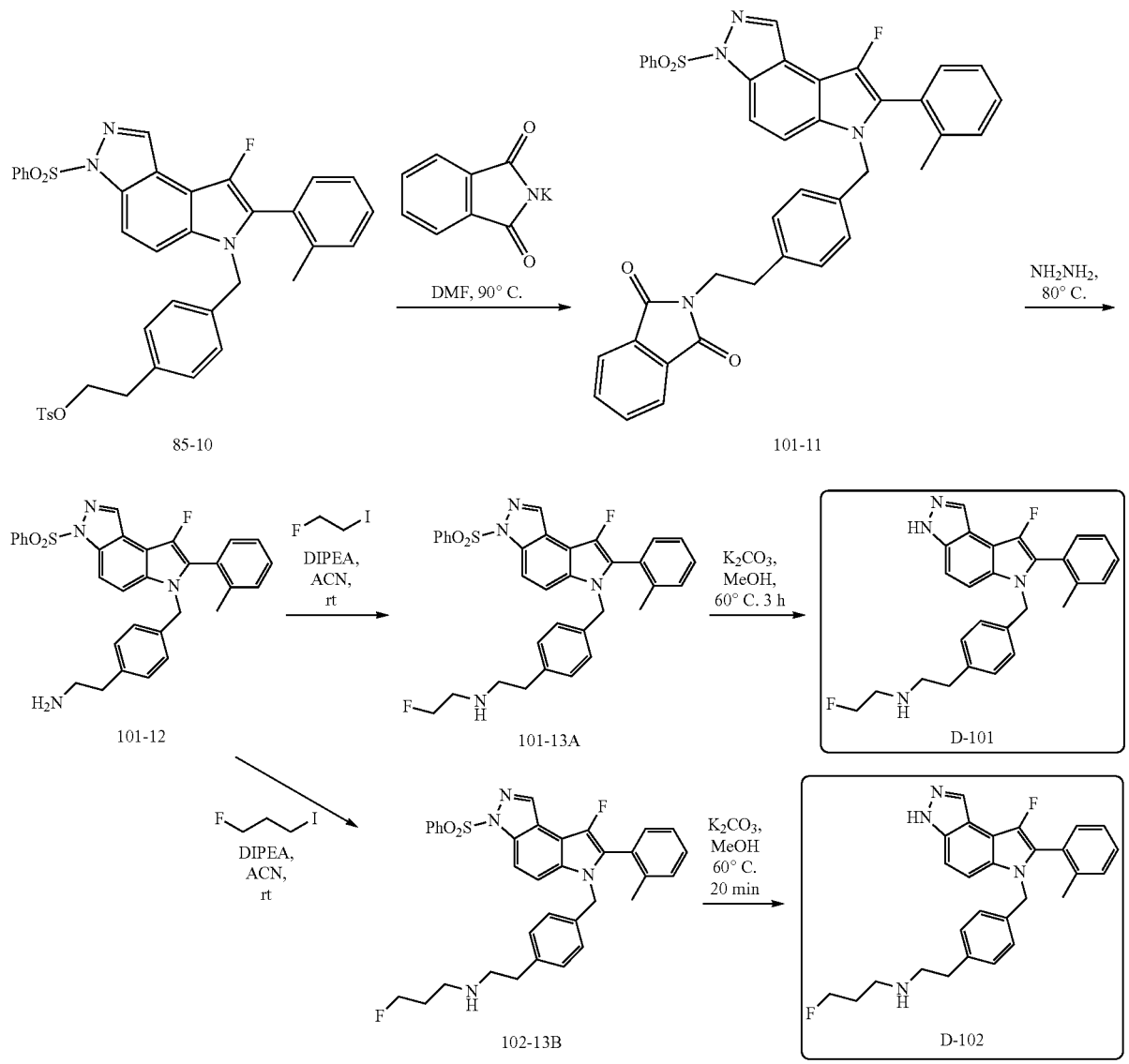
85-10 was also reacted with potassium phthalimide, and subsequently, with hydrazine to give 101-12. Primary amine 101-12 was reacted with either fluoroiodo ethane or fluoroiodopropane and thereafter desulfonyled in the presence of basic methanol/water to provide, respectively, D-101 and D-102.
SCHEME IX
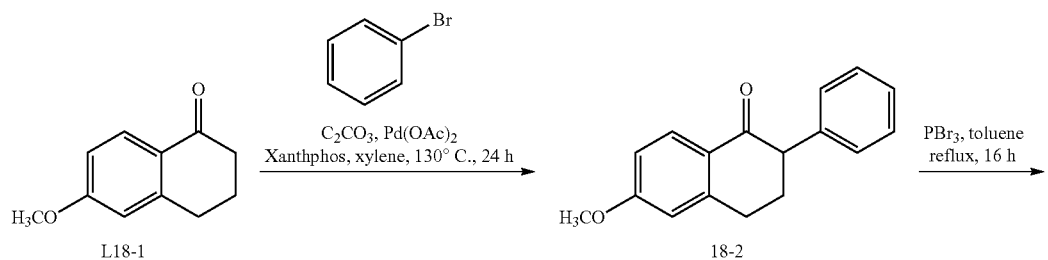

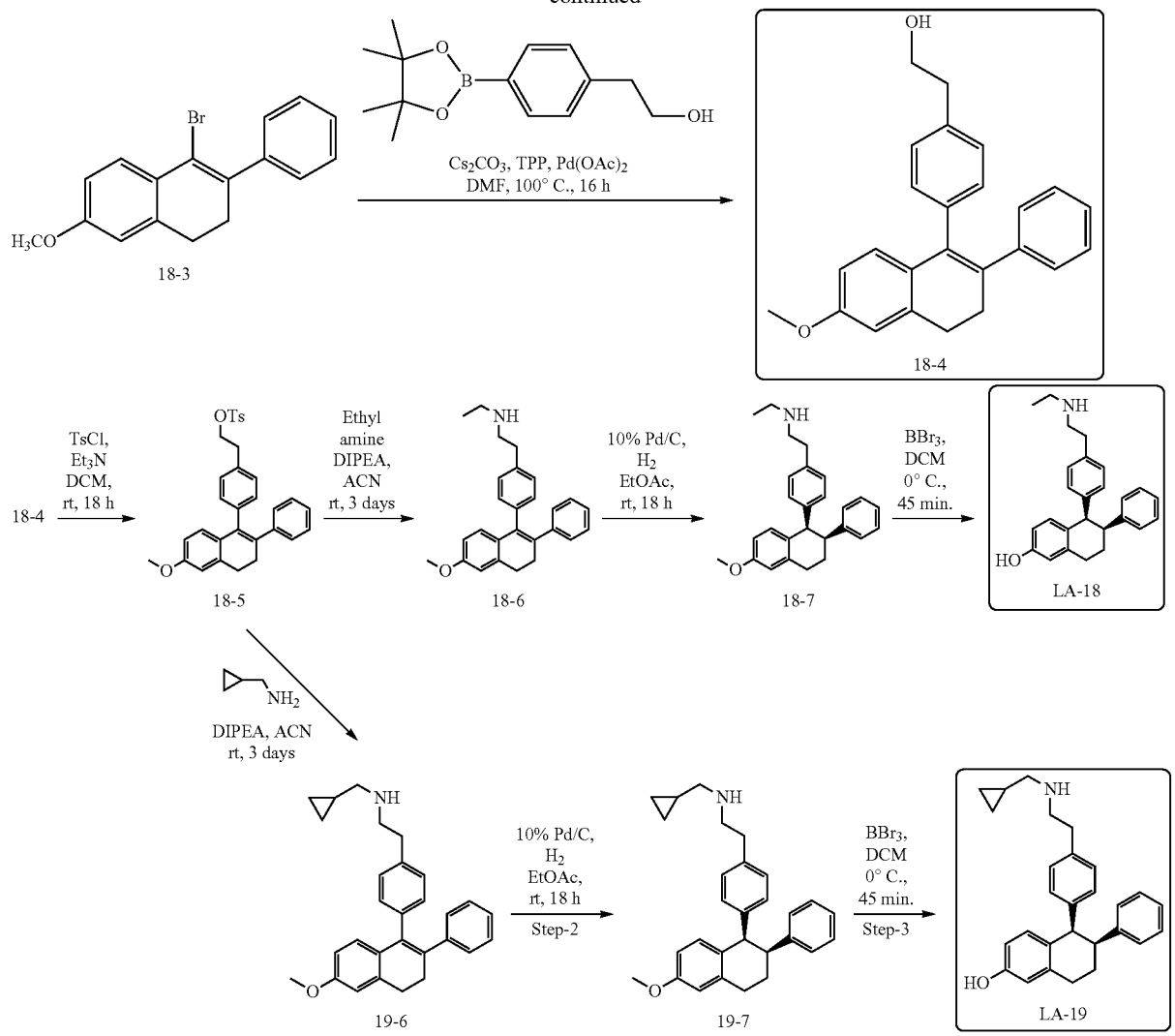

Compound L18-1 was arylated in the presence of palladium acetate and resultant ketone L18-2 was converted to the corresponding vinylic bromide with PBr₃. Compound L18-3 was arylated with 2-(4-(4,4,5,5-tetramethyl-1,3,2-dioxaborolan-2-yl)phenyl)ethan-1-ol to give L18-4, which was tosylated to L18-5 and reacted with ethylamine to L18-6. Reduction of the tetrasubstituted double bond in L18-6 gave the cis compound L18-7, which was demethylated to LA-18 with BBr₃. (Scheme IX) L18-5 was also treated with cyclopropylmethylamine followed by reduction and demethylation to yield LA-19.

SCHEME IXb

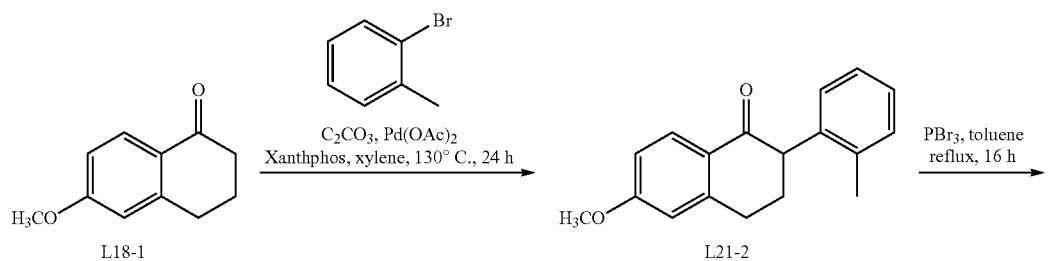

115
-continued
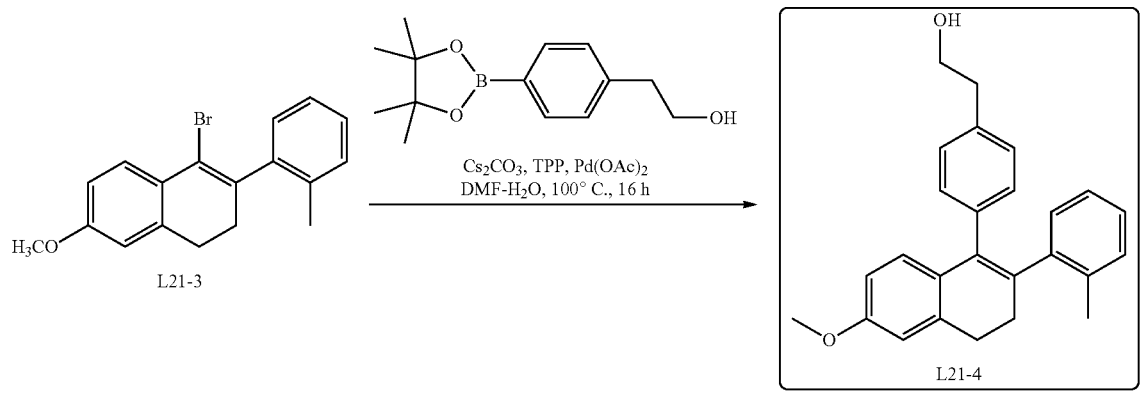
116
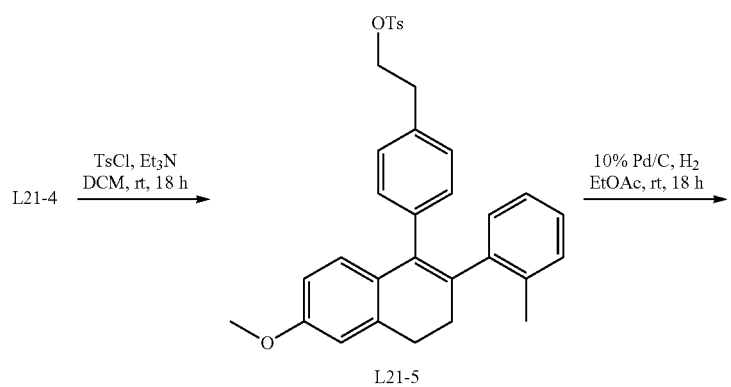
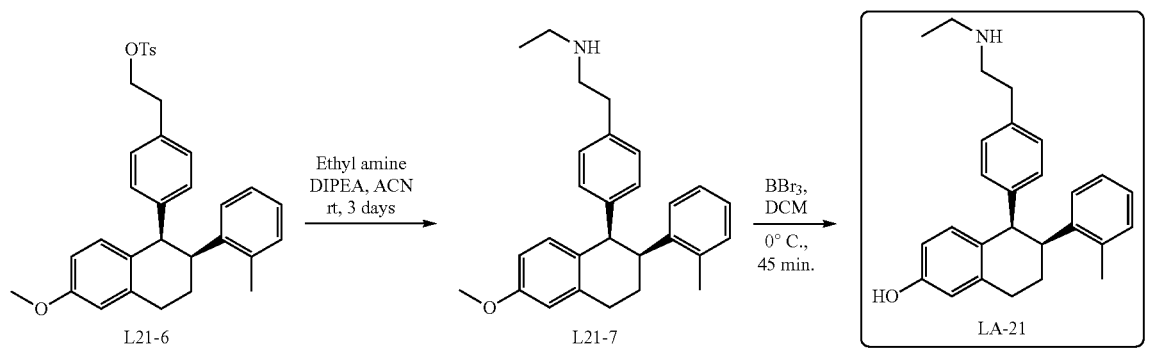
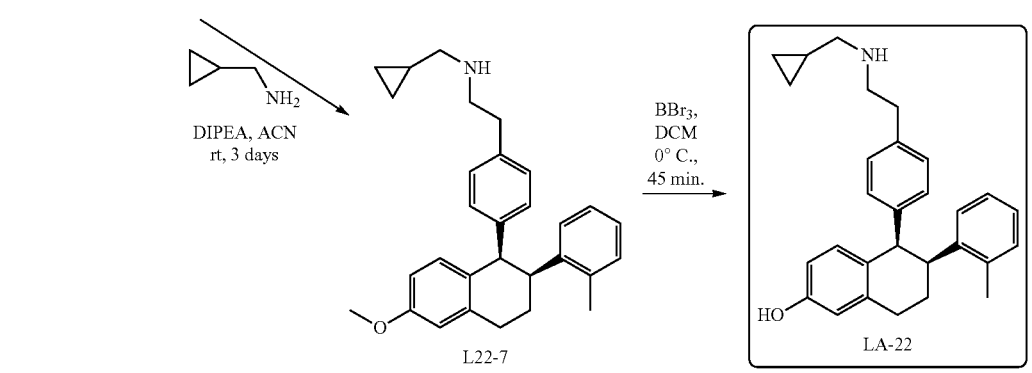

Compound L18-1 was arylated (2-methyl-bromobenzene) in the presence of palladium acetate and resultant ketone L21-2 was converted to the corresponding vinylic bromide with $PBr_3$. Compound L21-3 was arylated with 2-(4-(4,4,5,5-tetramethyl-1,3,2-dioxaborolan-2-yl)phenyl)ethan-1-ol to give L21-4, which was tosylated to L21-5 and reacted with ethylamine to L21-6. Reduction of the tetrasubstituted double bond in L21-6 gave the cis compound L21-7, which was demethylated to LA-21 with $BBr_3$. (Scheme IXb) L21-5 was also treated with cyclopropylmethylamine followed by reduction and demethylation to yield LA-22.

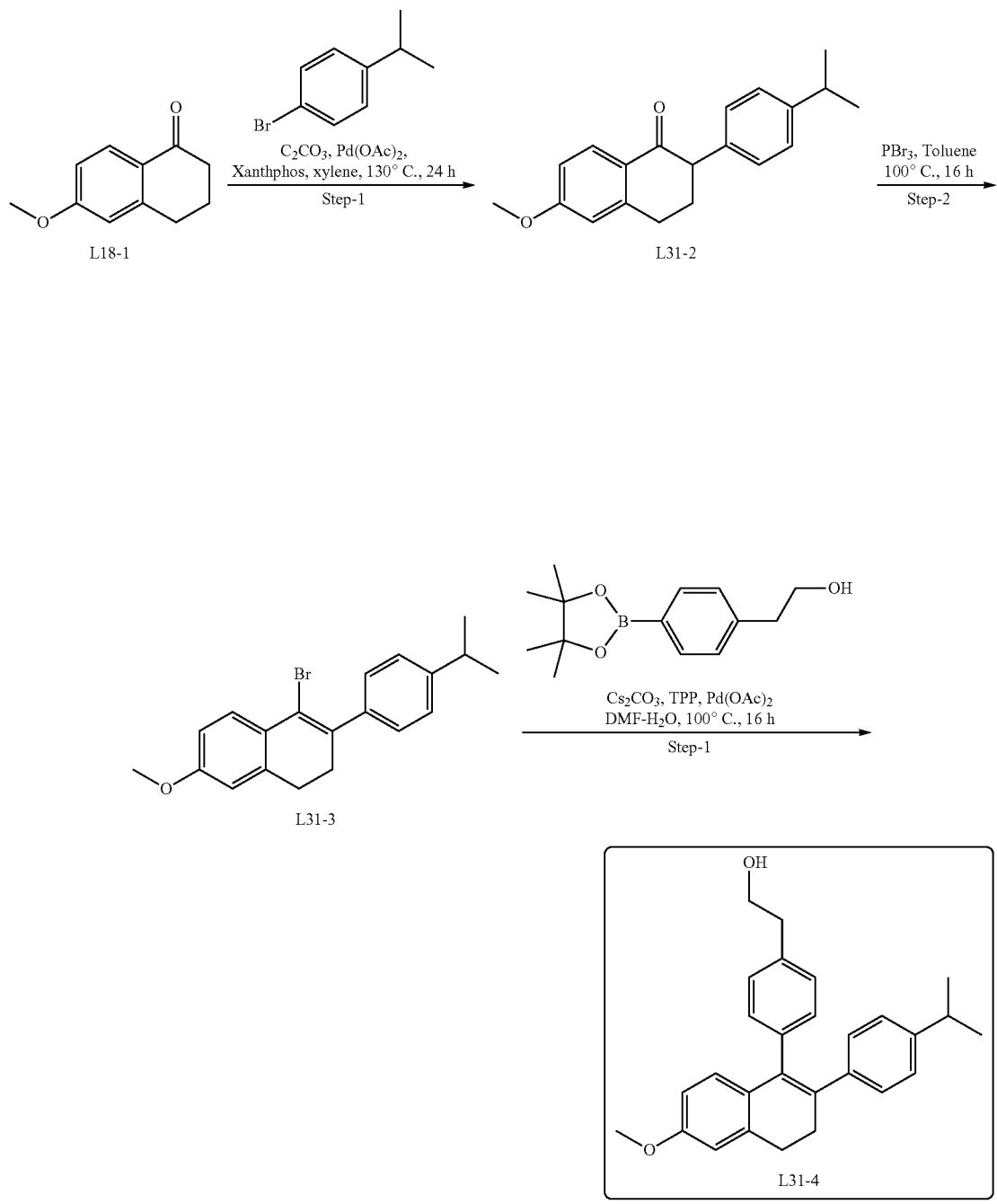

SCHEME IXc

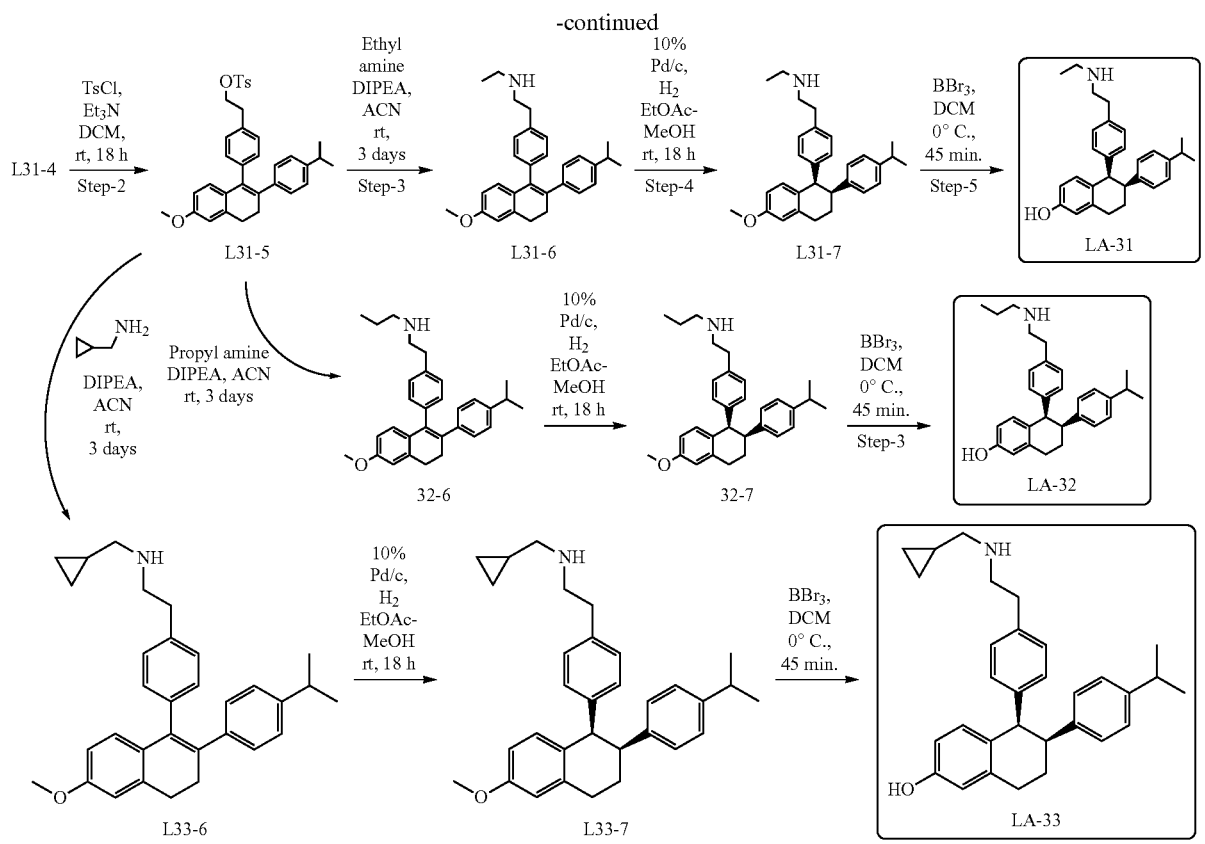

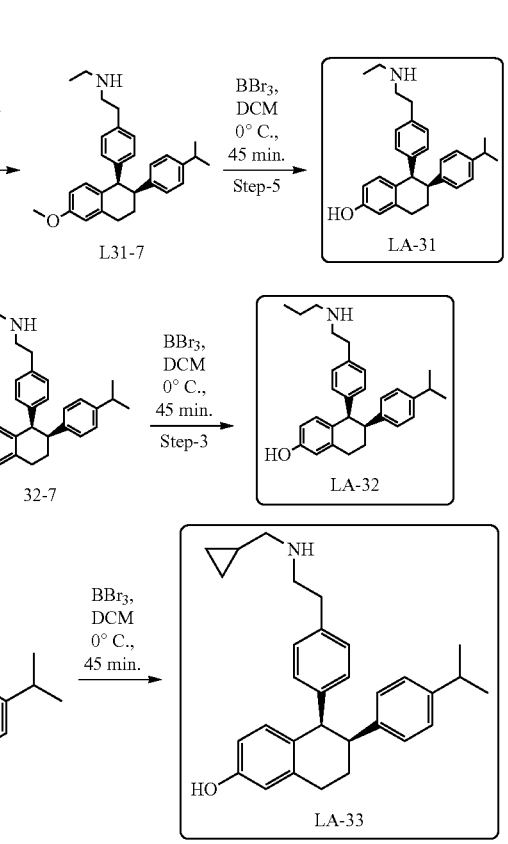

Compound L18-1 was arylated (4-isopropyl-bromobenzene) in the presence of palladium acetate and resultant ketone L31-2 was converted to the corresponding vinylic bromide with PBr₃. Compound L31-3 was arylated with 2-(4-(4,4,5,5-tetramethyl-1,3,2-dioxaborolan-2-yl)phenyl)ethan-1-ol to give L31-4, which was tosylated to L31-5 and reacted with ethylamine to L31-6. Reduction of the tetrasubstituted double bond in L31-6 gave the cis compound L31-7, which was demethylated to LA-31 with BBr₃. (Scheme IXc) L31-5 was also treated with cyclopropylmethylamine followed by reduction and demethylation to yield LA-33.

SCHEME X

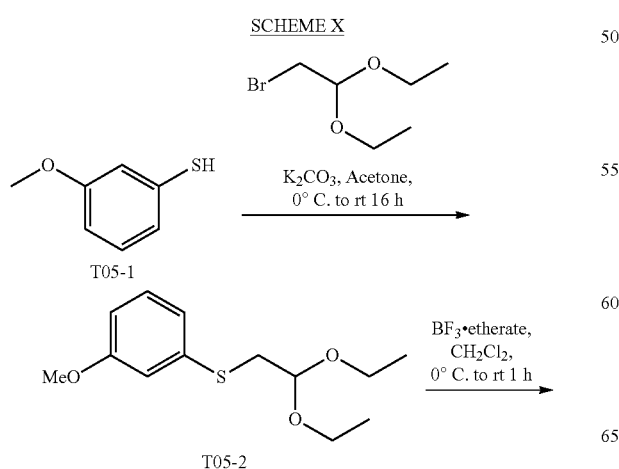

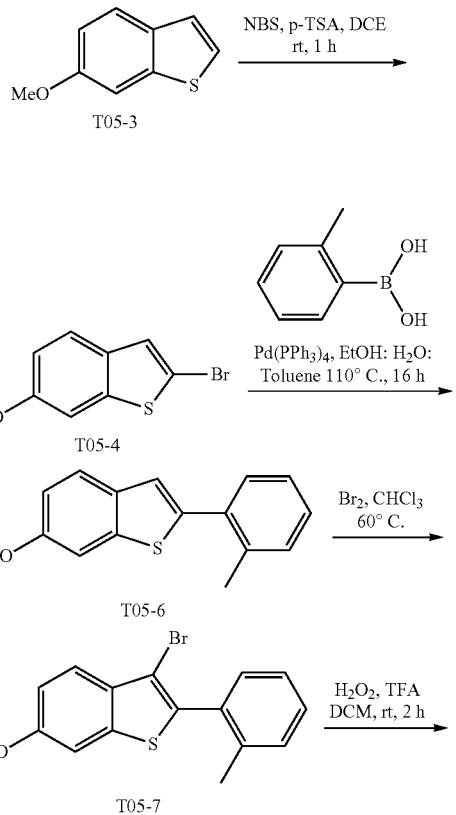

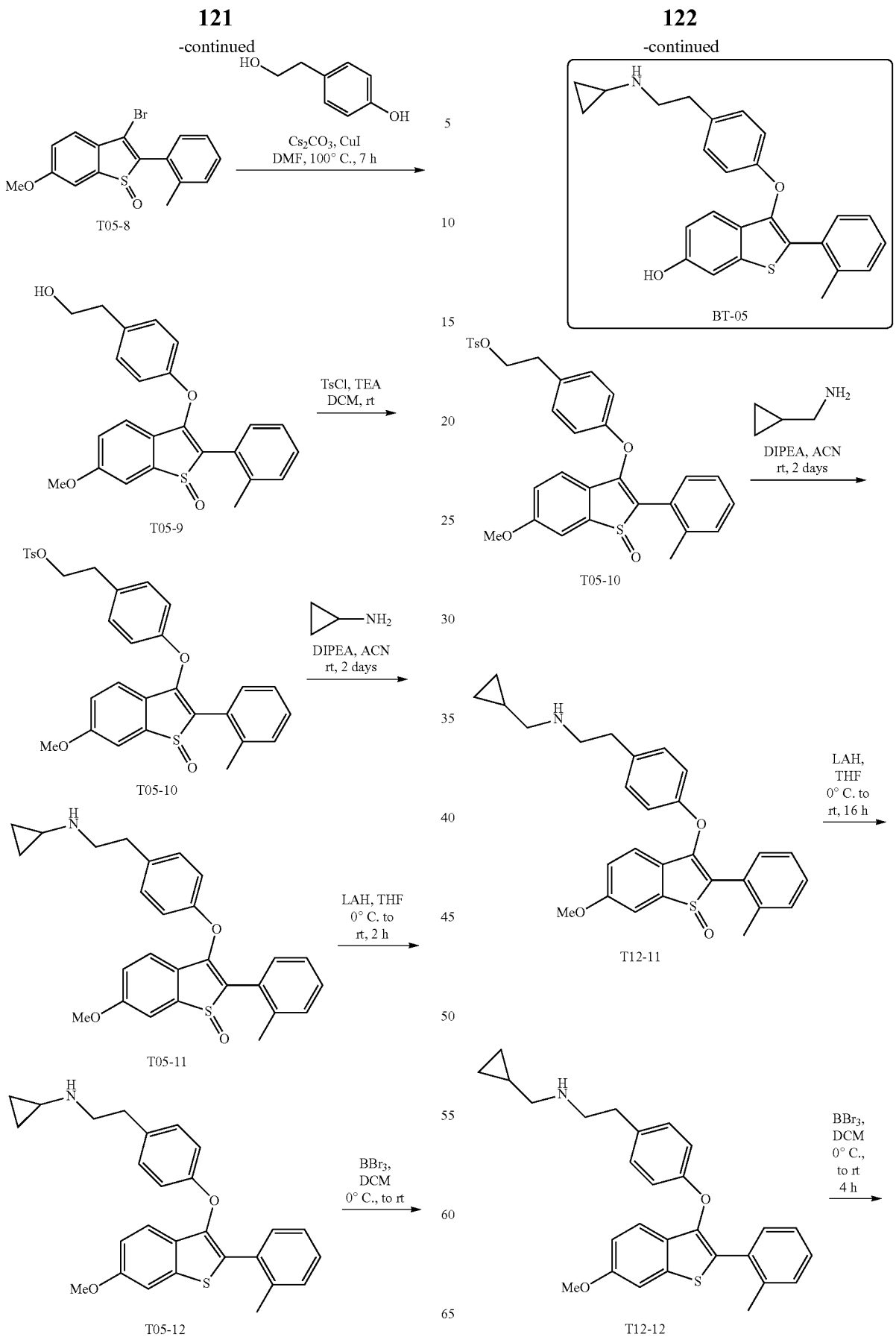

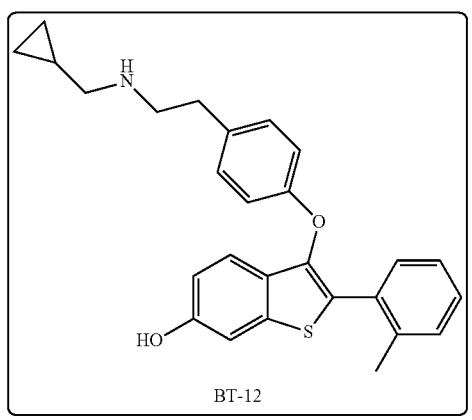

Compound T05-1 was alkylated with 2-bromo-1,1-diethoxyethane and subsequently cyclized in the presence of Lewis acid to the corresponding benzo{b}thiophene T05-3. After bromination with NBS, the heteroaryl bromide was coupled with o-tolylboronic acid in the presence of a palladium catalyst to yield T05-6. Bromination followed by oxidation of the sulfur atom led to T05-8. Displacement of the bromide with para hydroxyethylphenol and tosylation of the hydroxyethyl functionality gave T05-10. Intermediate T05-10 was treated with cyclopropylamine followed by reduction of the sulfonyl group and demethylation to yield BT-05. (Scheme X). In similar fashion, Intermediate T05-10 was treated with cyclopropylmethylamine followed by reduction of the sulfonyl group and demethylation to yield BT-12.

SCHEME XI

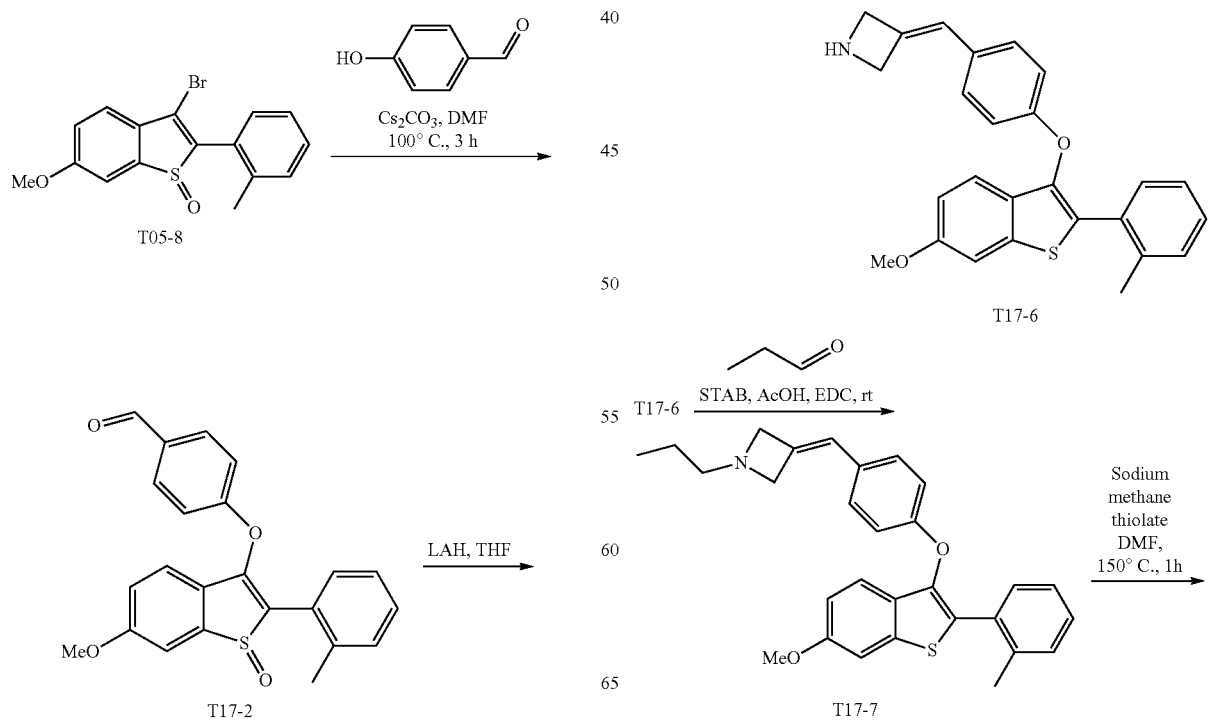

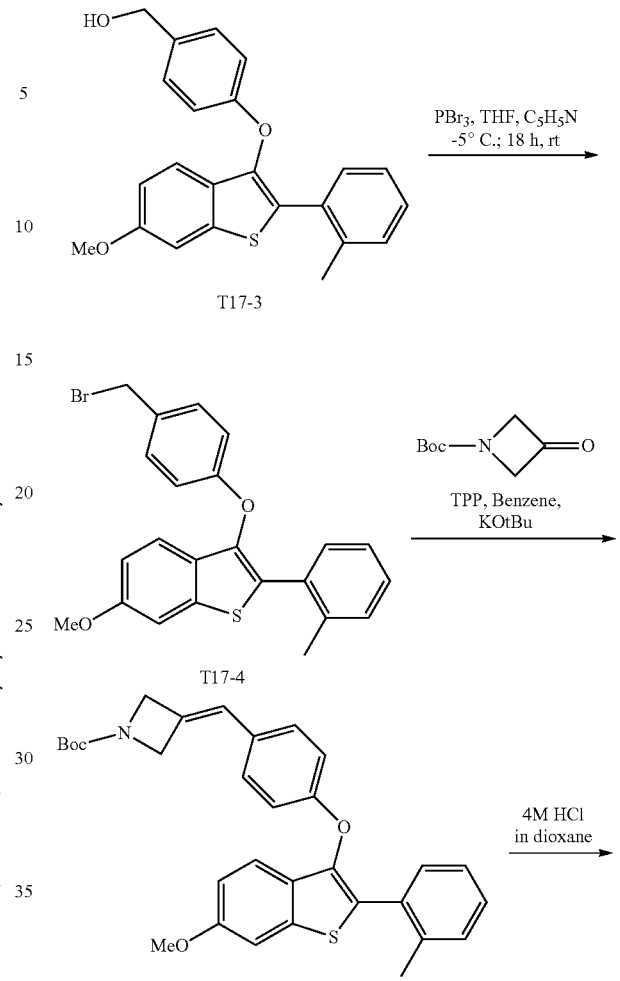

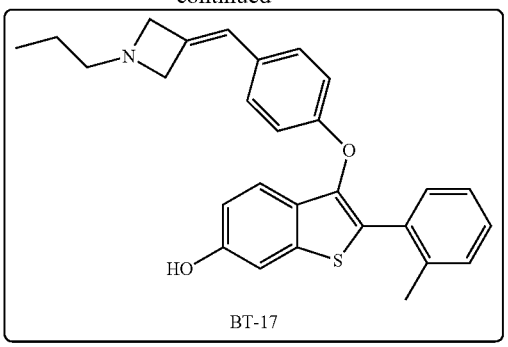

BT-17

Displacement of the bromide with para hydroxybenzaldehyde, subsequent reduction of the aldehyde with LAH, and conversion of the resultant benzylic alcohol with phosphorus tribromide yielded benzylic bromide T17-4. Wittig olefination of T17-4 with tert-butyl 3-oxoazetidine-1-carboxylate in the presence of triphenylphosphine led to T17-5. Removal of the Boc protecting group with acid gave T17-6, which was alkylated with propanal in the presence of sodium triacetoxyborohydride to form T17-7. Penultimate intermediate T17-7 was demethylated to give BT-17. (Scheme XI)

SCHEME XII

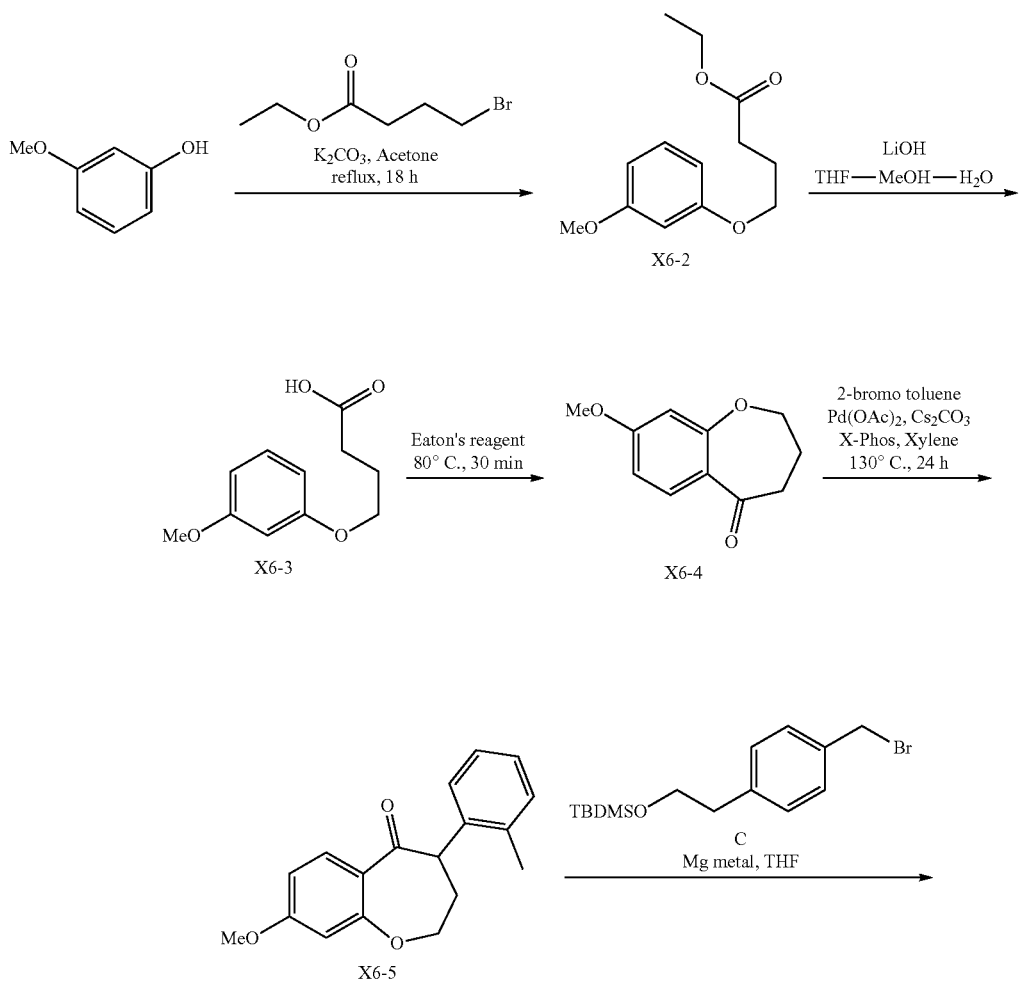

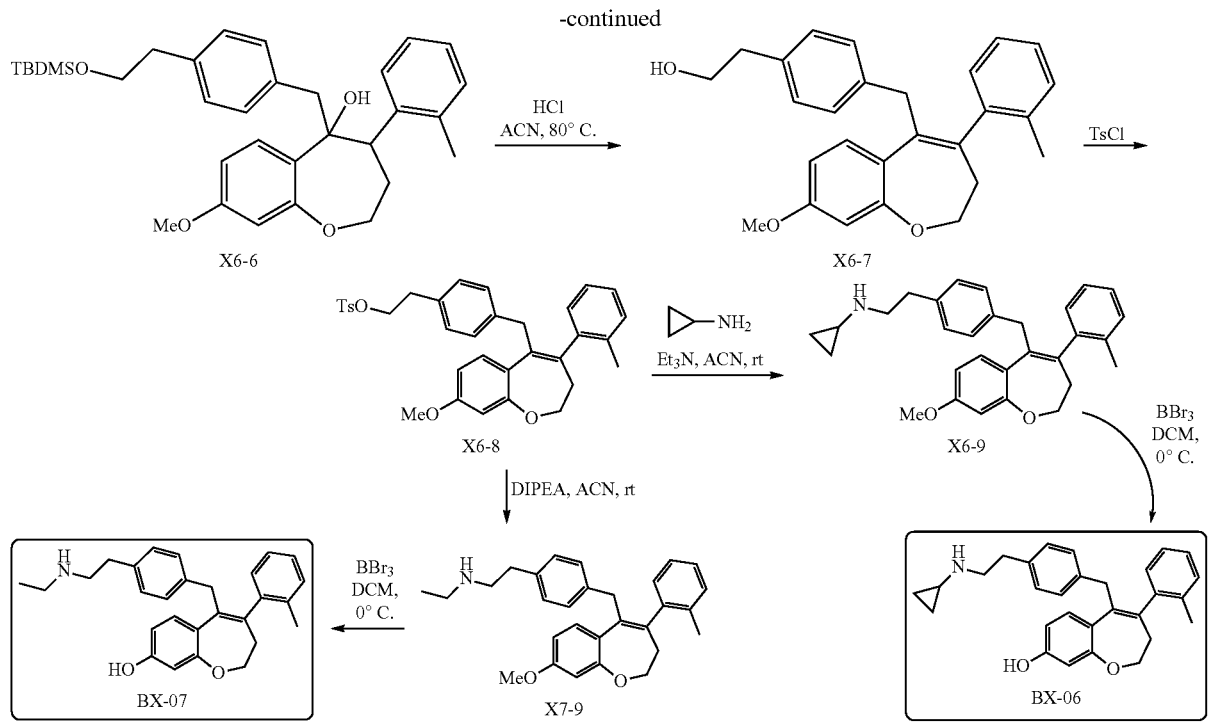

-continued

O-Alkylation of meta-methoxyphenol under basic conditions gave X6-2, which was de-esterified using LiOH and subsequently cyclized with Eaton's reagent to produce X6-4. Coupling of X6-4 with 2-bromotoluene in the presence of palladium acetate led to ketone X6-5, which was treated with a Grignard reagent formed from (4-(bromomethyl)phenethoxy)(tert-butyl)dimethylsilane to yield primary alcohol X6-7 after dehydration and loss of the protecting group with acid. After tosylation of the alcohol, tosylate was displaced with cyclopropylamine and demethoxylated to give BX-06 (Scheme XII). In similar fashion, tosylate X6-8 was reacted with ethylamine and demethoxylated with BBr3 to produce BX-07.

EXAMPLES

Materials: all chemicals were reagent grade and used without further purification. Chromatographic elution solvent systems are reported as volume:volume ratios. LC-MS data were obtained using a LC Thermo Finnigan Surveyor-MS Thermo Finnigan AQA in either positive mode or negative mode as described below:
LCMS-Condition 01: Method:—LCMS_X-Select (Formic Acid)
Column: X-Select CSH C18 (4.6*50) mm 2.5u, Mobile Phase: A.0.1% Formic acid in water B. 0.1% Formic acid in Acetonitrile, Inj Volume: 5.0 µL, Flow Rate: 1.0. mL/minute, Gradient program: 2% B to 98% B in 2.8 minute, Hold till 4.8 min, At 5.0 min B conc is 2% up to 7.0 min.
LCMS-Condition 02: Method:—LCMS_X-Bridge (NH$_3$)
Column: X-Bridge C18 (3.0*50) mm 2.5µ; Mobile Phase: A. 0.05% NH$_3$ in water; B. 0.05% NH$_3$ in Acetonitrile, Inj Volume: 0.2 µL, Flow Rate: 1.0 mL/minute; Gradient program: 1% B to 90% B in 1.5 minute, 100% B in 2.5 minute, Hold till 2.8 minute, At 3.0 minute B conc is 1% up to 4.0 min.

LCMS-Condition 03: Method:—LCMS_X-Select (Ammonium Bicarbonate)
Column: X-Select CSH C18 (3.0*50) mm 2.5u; Mobile Phase: A: 5 mM Ammonium Bicarbonate) in water; B: Acetonitrile; Inj Volume: 2 µL, Flow Rate: 1.2 mL/minute; Column oven temp. 50° C.; Gradient program: 0% B to 98% B in 2.0 minute, hold till 3.0 min, at 3.2 min B conc is 0% up to 4.0 min.

1-(4-(2-(Ethylamino)ethyl)benzyl)-2-(4-methoxyphenyl)-3-methyl-1H-indol-5-ol (D-01)

To 1-(4-methoxyphenyl)propan-1-one 1-1 (5 g, 30.45 mmol) in diethyl ether (50 mL) was added bromine (1.72 mL, 33.49 mmol) drop wise at 0° C. and stirred at room temperature for 2 h. After completion of the reaction, the reaction mixture was quenched with saturated Na2S2O3 solution and extracted with diethyl ether (3×). The combined organic layer was dried over anhydrous Na$_2$SO$_4$, filtered and concentrated under reduced pressure. The crude compound was purified by silica gel column chromatography eluting with 0-40% ethyl acetate in n-hexane to afford 4.5 g (61% yield) of compound 1-2 as off white solid.
LCMS-Condition 01: [M+H]$^+$=242.90; Rt=3.08 min
$^1$H NMR (400 MHz, DMSO-d$_6$) δ: 8.03 (d, J=8.80 Hz, 2H), 7.07 (d, J=8.80 Hz, 2H), 5.78 (q, J=6.36 Hz, 1H), 3.86 (s, 3H), 1.76 (d, J=6.36 Hz, 3H).
To 2-bromo-1-(4-methoxyphenyl)propan-1-one 1-2 (3 g, 12.34 mmol) in DMF (30 mL) was added 4-(benzyloxy) aniline (3.68 g, 18.51 mmol) at room temperature and degassed with argon for 15 min. The reaction mixture was then heated at 150° C. for 3 h. After completion of the reaction, the reaction mixture was cooled to room temperature, quenched with water and extracted with ethyl acetate (3×). Combined organic layer was dried over anhydrous Na$_2$SO$_4$, filtered and concentrated under reduced pressure. The crude compound was purified by silica gel column chromatography eluting with 0-20% ethyl acetate in n-hexane to afford 2.60 g (61% yield) of compound 1-4 as off white solid.

LCMS-Condition 01: [M+H]$^+$=343.05; Rt=3.65 min $^1$H NMR (400 MHz, DMSO-d$_6$) δ: 10.88 (s, 1H), 7.57 (d, J=8.31 Hz, 2H), 7.49 (d, J=7.34 Hz, 2H), 7.37-7.42 (m, 3H), 7.22 (d, J=8.80 Hz, 1H), 7.04-7.09 (m, 4H), 5.12 (s, 2H), 3.81 (s, 3H), 2.33 (s, 3H).

To 5-(benzyloxy)-2-(4-methoxyphenyl)-3-methyl-1H-indole 1-4 (1.50 g, 4.367 mmol) in DMF (15 mL) at 0° C. was added sodium hydride (60% dispersion in oil, 524 mg, 13.10 mmol) portion wise and stirred for 30 min. To the resulting solution at 0° C. was added 2-(4-(bromomethyl)phenyl)-N-ethylacetamide (1.23 g, 4.803 mmol). The reaction mixture was further stirred at room temperature for 18 h. After completion of the reaction, the reaction mixture was quenched with ice cold water, extracted with ethyl acetate (3×). Combined organic layer was dried over anhydrous Na$_2$SO$_4$, filtered and concentrated under reduced pressure. The crude compound was purified by silica gel column chromatography eluting with 0-40% ethyl acetate in n-hexane to afford 1.3 g (57% yield) of compound 1-5 as off white solid.

LCMS-Condition 01: [M+H]$^+$=519.30; Rt=3.28/3.66 min $^1$H NMR (400 MHz, DMSO-d$_6$) δ: 8.17 (d, J=8.80 Hz, 1H), 7.85 (t, J=5.14 Hz, 1H), 7.46-7.53 (m, 2H), 7.39-7.44 (m, 2H), 7.37 (d, J=5.38 Hz, 1H), 7.31 (d, J=8.31 Hz, 1H), 7.25-7.27 (m, 1H), 7.05-7.10 (m, 2H), 6.88 (dd, J=2.45, 8.80 Hz, 1H), 6.80 (dd, J=2.45, 8.80 Hz, 1H), 6.76 (d, J=7.83 Hz, 1H), 6.72 (d, J=8.31 Hz, 1H), 6.36 (d, J=7.83 Hz, 1H), 5.16-5.21 (m, 2H), 5.12 (s, 2H), 3.86 (s, 3H), 3.79 (s, 2H), 2.95-3.03 (m, 2H), 2.49 (s, 3H), 0.91-1.00 (m, 3H).

To 2-(4-((5-(benzyloxy)-2-(4-methoxyphenyl)-3-methyl-1H-indol-1-yl)methyl)phenyl)-N-ethylacetamide 1-5 (400 mg, 0.771 mmol) in THF (20 mL) at 0° C. was added lithium aluminium hydride (292 mg, 7.712 mmol) portion wise. The reaction mixture was further heated to 70° C. for 24 h. After completion of the reaction, the reaction mixture was cooled to room temperature, quenched with saturated Na$_2$SO$_4$ solution and extracted with ethyl acetate (3×). Combined organic layer was dried over anhydrous Na$_2$SO$_4$, filtered and concentrated under reduced pressure. The crude compound was purified by preparative HPLC purification to afford 16 mg (5% yield) of D-01 as off white solid.

LCMS-Condition 01: [M+H]$^+$=415.05; Rt=2.17 min $^1$H NMR (400 MHz, CD$_3$OD) δ: 8.44 (br. s, 1H), 7.97 (t, J=9.54 Hz, 1H), 7.13 (d, J=8.80 Hz, 2H), 6.99 (d, J=7.83 Hz, 2H), 6.87 (d, J=8.80 Hz, 3H), 6.81 (d, J=1.96 Hz, 1H), 6.73 (d, J=7.83 Hz, 2H), 6.53 (dd, J=2.45, 8.80 Hz, 1H), 5.07 (s, 2H), 3.72 (s, 3H), 2.94-3.00 (m, 2H), 2.84 (q, J=7.17 Hz, 2H), 2.72-2.78 (m, 2H), 2.07 (s, 3H), 1.13 (t, J=7.34 Hz, 3H).

1-(4-(2-(Cyclopropylamino)ethyl)benzyl)-2-(4-methoxyphenyl)-3-methyl-1H-indol-5-ol (D-02)

To a solution of 5-(benzyloxy)-1-(4-(2-iodoethyl)benzyl)-2-(4-methoxyphenyl)-3-methyl-1H-indole 3-7 (70 mg, 0.119 mmol) and cyclopropanamine (20 mg, 0.357 mmol) in DMF (5 mL) was added triethylamine (0.05 mL, 0.357 mmol) at room temperature and stirred for 16 h. After completion of the reaction, the reaction mixture was quenched with water and extracted with ethyl acetate (3×). Combined organic layer was dried over anhydrous Na2SO$_4$, filtered and concentrated under reduced pressure to afford 70 mg (crude) of compound 2-2 as light brown solid, which was used as such in the next step without further purification.

LCMS-Condition 01: [M+H]$^+$=517.25; Rt=1.85 min

To a solution of N-(4-((5-(benzyloxy)-2-(4-methoxyphenyl)-3-methyl-1H-indol-1-yl)methyl)phenethyl)cyclopropanamine 2-2 (70 mg, 0.135 mmol) in toluene (1 mL) was added trifluoroacetic acid (0.1 mL) at room temperature. The reaction mixture was then heated at 90° C. for 16 h. After completion of the reaction, the reaction mixture was quenched with saturated NaHCO$_3$ solution and extracted with DCM (3×). Combined organic layer was dried over anhydrous Na$_2$SO$_4$, filtered and concentrated under reduced pressure. The crude compound was purified by preparative HPLC column chromatography to afford 6 mg (10% yield) of D-02 as off white solid.

LCMS-Condition 01: [M+H]$^+$=427.05; Rt=1.40 min $^1$H NMR (400 MHz, CDCl$_3$) δ: 7.24 (d, J=8.80 Hz, 2H), 7.06 (d, J=8.31 Hz, 2H), 6.98-7.01 (m, 2H), 6.93 (d, J=8.80 Hz, 2H), 6.87 (d, J=8.31 Hz, 2H), 6.70 (dd, J=2.45, 8.80 Hz, 1H), 5.14 (s, 2H), 3.84 (s, 3H), 2.90-2.96 (m, 2H), 2.73-2.80 (m, 2H), 2.22 (s, 3H), 2.10-2.18 (m, 1H), 0.43-0.47 (m, 2H), 0.38-0.43 (m, 2H).

1-(4-(2-((Cyclopropylmethyl)amino)ethyl)benzyl)-2-(4-methoxyphenyl)-3-methyl-1H-indol-5-ol (D-03)

To 2-(4-(bromomethyl)phenyl)acetic acid (20 g, 87.30 mmol) in THF (200 mL) at 0° C. was added borane-dimethyl sulfide (12.4 mL, 130.96 mmol) drop wise. The reaction mixture was stirred at room temperature for 3 h. After completion of the reaction, the reaction mixture was cooled to 0° C. and quenched with dropwise addition of methanol. The resulting reaction mixture was concentrated under reduced pressure and the solid obtained was filtered and washed with n-hexane to afford 14 g of compound 3-2 as off white solid which was used as such in the next step without further purification.

$^1$H NMR (400 MHz, CDCl$_3$) δ: 7.35 (d, J=7.83 Hz, 2H), 7.21 (d, J=7.83 Hz, 2H), 4.49 (s, 2H), 3.86 (t, J=6.36 Hz, 2H), 2.87 (t, J=6.60 Hz, 2H)

To 2-(4-(bromomethyl)phenyl)ethan-1-ol 3-2 (1 g, 4.649 mmol) in DCM (15 mL) at 0° C. was added imidazole (0.77 mL, 13.94 mmol) and stirred for 15 min. To the resulting solution was added tert-butyldimethylsilyl chloride (840 mg, 5.579 mmol) at the same temperature. The reaction mixture was then stirred at room temperature for 16 h. After completion of the reaction, the reaction mixture was quenched with water and extracted with DCM (3×). Combined organic layer dried over anhydrous Na$_2$SO$_4$, filtered and concentrated under reduced pressure. The crude compound was purified by silica gel column chromatography eluting with 0-30% ethyl acetate in n-hexane to afford 1.2 g (78% yield) of compound 3-3 as colourless oil.

$^1$H NMR (400 MHz, CDCl$_3$) δ: 7.32 (d, J=7.82 Hz, 2H), 7.20 (d, J=7.82 Hz, 2H), 4.51 (s, 2H), 3.81 (t, J=7.09 Hz, 2H), 2.83 (t, J=7.09 Hz, 2H), 0.88 (s, 9H), 0.02 (s, 6H).

To 5-(benzyloxy)-2-(4-methoxyphenyl)-3-methyl-1H-indole 3-4 (470 mg, 1.368 mmol) in DMF (5 mL) at 0° C. was added sodium hydride (60% dispersion in oil, 109 mg, 2.737 mmol) portion wise and stirred for 30 min. To the resulting solution was added (4-(bromomethyl)phenethoxy)(tert-butyl)dimethylsilane 3 (584 mg, 1.779 mmol) at the same temperature. The reaction mixture was further stirred at room temperature for 3 h. After completion of the reaction, the reaction mixture was quenched with ice cold water and extracted with ethyl acetate (3×). The combined organic layer was dried over anhydrous Na2SO$_4$, filtered and concentrated under reduced pressure. The crude compound was purified by silica gel column chromatography eluting with 0-30% ethyl acetate in n-hexane to afford 660 mg (81% yield) of 3-5 as brown liquid.

LCMS-Condition 01: [M+H]$^+$=592.30; Rt=2.86 min

To 5-(benzyloxy)-1-(4-(2-((tert-butyldimethylsilyl)oxy)ethyl)benzyl)-2-(4-methoxyphenyl)-3-methyl-1H-indole 3-5 (650 mg, 1.098 mmol) in THF (5 mL) was added 1M solution of tetrabutylammonium fluoride in THF (1.3 mL, 1.317 mmol) drop wise at room temperature and stirred for 1 h. After completion of the reaction, the reaction mixture was quenched with saturated NaHCO$_3$ solution and extracted with ethyl acetate. Combined organic layer was dried over anhydrous Na$_2$SO$_4$, filtered and concentrated under reduced pressure. The crude compound was purified by silica gel column chromatography eluting with 0-40% ethyl acetate in n-hexane to afford 425 mg (81% yield) of compound 3-6 as off white solid.

LCMS-Condition 01: [M+H]$^+$=478.15; Rt=2.32 min $^1$H NMR (400 MHz, CDCl$_3$) δ: 7.49 (d, J=7.34 Hz, 2H), 7.39 (t, J=7.58 Hz, 2H), 7.32 (d, J=7.34 Hz, 1H), 7.22-7.25 (m, 3H), 7.15 (d, J=1.96 Hz, 1H), 7.08 (d, J=7.83 Hz, 2H), 7.04 (d, J=8.80 Hz, 1H), 6.92-6.96 (m, 2H), 6.90 (d, J=8.31 Hz, 2H), 5.16 (s, 2H), 5.13 (s, 2H), 3.84 (s, 3H), 3.79-3.83 (m, 2H), 2.80 (t, J=6.36 Hz, 2H), 2.25 (s, 3H).

To a solution of triphenylphosphine (1.15 g, 4.396 mmol) in DCM (30 mL) at 0° C. was added imidazole (300 mg, 4.396 mmol) and iodine (1.11 g, 4.396 mmol). The reaction mixture was allowed to attain room temperature and stirred for 1 h. To the resulting solution was added 2-(4-((5-(benzyloxy)-2-(4-methoxyphenyl)-3-methyl-1H-indol-1-yl)methyl)phenyl)ethan-1-ol 3-6 (420 mg, 0.879 mmol) and stirred at room temperature for 16 h. After completion of the reaction, the reaction mixture was quenched with water and extracted with DCM (3×). Combined organic layer was dried over anhydrous Na$_2$SO$_4$, filtered and concentrated under reduced pressure. The crude compound was purified by silica gel column chromatography eluting with 0-20% ethyl acetate in n-hexane to afford 425 mg (82% yield) of compound 3-7 as off white solid.

LCMS-Condition 01: [M+H]$^+$=588.05; Rt=2.55 min $^1$H NMR (400 MHz, CDCl$_3$) δ: 7.49 (d, J=7.83 Hz, 2H), 7.39 (t, J=7.34 Hz, 2H), 7.29-7.34 (m, 1H), 7.22 (d, J=8.80 Hz, 2H), 7.14 (d, J=2.45 Hz, 1H), 7.02-7.06 (m, 3H), 6.85-6.95 (m, 5H), 5.14 (br. s, 2H), 5.13 (br. s, 2H), 3.84 (s, 3H), 3.26-3.32 (m, 2H), 3.06-3.14 (m, 2H), 2.24 (s, 3H).

To a solution of 5-(benzyloxy)-1-(4-(2-iodoethyl)benzyl)-2-(4-methoxyphenyl)-3-methyl-1H-indole 3-7 (200 mg, 0.340 mmol) and cyclopropylmethanamine (72 mg, 1.021 mmol) in DMF (5 mL) was added triethylamine (0.14 mL, 1.021 mmol) at room temperature and stirred for 16 h. After completion of the reaction, the reaction mixture was quenched with water and extracted with ethyl acetate (3×). The combined organic layer was dried over anhydrous Na$_2$SO$_4$, filtered and concentrated under reduced pressure. The crude compound was purified by silica gel column chromatography eluting with 0-5% methanol in DCM to afford 80 mg (44% yield) of compound 3-8 as light brown solid.

LCMS-Condition 01: [M+H]$^+$=531.30; Rt=1.85 min $^1$H NMR (400 MHz, CDCl$_3$) δ: 7.48 (d, J=7.34 Hz, 2H), 7.38-7.41 (m, 1H), 7.36 (d, J=4.40 Hz, 1H), 7.30-7.34 (m, 1H), 7.22 (d, J=8.80 Hz, 2H), 7.14 (d, J=2.45 Hz, 1H), 7.07 (d, J=7.83 Hz, 2H), 7.02 (d, J=8.31 Hz, 1H), 6.92 (d, J=8.80 Hz, 2H), 6.87 (d, J=8.31 Hz, 3H), 5.13 (s, 2H), 5.12 (s, 2H), 3.81 (s, 3H), 3.18 (br. s, 4H), 2.75 (d, J=7.34 Hz, 2H), 2.24 (s, 3H), 1.14-1.21 (m, 1H), 0.57-0.64 (m, 2H), 0.32-0.39 (m, 2H).

To 2-(4-((5-(benzyloxy)-2-(4-methoxyphenyl)-3-methyl-1H-indol-1-yl)methyl)phenyl)-N-(cyclopropylmethyl)ethan-1-amine 3-8 (100 mg, 0.188 mmol) in toluene (1 mL) was added trifluoroacetic acid (0.1 mL) at room temperature. The reaction mixture was heated at 90° C. for 16 h. After completion of the reaction, the reaction mixture was quenched with saturated NaHCO$_3$ solution and extracted with DCM (3×). The combined organic layer was dried over anhydrous Na$_2$SO$_4$, filtered and concentrated under reduced pressure. The crude compound was purified by preparative HPLC column chromatography to afford 8 mg (9% yield) of D-03 as off white solid.

LCMS-Condition 01: [M+H]$^+$=441.25; Rt=1.48 min $^1$H NMR (400 MHz, CDCl$_3$) δ: 8.58 (s, 1H), 7.21 (d, J=8.31 Hz, 2H), 6.99 (d, J=1.96 Hz, 1H), 6.89-6.95 (m, 4H), 6.87 (d, J=8.31 Hz, 1H), 6.82 (d, J=7.83 Hz, 2H), 6.68 (d, J=6.85 Hz, 1H), 5.07 (s, 2H), 3.82 (s, 3H), 2.99-3.06 (m, 2H), 2.85-2.92 (m, 2H), 2.70 (d, J=7.34 Hz, 2H), 2.21 (s, 3H), 0.79-0.90 (m, 1H), 0.56 (d, J=7.34 Hz, 2H), 0.25 (d, J=4.40 Hz, 2H).

1-(4-(2-(Isopropylamino)ethyl)benzyl)-2-(4-methoxyphenyl)-3-methyl-1H-indol-5-ol (D-08)

To a solution of 5-(benzyloxy)-1-(4-(2-iodoethyl)benzyl)-2-(4-methoxyphenyl)-3-methyl-1H-indole 3-7 (300 mg, 0.510 mmol) and propan-2-amine (90 mg, 1.531 mmol) in DMF (3 mL) was added triethylamine (0.21 mL, 1.531 mmol) at room temperature. The reaction mixture was stirred at room temperature for 16 h. After completion of the reaction, the reaction mixture was quenched with water and extracted with ethyl acetate (3×). The combined organic layer was dried over anhydrous Na$_2$SO$_4$, filtered and concentrated under reduced pressure. The resulting crude compound was purified by silica gel column chromatography eluting with 0-5% methanol in DCM to afford 145 mg (55% yield) of compound 8-2 as light brown solid.

LCMS-Condition 01: [M+H]$^+$=519.25; Rt=1.77 min $^1$H NMR (400 MHz, CDCl$_3$) δ: 7.48 (d, J=7.34 Hz, 2H), 7.38 (t, J=7.34 Hz, 2H), 7.28-7.34 (m, 1H), 7.23 (d, J=8.80 Hz, 2H), 7.14 (d, J=2.45 Hz, 1H), 7.07 (d, J=7.82 Hz, 2H), 7.03 (d, J=8.80 Hz, 1H), 6.93 (d, J=8.80 Hz, 2H), 6.87 (d, J=7.82 Hz, 3H), 5.13 (br. s, 2H), 5.12 (s, 2H), 3.83 (s, 3H), 3.00-3.05 (m, 1H), 2.87-2.99 (m, 4H), 2.24 (s, 3H), 1.22 (d, J=6.36 Hz, 6H).

To N-(4-((5-(benzyloxy)-2-(4-methoxyphenyl)-3-methyl-1H-indol-1-yl)methyl)phenethyl)propan-2-amine 8-2 (30 mg, 0.057 mmol) in THF:EtOAc (1:1) was added palladium hydroxide (5 mg) at room temperature. The reaction mixture was stirred under hydrogen atmosphere at room temperature for 16 h. After completion of the reaction, the reaction mixture was filtered through pad of Celite™ and the filtrate was concentrated under reduced pressure. The resulting crude compound was purified by preparative HPLC to afford 6 mg (40% yield) of D-08 as off white solid.

LCMS-Condition-1: [M+H]$^+$=429.30; Rt=1.45 min $^1$H NMR (400 MHz, CDCl$_3$) δ: 8.64 (br. s, 1H), 7.21 (d, J=8.31 Hz, 2H), 7.00 (br. s, 1H), 6.90 (d, J=8.31 Hz, 4H), 6.85 (d, J=8.80 Hz, 2H), 6.80 (d, J=7.34 Hz, 2H), 6.69 (d, J=7.82 Hz, 1H), 5.05 (s, 2H), 3.82 (s, 3H), 2.83-3.23 (m, 6H), 2.20 (s, 3H), 1.09-1.18 (m, 6H).

1-(4-(2-(Cyclohexylamino)ethyl)benzyl)-2-(4-methoxyphenyl)-3-methyl-1H-indol-5-ol (D-09)

To a solution of 5-(benzyloxy)-1-(4-(2-iodoethyl)benzyl)-2-(4-methoxyphenyl)-3-methyl-1H-indole 3-7 (150 mg, 0.255 mmol) and cyclohexanamine (76 mg, 0.765 mmol) in DMF (3 mL) was added triethylamine (0.10 mL, 0.765 mmol) at room temperature. The reaction mixture was stirred at room temperature for 16 h. After completion of the reaction, the reaction mixture was quenched with water, extracted with ethyl acetate (3×). The combined organic layer was dried over anhydrous $Na_2SO_4$, filtered and concentrated under reduced pressure. The resulting crude compound was purified by silica gel column chromatography eluting with 0-5% methanol in DCM to afford 105 mg (74% yield) of compound 9-2 as light brown solid.

LCMS-Condition 01: $[M+H]^+$=559.35; Rt=1.86 min

To a solution of N-(4-((5-(benzyloxy)-2-(4-methoxyphenyl)-3-methyl-1H-indol-1-yl)methyl)phenethyl)cyclohexanamine 9-2 (100 mg, 0.178 mmol) in EtOAc (20 mL) was added palladium hydroxide (10 mg) at room temperature. The reaction mixture was stirred under hydrogen atmosphere at room temperature for 16 h. After completion of the reaction, the reaction mixture was filtered through a pad of Celite™, filtrate was concentrated. The resulting crude compound was purified by prep HPLC column chromatography to afford 50 mg (60% yield) of the title compound D-09 as off white solid.

LCMS-Condition 01: $[M+H]^+$=469.20; Rt=1.55 min $^1$H NMR (400 MHz, DMSO-$d_6$) δ: 8.72 (s, 1H), 7.29 (d, J=7.82 Hz, 2H), 7.00-7.08 (m, 4H), 6.82 (s, 1H), 6.76 (d, J=7.82 Hz, 2H), 6.58 (d, J=7.82 Hz, 1H), 5.16 (s, 2H), 3.79 (s, 3H), 2.62-2.86 (m, 6H), 2.12 (s, 3H), 1.78-1.87 (m, 2H), 1.65 (d, J=11.74 Hz, 2H), 1.54 (d, J=9.29 Hz, 2H), 1.02-1.20 (m, 4H).

2-(4-Methoxyphenyl)-3-methyl-1-(4-(2-((2,2,2-trifluoroethyl)amino)ethyl)benzyl)-1H-indol-5-ol (D-12)

To 5-(benzyloxy)-2-(4-methoxyphenyl)-3-methyl-1H-indole 3-4 (1.5 g, 4.373 mmol) in DMF (10 mL) at 0° C. was added 60% dispersion of sodium hydride in oil (420 mg, 17.49 mmol) portion wise and stirred at the same temperature for 30 min. To the resulting solution was added 2-(4-(bromomethyl)phenyl)-N-(2,2,2-trifluoroethyl)acetamide (1.62 g, 52.47 mmol) in DMF and stirred at room temperature for 16 h. After completion of the reaction, the reaction mixture was quenched with ice cold water and extracted with ethyl acetate (3×). Combined organic layer was dried over anhydrous $Na_2SO_4$, filtered and concentrated under reduced pressure. The resulting crude compound was purified by silica gel column chromatography eluting with 0-10% methanol in DCM to afford 510 mg (20% yield) of the compound 12-5 as brown oil.

$^1$H NMR (400 MHz, DMSO-$d_6$) δ: 8.66 (t, J=5.87 Hz, 1H), 7.44-7.49 (m, 2H), 7.38 (t, J=7.58 Hz, 2H), 7.27-7.34 (m, 3H), 7.11-7.18 (m, 2H), 7.04 (dd, J=8.07, 14.92 Hz, 4H), 6.73-6.81 (m, 3H), 5.19 (s, 2H), 5.11 (s, 2H), 3.82-3.90 (m, 2H), 3.78 (s, 3H), 3.39 (s, 2H), 2.16 (s, 3H).

To 2-(4-((5-(benzyloxy)-2-(4-methoxyphenyl)-3-methyl-1H-indol-1-yl)methyl)phenyl)-N-(2,2,2-trifluoroethyl)acetamide 12-5 (250 mg, 437.1 mmol) in ethyl acetate (40 mL) was added 20% palladium hydroxide on carbon (100 mg, 50% moisture) at room temperature. The reaction mixture was stirred under hydrogen atmosphere for 16 h. After completion of the reaction, the reaction mixture was filtered through a pad of Celite™ and washed with ethyl acetate. The filtrate was concentrated under reduced pressure and the crude compound was purified by preparative HPLC to afford 210 mg (99% yield) of compound 12-6 as off white sticky solid.

LCMS-Condition-1: $[M+H]^+$=483.10; Rt=2.01 min $^1$H NMR (400 MHz, DMSO-$d_6$) δ: 8.72 (s, 1H), 7.29 (d, J=8.31 Hz, 2H), 7.01-7.09 (m, 5H), 6.82 (d, J=1.96 Hz, 1H), 6.77 (d, J=8.31 Hz, 2H), 6.58 (dd, J=1.96, 8.80 Hz, 1H), 5.16 (s, 2H), 3.82-3.89 (m, 2H), 3.79 (s, 3H), 3.40 (s, 2H), 2.12 (s, 3H).

To 2-(4-((5-hydroxy-2-(4-methoxyphenyl)-3-methyl-1H-indol-1-yl)methyl)phenyl)-N-(2,2,2-trifluoroethyl)acetamide 12-6 (195 mg, 403.7 mmol) in THF (30 mL) at 0° C. was added lithium aluminium hydride (46 mg, 1211.1 mmol) portion wise. The reaction mixture was then heated at 70° C. for 16 h. After completion of the reaction, the reaction mixture was cooled and quenched with saturated $Na_2SO_4$ solution, filtered through a pad of Celite™ and washed with ethyl acetate. The separated organic layer was dried over anhydrous $Na_2SO_4$, filtered and concentrated under reduced pressure. The crude compound was purified by preparative HPLC purification to afford 13 mg (7% yield) of D-12 as pale yellow solid.

LCMS-Condition-1: $[M+H]^+$=469.20; Rt=1.80 min $^1$H NMR (400 MHz, DMSO-$d_6$) δ: 8.70 (s, 1H), 7.27 (d, J=8.80 Hz, 2H), 6.99-7.07 (m, 5H), 6.79-6.82 (m, 1H), 6.70-6.76 (m, 2H), 6.57 (dd, J=2.20, 8.56 Hz, 1H), 5.14 (s, 2H), 3.78 (s, 3H), 3.13-3.23 (m, 2H), 2.70-2.74 (m, 2H), 2.56-2.61 (m, 2H), 2.11 (s, 3H).

1-(4-(2-(Cyclopropylamino)ethyl)benzyl)-3-fluoro-2-(4-methoxyphenyl)-1H-indol-5-ol (D-15)

To 5-(benzyloxy)-2-(4-methoxyphenyl)-1H-indole 3-4 (1.78 g, 5.410 mmol) in dry Acetonitrile:DMSO (3:2; 20 mL) at −10° C. was added selectfluor (1.53 g, 4.328 mmol) under argon atmosphere. The reaction mixture was further stirred at 0° C. for 2 h. After completion of the reaction, the reaction mixture was concentrated under reduced pressure, the residue was dissolved in ethyl acetate (100 mL) and washed with water (40 mL) followed by brine (30 mL). The separated organic layer was dried over anhydrous $Na_2SO_4$, filtered and concentrated under reduced pressure. The resulting crude compound was purified by silica gel column chromatography eluting with 0-20% ethyl acetate in n-hexane to afford 402 mg (21% yield) of compound 15-5 as off white solid.

LCMS-Condition 01: $[M+18]f$=366.10; Rt=2.24 min $^1$H NMR (400 MHz, DMSO-$d_6$) δ: 11.07 (s, 1H), 7.71-7.75 (m, 2H), 7.47 (d, J=6.85 Hz, 2H), 7.39 (t, J=7.34 Hz, 2H), 7.30-7.33 (m, 1H), 7.25 (dd, J=2.45, 8.80 Hz, 1H), 7.07 (d, J=8.80 Hz, 2H), 7.04 (d, J=2.45 Hz, 1H), 6.84 (dd, J=2.45, 8.80 Hz, 1H), 5.12 (s, 2H), 3.80 (s, 3H).

To 5-(benzyloxy)-3-fluoro-2-(4-methoxyphenyl)-1H-indole 15-5 (590 mg, 1.705 mmol) in DMF (10 mL) at 0° C. was added sodium hydride (60% dispersion in oil, 203 mg, 5.115 mmol) portion wise. The reaction mixture was further stirred at 0° C. for 30 min. To the resulting solution was added (4-(bromomethyl)phenethoxy)(tert-butyl)dimethylsilane (671 mg, 2.046 mmol). The reaction mixture was stirred at room temperature for 18 h. After completion of the reaction, the reaction mixture was quenched with ice cold water and extracted with ethyl acetate (3×). The combined organic layer was dried over anhydrous Na2SO4, filtered and concentrated under reduced pressure. The resulting crude compound was purified by silica gel column chromatography eluting with 0-80% ethyl acetate in n-hexane to afford 405 mg (49% yield) of compound 15-6 as brownish solid.

LCMS-Condition 01: $[M-18]^+$=464.25; Rt=2.34 min $^1$H NMR (400 MHz, DMSO-$d_6$) δ: 7.52-7.56 (m, 2H), 7.44-7.51 (m, 4H), 7.37-7.42 (m, 2H), 7.19 (d, J=2.45 Hz, 1H), 7.14 (t, J=8.07 Hz, 4H), 6.95 (dd, J=2.45, 8.80 Hz, 1H), 6.84 (d, J=8.31 Hz, 2H), 5.36 (s, 2H), 5.21 (s, 2H), 4.64 (t, J=5.38 Hz, 1H), 3.87 (s, 3H), 3.55-3.61 (m, 2H), 2.69 (t, J=6.85 Hz, 2H).

To 2-(4-((5-(benzyloxy)-3-fluoro-2-(4-methoxyphenyl)-1H-indol-1-yl)methyl)phenyl)ethan-1-ol 15-6 (405 mg, 0.842 mmol) in $CH_2Cl_2$ (10 mL) at 0° C. was added triethylamine (0.35 mL, 2.526 mmol) followed by p-TsCl (241 mg, 1.263 mmol). The reaction mixture was stirred at room temperature for 18 h. After completion of the reaction, the reaction mixture was diluted with $CH_2Cl_2$ (100 mL) and washed with water (30 mL) and brine (30 mL). The combined organic layer was dried over anhydrous $Na_2SO_4$, filtered and concentrated under reduced pressure to afford 365 mg (68% yield) of compound 15-7 as brown solid.

LCMS-Condition 01: [M+H]$^+$=636.35; Rt=2.54 min $^1$H NMR (400 MHz, DMSO-d$_6$) δ: 7.63 (d, J=7.83 Hz, 2H), 7.51 (d, J=7.34 Hz, 2H), 7.40-7.47 (m, 4H), 7.31-7.39 (m, 4H), 7.18 (d, J=2.45 Hz, 1H), 7.11 (d, J=8.31 Hz, 2H), 7.02 (d, J=8.31 Hz, 2H), 6.93 (dd, J=2.20, 9.05 Hz, 1H), 6.79 (d, J=7.83 Hz, 2H), 5.33 (s, 2H), 5.18 (s, 2H), 4.18 (t, J=6.36 Hz, 2H), 3.83 (s, 3H), 2.82 (t, J=6.36 Hz, 2H), 2.39 (s, 3H).

To 4-((5-(benzyloxy)-3-fluoro-2-(4-methoxyphenyl)-1H-indol-1-yl)methyl)phenethyl 4-methylbenzenesulfonate 15-7 (170 mg, 0.267 mmol) in acetonitrile (5 mL) was added DIPEA (0.81 mL, 1.072 mmol) and cyclopropyl amine (mL, 2.670 mmol) in a sealed tube. The reaction mixture was stirred at room temperature for 24 h. After completion of the reaction, the reaction mixture was concentrated under reduced pressure, washed with n-hexane (2×10 mL) and decanted followed by drying to afford to afford 135 mg (96% yield) of compound 15-8 as white solid.

LCMS-Condition 01: [M+H]$^+$=521.31; Rt=1.74 min $^1$H NMR (400 MHz, DMSO-d$_6$) δ: 7.47 (d, J=6.85 Hz, 2H), 7.36-7.44 (m, 5H), 7.33 (d, J=7.34 Hz, 2H), 7.10-7.14 (m, 1H), 7.05 (t, J=8.80 Hz, 4H), 6.88 (d, J=8.80 Hz, 1H), 6.77 (d, J=7.34 Hz, 2H), 5.28 (br. s, 2H), 5.14 (s, 2H), 3.80 (s, 3H), 2.67-2.73 (m, 2H), 2.54-2.62 (m, 2H), 2.03 (d, J=2.93 Hz, 1H), 0.31 (d, J=5.87 Hz, 2H), 0.15 (d, J=1.96 Hz, 2H).

To N-(4-((5-(benzyloxy)-3-fluoro-2-(4-methoxyphenyl)-1H-indol-1-yl)methyl)phenethyl)cyclopropanamine 15-8 (140 mg, 0.269 mmol) in TFA (0.81 mL) at 0° C. was added methane sulphonic acid (0.13 mL, 2.002 mmol) and triethyl silane (0.41 mL, 2.566 mmol) under argon atmosphere. The reaction mixture was stirred at room temperature for 2 h under argon atmosphere. After completion of the reaction, the reaction mixture was concentrated under reduced pressure and diluted with ethyl acetate (50 mL). Organic layer was washed with saturated NaHCO$_3$ (15 mL) followed by brine (15 mL), dried over anhydrous Na$_2$SO$_4$, filtered and concentrated under reduced pressure. The crude material was purified by preparative HPLC to afford 18 mg (16% yield) of D-15 as white solid.

LCMS-Condition 01: [M+H]$^+$=431.20; Rt=1.46 min $^1$H NMR (400 MHz, DMSO-d$_6$) δ: 9.04 (s, 1H), 7.40 (d, J=8.31 Hz, 2H), 7.18-7.23 (m, 1H), 7.03-7.08 (m, 4H), 6.82 (d, J=1.96 Hz, 1H), 6.77 (d, J=7.82 Hz, 2H), 6.67 (dd, J=2.20, 9.05 Hz, 1H), 5.24 (s, 2H), 3.80 (s, 3H), 2.67-2.74 (m, 2H), 2.56-2.63 (m, 2H), 2.03 (tt, J=3.36, 6.66 Hz, 1H), 0.28-0.34 (m, 2H), 0.11-0.17 (m, 2H).

1-(4-(2-(Ethylamino)ethyl)benzyl)-3-fluoro-2-(4-methoxyphenyl)-1H-indol-5-ol (D-16)

To 4-((5-(benzyloxy)-3-fluoro-2-(4-methoxyphenyl)-1H-indol-1-yl)methyl)phenethyl-4-methylbenzenesulfonate 15-7 (175 mg, 0.276 mmol) in acetonitrile (10 mL) was added DIPEA (0.24 mL, 1.380 mmol) followed by 2N ethyl amine in THF (1.37 mL, 2.760 mmol) in a sealed tube. The reaction mixture was stirred at room temperature for 24 h. After completion of the reaction, the reaction mixture was concentrated under reduced pressure, washed with n-hexane (2×10 mL) and decanted followed by drying to afford to afford 135 mg (95% yield) of compound 16-8 as white solid.

LCMS-Condition 01: [M-18]$^+$=491.30; Rt=1.76 min $^1$H NMR (400 MHz, DMSO-d$_6$) δ: 7.54-7.58 (m, 3H), 7.46-7.53 (m, 4H), 7.39-7.43 (m, 2H), 7.17-7.23 (m, 4H), 7.15 (s, 1H), 6.97 (dd, J=2.20, 9.05 Hz, 1H), 6.91 (d, J=8.31 Hz, 2H), 5.40 (s, 2H), 5.22 (s, 2H), 3.89 (s, 3H), 3.03-3.09 (m, 2H), 2.93 (q, J=7.34 Hz, 2H), 2.81-2.87 (m, 2H), 1.20 (t, J=7.34 Hz, 3H).

To 2-(4-((5-(benzyloxy)-3-fluoro-2-(4-methoxyphenyl)-1H-indol-1-yl)methyl)phenyl)-N-ethylethan-1-amine 16-8 (145 mg, 0.285 mmol) in TFA (1 mL) at 0° C. was added methane sulphonic acid (0.18 mL, 2.772 mmol) and triethyl silane (0.48 mL, 3.005 mmol) under argon atmosphere. The reaction mixture was stirred at room temperature for 2 h under argon atmosphere. After completion of the reaction, the reaction mixture was concentrated under reduced pressure and diluted with ethyl acetate (50 mL). Organic layer was washed with saturated NaHCO$_3$ solution (15 mL) followed by brine (15 mL), dried over anhydrous Na$_2$SO$_4$, filtered and concentrated under reduced pressure. The crude compound was purified by preparative HPLC purification to afford 9 mg (7% yield) of D-16 as white solid.

LCMS-Condition 01: [M+H]$^+$=419.20; Rt=1.39 min $^1$H NMR (400 MHz, DMSO-d$_6$) δ: 9.06 (br. s, 1H), 7.41 (d, J=8.80 Hz, 2H), 7.20 (d, J=8.80 Hz, 1H), 7.06 (dd, J=2.69, 8.56 Hz, 4H), 6.82 (d, J=1.96 Hz, 1H), 6.78 (d, J=7.82 Hz, 2H), 6.67 (dd, J=1.96, 8.80 Hz, 1H), 5.24 (s, 2H), 3.80 (s, 3H), 2.59-2.73 (m, 5H), 2.56 (d, J=6.85 Hz, 2H), 0.99 (t, J=7.09 Hz, 3H). 3-Chloro-1-(4-(2-(ethylamino)ethyl)benzyl)-2-(4-methoxyphenyl)-1H-indol-5-ol (D-13)

To 5-hydroxy-2-nitrobenzaldehyde 13-1 (15 g, 89.82 mmol) in DMF (100 mL) at 0° C. was added potassium carbonate (18.6 g, 134.7 mmol) and benzyl bromide (12 mL, 98.80 mmol) under argon atmosphere. The reaction mixture was then heated at 80° C. for 3 h. After completion of the reaction, the reaction mixture was quenched with ice cold water and extracted with ethyl acetate (3×). Combined organic layer was dried over anhydrous Na$_2$SO$_4$, filtered and concentrated under reduced pressure. The resulting crude compound was purified by trituration in n-hexane to afford 22 g (95% yield) of compound 13-2 as off white solid.

LCMS-Condition 01: [M+H]$^+$=257.95; Rt=1.94 min

To 5-(benzyloxy)-2-nitrobenzaldehyde 13-2 (20 g, 77.82 mmol) in $CH_2Cl_2$ (200 mL) at 0° C. was added carbon tetrabromide (39 g, 116.7 mmol) and solution of triphenyl phosphine (60 g, 233.46 mmol) in dry $CH_2Cl_2$ (50 mL) drop wise. The reaction mixture was stirred at room temperature for 2 h. After completion of the reaction, the reaction mixture was filtered through a silica pad and washed with $CH_2Cl_2$. The filtrate was concentrated under reduced pressure and the crude intermediate was dissolved in ethanol (200 mL) and SnCl$_2$ (52 g, 233.46 mmol) was added to it at room temperature. The reaction mixture was then heated to 80° C. and stirred for 2.5 h. After completion of the reaction, the reaction mixture was diluted with ethyl acetate and quenched with solid potassium carbonate (100 g), stirred and filtered. The filtrate was washed with brine (600 mL), dried over anhydrous Na2SO$_4$, filtered and concentrated under reduced pressure. The resulting crude compound was purified by silica gel column chromatography eluting with 0-30% ethyl acetate in n-hexane to afford 14 g (48% yield) of compound 13-3 as deep brown liquid.

LCMS-Condition 01: [M+H]$^+$=383.95; Rt=2.13 min $^1$H NMR (400 MHz, DMSO-d$_6$) δ: 7.46-7.48 (m, 1H), 7.26-7.41 (m, 5H), 6.97 (d, J=2.45 Hz, 1H), 6.80 (dd, J=2.69, 8.56 Hz, 1H), 6.62 (d, J=8.80 Hz, 1H), 4.96 (s, 2H), 4.85 (s, 2H).

To 4-(benzyloxy)-2-(2,2-dibromovinyl)aniline 13-3 (14 g, 36.55 mmol) in toluene (100 mL) was added (4-methoxyphenyl)boronic acid (8.33 g, 54.83 mmol), K$_3$PO$_4$ (36.5 g, 182.7 mmol) simultaneously at room temperature under argon atmosphere and degassed for 10 min. The solution of Pd(OAc)$_2$ (1.5 g, 0.365 mmol) and S-Phos (2 g, 0.731 mmol) in toluene (50 mL) prepared in another flask was degassed with argon for 10 min and added to the above reaction mixture at room temperature under argon atmosphere. The reaction mixture was heated at 90° C. and stirred for 4 h. After completion of the reaction, the reaction mixture was diluted with water and extracted with ethyl acetate (3×). The combined organic layer was dried over anhydrous Na$_2$SO$_4$, filtered and concentrated under reduced pressure. The resulting crude compound was purified by silica gel column chromatography eluting with 0-30% ethyl acetate in n-hexane to afford 4.8 g (40% yield) of compound 13-4 as off white solid.

LCMS-Condition 01: [M+H]$^+$=330.00; Rt=2.19 min $^1$H NMR (400 MHz, DMSO-d$_6$) δ: 11.23 (s, 1H), 7.74 (d, J=8.80 Hz, 2H), 7.46 (d, J=7.34 Hz, 2H), 7.35-7.41 (m, 2H), 7.27-7.32 (m, 1H), 7.24 (d, J=8.80 Hz, 1H), 7.06 (d, J=2.45 Hz, 1H), 7.00 (d, J=8.80 Hz, 2H), 6.77 (dd, J=2.45, 8.80 Hz, 1H), 6.65 (d, J=1.5 Hz, 1H), 5.08 (s, 2H), 3.78 (s, 3H).

To 5-(benzyloxy)-2-(4-methoxyphenyl)-1H-indole 13-4 (1.75 g, 5.319 mmol) in CH$_2$Cl$_2$ (20 mL) at −10° C. was added N-chlorosuccinimide (568 mg, 4.255 mmol). The reaction mixture was then stirred at −10° C. for 1 h. After completion of the reaction, the reaction mixture was diluted with CH$_2$Cl$_2$ (50 mL), washed with aqueous sodium sulfite solution (20 mL), dried over anhydrous Na$_2$SO$_4$, filtered and concentrated under reduced pressure. The resulting crude compound was stirred in methanol (2 mL) for 10 min, filtered and dried to afford 825 mg (43% yield) of compound 13-5 as off white solid.

LCMS-Condition 01: [M+H]$^+$=363.95; Rt=2.30 min.

To 5-(benzyloxy)-3-chloro-2-(4-methoxyphenyl)-1H-indole 13-5 (820 mg, 2.525 mmol) in DMF (10 mL) at 0° C. was added sodium hydride (60% dispersion in oil, 320 mg, 6.756 mmol) portion wise. The reaction mixture was further stirred at 0° C. for 30 min. To the resulting solution was added (4-(bromomethyl)phenethoxy)(tert-butyl)dimethylsilane (960 mg, 2.929 mmol). The reaction mixture was stirred at room temperature for 18 h. After completion of the reaction, the reaction mixture was quenched with ice cold water and extracted with ethyl acetate (3×). Combined organic layer was dried over anhydrous Na2SO$_4$, filtered and concentrated under reduced pressure. The resulting crude compound was purified by silica gel column chromatography eluting with 0-80% ethyl acetate in n-hexane to afford 605 mg (54% yield) of compound 13-7 as off white sticky solid.

LCMS-Condition 01: [M+H]$^+$=498.10; Rt=2.32 min $^1$H NMR (400 MHz, DMSO-d$_6$) δ: 7.46-7.50 (m, 2H), 7.31-7.43 (m, 6H), 7.04-7.10 (m, 5H), 6.91 (dd, J=2.45, 8.80 Hz, 1H), 6.73-6.78 (m, 2H), 5.29 (s, 2H), 5.15 (s, 2H), 3.81 (s, 3H), 3.47-3.54 (m, 2H), 2.61 (t, J=7.09 Hz, 2H).

To 2-(4-((5-(benzyloxy)-3-chloro-2-(4-methoxyphenyl)-1H-indol-1-yl)methyl)phenyl)ethan-1-ol 13-7 (550 mg, 1.106 mmol) in CH$_2$Cl$_2$ (10 mL) at 0° C. was added triethylamine (0.46 mL, 3.319 mmol) followed by p-TsCl (318 mg, 1.660 mmol). The reaction mixture was stirred at room temperature for 18 h. After completion of the reaction, the reaction mixture was diluted with CH$_2$Cl$_2$ (100 mL) and washed with water (30 mL) and brine (30 mL). The combined organic layer was dried over anhydrous Na$_2$SO$_4$, filtered and concentrated under reduced pressure to afford 590 mg (81% yield) of compound 13-8 as off white solid.

LCMS-Condition 01: [M+H]$^+$=652.25; Rt=2.57 min $^1$H NMR (400 MHz, DMSO-d$_6$) δ: 7.67 (d, J=7.82 Hz, 2H), 7.57 (d, J=7.34 Hz, 2H), 7.45-7.51 (m, 4H), 7.40-7.45 (m, 2H), 7.37 (d, J=8.31 Hz, 2H), 7.15-7.19 (m, 3H), 7.06 (d, J=7.82 Hz, 2H), 7.01 (dd, J=1.96, 8.80 Hz, 1H), 6.83 (d, J=7.82 Hz, 2H), 5.39 (s, 2H), 5.25 (s, 2H), 4.23 (t, J=6.36 Hz, 2H), 3.90 (s, 3H), 2.87 (t, J=6.36 Hz, 2H), 2.44 (s, 3H).

To 4-((5-(benzyloxy)-3-chloro-2-(4-methoxyphenyl)-1H-indol-1-yl)methyl)phenethyl4-methylbenzenesulfonate 13-8 (580 mg, 0.891 mmol) in acetonitrile (15 mL) was added 2N ethyl amine in THF (4.4 mL, mmol) and DIPEA (0.5 mL, 2.673 mmol) in a seal tube. The reaction mixture was then stirred at room temperature for 24 h. After completion of the reaction, the reaction mixture was concentrated under reduced pressure, washed with n-hexane (2×10 mL) and decanted followed by drying to afford 252 mg (53% yield) of compound 13-9 as white solid.

LCMS-Condition 01: [M+H]$^+$=525.15; Rt=1.82 min $^1$H NMR (400 MHz, DMSO-d$_6$) δ: 7.54-7.58 (m, 3H), 7.46-7.53 (m, 4H), 7.40-7.45 (m, 2H), 7.15-7.22 (m, 5H), 7.00 (dd, J=2.20, 9.05 Hz, 1H), 6.91 (d, J=8.31 Hz, 2H), 5.40 (s, 2H), 5.24 (s, 2H), 3.90 (s, 3H), 3.07-3.12 (m, 2H), 2.97 (q, J=7.34 Hz, 2H), 2.83-2.89 (m, 2H), 1.21 (t, J=7.09 Hz, 3H).

To 2-(4-((5-(benzyloxy)-3-chloro-2-(4-methoxyphenyl)-1H-indol-1-yl)methyl)phenyl)-N-ethylethan-1-amine 13-9 (250 mg, 0.476 mmol) in TFA (1.5 mL) at 0° C. was added methane sulphonic acid (0.25 mL, 3.850 mmol) and triethyl silane (0.75 mL, 4.695 mmol) under argon atmosphere. The reaction mixture was stirred at room temperature for 2 h under argon atmosphere. After completion of the reaction, the reaction mixture was concentrated under reduced pressure and diluted with ethyl acetate (100 mL). The separated organic layer was washed with saturated NaHCO$_3$ (30 mL) followed by brine (30 mL), dried over anhydrous Na$_2$SO$_4$, filtered and concentrated under reduced pressure. The crude compound was purified by preparative HPLC to afford 45 mg (22% yield) of D-13 as white solid.

LCMS-Condition 01: [M+H]$^+$=435.20; Rt=1.46 min $^1$H NMR (400 MHz, DMSO-d$_6$) δ: 8.32 (s, 1H), 7.39 (d, J=8.80 Hz, 2H), 7.21 (d, J=8.80 Hz, 1H), 7.06 (d, J=8.80 Hz, 4H), 6.81 (d, J=2.45 Hz, 1H), 6.78 (d, J=7.82 Hz, 2H), 6.65-6.70 (m, 1H), 5.24 (s, 2H), 3.80 (s, 3H), 2.75-2.82 (m, 2H), 2.62-2.69 (m, 4H), 1.02 (t, J=7.34 Hz, 3H).

1-(4-(2-(Cyclopropylamino)ethyl)benzyl)-3-fluoro-2-(o-tolyl)-1H-indol-5-ol (D-28)

To 4-(benzyloxy)-2-(2,2-dibromovinyl)aniline 13-3 (5.5 g, 14.360 mmol) in toluene:ethanol (9:1; 60 mL) was added 2-methyl-phenyl boronic acid (2.54 g, 18.66 mmol) and 2M solution of Na$_2$CO$_3$ (4.56 g, 43.08 mmol) at room temperature under argon atmosphere and the mixture was degassed with argon for 30 min. To the resulting solution was added Pd(PPh$_3$)$_4$ (830 mg, 0.718 mmol) and degassing was continued for another 10 min at room temperature. The reaction mixture was then heated at 90° C. and stirred for 18 h. After completion of the reaction, the reaction mixture was diluted with water and extracted with ethyl acetate (3×50 mL). The combined organic layer was dried over anhydrous $Na_2SO_4$, filtered and concentrated under reduced pressure. The resulting crude compound was purified by silica gel column chromatography eluting with 0-15% ethyl acetate in n-hexane to afford 2.35 g (52% yield) of compound 28-1 as thick oil.

LCMS-Condition 01: [M+H]$^+$=314.10; Rt=2.38 min $^1$H NMR (400 MHz, CDCl$_3$) δ: 8.03 (br. s, 1H), 7.48 (d, J=7.46 Hz, 2H), 7.43-7.46 (m, 1H), 7.39 (t, J=7.46 Hz, 2H), 7.22-7.34 (m, 5H), 7.18 (d, J=1.96 Hz, 1H), 6.95 (dd, J=1.90, 8.74 Hz, 1H), 6.51-6.54 (m, 1H), 5.12 (s, 2H), 2.49 (s, 3H).

To 5-(benzyloxy)-2-(o-tolyl)-1H-indole 28-1 (2.34 g, 7.667 mmol) in dry ACN:DMSO (3:2; 25 mL) at −10° C. was added selectfluor (2.1 g, 6.134 mmol) under argon atmosphere. The reaction mixture was then stirred at 0° C. for 2 h. After completion of the reaction, the reaction mixture was concentrated under reduced pressure, the residue was dissolved in ethyl acetate (100 mL) and washed with water (40 mL) followed by brine (30 mL). The separated organic layer was dried over anhydrous $Na_2SO_4$, filtered and concentrated under reduced pressure. The resulting crude compound was purified by silica gel column chromatography eluting with 0-15% ethyl acetate in n-hexane followed by preparative TLC to afford 820 mg (33% yield) of compound 28-2 as off white solid.

LCMS-Condition 01: [M-18]f=314.11; Rt=2.38 min $^1$H NMR (400 MHz, CDCl$_3$) δ: 8.04 (s, 1H), 7.47-7.51 (m, 2H), 7.38-7.45 (m, 3H), 7.26-7.33 (m, 4H), 7.21-7.25 (m, 1H), 7.16 (d, J=2.45 Hz, 1H), 6.95-7.00 (m, 1H), 5.14 (s, 2H), 2.43 (3, 3H).

To 5-(benzyloxy)-3-fluoro-2-(o-tolyl)-1H-indole 28-2 (450 mg, 1.364 mmol) in DMF (10 mL) at 0° C. was added sodium hydride (60% dispersion in oil, 163 mg, 4.092 mmol) portion wise. The reaction mixture was then stirred at 0° C. for 30 min. To the resulting solution was added tert-butyl(4-(bromomethyl)phenethoxy)dimethylsilane (591 mg, 1.773 mmol). The reaction mixture was stirred at room temperature for 2 h. After completion of the reaction, the reaction mixture was quenched with ice cold water and extracted with ethyl acetate (3×25 mL). The combined organic layer was dried over anhydrous $Na_2SO_4$, filtered and concentrated under reduced pressure to afford 902 mg (crude) of compound 28-3 as colourless thick liquid.

LCMS-Condition 01: [M-18]$^+$=562.30; Rt=3.09 min $^1$H NMR (400 MHz, DMSO-d$_6$) δ: 7.44-7.48 (m, 2H), 7.35-7.42 (m, 4H), 7.28-7.34 (m, 3H), 7.11-7.16 (m, 2H), 7.00 (d, J=7.83 Hz, 2H), 6.88 (dd, J=1.96, 8.80 Hz, 1H), 6.66 (d, J=7.83 Hz, 2H), 5.13 (s, 1H), 5.12 (s, 1H), 5.09 (br. s, 1H), 5.07 (br. s, 1H), 3.65 (t, J=6.60 Hz, 2H), 2.61 (t, J=6.85 Hz, 2H), 2.09 (s, 3H), 0.76 (s, 9H), −0.13 (s, 6H).

To 5-(benzyloxy)-1-(4-(2-((tert-butyldimethylsilyl)oxy) ethyl)benzyl)-3-fluoro-2-(o-tolyl)-1H-indole 28-3 (900 mg, 1.559 mmol) in THF (10 mL) at 0° C. was added 1M solution of tetrabutylammonium fluoride in THF (2.3 mL, 2.339 mmol) dropwise at room temperature and stirred for 2 h. After completion of the reaction, the reaction mixture was concentrated under reduced pressure and diluted with ethyl acetate. The separated organic layer was dried over anhydrous $Na_2SO_4$, filtered and concentrated under reduced pressure to afford 780 mg (crude) of compound 28-4 as colourless thick liquid which was used as such in the next step without further purification.

LCMS-Condition 01: [M-18]f=448.10; Rt=2.39 min $^1$H NMR (400 MHz, CDCl$_3$) δ: 7.45-7.51 (m, 2H), 7.37-7.43 (m, 2H), 7.29-7.35 (m, 3H), 7.22-7.24 (m, 2H), 7.17 (d, J=2.45 Hz, 1H), 7.13 (dd, J=2.20, 9.05 Hz, 1H), 7.04 (d, J=7.83 Hz, 2H), 6.92 (dd, J=2.45, 8.80 Hz, 1H), 6.78 (d, J=7.83 Hz, 2H), 5.13 (s, 1H), 5.12 (s, 1H), 5.07 (s, 1H), 5.03 (s, 1H), 3.79 (t, J=6.36 Hz, 2H), 3.48 (q, J=6.85 Hz, 1H), 2.78 (t, J=6.36 Hz, 2H), 2.19 (s, 3H).

To 2-(4-((5-(benzyloxy)-3-fluoro-2-(o-tolyl)-1H-indol-1-yl)methyl)phenyl)ethan-1-ol 28-4 (750 mg, 1.613 mmol) in CH$_2$Cl$_2$ (10 mL) at 0° C. was added triethylamine (0.67 mL, 4.839 mmol) followed by tosyl chloride (371 mg, 1.936 mmol). The reaction mixture was stirred at room temperature for 18 h. After completion of the reaction, the reaction mixture was diluted with DCM, and washed with water, and brine. Organic layer was dried over anhydrous $Na_2SO_4$, filtered and concentrated under reduced pressure. The resulting crude compound was purified by silica gel column chromatography eluting with 0-30% ethyl acetate in n-hexane to afford 451 mg (45% yield) of compound 28-5 as colourless sticky solid.

LCMS-Condition 01: [M-18]$^+$=602.22; Rt=2.62 min $^1$H NMR (400 MHz, CDCl$_3$) δ: 7.63 (d, J=8.31 Hz, 2H), 7.46-7.50 (m, 2H), 7.39-7.42 (m, 1H), 7.38 (s, 2H), 7.30-7.36 (m, 3H), 7.23 (d, J=4.40 Hz, 3H), 7.12-7.17 (m, 2H), 6.92 (d, J=7.83 Hz, 3H), 6.72 (d, J=7.83 Hz, 2H), 5.12 (s, 1H), 5.11 (s, 1H), 5.07 (s, 1H), 5.01 (s, 1H), 4.12 (t, J=6.85 Hz, 2H), 2.85 (t, J=6.85 Hz, 2H), 2.39 (s, 3H), 2.16 (s, 3H).

To 4-((5-(benzyloxy)-3-fluoro-2-(o-tolyl)-1H-indol-1-yl)methyl)phenethyl 4-methylbenzenesulfonate 28-5 (225 mg, 0.363 mmol) in acetonitrile (5 mL) was added DIPEA (0.6 mL, 3.635 mmol) and cyclopropyl amine (208 mg, 3.635 mmol) and in a sealed tube. The reaction mixture was stirred at room temperature for 72 h. After completion of the reaction, the reaction mixture was concentrated under reduced pressure, and diluted with ethyl acetate. Organic layer was washed with water and brine, dried over anhydrous $Na_2SO_4$, filtered and concentrated under reduced pressure 210 mg (crude) of compound 28-6 as off white solid which was used as such in the next step without further purification.

LCMS-Condition 01: [M+H]$^+$=505.35; Rt=1.48 min $^1$H NMR (400 MHz, CDCl$_3$) δ: 7.46-7.50 (m, 2H), 7.36-7.42 (m, 2H), 7.28-7.35 (m, 2H), 7.20-7.23 (m, 2H), 7.13-7.18 (m, 3H), 6.96 (d, J=8.31 Hz, 2H), 6.92 (dd, J=2.45, 8.80 Hz, 1H), 6.72 (d, J=7.83 Hz, 2H), 5.12 (s, 1H), 5.11 (s, 1H), 5.04 (s, 1H), 4.99 (s, 1H), 3.02-3.07 (m, 2H), 2.89-2.95 (m, 2H), 2.35-2.40 (m, 1H), 2.32 (s, 3H), 1.40-1.50 (m, 4H).

To N-(4-((5-(benzyloxy)-3-fluoro-2-(o-tolyl)-1H-indol-1-yl)methyl)phenethyl)cyclopropanamine 28-6 (280 mg, 0.555 mmol) in ethyl acetate:methanol (4:1; 7 mL) was added 20% palladium hydroxide on carbon (55 mg, 20% w/w) at room temperature. The reaction mixture was stirred under hydrogen atmosphere for 18 h. After completion of the reaction, the reaction mixture was filtered through a pad of Celite™ and washed with ethyl acetate. The filtrate was concentrated under reduced pressure and the crude compound was purified by preparative HPLC to afford 28 mg (12% yield) of D-28 as white solid.

LCMS-Condition 01: [M+H]$^+$=415.22; Rt=1.52 min $^1$H NMR (400 MHz, DMSO-d$_6$) δ: 9.05 (s, 1H), 7.27-7.34 (m, 5H), 6.98 (d, J=7.78 Hz, 2H), 6.83 (d, J=2.01 Hz, 1H), 6.69 (dd, J=2.13, 8.91 Hz, 1H), 6.64 (d, J=7.78 Hz, 2H), 5.01-5.11 (m, 2H), 2.67-2.69 (m, 2H), 2.55-2.58 (m, 2H), 2.07 (s, 3H), 1.99-2.03 (m, 1H), 0.18-0.25 (m, 2H), 0.02-0.08 (m, 2H). 3-Fluoro-2-(2-methoxyphenyl)-1-(4-(2-(propylamino)ethyl)benzyl)-1H-indol-5-ol (D-87)

To 4-(benzyloxy)-2-(2,2-dibromovinyl)aniline 13-3 (15 g, 39.16 mmol) in toluene:ethanol (3:1, 80 mL) was added 2-methoxyphenyl boronic acid (7.73 g, 50.86 mmol) and aq.

solution of Na$_2$CO$_3$ (12.45 g, 117.45 mmol) simultaneously at room temperature under argon atmosphere and degassed for 30 min. To the resulting solution was added Pd(PPh$_3$)$_4$ (2.26 g, 1.956 mmol) and degassing was continued for another 10 min. The reaction mixture was further heated to 90° C. and stirred for 18 h. After completion of the reaction, the reaction mixture was diluted with water and extracted with ethyl acetate (3×50 mL). The combined organic layer was dried over anhydrous Na$_2$SO$_4$, filtered and concentrated under reduced pressure. The crude compound was purified by silica gel column chromatography eluting with 0-8% ethyl acetate in n-hexane to afford 5 g (39% yield) of compound 87-2 as sticky solid.

LCMS-Condition-1: [M+H]$^+$=329.70; Rt=2.21 min $^1$H NMR (400 MHz, DMSO-d$_6$) δ: 11.02 (s, 1H), 7.77 (dd, J=1.47, 7.83 Hz, 1H), 7.46-7.49 (m, 2H), 7.39 (t, J=7.34 Hz, 2H), 7.29-7.36 (m, 3H), 7.10-7.15 (m, 2H), 7.01-7.07 (m, 1H), 6.79-6.84 (m, 2H), 5.10 (s, 2H), 3.93 (s, 3H).

To a solution of 5-(benzyloxy)-2-(2-methoxyphenyl)-1H-indole 87-2 (4.5 g, 13.67 mmol) in dry Acetonitrile:DMSO (5:2, 35 mL) at −10° C. was added selectfluor (4.84 g, 13.67 mmol) under argon atmosphere. The reaction mixture was stirred at room temperature for 4 h. After completion of the reaction (monitored by TLC and LCMS), the reaction mixture was concentrated under reduced pressure, the residue was dissolved in ethyl acetate (100 mL) and washed with water (40 mL) followed by brine (30 mL). The separated organic layer was dried over anhydrous Na$_2$SO$_4$, filtered and concentrated under reduced pressure. The crude compound was purified by silica gel column chromatography eluting with 0-5% ethyl acetate in n-hexane followed by preparative TLC to afford 2.2 g (46% yield) of compound 87-3 as brown solid.

LCMS-Condition-1: [M+H]$^+$=348.10; Rt=2.29 min $^1$H NMR (400 MHz, DMSO-d$_6$) δ: 10.64 (s, 1H), 7.54 (d, J=7.53 Hz, 1H), 7.36-7.40 (m, 2H), 7.26-7.33 (m, 3H), 7.21-7.26 (m, 2H), 7.06-7.10 (m, 1H), 6.95-6.99 (m, 2H), 6.77 (dd, J=2.13, 8.91 Hz, 1H), 5.04 (s, 2H), 3.79 (s, 3H).

To a solution of 5-(benzyloxy)-3-fluoro-2-(2-methoxyphenyl)-1H-indole 87-3 (1.5 g, 4.319 mmol) in DMF (10 mL) at 0° C. was added sodium hydride (60% dispersion in oil, 863 mg, 21.58 mmol) portion wise and stirred at 0° C. for 30 min. To the resulting solution was added (4-(bromomethyl)phenethoxy)(tert-butyl)dimethylsilane (1.7 g, 5.182 mmol). Then the reaction mixture was stirred at room temperature for 2 h. After completion of the reaction (monitored by TLC and LCMS), the reaction mixture was quenched with ice cold water and extracted with ethyl acetate (3×75 mL). The combined organic layer was dried over anhydrous Na$_2$SO$_4$, filtered and concentrated under reduced pressure. The crude compound was purified by silica gel column chromatography eluting with 0-4% ethyl acetate in n-hexane to afford 2 g (77% yield) of compound 87-4 as thick yellow oil.

LCMS-Condition-1: [M+Na]$^+$=618.35; Rt=2.76 min $^1$H NMR (400 MHz, DMSO-d$_6$) δ: 7.44 (d, J=7.82 Hz, 2H), 7.37 (t, J=7.58 Hz, 2H), 7.29 (d, J=5.87 Hz, 2H), 7.22-7.26 (m, 1H), 7.11-7.18 (m, 2H), 7.02-7.05 (m, 1H), 7.00 (d, J=7.34 Hz, 3H), 6.83 (dd, J=2.45, 9.29 Hz, 1H), 6.74 (d, J=7.83 Hz, 2H), 5.74 (s, 2H), 5.11 (s, 2H), 3.71 (s, 3H), 3.60-3.68 (m, 2H), 2.60 (t, J=6.60 Hz, 2H), 0.76 (s, 9H), −0.13 (s, 6H).

To a solution of 5-(benzyloxy)-1-(4-(2-((tert-butyldimethylsilyl)oxy)ethyl)benzyl)-3-fluoro-2-(2-methoxyphenyl)-1H-indole 87-4 (2 g, 3.361 mmol) in THF (20 mL) at 0° C. was added 1M solution of tetrabutylammonium fluoride in THF (5 mL, 5.042 mmol) drop wise at room temperature and stirred for 2 h. After completion of the reaction (monitored by TLC and LCMS), the reaction mixture was concentrated under reduced pressure, diluted with water and extracted with ethyl acetate (2×10 mL). The combined organic layer was dried over anhydrous Na$_2$SO$_4$, filtered and concentrated under reduced pressure. The crude compound was purified by silica gel column chromatography eluting with 0-30% ethyl acetate in n-hexane to afford 1.3 g (81% yield) of compound 87-5 as colorless thick syrup.

LCMS-Condition-1: [M+Na]$^+$=504.15; Rt=2.35 min $^1$H NMR (400 MHz, DMSO-d$_6$) δ: 7.55 (d, J=7.34 Hz, 2H), 7.47 (t, J=7.34 Hz, 2H), 7.36-7.43 (m, 3H), 7.22-7.28 (m, 2H), 7.19 (d, J=2.45 Hz, 1H), 7.14 (t, J=7.34 Hz, 1H), 7.09 (d, J=7.83 Hz, 2H), 6.95 (dd, J=2.20, 9.05 Hz, 1H), 6.83 (d, J=7.82 Hz, 2H), 5.09-5.14 (m, 4H), 4.63 (t, J=5.14 Hz, 1H), 3.81 (s, 3H), 3.54-3.61 (m, 2H), 2.68 (t, J=6.85 Hz, 2H).

To 2-(4-((5-(benzyloxy)-3-fluoro-2-(2-methoxyphenyl)-1H-indol-1-yl)methyl)phenyl)ethan-1-ol 87-5 (1.3 g, 2.702 mmol) in CH$_2$Cl$_2$ (15 mL) at 0° C. was added triethylamine (1.1 mL, 8.108 mmol) followed by tosyl chloride (621 mg, 3.243 mmol) and the reaction mixture was stirred at room temperature for 3 h. After completion of the reaction (monitored by TLC and LCMS), the reaction mixture was concentrated under reduced pressure, diluted with water and extracted with ethyl acetate (2×50 mL). The combined organic layer was dried over anhydrous Na$_2$SO$_4$, filtered and concentrated under reduced pressure. The crude compound was purified by silica gel column chromatography eluting with 0-10% ethyl acetate in n-hexane to afford 1.3 g (76% yield) of compound 87-6 as light brown solid.

LCMS-Condition-1: [M+Na]$^+$=658.20; Rt=2.53 min $^1$H NMR (400 MHz, DMSO-d$_6$) δ: 7.54 (d, J=8.31 Hz, 2H), 7.45 (d, J=8.31 Hz, 3H), 7.34-7.40 (m, 2H), 7.27-7.33 (m, 3H), 7.24 (d, J=8.31 Hz, 2H), 7.12-7.19 (m, 1H), 7.10 (d, J=1.96 Hz, 1H), 7.04 (t, J=7.34 Hz, 1H), 6.91 (d, J=7.82 Hz, 2H), 6.86 (dd, J=2.20, 9.05 Hz, 1H), 6.71 (d, J=7.82 Hz, 2H), 5.12 (s, 2H), 5.08 (s, 1H), 5.00 (br. s, 1H), 4.10 (t, J=6.36 Hz, 2H), 3.70 (s, 3H), 2.74 (t, J=6.36 Hz, 2H), 2.32 (s, 3H).

To a solution of 4-((5-(benzyloxy)-3-fluoro-2-(2-methoxyphenyl)-1H-indol-1-yl)methyl)phenethyl 4-methylbenzenesulfonate 87-6 (300 mg, 0.472 mmol) in acetonitrile (4 mL) was added DIPEA (0.5 mL, 2.834 mmol) and propyl amine (83 mg, 1.417 mmol) in a sealed tube. Then the reaction mixture was stirred at room temperature for 48 h. After completion of the reaction (monitored by TLC and LCMS), the reaction mixture was concentrated under reduced pressure, diluted with water and extracted with ethyl acetate (2×20 mL). The combined organic layer was dried over anhydrous Na$_2$SO$_4$, filtered and concentrated under reduced pressure. The crude compound was purified by silica gel column chromatography eluting with 0-5% methanol in DCM to afford 200 mg (65% yield) of compound 87-7 as yellow sticky solid.

LCMS-Condition-1: [M+H]$^+$=523.30; Rt=1.94 min $^1$H NMR (400 MHz, DMSO-d$_6$) δ: 7.46 (d, J=7.88 Hz, 3H), 7.39 (t, J=7.63 Hz, 2H), 7.27-7.34 (m, 3H), 7.15-7.20 (m, 1H), 7.11 (d, J=1.97 Hz, 1H), 7.05-7.08 (m, 1H), 7.03 (d, J=8.37 Hz, 2H), 6.86 (dd, J=2.46, 8.86 Hz, 1H), 6.78 (d, J=8.37 Hz, 2H), 5.14 (s, 2H), 4.96-5.13 (m, 2H), 3.73 (s, 3H), 2.74-2.81 (m, 2H), 2.62-2.69 (m, 2H), 2.58 (t, J=7.38 Hz, 2H), 1.38-1.47 (m, 2H), 1.23 (br. s, 1H), 0.80-0.86 (m, 3H).

To a solution of N-(4-((5-(benzyloxy)-3-fluoro-2-(2-methoxyphenyl)-1H-indol-1-yl)methyl)phenethyl)propan-1-amine 87-7 (200 mg, 0.361 mmol) in ethyl acetate:

methanol (1:1; 3 mL) was added 20% palladium hydroxide on carbon (100 mg) at room temperature and the reaction mixture was stirred under hydrogen atmosphere for 18 h. After completion of the reaction (monitored by TLC and LCMS), the reaction mixture was filtered through a pad of Celite™ and washed with ethyl acetate. The filtrate was concentrated under reduced pressure and the crude compound was purified by preparative HPLC to afford 55 mg (16% yield) of D-87 as off white solid.

LCMS-Condition-1: [M+H]$^+$=433.20; Rt=1.39 min $^1$H NMR (400 MHz, DMSO-d$_6$) δ: 9.04 (br. s, 1H), 7.43-7.49 (m, 1H), 7.31 (dd, J=1.71, 7.58 Hz, 1H), 7.14-7.20 (m, 2H), 6.98-7.07 (m, 3H), 6.81 (d, J=2.45 Hz, 1H), 6.74 (d, J=8.31 Hz, 2H), 6.65 (dd, J=2.45, 8.80 Hz, 1H), 5.06-5.20 (m, 1H), 4.87-5.02 (m, 1H), 3.72 (s, 3H), 2.53-2.64 (m, 4H), 2.41 (t, J=7.09 Hz, 2H), 1.23-1.38 (m, 3H), 0.80 (t, J=7.58 Hz, 3H).

1-(4-(2-(Cyclobutylamino)ethyl)benzyl)-2-(2,6-dimethylphenyl)-3-fluoro-1H-indol-5-ol (D-50)

To 4-(benzyloxy)-2-(2,2-dibromovinyl)aniline 13-3 (5 g, 13.05 mmol) in toluene-ethanol (35:6 mL) was added 2,6-dimethyl-phenyl boronic acid (2.5 g, 16.78 mmol) and solution of Na$_2$CO$_3$ (4.1 g, 38.67 mmol) in water (3 mL) simultaneously at room temperature under argon atmosphere and degassed for 30 min. To the resulting solution was added Pd(PPh$_3$)$_4$ (753 mg, 0.652 mmol) and degassing was continued for another 10 min at room temperature. The reaction mixture was then heated to 90° C. for 18 h. After completion of the reaction (monitored by TLC and LCMS), the reaction mixture was diluted with water and extracted with ethyl acetate (3×50 mL). The combined organic layer was dried over anhydrous Na$_2$SO$_4$, filtered and concentrated under reduced pressure. The crude compound was purified by silica gel column chromatography eluting with 0-15% ethyl acetate in n-hexane to afford 1 g (24% yield) of compound 50-1 as thick brown syrup.

LCMS-Condition 01: [M+H]$^+$=328.20; Rt=2.38 min $^1$H NMR (400 MHz, DMSO-d$_6$) δ: 10.95 (br. s, 1H), 7.45-7.50 (m, 2H), 7.40 (t, J=7.34 Hz, 2H), 7.33 (d, J=7.34 Hz, 1H), 7.22 (t, J=7.83 Hz, 2H), 7.14 (d, J=7.82 Hz, 3H), 6.80 (dd, J=1.96, 8.80 Hz, 1H), 6.20 (s, 1H), 5.11 (s, 2H), 2.11 (s, 6H).

To 5-(benzyloxy)-2-(2,6-dimethylphenyl)-1H-indole 50-1 (1 g, 3.058 mmol) in dry Acetonitrile:DMSO (3:1 mL) at −10° C. was added selectfluor (1.08 g, 3.051 mmol) under argon atmosphere. The reaction mixture was further stirred at 0° C. for 2 h. After completion of the reaction (monitored by TLC and LCMS), the reaction mixture was concentrated under reduced pressure, the residue was dissolved in ethyl acetate (100 mL) and washed with water (40 mL) followed by brine (30 mL). The separated organic layer dried over anhydrous Na$_2$SO$_4$, filtered and concentrated under reduced pressure. The resulting crude compound was purified by silica gel column chromatography eluting with 0-10% ethyl acetate in n-hexane followed by preparative TLC to afford 500 mg (52% yield) of the title compound 50-2 as brown solid.

LCMS-Condition 01: [M+18]$^+$=364.00; Rt=2.49 min $^1$H NMR (400 MHz, DMSO-d$_6$) δ: 10.83 (br. s, 1H), 7.48 (d, J=7.34 Hz, 3H), 7.36-7.43 (m, 2H), 7.28-7.36 (m, 2H), 7.15-7.26 (m, 4H), 5.14 (s, 2H), 2.14 (s, 6H).

To a solution of 5-(benzyloxy)-2-(2,6-dimethylphenyl)-3-fluoro-1H-indole 50-2 (500 mg, 1.449 mmol) in DMF (5 mL) at 0° C. was added sodium hydride (60% dispersion in oil, 145 mg, 6.041 mmol) portion wise and stirred for 30 min. To the resulting solution was added tert-butyl(4-(chloromethyl)phenethoxy)dimethylsilane (572 mg, 1.738 mmol). Then the reaction mixture was stirred at room temperature for 2 h. After completion of the reaction (monitored by TLC and LCMS), the reaction mixture was quenched with ice cold water and extracted with ethyl acetate (3×25 mL). The combined organic layer was dried over anhydrous Na$_2$SO$_4$, filtered and concentrated under reduced pressure. The resulting crude compound was purified by silica gel column chromatography eluting with 0-10% ethyl acetate in n-hexane to afford 500 mg (60% yield) of compound 50-3 as thick oil.

LCMS-Condition 01: [M+H]$^+$=594.20; Rt=3.17 min $^1$H NMR (400 MHz, DMSO-d$_6$) δ: 7.39-7.49 (m, 4H), 7.28-7.35 (m, 2H), 7.14-7.22 (m, 4H), 6.98 (d, J=6.85 Hz, 2H), 6.88 (d, J=9.29 Hz, 1H), 6.66 (d, J=6.85 Hz, 2H), 5.15 (s, 2H), 4.95 (s, 2H), 3.73 (t, J=6.85 Hz, 2H), 2.70 (t, J=6.36 Hz, 2H), 1.90 (s, 6H), 0.78 (s, 9H), −0.09 (s, 6H).

To a solution of 5-(benzyloxy)-1-(4-(2-((tert-butyldimethylsilyl)oxy)ethyl)benzyl)-2-(2,6-dimethylphenyl)-3-fluoro-1H-indole 50-3 (500 mg, 0.842 mmol) in THF (10 mL) was added 1M solution of tetrabutylammonium fluoride in THF (1.25 mL, 4.809 mmol) dropwise at room temperature and stirred for 1 h. After completion of the reaction (monitored by TLC and LCMS), the reaction mixture was quenched with saturated NaHCO$_3$ solution and extracted with ethyl acetate (20 mL×3). The combined organic layer was dried over anhydrous Na$_2$SO$_4$, filtered and concentrated under reduced pressure. The crude compound was purified by silica gel column chromatography eluting with 0-40% ethyl acetate in n-hexane to afford 400 mg (82% yield) of compound 50-4 as off white solid.

LCMS-Condition 01: [M-18]$^+$=462.50; Rt=2.36 min $^1$H NMR (400 MHz, DMSO-d$_6$) δ: 7.54 (d, J=6.85 Hz, 3H), 7.43-7.48 (m, 2H), 7.36-7.41 (m, 3H), 7.31 (d, J=7.82 Hz, 1H), 7.22 (d, J=7.34 Hz, 2H), 7.06 (d, J=7.83 Hz, 2H), 6.72 (d, J=7.82 Hz, 2H), 5.21 (s, 2H), 5.00 (s, 2H), 4.59-4.64 (m, 1H), 3.61-3.67 (m, 2H), 2.75-2.81 (m, 2H), 1.98 (s, 6H).

To 2-(4-((5-(benzyloxy)-2-(2,6-dimethylphenyl)-3-fluoro-1H-indol-1-yl)methyl)phenyl)ethan-1-ol 50-4 (400 mg, 0.834 mmol) in CH$_2$Cl$_2$ (10 mL) at 0° C. was added triethylamine (0.46 mL, 3.366 mmol) followed by tosyl chloride (236 mg, 1.248 mmol). Then the reaction mixture was stirred at room temperature for 18 h. After completion of the reaction (monitored by TLC and LCMS), the reaction mixture was diluted with CH$_2$Cl$_2$. The combined organic layer was washed with brine, dried over anhydrous Na$_2$SO$_4$, filtered and concentrated under reduced pressure to afford 400 mg (78% yield) of compound 50-5 as colourless sticky oil.

LCMS-Condition 01: [M+H]$^+$=634.25; Rt=2.62 min $^1$H NMR (400 MHz, DMSO-d$_6$) δ: 7.64 (d, J=7.83 Hz, 2H), 7.54 (d, J=4.89 Hz, 2H), 7.43-7.49 (m, 3H), 7.35 (t, J=6.60 Hz, 4H), 7.19-7.24 (m, 3H), 6.99 (d, J=7.83 Hz, 3H), 6.69 (d, J=7.82 Hz, 2H), 5.16 (s, 2H), 4.96 (s, 2H), 4.15-4.21 (m, 2H), 2.83 (t, J=5.87 Hz, 2H), 2.40 (s, 3H), 1.97 (s, 6H).

To 4-((5-(benzyloxy)-2-(2,6-dimethylphenyl)-3-fluoro-1H-indol-1-yl)methyl)phenethyl 4-methylbenzenesulfonate 50-5 (200 mg, 0.316 mmol) in acetonitrile (2 mL) was added 3-methylazetidine hydrochloride (112 mg, 1.577 mmol) and DIPEA (0.4 mL, 2.158 mmol) in a seal tube. The reaction mixture was further stirred at room temperature for 48 h. After completion of the reaction, the reaction mixture was concentrated under reduced pressure, washed with ethyl acetate (2×10 mL). The combined organic layer dried over anhydrous Na$_2$SO$_4$, filtered and concentrated under reduced pressure. The crude compound was purified by silica gel column chromatography eluting with 0-10% methanol in CH$_2$Cl$_2$ to afford 100 mg (60% yield) of the title compound 50-6 as thick oil.

LCMS-Condition 01: [M+H]$^+$=533.65; Rt=1.81 min $^1$H NMR (400 MHz, DMSO-d$_6$) δ: 7.45-7.51 (m, 3H), 7.40 (t, J=7.58 Hz, 2H), 7.31 (dd, J=7.58, 15.89 Hz, 2H), 7.11-7.19 (m, 3H), 6.98-7.04 (m, 2H), 6.93 (dd, J=1.96, 8.80 Hz, 1H), 6.67 (d, J=7.83 Hz, 2H), 5.15 (s, 2H), 4.95 (s, 2H), 3.19-3.29 (m, 1H), 2.55-2.67 (m, 4H), 2.01-2.12 (m, 2H), 1.91 (s, 6H), 1.49-1.74 (m, 5H).

To a solution of N-(4-((5-(benzyloxy)-2-(2,6-dimethylphenyl)-3-fluoro-1H-indol-1-yl)methyl)phenethyl)cyclobutanamine 50-6 (100 mg, 0.187 mmol) in ethyl acetate-methanol (1:1, 4 mL) was added 20% palladium hydroxide on carbon (25 mg) at room temperature. Then the reaction mixture was stirred under hydrogen atmosphere for 18 h. After completion of the reaction (monitored by TLC and LCMS), the reaction mixture was filtered through a pad of Celite™ and washed with ethyl acetate. The filtrate was concentrated under reduced pressure and the crude compound was purified by preparative HPLC to afford 20 mg (24% yield) of D-50 as off white solid.

LCMS-Condition 01: [M+H]$^+$=443.15; Rt=1.61 min $^1$H NMR (400 MHz, DMSO-d$_6$) δ: 9.06 (br. s, 1H), 7.37 (dd, J=2.45, 8.80 Hz, 1H), 7.27-7.32 (m, 1H), 7.15 (d, J=7.34 Hz, 2H), 6.98 (d, J=7.83 Hz, 2H), 6.84 (d, J=1.96 Hz, 1H), 6.72 (dd, J=2.20, 9.05 Hz, 1H), 6.65 (d, J=8.31 Hz, 2H), 4.90 (s, 2H), 3.06-3.12 (m, 1H), 2.52-2.55 (m, 3H), 2.00-2.08 (m, 2H), 1.91 (s, 6H), 1.49-1.63 (m, 5H).

2-(2,6-Dimethylphenyl)-1-(4-(2-(ethylamino)ethyl)benzyl)-3-fluoro-1H-indol-5-ol (D-78)

To a solution of 4-((5-(benzyloxy)-2-(2,6-dimethylphenyl)-3-fluoro-1H-indol-1-yl)methyl)phenethyl 4-methylbenzenesulfonate 50-5 (200 mg, 0.315 mmol) in acetonitrile (0.5 mL) was added ethyl amine (2M in THF, 1.57 mL, 3.15 mmol) and DIPEA (326 mg, 2.52 mmol) in a sealed tube. Then the reaction mixture was stirred at room temperature for 4 days. After completion of the reaction (monitored by TLC and LCMS), the reaction mixture was concentrated under reduced pressure, and the crude compound was purified by silica gel column chromatography eluting with 0-20% ethyl acetate in n-hexane to afford 100 mg (60% yield) of compound 78-1 as semi-solid.

LCMS-Condition 1: [M+H]$^+$=507.30; Rt=1.87 min $^1$H NMR (400 MHz, DMSO-d$_6$) δ: 7.45-7.49 (m, 3H), 7.39-7.43 (m, 2H), 7.29-7.35 (m, 2H), 7.05-7.19 (m, 5H), 6.91-6.94 (m, 1H), 6.73 (d, J=8.0 Hz, 2H), 5.16 (s, 2H), 4.97 (s, 2H), 2.99-3.01 (m, 2H), 2.87 (d, J=7.6 Hz, 2H), 2.74-2.79 (m, 2H), 2.28 (br. S, 1H), 1.94 (s, 6H), 1.12 (t, J=7.6 Hz, 3H).

To a solution of 2-(4-((5-(benzyloxy)-2-(2,6-dimethylphenyl)-3-fluoro-1H-indol-1-yl)methyl)phenyl)-N-ethylethan-1-amine 78-1 (100 mg, 0.196 mmol) in ethyl acetate-methanol (1:1; 4 mL) was added 20% palladium hydroxide on carbon (25 mg) at room temperature. Then the reaction mixture was stirred under hydrogen atmosphere for 18 h. After completion of the reaction (monitored by TLC and LCMS), the reaction mixture was filtered through a pad of Celite™ and washed with ethyl acetate. The filtrate was concentrated under reduced pressure and the crude compound was purified by preparative HPLC to afford 18 mg (10% yield) of D-78 as off white solid.

LCMS-Condition 1: [M+H]$^+$=417.50; Rt=1.45 min $^1$H NMR (400 MHz, DMSO-d$_6$) δ: 9.02 (s, 1H), 7.38 (dd, J=1.96, 8.80 Hz, 1H), 7.26-7.32 (m, 1H), 7.15 (d, J=7.34 Hz, 2H), 6.99 (d, J=7.82 Hz, 2H), 6.84 (d, J=1.96 Hz, 1H), 6.72 (dd, J=2.45, 8.80 Hz, 1H), 6.66 (d, J=8.31 Hz, 2H), 4.90 (s, 2H), 2.53-2.68 (m, 6H), 1.91 (s, 6H), 0.95 (t, J=7.09 Hz, 3H).

1-(4-(2-(Cyclopropylamino)ethyl)benzyl)-3-fluoro-2-(4-hydroxy-2-methylphenyl)-1H-indol-5-ol (D-52)

To a solution of 4-(benzyloxy)-2-(2,2-dibromovinyl)aniline 13-3 (6 g, 15.66 mmol) in toluene-ethanol (1:1, 50 mL) was added 2-methyl-4-methoxy-phenyl boronic acid (3.4 g, 20.36 mmol) and saturated solution of Na$_2$CO$_3$ (5.06 g, 46.99 mmol) simultaneously at room temperature under argon atmosphere and degassed for 30 min. To the resulting solution was added Pd(PPh$_3$)$_4$ (906 mg, 0.784 mmol) and degassing was continued for another 10 min at room temperature. The reaction mixture was then heated at 90° C. and stirred for 18 h. After completion of the reaction (monitored by TLC and LCMS), the reaction mixture was diluted with water and extracted with ethyl acetate (3×50 mL). The combined organic layer was washed with water (50 mL), brine (50 mL) dried over anhydrous Na$_2$SO$_4$, filtered and concentrated under reduced pressure. The crude compound was purified by silica gel column chromatography eluting with 0-10% ethyl acetate in n-hexane to afford 1.91 g (36% yield) of compound 52-1 as thick brown syrup.

LCMS-Condition 1: [M+H]$^+$=344.10; Rt=2.35 min $^1$H NMR (400 MHz, DMSO-d$_6$) δ: 11.08 (s, 1H), 7.52 (t, J=7.09 Hz, 3H), 7.45 (t, J=7.34 Hz, 2H), 7.39 (d, J=7.34 Hz, 1H), 7.32 (d, J=8.31 Hz, 1H), 7.17 (d, J=2.45 Hz, 1H), 6.97 (d, J=2.45 Hz, 1H), 6.93 (dd, J=2.45, 8.80 Hz, 1H), 6.86 (dd, J=2.45, 8.80 Hz, 1H), 6.45 (d, J=1.96 Hz, 1H), 5.16 (s, 2H), 3.85 (s, 3H), 2.49 (s, 3H).

To a solution of 5-(benzyloxy)-2-(4-methoxy-2-methylphenyl)-1H-indole 52-1 (1.9 g, 5.539 mmol) in dry Acetonitrile:DMSO (4:1, 30 mL) at −10° C. was added selectfluor (1.76 g, 4.98 mmol) under argon atmosphere. The reaction mixture was then stirred at 0° C. for 2 h. After completion of the reaction (monitored by TLC and LCMS), the reaction mixture was concentrated under reduced pressure, the residue was dissolved in ethyl acetate (100 mL) and washed with water (40 mL) followed by brine (30 mL). The organic layer was dried over anhydrous Na$_2$SO$_4$, filtered and concentrated under reduced pressure. The crude compound was purified by silica gel column chromatography eluting with 0-10% ethyl acetate in n-hexane followed by preparative TLC to afford 790 mg (40% yield) of compound 52-2 as brown solid.

LCMS-Condition 1: [M-18]$^+$=344.05; Rt=2.39 min $^1$H NMR (400 MHz, DMSO-d$_6$) δ: 10.84 (s, 1H), 7.45-7.49 (m, 2H), 7.36-7.41 (m, 2H), 7.30-7.34 (m, 2H), 7.24 (dd, J=2.22, 8.61 Hz, 1H), 7.06 (d, J=1.97 Hz, 1H), 6.93 (d, J=2.46 Hz, 1H), 6.87 (ddd, J=2.46, 8.86, 10.83 Hz, 2H), 5.13 (s, 2H), 3.79 (s, 3H), 2.31 (s, 3H).

To a solution of 5-(benzyloxy)-3-fluoro-2-(4-methoxy-2-methylphenyl)-1H-indole 52-2 (800 mg, 2.216 mmol) in DMF (10 mL) at 0° C. was added sodium hydride (60% dispersion in oil, 320 mg, 6.630 mmol) portion wise and stirred at 0° C. for 30 min. To the resulting solution was added tert-butyl(4-(chloromethyl)phenethoxy)dimethylsilane (904 mg, 2.756 mmol). The reaction mixture was stirred at room temperature for 18 h. After completion of the reaction (monitored by TLC), the reaction mixture was quenched with ice cold water, extracted with ethyl acetate (3×25 mL) and washed with water (50 mL) and brine (20 mL). The combined organic layer was dried over anhydrous Na$_2$SO$_4$, filtered and concentrated under reduced pressure.

The crude compound was purified by silica gel column chromatography eluting with 0-10% ethyl acetate in n-hexane to afford 960 mg (72% yield) of compound 52-3 as brown thick oil.

LCMS-Condition 1: [M+H]$^+$=609.86; Rt=2.27 min $^1$H NMR (400 MHz, CDCl$_3$) δ: 7.46-7.50 (m, 2H), 7.37-7.42 (m, 3H), 7.15-7.17 (m, 1H), 7.09 (dd, J=2.46, 8.86 Hz, 1H), 7.02 (d, J=7.88 Hz, 3H), 6.89 (dd, J=2.46, 8.86 Hz, 1H), 6.83 (d, J=2.46 Hz, 1H), 6.75-6.79 (m, 3H), 5.13 (s, 2H), 4.97-5.10 (m, 2H), 3.84 (s, 3H), 3.72 (t, J=7.14 Hz, 2H), 2.73 (t, J=6.89 Hz, 2H), 2.17 (s, 3H), 0.85 (s, 9H), 0.01 (s, 3H).

To a solution of 5-(benzyloxy)-1-(4-(2-((tert-butyldimethylsilyl)oxy)ethyl)benzyl)-3-fluoro-2-(4-methoxy-2-methylphenyl)-1H-indole 52-3 (900 mg, 1.477 mmol) in THF (10 mL) was added 1M solution of tetrabutylammonium fluoride in THF (0.58 mL, 0.580 mmol) drop wise at room temperature and stirred for 1 h. After completion of the reaction (monitored by TLC), the reaction mixture was quenched with saturated NaHCO$_3$ solution and extracted with ethyl acetate (3×25 mL). The combined organic layer was dried over anhydrous Na$_2$SO$_4$, filtered and concentrated under reduced pressure. The crude compound was purified by silica gel column chromatography eluting with 0-40% ethyl acetate in n-hexane to afford 600 mg (82% yield) of compound 52-4 as colourless sticky oil.

LCMS-Condition 1: [M+H]$^+$=496.10; Rt=2.39 min $^1$H NMR (400 MHz, DMSO-d$_6$) δ: 7.49-7.53 (m, 2H), 7.35-7.47 (m, 4H), 7.28 (d, J=8.37 Hz, 1H), 7.16 (d, J=1.97 Hz, 1H), 7.06 (d, J=7.88 Hz, 2H), 6.98 (d, J=2.46 Hz, 1H), 6.92 (ddd, J=2.46, 5.66, 8.61 Hz, 2H), 6.73 (d, J=7.88 Hz, 2H), 5.79-5.80 (m, 2H), 5.18 (s, 2H), 4.59 (t, J=5.17 Hz, 1H), 3.83 (s, 3H), 3.50-3.58 (m, 2H), 2.64 (t, J=6.89 Hz, 2H), 2.12 (s, 3H).

To a solution of 2-(4-((5-(benzyloxy)-3-fluoro-2-(4-methoxy-2-methylphenyl)-1H-indol-1-yl)methyl)phenyl)ethan-1-ol 52-4 (600 mg, 1.212 mmol) in CH$_2$Cl$_2$ (10 mL) at 0° C. was added triethylamine (0.5 mL, 3.597 mmol) followed by tosyl chloride (385 mg, 1.816 mmol). The reaction mixture was stirred at room temperature for 18 h. After completion of the reaction (monitored by TLC and LCMS), the reaction mixture was diluted with CH$_2$Cl$_2$ (3×30 mL). The combined organic layer was dried over anhydrous Na$_2$SO$_4$, filtered and concentrated under reduced pressure to afford 600 mg (76% yield) of compound 52-5 as colorless sticky oil.

LCMS-Condition 1: [M+H]$^+$=650.25; Rt=2.59 min $^1$H NMR (400 MHz, DMSO-d$_6$) δ: 7.57 (d, J=8.31 Hz, 2H), 7.45-7.49 (m, 2H), 7.37-7.43 (m, 3H), 7.33 (d, J=6.85 Hz, 1H), 7.26 (dd, J=8.31, 16.63 Hz, 3H), 7.11-7.17 (m, 1H), 6.92-6.96 (m, 3H), 6.85-6.91 (m, 2H), 6.66 (d, J=7.82 Hz, 2H), 5.06-5.15 (m, 4H), 4.13 (t, J=6.60 Hz, 2H), 3.78 (s, 3H), 2.77 (t, J=5.87 Hz, 2H), 2.34 (s, 3H), 2.06 (s, 3H).

To a solution of 4-((5-(benzyloxy)-3-fluoro-2-(4-methoxy-2-methylphenyl)-1H-indol-1-yl)methyl)phenethyl 4-methylbenzenesulfonate 52-5 (300 mg, 0.461 mmol) in acetonitrile (3 mL) was added DIPEA (0.7 mL, 3.736 mmol) and cyclopropyl amine (0.26 mL, 4.61 mmol) at room temperature in a sealed tube. The reaction mixture was stirred at room temperature for 72 h. After completion of the reaction (monitored by TLC and LCMS), the reaction mixture was concentrated under reduced pressure, washed with ethyl acetate (2×15 mL). The combined organic layer was dried over anhydrous Na$_2$SO$_4$, filtered and concentrated under reduced pressure. The crude compound was purified by silica gel column chromatography eluting with 0-10% methanol in CH$_2$Cl$_2$ to afford 180 mg (73% yield) of compound 52-6 as colourless oil.

LCMS-Condition 1: [M+H]$^+$=535.25; Rt=1.87 min $^1$H NMR (400 MHz, DMSO-d$_6$) δ: 7.44-7.49 (m, 2H), 7.36-7.43 (m, 3H), 7.31-7.35 (m, 1H), 7.23 (d, J=7.83 Hz, 1H), 7.11 (br. s, 1H), 7.01 (d, J=7.34 Hz, 2H), 6.84-6.93 (m, 3H), 6.68 (d, J=7.83 Hz, 2H), 5.14 (s, 2H), 5.03-5.13 (m, 2H), 3.79 (s, 3H), 2.67-2.72 (m, 2H), 2.54-2.61 (m, 2H), 2.04 (s, 3H), 2.04-2.07 (m, 1H), 1.23 (br. s, 1H), 0.28-0.35 (m, 2H), 0.12-0.19 (m, 2H).

To a solution of N-(4-((5-(benzyloxy)-3-fluoro-2-(4-methoxy-2-methylphenyl)-1H-indol-1-yl)methyl)phenethyl)cyclopropanamine 52-6 (140 mg, 0.261 mmol) in DCM (14 mL) at 0° C. was added BBr$_3$ (130 mg, 0.520 mmol) drop wise. The reaction mixture was stirred at the same temperature for 30 min. After completion of the reaction (monitored by TLC and LCMS), the reaction mixture was quenched with saturated sodium bicarbonate solution and extracted with DCM (3×15 mL). The combined organic layer was dried over anhydrous Na$_2$SO$_4$, filtered and concentrated under reduced pressure. The crude compound was purified by preparative HPLC to afford 10 mg (10% yield) of D-52 as off white solid.

LCMS-Condition 1: [M+H]$^+$=431.25; Rt=1.41 min $^1$H NMR (400 MHz, DMSO-d$_6$) δ: δ 9.63 (s, 1H), 8.98 (s, 1H), 7.24 (d, J=9.29 Hz, 1H), 7.09 (d, J=7.82 Hz, 1H), 7.01 (d, J=7.34 Hz, 2H), 6.81 (s, 1H), 6.64-6.74 (m, 5H), 4.96-5.10 (m, 2H), 2.66-2.74 (m, 2H), 2.57-2.62 (m, 2H), 2.00-2.07 (m, 1H), 1.98 (s, 3H), 1.07-1.98 (m, 1H), 0.09-0.19 (m, 4H).

3-Fluoro-1-(4-(2-((2-fluoroethyl)amino)ethyl)benzyl)-2-(4-methoxy-2-methylphenyl)-1H-indol-5-ol (D-103)

To 5-(benzyloxy)-3-fluoro-2-(4-methoxy-2-methylphenyl)-1H-indole 52-2 (2 g, 5.540 mmol) in DMF (15 mL) at 0° C. was added 60% dispersion sodium hydride in oil (1.1 g, 27.66 mmol) portionwise. The reaction mixture was further stirred at 0° C. for 30 min. To the resulting solution was added (4-(bromomethyl)phenethoxy)(tert-butyl)dimethylsilane (2.18 g, 6.643 mmol). The reaction mixture was stirred at room temperature for 2 h. After completion of the reaction, the reaction mixture was quenched with ice cold water and extracted with ethyl acetate (3×25 mL). The combined organic layer dried over anhydrous Na$_2$SO$_4$, filtered and concentrated under reduced pressure. The crude compound was purified by silica gel column chromatography eluting with 0-30% ethyl acetate in n-hexane to afford 2 g (60% yield) of compound 103-7 as thick yellow oil.

LCMS-Condition-1: [M+H]$^+$=610.25; Rt=3.14 min $^1$H NMR (400 MHz, DMSO-d$_6$) δ: 7.45-7.49 (m, 2H), 7.39 (t, J=7.34 Hz, 2H), 7.31-7.36 (m, 2H), 7.22 (d, J=8.31 Hz, 1H), 7.11 (d, J=2.45 Hz, 1H), 7.03 (d, J=7.83 Hz, 2H), 6.93 (d, J=2.45 Hz, 1H), 6.86 (ddd, J=2.45, 5.75, 8.44 Hz, 2H), 6.69 (d, J=7.83 Hz, 2H), 5.14 (s, 2H), 3.79 (s, 2H), 3.67 (t, J=6.60 Hz, 2H), 2.63 (t, J=6.85 Hz, 2H), 2.06-2.10 (m, 3H), 1.99 (s, 3H), 0.77 (s, 9H), −0.12 (s, 6H).

To 5-(benzyloxy)-1-(4-(2-((tert-butyldimethylsilyl)oxy)ethyl)benzyl)-3-fluoro-2-(4-methoxy-2-methylphenyl)-1H-indole 103-7 (2.5 g, 4.099 mmol) in THF (30 mL) at 0° C. was added 1M solution of tetrabutylammonium fluoride in THF (6.1 mL, 6.149 mmol) dropwise at room temperature and stirred for 2 h. After completion of the reaction, the reaction mixture was diluted with water and extracted with ethyl acetate (3×50 mL). The combined organic layer dried over anhydrous Na$_2$SO$_4$, filtered and concentrated under reduced pressure. The crude compound was purified by silica gel column chromatography eluting with 0-30% ethyl acetate in n-hexane to afford 2 g (98% yield) of compound 103-8 as brown sticky solid.

LCMS-Condition-1: [M+H]$^+$=496.20; Rt=2.49 min $^1$H NMR (400 MHz, DMSO-d$_6$) δ: 7.45-7.49 (m, 2H), 7.32-7.42 (m, 4H), 7.24 (d, J=8.31 Hz, 1H), 7.12 (d, J=2.45 Hz, 1H), 7.02 (d, J=8.31 Hz, 2H), 6.94 (d, J=2.45 Hz, 1H), 6.85-6.91 (m, 2H), 6.69 (d, J=8.31 Hz, 2H), 5.14 (s, 2H), 4.56 (t, J=5.38 Hz, 1H), 3.79 (s, 3H), 3.46-3.52 (m, 2H), 2.60 (t, J=7.09 Hz, 2H), 2.07 (s, 3H), 1.99 (s, 2H).

To 2-(4-((5-(benzyloxy)-3-fluoro-2-(4-methoxy-2-methylphenyl)-1H-indol-1-yl)methyl)phenyl)ethan-1-ol 103-8 (2 g, 4.036 mmol) in CH$_2$Cl$_2$ (30 mL) at 0° C. was added triethylamine (1.6 mL, 12.12 mmol) followed by tosyl chloride (928 mg, 4.845 mmol). The reaction mixture was stirred at room temperature for 12 h. After completion of the reaction, the reaction mixture was diluted with water and extracted with CH$_2$Cl$_2$ (3×30 mL). The combined organic layer dried over anhydrous Na$_2$SO$_4$, filtered and concentrated under reduced pressure. The crude compound was purified by silica gel column chromatography eluting with 0-10% ethyl acetate in n-hexane to afford to afford 2.4 g (90% yield) of compound 103-9 as white sticky solid.

LCMS-Condition-1: [M+H]$^+$=650.80; Rt=2.50 min $^1$H NMR (400 MHz, DMSO-d$_6$) δ: 7.66 (d, J=8.31 Hz, 2H), 7.54-7.58 (m, 2H), 7.46-7.51 (m, 3H), 7.42 (d, J=6.85 Hz, 1H), 7.36 (d, J=7.83 Hz, 2H), 7.32 (d, J=8.80 Hz, 1H), 7.22 (d, J=2.45 Hz, 1H), 7.01-7.05 (m, 3H), 6.94-7.01 (m, 2H), 6.75 (d, J=7.83 Hz, 2H), 5.22-5.25 (m, 2H), 4.22 (t, J=6.36 Hz, 2H), 3.87 (s, 3H), 3.41 (s, 3H), 2.86 (t, J=6.36 Hz, 2H), 2.43 (s, 3H), 2.15 (s, 2H).

To 4-((5-(benzyloxy)-3-fluoro-2-(4-methoxy-2-methylphenyl)-1H-indol-1-yl)methyl)phenethyl 4-methylbenzenesulfonate 103-9 (1.5 g, 2.309 mmol) in DMF (5 mL) was added potassium pthalimide (512 mg, 2.771 mmol) at room temperature. The reaction mixture was further heated to 80° C. and stirred for 3 h. After completion of the reaction, the reaction mixture was diluted with water and extracted with ethyl acetate (3×50 mL). The combined organic layer dried over anhydrous Na$_2$SO$_4$, filtered and concentrated under reduced pressure. The crude compound was purified by silica gel column chromatography eluting with 0-10% ethyl acetate in n-hexane to afford 1.4 g (98% yield) of compound 103-10 as pale brown solid.

LCMS-Condition-1: [M+H]$^+$=625.10; Rt=2.47 min $^1$H NMR (400 MHz, DMSO-d$_6$) δ: 7.80-7.85 (m, 4H), 7.45-7.50 (m, 2H), 7.40 (t, J=7.34 Hz, 2H), 7.31-7.37 (m, 2H), 7.16 (d, J=8.31 Hz, 1H), 7.11 (d, J=2.45 Hz, 1H), 7.02 (d, J=8.31 Hz, 2H), 6.86-6.91 (m, 2H), 6.82-6.85 (m, 1H), 6.66 (d, J=7.83 Hz, 2H), 5.15 (s, 2H), 5.03-5.10 (m, 2H), 3.79 (s, 3H), 3.73 (t, J=7.34 Hz, 2H), 2.83 (t, J=7.09 Hz, 2H), 1.99 (s, 3H).

To 2-(4-((5-(benzyloxy)-3-fluoro-2-(4-methoxy-2-methylphenyl)-1H-indol-1-yl)methyl)phenethyl)isoindoline-1,3-dione 103-10 (1.4 g, 2.241 mmol) in ethanol (15 mL) was added hydrazine hydrate (112 mg, 2.241 mmol) at room temperature. The reaction mixture was further heated to 80° C. and stirred for 4 h. After completion of the reaction, the reaction mixture was filtered, washed with DCM (50 mL) and the filtrate was concentrated under reduced pressure. The resulting crude compound was purified by silica gel column chromatography eluting with 0-3% methanol in DCM to afford 828 mg (73% yield) of compound 103-11 as white solid.

LCMS-Condition-1: [M+H]$^+$=495.25; Rt=1.70 min $^1$H NMR (400 MHz, DMSO-d$_6$) δ: 8.07 (dd, J=3.18, 5.62 Hz, 1H), 7.88 (dd, J=3.42, 5.87 Hz, 1H), 7.45-7.50 (m, 2H), 7.30-7.43 (m, 4H), 7.24 (d, J=8.31 Hz, 1H), 7.12 (d, J=2.45 Hz, 1H), 7.02 (d, J=7.83 Hz, 2H), 6.94 (d, J=2.45 Hz, 1H), 6.88 (dt, J=2.69, 8.44 Hz, 2H), 6.70 (d, J=7.83 Hz, 2H), 5.15 (s, 2H), 5.06-5.12 (m, 2H), 3.79 (s, 3H), 2.69-2.75 (m, 2H), 2.56 (t, J=7.34 Hz, 2H), 2.06 (s, 3H).

To 2-(4-((5-(benzyloxy)-3-fluoro-2-(4-methoxy-2-methylphenyl)-1H-indol-1-yl)methyl)phenyl)ethan-1-amine 103-11 (300 mg, 0.606 mmol) in acetonitrile (4 mL) was added potassium carbonate (83.7 mg, 0.606 mmol) and 1-fluoro-2-iodoethane (105 mg, 0.606 mmol) and in a seal tube. The reaction mixture was further stirred at room temperature for 24 h. After completion of the reaction, the reaction mixture was diluted with water and extracted with ethyl acetate (2×10 mL). The combined organic layer dried over anhydrous Na$_2$SO$_4$, filtered and concentrated under reduced pressure. The crude compound was purified by silica gel column chromatography eluting with 0-3% methanol in DCM to afford 250 mg (76% yield) of compound 103-12 as colorless sticky solid.

LCMS-Condition-1: [M+H]$^+$=541.35; Rt=1.73 min

To N-(4-((5-(benzyloxy)-3-fluoro-2-(4-methoxy-2-methylphenyl)-1H-indol-1-yl)methyl)phenethyl)-2-fluoroethan-1-amine 103-12 (250 mg, 0.455 mmol) in ethyl acetate: methanol (1:1; 10 mL) was added 20% palladium hydroxide on carbon (75 mg, 20% w/w) at room temperature. The reaction mixture was further stirred under hydrogen atmosphere for 1 h. After completion of the reaction, the reaction mixture was filtered through pad of a Celite™ and washed with ethyl acetate. The filtrate was concentrated under reduced pressure and the crude compound was purified by preparative HPLC to afford 20 mg (9.6% yield) of D-103 as off white solid.

LCMS-Condition-1: [M+H]$^+$=451.25; Rt=1.54 min $^1$H NMR (400 MHz, DMSO-d$_6$) δ: 9.01 (s, 1H), 7.24-7.27 (m, 1H), 7.22 (d, J=8.31 Hz, 1H), 7.02 (d, J=8.31 Hz, 2H), 6.92 (d, J=2.45 Hz, 1H), 6.86 (dd, J=2.45, 8.31 Hz, 1H), 6.82 (d, J=2.45 Hz, 1H), 6.65-6.70 (m, 3H), 4.97-5.12 (m, 2H), 4.47 (t, J=5.14 Hz, 1H), 4.35 (t, J=5.14 Hz, 1H), 3.78 (s, 3H), 2.79 (t, J=5.14 Hz, 1H), 2.72 (t, J=5.14 Hz, 1H), 2.65-2.70 (m, 2H), 2.55-2.61 (m, 2H), 2.06 (s, 3H).

3-Fluoro-1-(4-(2-((3-fluoropropyl)amino)ethyl)benzyl)-2-(4-methoxy-2-methylphenyl)-1H-indol-5-ol
(D-104)

To a solution of 2-(4-((5-(benzyloxy)-3-fluoro-2-(4-methoxy-2-methylphenyl)-1H-indol-1-yl)methyl)phenyl)ethan-1-amine 103-11 (300 mg, 0.606 mmol) in acetonitrile (4 mL) was added potassium carbonate (83.7 mg, 0.606 mmol) and 1-fluoro-3-iodopropane (114 mg, 0.606 mmol) in a sealed tube. The reaction mixture was stirred at room temperature for 24 h. After completion of the reaction (monitored by TLC and LCMS), the reaction mixture was diluted with water and extracted with ethyl acetate (2×10 mL). The combined organic layer was dried over anhydrous Na$_2$SO$_4$, filtered and concentrated under reduced pressure. The crude compound was purified by silica gel column chromatography eluting with 0-3% methanol in DCM to afford 250 mg (74% yield) of compound 104-12 as colourless sticky solid.

LCMS-Condition-1: [M+H]$^+$=555.25; Rt=1.76 min $^1$H NMR (400 MHz, DMSO-d$_6$) δ: 7.46-7.49 (m, 2H), 7.32-7.42 (m, 4H), 7.24 (d, J=8.31 Hz, 1H), 7.12 (d, J=2.45 Hz, 1H), 7.03 (d, J=7.83 Hz, 2H), 6.94 (d, J=2.45 Hz, 1H), 6.85-6.91 (m, 2H), 6.70 (d, J=8.31 Hz, 2H), 5.02-5.14 (m, 4H), 4.51 (t, J=6.11 Hz, 1H), 4.39 (t, J=5.87 Hz, 1H), 3.79 (s, 3H), 2.58-2.73 (m, 6H), 2.06 (s, 3H), 1.70-1.83 (m, 2H).

To a solution of N-(4-((5-(benzyloxy)-3-fluoro-2-(4-methoxy-2-methylphenyl)-1H-indol-1-yl)methyl)phenethyl)-3-fluoropropan-1-amine 104-12 (250 mg, 0.458 mmol) in ethyl acetate:methanol (1:1; 10 mL) was added 20% palladium hydroxide on carbon (75 mg, 20% w/w) at room temperature. The reaction mixture was stirred under hydrogen atmosphere for 12 h. After completion of the reaction (monitored by TLC and LCMS), the reaction mixture was filtered through a pad of Celite™ and washed with methanol. The filtrate was concentrated under reduced pressure and the crude compound was purified by preparative HPLC to afford 50 mg (23% yield) of D-104 as off white solid.

LCMS-Condition-1: [M+H]$^+$=465.25; Rt=1.88 min $^1$H NMR (400 MHz, DMSO-d$_6$) δ: 9.01 (s, 1H), 7.24-7.27 (m, 1H), 7.22 (d, J=8.31 Hz, 1H), 7.01 (d, J=8.31 Hz, 2H), 6.92 (d, J=2.45 Hz, 1H), 6.86 (dd, J=2.69, 8.56 Hz, 1H), 6.82 (d, J=1.96 Hz, 1H), 6.69 (d, J=1.47 Hz, 1H), 6.65-6.68 (m, 2H), 4.97-5.09 (m, 2H), 4.50 (t, J=6.11 Hz, 1H), 4.38 (t, J=5.87 Hz, 1H), 3.78 (s, 3H), 2.53-2.64 (m, 6H), 2.06 (s, 3H), 1.64-1.78 (m, 2H).

1-(4-(2-(Cyclopropylamino)ethyl)benzyl)-3-fluoro-2-(4-fluoro-2-methylphenyl)-1H-indol-5-ol (D-36)

To 4-(benzyloxy)-2-(2,2-dibromovinyl)aniline D-13-3 (15 g, 39.16 mmol) in toluene (60 mL) was added 2-methyl-4-fluoro-phenyl boronic acid (7.2 g, 46.96 mmol), Na$_2$CO$_3$ (12.4 g, 117.4 mmol) at room temperature and degassed with argon for 10 min. To the resulting solution was added Pd(PPh$_3$)$_4$ (2.25 g, 1.950 mmol) and degassed with argon for another 10 min. The reaction mixture was further heated to 90° C. and stirred for 18 h. After completion of the reaction, the reaction mixture was diluted with water and extracted with ethyl acetate (thrice). The combined organic layer dried over anhydrous Na$_2$SO$_4$, filtered and concentrated under reduced pressure. The resulting crude compound was purified by silica gel column chromatography eluting with 0-8% ethyl acetate in n-hexane to afford 5 g (38% yield) of compound 36-1 as brown solid LCMS: [M+H]$^+$=333.35; Rt=2.29 min $^1$H NMR (400 MHz, DMSO-d$_6$) δ: 11.13 (br. s, 1H), 7.50-7.56 (m, 1H), 7.45-7.50 (m, 2H), 7.39 (t, J=7.34 Hz, 2H), 7.26-7.34 (m, 2H), 7.20 (d, J=10.27 Hz, 1H), 7.13 (br. s, 2H), 6.83 (d, J=8.80 Hz, 1H), 6.46 (s, 1H), 5.11 (s, 2H), 2.45 (s, 3H).

To a solution of 5-(benzyloxy)-2-(4-fluoro-2-methylphenyl)-1H-indole 36-1 (10 g, 30.21 mmol) in dry acetonitrile: DMSO (3:2; 80 mL) at −10° C. was added selectfluor (10.6 g, 30.16 mmol) under argon atmosphere. The reaction mixture was allowed to attain room temperature and stirred for 4 h. After completion of the reaction, the reaction mixture was the reaction mixture was quenched with water and extracted with ethyl acetate (3×20 mL). The combined organic layer dried over anhydrous Na$_2$SO$_4$, filtered and concentrated under reduced pressure. The resulting crude compound was purified by silica gel column chromatography eluting with 0-5% ethyl acetate in n-hexane to afford 1 g (9.5% yield) of compound 36-2 as brown solid.

LCMS: [M+H]$^+$=350.30; Rt=2.30 min $^1$H NMR (400 MHz, DMSO-d$_6$) δ: 11.01 (br. s, 1H), 7.49-7.55 (m, 3H), 7.44 (t, J=7.34 Hz, 2H), 7.37 (d, J=7.34 Hz, 1H), 7.30 (t, J=9.29 Hz, 1H), 7.21 (t, J=8.56 Hz, 1H), 7.13 (s, 1H), 6.94 (d, J=8.80 Hz, 1H), 5.18 (s, 2H), 2.39 (s, 3H).

To a solution of 5-(benzyloxy)-3-fluoro-2-(4-fluoro-2-methylphenyl)-1H-indole 36-2 (400 mg, 1.136 mmol) in DMF (10 mL) at 0° C. was added sodium hydride (60% dispersion in oil, 82 mg, 3.410 mmol) portionwise and stirred for 30 min. To the resulting solution was added (4-(bromomethyl)phenethoxy)(tert-butyl)dimethylsilane (487 mg, 1.478 mmol). Then the reaction mixture was stirred at room temperature for 18 h. After completion of the reaction (monitored by TLC and LCMS), the reaction mixture was quenched with ice cold water and extracted with ethyl acetate (3×15 mL). The combined organic layer was washed with brine, dried over anhydrous Na$_2$SO$_4$, filtered and concentrated under reduced pressure. The crude compound was purified by silica gel column chromatography eluting with 0-4% ethyl acetate in n-hexane to afford 550 mg (92% yield) of compound 36-3 as yellowish oil.

LCMS-Condition 01: [M-18]$^+$=580.30; Rt=2.87 min $^1$H NMR (400 MHz, CDCl$_3$) δ: 7.48 (d, J=7.34 Hz, 2H), 7.37-7.43 (m, 2H), 7.32-7.36 (m, 1H), 7.10-7.21 (m, 4H), 7.02 (d, J=8.07 Hz, 2H), 6.84-6.95 (m, 2H), 6.74 (d, J=8.07 Hz, 2H), 5.13 (m, 2H), 4.95-5.09 (m, 2H), 3.72 (t, J=6.91 Hz, 2H), 2.73 (t, J=6.85 Hz, 2H), 2.15 (s, 3H), 0.87 (s, 9H), 0.00 (s, 6H).

To a solution of 5-(benzyloxy)-1-(4-(2-((tert-butyldimethylsilyl)oxy)ethyl)benzyl)-3-fluoro-2-(4-fluoro-2-methylphenyl)-1H-indole 36-3 (550 mg, 0.920 mmol) in THF (10 mL) at 0° C. was added TBAF (361 mg, 1.380 mmol). The reaction mixture was then stirred at room temperature for 1 h. After completion of the reaction (monitored by TLC and LCMS), the reaction mixture was quenched with ice cold water and extracted with ethyl acetate (3×20 mL). The combined organic layer was washed with water (20 mL) and brine (20 mL) dried over anhydrous Na$_2$SO$_4$, filtered and concentrated under reduced pressure. The compound was purified by silica gel column chromatography eluting with 0-50% ethyl acetate in n-hexane to afford 500 mg crude of compound 36-4 as yellowish oil.

LCMS-Condition 01: [M-18]$^+$=466.05; Rt=2.33 min $^1$H NMR (400 MHz, CDCl$_3$) δ: 7.47-7.50 (m, 2H), 7.28-7.43 (m, 3H), 7.18-7.23 (m, 1H), 7.17 (d, J=2.45 Hz, 1H), 7.12-7.15 (m, 1H), 7.05 (d, J=8.31 Hz, 2H), 6.89-7.02 (m, 3H), 6.77 (d, J=7.83 Hz, 2H), 5.14 (s, 2H), 4.97-5.13 (m, 2H), 3.77-3.82 (m, 2H), 2.79 (t, J=6.60 Hz, 2H), 2.14 (s, 3H).

To a solution of 2-(4-((5-(benzyloxy)-3-fluoro-2-(4-fluoro-2-methylphenyl)-1H-indol-1-yl)methyl)phenyl)ethan-1-ol 36-4 (500 mg, 1.033 mmol) in CH$_2$Cl$_2$ (10 mL) at 0° C. was added triethylamine (0.43 mL, 3.102 mmol) followed by p-TsCl (256 mg, 1.344 mmol) and the reaction mixture was stirred at room temperature for 2 h. After completion of the reaction (monitored by TLC and LCMS), the reaction mixture was diluted with water (30 mL) and extracted with DCM (3×20 mL). The combined organic layer was washed with saturated sodium bicarbonate solution (20 mL), dried over anhydrous Na$_2$SO$_4$, filtered and concentrated under reduced pressure to afford 500 mg (76% yield) of compound 36-5 as yellow solid.

LCMS-Condition 01: [M+H]$^+$=638.20; Rt=2.51 min $^1$H NMR (400 MHz, CDCl$_3$) δ: 7.63-7.72 (m, 2H), 7.48 (d, J=7.34 Hz, 2H), 7.37-7.43 (m, 2H), 7.23 (d, J=7.83 Hz, 2H), 7.08-7.20 (m, 4H), 6.97-7.02 (m, 1H), 6.91-6.96 (m, 4H), 6.68-6.75 (m, 2H), 5.13 (s, 2H), 4.94-5.08 (s, 2H), 4.13 (t, J=7.09 Hz, 2H), 2.87 (t, J=6.85 Hz, 2H), 2.40 (s, 3H), 2.13 (s, 3H).

To a solution of 4-((5-(benzyloxy)-3-fluoro-2-(4-fluoro-2-methylphenyl)-1H-indol-1-yl)methyl)phenethyl 4-methylbenzenesulfonate 36-5 (250 mg, 0.392 mmol) in acetonitrile (1 mL) was added cyclopropanamine (224 mg, 3.920 mmol) and DIPEA (0.68 mL, 3.920 mmol) in a sealed tube. The reaction mixture was then stirred at room temperature for 72 h. After completion of the reaction (monitored by TLC and LCMS), the reaction mixture was concentrated under reduced pressure and diluted with ethyl acetate. The separated organic layer was dried over anhydrous $Na_2SO_4$, filtered and concentrated under reduced pressure. The crude compound was purified by silica gel column chromatography eluting with 0-50% ethyl acetate in n-hexane to afford 160 mg (78% yield) of compound 36-6 as off white solid.

LCMS-Condition 01: $[M+H]^+=523.20$; Rt=1.85 min $^1$H NMR (400 MHz, $CDCl_3$) δ: 7.49 (d, J=7.34 Hz, 2H), 7.38-7.43 (m, 2H), 7.30-7.36 (m, 1H), 7.14-7.22 (m, 3H), 7.03 (d, J=7.83 Hz, 2H), 6.87-7.01 (m, 3H), 6.74 (d, J=7.80 Hz, 2H), 5.14 (s, 2H), 4.97-5.09 (m, 2H), 2.86-2.92 (m, 2H), 2.70-2.76 (m, 2H), 2.14 (s, 3H), 2.07-2.11 (m, 1H), 0.40-0.48 (m, 2H), 0.30-0.39 (m, 2H).

To a solution of N-(4-((5-(benzyloxy)-3-fluoro-2-(4-fluoro-2-methylphenyl)-1H-indol-1-yl)methyl)phenethyl) cyclopropanamine 36-6 (160 mg, 0.3061 mmol) in ethyl acetate (5 mL) was added 20% palladium hydroxide on carbon (40 mg) at room temperature. Then the reaction mixture was stirred under hydrogen atmosphere for 18 h. After completion of the reaction (monitored by TLC and LCMS), the reaction mixture was filtered through pad of a Celite™ and washed with ethyl acetate. The filtrate was concentrated under reduced pressure and the crude compound was purified by preparative HPLC to afford 28 mg (21% yield) of D-36 as white solid.

LCMS-Condition 01: $[M+H]^+=433.10$; Rt=1.54 min $^1$H NMR (400 MHz, $CDCl_3$) δ: 7.18 (dd, J=6.11, 8.07 Hz, 1H), 7.06-7.11 (m, 1H), 6.96-7.04 (m, 4H), 6.87-6.94 (m, 1H), 6.70-6.78 (m, 3H), 4.93-5.07 (m, 2H), 2.89-2.95 (m, 2H), 2.70-2.76 (m, 2H), 2.12 (s, 3H), 0.81-0.92 (m, 1H), 0.44 (d, J=6.36 Hz, 2H), 0.35-0.41 (m, 2H).

3-Fluoro-2-(4-methoxy-2-methylphenyl)-1-(4-(2-(propylamino)ethyl)benzyl)-1H-indol-5-ol (D-96)

To 4-(benzyloxy)-2-(2,2-dibromovinyl)aniline 13-3 (10 g, 26.10 mmol) in toluene:ethanol (60:20 mL) was added (4-methoxy-2-methylphenyl)boronic acid (5.6 g, 33.94 mmol) and solution of $Na_2CO_3$ (8.3 g, 78.32 mmol) simultaneously at room temperature under argon atmosphere and degassed for 30 min. To the resulting solution was added catalyst Pd(PPh$_3$)$_4$ (1.5 g, 1.305 mmol) and degassed with argon for another 10 min at room temperature. The reaction mixture was further heated to 90° C. and stirred for 18 h. After completion of the reaction, the reaction mixture was diluted with water and extracted with ethyl acetate (3×50 mL). The combined organic layer dried over anhydrous $Na_2SO_4$, filtered and concentrated under reduced pressure. The resulting crude compound was purified by silica gel column chromatography eluting with 0-20% ethyl acetate in n-hexane to afford 3 g (33% yield) of compound 96- as yellow solid.

LCMS-Condition-1: $[M+H]^+=344.15$; Rt=2.24 min $^1$H NMR (400 MHz, DMSO-$d_6$) δ: 11.01 (br. s, 1H), 7.44-7.49 (m, 2H), 7.42 (d, J=6.36 Hz, 1H), 7.36-7.40 (m, 2H), 7.32 (d, J=7.34 Hz, 1H), 7.26 (d, J=8.80 Hz, 1H), 7.10 (s, 1H), 6.90 (s, 1H), 6.87 (d, J=9.29 Hz, 1H), 6.77-6.82 (m, 1H), 6.38 (s, 1H), 5.10 (s, 2H), 3.79 (s, 3H), 2.43 (s, 3H).

To 5-(benzyloxy)-2-(4-methoxy-2-methylphenyl)-1H-indole 96-1 (2.5 g, 7.288 mmol) in dry Acetonitrile:DMSO (15:5 mL) at −10° C. was added selectfluor (2.58 g, 7.288 mmol) under argon atmosphere. The reaction mixture was further stirred at room temperature for 4 h. After completion of the reaction, the reaction mixture was diluted with water and extracted with ethyl acetate (3×50 mL). The combined organic layer dried over anhydrous $Na_2SO_4$, filtered and concentrated under reduced pressure. The resulting crude compound was purified by silica gel column chromatography eluting with 0-5% ethyl acetate in n-hexane to afford 1.2 g (46% yield) of compound 96-2 as brown solid.

LCMS-Condition-1: $[M-18]^+=344.05$; Rt=2.23 min $^1$H NMR (400 MHz, DMSO-$d_6$) δ: 10.85 (s, 1H), 7.48 (d, J=7.34 Hz, 2H), 7.40 (t, J=7.58 Hz, 2H), 7.34 (d, J=8.31 Hz, 2H), 7.25 (dd, J=2.20, 9.05 Hz, 1H), 7.07 (d, J=1.96 Hz, 1H), 6.94 (s, 1H), 6.88 (ddd, J=2.20, 9.05, 11.74 Hz, 2H), 5.14 (s, 2H), 3.80 (s, 3H), 2.32 (s, 3H).

To 5-(benzyloxy)-3-fluoro-2-(4-methoxy-2-methylphenyl)-1H-indole 96-2 (400 mg, 1.108 mmol) in DMF (mL) at 0° C. was added 60% dispersion sodium hydride in oil (110 mg, 2.770 mmol) portionwise. The reaction mixture was further stirred at 0° C. for 30 min. To the resulting solution was added tert-butyl(4-(bromomethyl)phenethoxy)dimethylsilane (436 mg, 1.329 mmol). The reaction mixture was stirred at room temperature for 3 h. After completion of the reaction, the reaction mixture was quenched with ice cold water and extracted with ethyl acetate (3×25 mL). The combined organic layer dried over anhydrous $Na_2SO_4$, filtered and concentrated under reduced pressure. The crude compound was purified by silica gel column chromatography eluting with 0-8% ethyl acetate in n-hexane to afford _____ mg (crude) of compound 96-3 as thick oil.

LCMS-Condition-1: $[M+Na]^+=633.25$; Rt=3.05 min $^1$H NMR (400 MHz, DMSO-$d_6$) δ: 7.42-7.47 (m, 2H), 7.37 (t, J=7.34 Hz, 2H), 7.30-7.34 (m, 2H), 7.18-7.23 (m, 1H), 7.10 (d, J=2.45 Hz, 1H), 7.01 (d, J=7.82 Hz, 2H), 6.92 (d, J=2.45 Hz, 1H), 6.81-6.87 (m, 2H), 6.68 (d, J=7.82 Hz, 2H), 5.10-5.13 (m, 2H), 4.98-5.09 (m, 2H), 3.77 (s, 3H), 3.65 (t, J=6.85 Hz, 2H), 2.61 (t, J=6.60 Hz, 2H), 2.06 (s, 3H), 0.74-0.78 (m, 9H), −0.13 (s, 6H)

To 5-(benzyloxy)-1-(4-(2-((tert-butyldimethylsilyl)oxy)ethyl)benzyl)-3-fluoro-2-(4-methoxy-2-methylphenyl)-1H-indole 96-3 (400 mg, 0.656 mmol) in THF (3 mL) at 0° C. was added 1M solution of tetrabutylammonium fluoride in THF (0.98 mL, 0.985 mmol) dropwise. The reaction mixture was further stirred at room temperature for 2 h. After completion of the reaction, the reaction mixture was quenched with water and extracted with ethyl acetate. The separated organic layer was dried over anhydrous $Na_2SO_4$, filtered and concentrated under reduced pressure. The crude compound was purified by silica gel column chromatography eluting with 30% ethyl acetate in n-hexane to afford 280 mg (87% yield) of compound 96-4 as yellowish thick oil.

LCMS-Condition-1: $[M+H]^+=496.25$; Rt=2.40 min $^1$H NMR (400 MHz, DMSO-$d_6$) δ: 7.54-7.59 (m, 2H), 7.41-7.50 (m, 4H), 7.33 (d, J=8.31 Hz, 1H), 7.21 (d, J=2.45 Hz, 1H), 7.11 (d, J=8.31 Hz, 2H), 7.03 (d, J=2.45 Hz, 1H), 6.94-6.99 (m, 2H), 6.78 (d, J=8.31 Hz, 2H), 5.23 (s, 2H), 5.12-5.21 (m, 2H), 4.63-4.68 (m, 1H), 3.88 (s, 3H), 3.58 (dt, J=5.38, 7.09 Hz, 2H), 2.66-2.72 (m, 2H), 2.17 (s, 3H).

To 2-(4-((5-(benzyloxy)-3-fluoro-2-(4-methoxy-2-methylphenyl)-1H-indol-1-yl)methyl)phenyl)ethan-1-ol 96-4 (280 mg, 0.565 mmol) in $CH_2Cl_2$ (3 mL) at 0° C. was added triethylamine (0.23 mL, 1.696 mmol) followed by tosyl chloride (129 mg, 0.678 mmol). The reaction mixture was stirred at room temperature for 18 h. After completion of the reaction, the reaction mixture was diluted with $CH_2Cl_2$ (3×30 mL). The combined organic layer dried over anhydrous $Na_2SO_4$, filtered and concentrated under reduced pressure. The crude compound was purified by silica gel column chromatography eluting with 0-10% ethyl acetate in n-hexane to afford 310 mg (84% yield) of compound 96-5 as off white solid.

LCMS-Condition-1: [M-18]$^+$=632.20; Rt=2.58 min $^1$H NMR (400 MHz, DMSO-d$_6$) δ: 7.66 (d, J=7.83 Hz, 2H), 7.56 (d, J=6.85 Hz, 2H), 7.45-7.52 (m, 3H), 7.42 (d, J=6.85 Hz, 1H), 7.36 (d, J=7.83 Hz, 2H), 7.31-7.35 (m, 1H), 7.22 (d, J=2.45 Hz, 1H), 7.03 (d, J=7.83 Hz, 3H), 6.94-7.01 (m, 2H), 6.75 (d, J=7.83 Hz, 2H), 5.23 (s, 2H), 5.14-5.22 (m, 2H), 4.21 (t, J=6.11 Hz, 2H), 3.87 (s, 3H), 2.83-2.89 (m, 2H), 2.43 (s, 3H), 2.15 (s, 3H).

To 4-((5-(benzyloxy)-3-fluoro-2-(4-methoxy-2-methylphenyl)-1H-indol-1-yl)methyl)phenethyl 4-methylbenzenesulfonate 96-5 (309 mg, 0.476 mmol) in acetonitrile (3 mL) was added DIPEA (0.49 mL, 2.856 mmol) and propyl amine (84.2 mg, 1.428 mmol) and in a seal tube. The reaction mixture was further stirred at room temperature for 72 h. After completion of the reaction, the reaction mixture was concentrated under reduced pressure, was diluted with water and extracted with ethyl acetate (2×10 mL). The combined organic layer dried over anhydrous Na$_2$SO$_4$, filtered and concentrated under reduced pressure. The crude compound was purified by silica gel column chromatography eluting with 0-2% methanol in DCM to afford 210 mg (82% yield) of compound 96-6 as brownish thick oil.

LCMS-Condition-1: [M+H]$^+$=537.30; Rt=1.94 min $^1$H NMR (400 MHz, DMSO-d$_6$) δ: 7.39-7.44 (m, 2H), 7.25-7.37 (m, 4H), 7.17 (d, J=8.31 Hz, 1H), 7.06 (d, J=2.45 Hz, 1H), 6.96 (d, J=7.82 Hz, 2H), 6.87 (d, J=2.45 Hz, 1H), 6.82 (dt, J=2.45, 8.31 Hz, 2H), 6.64 (d, J=8.31 Hz, 2H), 5.08 (s, 2H), 5.03 (d, J=16.14 Hz, 2H), 3.73 (s, 3H), 2.62 (d, J=6.85 Hz, 2H), 2.52-2.57 (m, 2H), 2.00 (s, 3H), 1.27-1.36 (m, 2H), 1.17 (s, 3H), 0.76 (t, J=7.58 Hz, 3H).

To N-(4-((5-(benzyloxy)-3-fluoro-2-(4-methoxy-2-methylphenyl)-1H-indol-1-yl)methyl)phenethyl)propan-1-amine 96-6 (210 mg, 0.391 mmol) in ethyl acetate:methanol (1:1; 3 mL) was added 20% palladium hydroxide on carbon (100 mg) at room temperature. The reaction mixture was further stirred under hydrogen atmosphere for 18 h. After completion of the reaction, the reaction mixture was filtered through pad of a Celite™ and washed with ethyl acetate. The filtrate was concentrated under reduced pressure and the crude compound was purified by preparative HPLC to afford 35 mg (11% yield) of D-96 as off white solid.

LCMS-Condition-1: [M+H]$^+$=447.30; Rt=1.66 min $^1$H NMR (400 MHz, DMSO-d$_6$) δ: 9.01 (br. s, 1H), 7.20-7.28 (m, 2H), 7.01 (d, J=7.83 Hz, 2H), 6.92 (d, J=2.45 Hz, 1H), 6.86 (dd, J=2.45, 8.31 Hz, 1H), 6.82 (d, J=1.96 Hz, 1H), 6.64-6.71 (m, 3H), 4.96-5.11 (m, 2H), 3.78 (s, 3H), 2.55-2.66 (m, 4H), 2.43 (t, J=7.09 Hz, 2H), 2.06 (s, 3H), 1.31-1.40 (m, 2H), 1.23 (s, 1H), 0.81 (t, J=7.34 Hz, 3H).

2-([1,1'-Biphenyl]-2-yl)-3-fluoro-1-(4-(2-(propylamino)ethyl)benzyl)-1H-indol-5-ol (D-66)

To 4-(benzyloxy)-2-(2,2-dibromovinyl)aniline 13-3 (1 g, 2.610 mmol) in toluene:ethanol (5:1, 12 mL) was added [1,1'-biphenyl]-2-ylboronic acid (672 mg, 3.393 mmol) and solution of Na$_2$CO$_3$ (830 mg, 27.830 mmol) in water (2 mL) simultaneously at room temperature under argon atmosphere and degassed with argon for 30 min. To the resulting solution was added Pd(PPh$_3$)$_4$ (150 mg, 0.129 mmol) and degassing was continued for another 10 min. The reaction mixture was then heated to 90° C. and stirred for 18 h. After completion of the reaction (monitored by TLC and LCMS), the reaction mixture was diluted with water and extracted with ethyl acetate (3×50 mL). The combined organic layer was dried over anhydrous Na$_2$SO$_4$, filtered and concentrated under reduced pressure. The crude compound was purified by silica gel column chromatography eluting with 0-8% ethyl acetate in n-hexane to afford 400 mg (40% yield) of compound 66-3 as sticky solid.

LCMS-Condition-1: [M+H]$^+$=376.10; Rt=2.48 min $^1$H NMR (400 MHz, DMSO-d$_6$) δ: 10.99 (br. s, 1H), 7.65 (d, J=7.34 Hz, 1H), 7.40-7.51 (m, 4H), 7.34-7.40 (m, 4H), 7.31 (d, J=3.91 Hz, 4H), 7.22-7.26 (m, 2H), 7.18 (d, J=8.31 Hz, 1H), 6.91 (d, J=1.96 Hz, 1H), 6.74 (dd, J=1.96, 8.80 Hz, 1H), 5.02 (s, 2H).

To 2-([1,1'-biphenyl]-2-yl)-5-(benzyloxy)-1H-indole 66-3 (400 mg, 1.065 mmol) in dry Acetonitrile:DMSO (3:2, 5 mL) at −10° C. was added selectfluor (380 mg, 1.072 mmol) under argon atmosphere. The reaction mixture was then stirred at room temperature for 2 h. After completion of the reaction, the reaction mixture was concentrated under reduced pressure, the residue was dissolved in ethyl acetate (100 mL) and washed with water (40 mL) followed by brine (30 mL). The separated organic layer was dried over anhydrous Na$_2$SO$_4$, filtered and concentrated under reduced pressure. The crude compound was purified by silica gel column chromatography eluting with 0-4% ethyl acetate in n-hexane to afford 362 mg (86% yield) of compound 66-4 as yellow thick oil which was forwarded for the next reaction without further purification.

LCMS-Condition-1: [M-18]$^+$=376.15; Rt=2.48 min

To 2-([1,1'-biphenyl]-2-yl)-5-(benzyloxy)-3-fluoro-1H-indole 66-4 (362 mg, 0.920 mmol) in DMF (5 mL) at 0° C. was added sodium hydride (60% dispersion in oil, 92 mg, 2.300 mmol) portion wise. The reaction mixture was then stirred at 0° C. for 30 min. To the resulting solution was added (4-(bromomethyl)phenethoxy)(tert-butyl)dimethylsilane (454 mg, 1.378 mmol) and the reaction mixture was stirred at room temperature for 4 h. After completion of the reaction (monitored by TLC and LCMS), the reaction mixture was quenched with ice cold water and extracted with ethyl acetate (3×25 mL). The combined organic layer was dried over anhydrous Na$_2$SO$_4$, filtered and concentrated under reduced pressure. The crude compound was purified by silica gel column chromatography eluting with 0-4% ethyl acetate in n-hexane to afford 360 mg (61% yield) of compound 66-5 as pale yellow thick oil.

LCMS-Condition-1: [M-18]$^+$=624.35; Rt=2.90 min $^1$H NMR (400 MHz, CDCl$_3$) δ: 7.45-7.52 (m, 5H), 7.40 (ddd, J=2.22, 4.68, 6.89 Hz, 3H), 7.18-7.22 (m, 5H), 7.14-7.18 (m, 2H), 6.96 (d, J=7.88 Hz, 2H), 6.85-6.91 (m, 1H), 6.77-6.83 (m, 1H), 6.61 (d, J=8.37 Hz, 2H), 5.09 (s, 2H), 4.51 (s, 2H), 3.80 (t, J=7.14 Hz, 2H), 2.83 (t, J=6.89 Hz, 2H), 0.88 (s, 9H), 0.85 (s, 6H).

To 2-([1,1'-biphenyl]-2-yl)-5-(benzyloxy)-1-(4-(2-((tert-butyldimethylsilyl)oxy)ethyl)benzyl)-3-fluoro-1H-indole 66-5 (360 mg, 0.560 mmol) in THF (4 mL) at 0° C. was added 1M solution of tetrabutylammonium fluoride in THF (0.84 mL, 0.841 mmol) drop wise at room temperature and stirred for 3 h. After completion of the reaction, the reaction mixture was quenched with ice cold water and extracted with ethyl acetate (3×25 mL). The combined organic layer was dried over anhydrous Na$_2$SO$_4$, filtered and concentrated under reduced pressure. The crude compound was purified by silica gel column chromatography eluting with 20-30% ethyl acetate in n-hexane to afford 168 mg (57% yield) of compound 66-6 as pale brown semi-solid.

LCMS-Condition-1: [M+H]$^+$=528.15; Rt=2.35 min $^1$H NMR (400 MHz, CDCl$_3$) δ: 7.49-7.51 (m, 1H), 7.43-7.49 (m, 4H), 7.36-7.42 (m, 3H), 7.30-7.35 (m, 1H), 7.12-7.22 (m, 5H), 7.10 (d, J=2.42 Hz, 1H), 6.97 (d, J=8.07

Hz, 2H), 6.88-6.92 (m, 1H), 6.76-6.83 (m, 1H), 6.63 (d, J=8.07 Hz, 2H), 5.08 (s, 2H), 4.73 (s, 1H), 4.70 (s, 1H), 3.77 (q, J=5.79 Hz, 2H), 2.73-2.78 (m, 2H).

To 2-(4-((2-([1,1'-biphenyl]-2-yl)-5-(benzyloxy)-3-fluoro-1H-indol-1-yl)methyl)phenyl)ethan-1-ol 66-6 (160 mg, 0.303 mmol) in $CH_2Cl_2$ (3 mL) at 0° C. was added triethylamine (0.17 mL, 1.255 mmol) followed by tosyl chloride (92 mg, 0.480 mmol). The reaction mixture was stirred at room temperature for 16 h. After completion of the reaction, the reaction mixture was diluted water and extracted with $CH_2Cl_2$ (3×30 mL). The combined organic layer dried over anhydrous $Na_2SO_4$, filtered and concentrated under reduced pressure to afford 178 mg (83% yield) of the title compound 66-7 as pale yellow thick oil.

LCMS-Condition-1: [M+H]$^+$=682.20; Rt=2.54 min $^1$H NMR (400 MHz, CDCl$_3$) δ: 7.64 (d, J=8.28 Hz, 2H), 7.37-7.53 (m, 8H), 7.28-7.35 (m, 2H), 7.14-7.23 (m, 7H), 6.78-6.88 (m, 4H), 6.54-6.58 (m, 2H), 5.08 (s, 2H), 4.65-4.70 (m, 2H), 4.06-4.14 (m, 2H), 2.81-2.86 (m, 2H), 2.39 (s, 2H), 2.38 (s, 3H).

To 4-((2-([1,1'-biphenyl]-2-yl)-5-(benzyloxy)-3-fluoro-1H-indol-1-yl)methyl)phenethyl 4-methylbenzenesulfonate 66-7 (175 mg, 0.256 mmol) in acetonitrile (3 mL) was added DIPEA (0.27 mL, 1.539 mmol) and propyl amine (0.06 mL, 0.761 mmol). The reaction mixture was stirred at room temperature for 4 days in a sealed tube. After completion of the reaction, the reaction mixture was concentrated under reduced pressure, washed with ethyl acetate (2×10 mL). The combined organic layer was dried over anhydrous $Na_2SO_4$, filtered and concentrated under reduced pressure. The crude compound was purified by silica gel column chromatography eluting with 0-5% methanol in DCM to afford 131 mg (91% yield) of compound 66-8 as pale yellow solid.

LCMS-Condition-1: [M+H]$^+$=569.30; Rt=1.92 min $^1$H NMR (400 MHz, CDCl$_3$) δ: 7.72 (d, J=8.31 Hz, 1H), 7.31-7.50 (m, 10H), 7.12-7.20 (m, 6H), 6.90 (d, J=8.31 Hz, 2H), 6.57 (d, J=8.31 Hz, 2H), 5.07 (s, 2H), 4.67 (d, J=8.31 Hz, 2H), 2.97 (s, 3H), 2.76-2.82 (m, 2H), 2.31 (s, 2H), 1.72 (qd, J=7.50, 15.16 Hz, 2H), 0.85-0.92 (m, 3H).

To N-(4-((2-([1,1'-biphenyl]-2-yl)-5-(benzyloxy)-3-fluoro-1H-indol-1-yl)methyl)phenethyl)propan-1-amine 66-8 (120 mg, 0.211 mmol) in ethyl acetate:methanol (2:1, 3 mL) was added 20% palladium hydroxide on carbon (40 mg, 20% w/w) at room temperature. The reaction mixture was then stirred under hydrogen atmosphere at room temperature for 3 h. After completion of the reaction, the reaction mixture was filtered through pad of a Celite™ and washed with ethyl acetate. The filtrate was concentrated under reduced pressure and the crude compound was purified by preparative HPLC to afford 36 mg (36% yield) of D-66 as pale brown solid.

LCMS-Condition-1: [M+H]$^+$=479.30; Rt=1.53 min $^1$H NMR (400 MHz, CDCl$_3$) δ: 7.49 (d, J=3.42 Hz, 2H), 7.41-7.46 (m, 1H), 7.36-7.41 (m, 1H), 7.17 (d, J=5.87 Hz, 3H), 7.14 (br. s, 2H), 6.88-6.97 (m, 3H), 6.80 (d, J=7.34 Hz, 1H), 6.56-6.65 (m, 3H), 4.68 (q, J=16.47 Hz, 2H), 2.83-2.90 (m, 2H), 2.71-2.78 (m, 2H), 2.64 (t, J=7.34 Hz, 2H), 1.52 (qd, J=7.34, 14.67 Hz, 2H), 0.87 (t, J=7.34 Hz, 3H)

1-(4-(2-(Ethylamino)ethyl)benzyl)-3-fluoro-2-(o-tolyl)-1H-indol-5-ol (D-29)

To 4-((5-(benzyloxy)-3-fluoro-2-(o-tolyl)-1H-indol-1-yl)methyl)phenethyl 4-methylbenzenesulfonate 28-5 (225 mg, 0.363 mmol) in acetonitrile (5 mL) was added DIPEA (0.63 mL, 3.364 mmol) and 2M solution of ethyl amine in THF (1.8 mL, 164 mg, 3.634 mmol) and in a sealed tube. The reaction mixture was further stirred at room temperature for 72 h. After completion of the reaction, the reaction mixture was concentrated under reduced pressure, and diluted with ethyl acetate. Organic layer was washed with water and brine, dried over anhydrous $Na_2SO_4$, filtered and concentrated under reduced pressure to afford 175 mg (97% yield) of compound 29-1 as off white solid.

LCMS-Condition 01: [M+H]$^+$=493.29; Rt=1.49 min $^1$H NMR (400 MHz, CDCl$_3$) δ: 9.43 (s, 1H), 7.70-7.75 (m, 1H), 7.48 (d, J=7.34 Hz, 1H), 7.39 (t, J=7.09 Hz, 2H), 7.28-7.35 (m, 2H), 7.13-7.25 (m, 3H), 7.05-7.11 (m, 1H), 6.99 (d, J=7.83 Hz, 2H), 6.91 (dd, J=2.45, 8.80 Hz, 1H), 6.69-6.79 (m, 2H), 5.09-5.14 (m, 2H), 4.92-5.06 (m, 2H), 2.98-3.14 (m, 4H), 2.15-2.21 (m, 5H), 1.41 (t, J=7.34 Hz, 3H).

To 2-(4-((5-(benzyloxy)-3-fluoro-2-(o-tolyl)-1H-indol-1-yl)methyl)phenyl)-N-ethylethan-1-amine 29-1 (175 mg, 0.366 mmol) in ethyl acetate:methanol (4:1; 4 mL) was added 20% palladium hydroxide on carbon (35 mg, 20% w/w) at room temperature. The reaction mixture was further stirred under hydrogen atmosphere for 3 h. After completion of the reaction, the reaction mixture was filtered through a pad of Celite™ and washed with ethyl acetate. The filtrate was concentrated under reduced pressure and the crude compound was purified by preparative HPLC to afford 15 mg (11% yield) of D-29 as white solid.

LCMS-Condition 01: [M+H]$^+$=403.24; Rt=1.49 min $^1$H NMR (400 MHz, DMSO-d$_6$) δ: 9.04 (s, 1H), 7.27-7.41 (m, 5H), 7.00 (d, J=7.83 Hz, 2H), 6.84 (d, J=1.96 Hz, 1H), 6.70 (dd, J=2.45, 8.80 Hz, 1H), 6.66 (d, J=7.83 Hz, 2H), 5.00-5.13 (m, 2H), 2.54-2.68 (m, 4H), 2.46-2.49 (m, 2H), 2.08 (s, 3H), 1.22-1.26 (m, 1H), 0.95 (t, J=7.09 Hz, 3H).

1-(4-(2-((Cyclopropylmethyl)amino)ethyl)benzyl)-3-fluoro-2-(o-tolyl)-1H-indol-5-ol (D-39)

To 4-((5-(benzyloxy)-3-fluoro-2-(o-tolyl)-1H-indol-1-yl)methyl)phenethyl 4-methylbenzenesulfonate 28-5 (200 mg, 0.323 mmol) in acetonitrile (4 mL) was added cyclopropylmethanamine (229 mg, 3.230 mmol) and DIPEA (416 mg, mL, 3.230 mmol) in a sealed tube. The reaction mixture was then stirred at room temperature for 72 h. After completion of the reaction, the reaction mixture was concentrated under reduced pressure, diluted with ethyl acetate. Organic layer was washed with water (20 mL), brine (20 mL); dried over anhydrous $Na_2SO_4$, filtered and concentrated under reduced pressure to afford 140 mg (84% yield) of compound 39-1 as colourless thick oil.

LCMS-Condition 01: [M+H]$^+$=519.30; Rt=1.89 min

To 1-(4-(2-((cyclopropylmethyl)amino)ethyl)benzyl)-3-fluoro-2-(o-tolyl)-1H-indol-5-ol 39-1 (140 mg, 0.270 mmol) in ethyl acetate:methanol (1:1; 3 mL) was added 20% palladium hydroxide on carbon (45 mg) at room temperature under nitrogen atmosphere. The reaction mixture was then stirred under hydrogen atmosphere for 2 h. After completion of the reaction, the reaction mixture was filtered through a pad of Celite™ and washed with a mixture of methanol and ethyl acetate. The filtrate was concentrated under reduced pressure and the crude compound was purified by preparative HPLC to afford 22 mg (19% yield) of D-39 as off white solid.

LCMS-Condition 01: [M+H]$^+$=429.55; Rt=1.55 min $^1$H NMR (400 MHz, DMSO-d$_6$) δ: 8.99-9.01 (m, 1H), 7.30-7.37 (m, 2H), 7.24-7.29 (m, 3H), 6.97 (d, J=8.31 Hz, 2H), 6.80 (d, J=1.96 Hz, 1H), 6.67 (dd, J=1.96, 8.80 Hz, 1H), 6.63 (d, J=8.31 Hz, 2H), 5.03 (d, J=8.31 Hz, 2H), 2.60-2.65 (m, 2H), 2.51-2.57 (m, 2H), 2.40-2.43 (m, 1H), 2.31 (d, J=6.36 Hz, 2H), 2.04 (s, 3H), 1.20 (s, 1H), 0.73-0.82 (m, 2H), 0.29-0.35 (m, 2H).

1-(4-(2-(Cyclobutylamino)ethyl)benzyl)-3-fluoro-2-(o-tolyl)-1H-indol-5-ol (D-46)

To 4-((5-(benzyloxy)-3-fluoro-2-(o-tolyl)-1H-indol-1-yl)methyl)phenethyl 4-methylbenzenesulfonate 28-5 (200 mg, 0.323 mmol) in acetonitrile (4 mL) was added cyclobutyl amine (232 mg, 3.230 mmol) and DIPEA (0.56 mL, 3.230 mmol) in a sealed tube. The reaction mixture was then stirred at room temperature for 72 h. After completion of the reaction, the reaction mixture was concentrated under reduced pressure, and diluted with ethyl acetate. Organic layer was washed with water (20 mL), brine (20 mL) and dried over anhydrous $Na_2SO_4$, filtered and concentrated under reduced pressure to afford 150 mg (89% yield) of compound 46-1 as colourless oil which was used in the next reaction without further purification.

LCMS-Condition 01: $[M+H]^+$=519.35; Rt=1.95 min
$^1$H NMR (400 MHz, DMSO-$d_6$) δ: 7.47 (d, J=7.83 Hz, 4H), 7.37-7.43 (m, 4H), 7.29-7.35 (m, 3H), 7.11 (d, J=8.31 Hz, 2H), 7.04 (d, J=7.83 Hz, 2H), 6.91 (dd, J=1.96, 8.80 Hz, 1H), 6.71 (d, J=7.83 Hz, 1H), 5.15 (s, 2H), 5.11 (s, 2H), 2.90 (t, J=6.60 Hz, 2H), 2.67 (dt, J=7.34, 19.07 Hz, 5H), 2.28 (s, 3H), 2.09-2.13 (m, 2H), 0.9-1.2 (m, 2H).

To 1-(4-(2-(cyclobutylamino)ethyl)benzyl)-3-fluoro-2-(o-tolyl)-1H-indol-5-yl benzoate 46-1 (150 mg, 0.289 mmol) in ethyl acetate:methanol (1:1; 3 mL) was added 20% palladium hydroxide on carbon (49 mg, 30% w/w) at room temperature. The reaction mixture was stirred under hydrogen atmosphere for 2 h. After completion of the reaction, the reaction mixture was filtered through a pad of Celite™ and washed with ethyl acetate. The filtrate was concentrated under reduced pressure and the crude compound was purified by preparative HPLC to afford 50 mg (39% yield) of D-46 as brown solid.

LCMS-Condition 01: $[M+H]^+$=429.25; Rt=1.54 min
$^1$H NMR (400 MHz, DMSO-$d_6$) δ: 9.04 (s, 1H), 7.27-7.41 (m, 5H), 7.00 (d, J=7.83 Hz, 2H), 6.84 (d, J=1.96 Hz, 1H), 6.71 (d, J=1.96 Hz, 1H), 6.65-6.70 (m, 2H), 4.99-5.13 (m, 2H), 3.14-3.20 (m, 1H), 2.54-2.60 (m, 4H), 2.09 (s, 3H), 2.01-2.07 (m, 2H), 1.51-1.69 (m, 4H).

3-Fluoro-1-(4-(2-(propylamino)ethyl)benzyl)-2-(o-tolyl)-1H-indol-5-ol (D-67)

To 4-((5-(benzyloxy)-3-fluoro-2-(o-tolyl)-1H-indol-1-yl)methyl)phenethyl 4-methylbenzenesulfonate 28-5 (250 mg, 0.4038 mmol) in acetonitrile (4 mL) was added DIPEA (0.7 mL, 4.040 mmol) and propyl amine (238 mg, 4.040 mmol) in a sealed tube. The reaction mixture was then stirred at room temperature for 72 h. After completion of the reaction, the reaction mixture was concentrated under reduced pressure, and diluted with ethyl acetate. Organic layer was dried over anhydrous $Na_2SO_4$, filtered and concentrated under reduced pressure to afford 145 mg (70% yield) of compound 67-1 as colorless thick oil. LCMS: $[M+H]^+$=507.65; Rt=1.77 min $^1$H NMR (400 MHz, DMSO-$d_6$) δ: 7.47 (d, J=7.34 Hz, 3H), 7.30-7.43 (m, 7H), 7.15 (d, J=1.96 Hz, 1H), 7.11 (d, J=7.82 Hz, 1H), 7.06 (d, J=7.82 Hz, 2H), 6.91 (dd, J=2.45, 9.29 Hz, 1H), 6.73 (d, J=8.31 Hz, 1H), 5.15 (s, 2H), 5.09-5.13 (m, 2H), 2.90-2.98 (m, 2H), 2.75 (t, J=7.58 Hz, 4H), 2.28 (s, 3H), 2.11-2.13 (m, 3H), 1.47-1.58 (m, 2H), 0.87 (t, J=7.34 Hz, 3H).

To N-(4-((5-(benzyloxy)-3-fluoro-2-(o-tolyl)-1H-indol-1-yl)methyl)phenethyl)propan-1-amine 67-1 (140 mg, 0.276 mmol) in ethyl acetate:methanol (1:1; 4 mL) was added 20% palladium hydroxide on carbon (48.4 mg, 30% w/w) at room temperature. The reaction mixture was stirred under hydrogen atmosphere for 2 h. After completion of the reaction, the reaction mixture was filtered through a pad of Celite™ and washed with ethyl acetate. The filtrate was concentrated under reduced pressure and the crude compound was purified by preparative HPLC to afford 35 mg (30% yield) of D-67 as off white solid.

LCMS: $[M+H]^+$=417.45; Rt=1.43 min
$^1$H NMR (400 MHz, DMSO-$d_6$) δ: 9.05 (br. s, 1H), 7.28-7.41 (m, 5H), 7.00 (d, J=8.31 Hz, 2H), 6.84 (d, J=1.96 Hz, 1H), 6.70 (dd, J=2.45, 8.80 Hz, 1H), 6.66 (d, J=7.83 Hz, 2H), 5.00-5.12 (m, 2H), 2.53-2.64 (m, 4H), 2.42 (t, J=7.09 Hz, 2H), 2.08 (s, 3H), 1.29-1.40 (m, 2H), 1.23 (s, 1H), 0.81 (t, J=7.34 Hz, 3H).

1-(4-(2-(Butylamino)ethyl)benzyl)-3-fluoro-2-(o-tolyl)-1H-indol-5-ol (D-68)

To 4-((5-(benzyloxy)-3-fluoro-2-(o-tolyl)-1H-indol-1-yl)methyl)phenethyl 4-methylbenzenesulfonate 28-5 (250 mg, 0.4038 mmol) in acetonitrile (4 mL) was added butyl amine (295 mg, 4.040 mmol) and DIPEA (0.7 mL, 4.040 mmol) in a sealed tube. The reaction mixture was stirred at room temperature for 72 h. After completion of the reaction, the reaction mixture was concentrated under reduced pressure, and diluted with ethyl acetate. Organic layer was dried over anhydrous $Na_2SO_4$, filtered and concentrated under reduced pressure to afford 240 mg (crude) of compound 68-1 as off white solid.

LCMS: $[M+H]^+$=521.75; Rt=1.80 min
$^1$H NMR (400 MHz, DMSO-$d_6$) δ: 7.47 (d, J=7.82 Hz, 4H), 7.37-7.43 (m, 3H), 7.25-7.36 (m, 4H), 7.11 (d, J=7.83 Hz, 2H), 7.05 (d, J=7.82 Hz, 1H), 6.91 (dd, J=2.20, 9.05 Hz, 1H), 6.73 (d, J=7.83 Hz, 1H), 5.15 (s, 2H), 2.90-2.98 (m, 2H), 2.70-2.80 (m, 4H), 2.28 (s, 3H), 2.10-2.14 (m, 2H), 1.45-1.49 (m, 2H), 1.28 (dq, J=6.60, 14.43 Hz, 3H), 0.83-0.90 (m, 3H).

To N-(4-((5-(benzyloxy)-3-fluoro-2-(o-tolyl)-1H-indol-1-yl)methyl)phenethyl)butan-1-amine 68-1 (240 mg, 0.4615 mmol) in ethyl acetate:methanol (1:1; 4 mL) was added 20% palladium hydroxide on carbon (77.5 mg, 30% w/w) at room temperature. The reaction mixture was further stirred under hydrogen atmosphere for 18 h. After completion of the reaction, the reaction mixture was filtered through a pad of Celite™ and washed with ethyl acetate. The filtrate was concentrated under reduced pressure and the crude compound was purified by preparative HPLC to afford 50 mg (25% yield) of D-68 as light brown solid.

LCMS: $[M+H]^+$=431.20; Rt=1.59 min
$^1$H NMR (400 MHz, DMSO-$d_6$) δ: 9.02-9.15 (m, 1H), 7.27-7.41 (m, 5H), 6.99 (d, J=8.31 Hz, 2H), 6.84 (d, J=2.45 Hz, 1H), 6.70 (dd, J=1.96, 8.80 Hz, 1H), 6.66 (d, J=7.82 Hz, 2H), 5.00-5.12 (m, 2H), 2.58 (qd, J=5.79, 11.49 Hz, 4H), 2.44 (t, J=6.85 Hz, 2H), 2.08 (s, 3H), 1.20-1.36 (m, 5H), 0.80-0.86 (m, 3H).

3-Fluoro-1-(4-(2-((3-fluoropropyl)amino)ethyl)benzyl)-2-(o-tolyl)-1H-indol-5-ol (D-69)

To a solution of 4-((5-(benzyloxy)-3-fluoro-2-(o-tolyl)-1H-indol-1-yl)methyl)phenethyl 4-methylbenzenesulfonate 28-5 (500 mg, 0.807 mmol) in DMF (10 mL) was added potassium phthalimide (164 mg, 0.886 mmol) at room temperature. The reaction mixture was then heated to 80° C. for 3 h. After completion of the reaction, the reaction mixture was cooled to room temperature, diluted with ethyl acetate (100 mL) washed with water (30 mL), brine (30 mL). Organic layer was dried over anhydrous $Na_2SO_4$, filtered and concentrated under reduced pressure to afford 510 mg (crude) of compound 69-6 as yellowish solid which was forwarded for the next reaction without further purification.

LCMS-Condition-1: $[M+H]^+=595.30$; Rt=2.66 min

To a solution of 2-(4-((5-(benzyloxy)-3-fluoro-2-(o-tolyl)-1H-indol-1-yl)methyl)phenethyl)isoindoline-1,3-dione 69-6 (550 mg, 0.925 mmol) in ethanol (8 mL) was added hydrazine hydrate (55.6 mg, 1.018 mmol) at room temperature. The reaction mixture was then heated at 80° C. for 2 h. After completion of the reaction (monitored by TLC), the reaction mixture was concentrated under reduced pressure. The crude compound was purified by silica gel column chromatography eluting with 0-3% methanol in DCM to afford 265 mg (62% yield) of compound 69-7 as white solid.

LCMS-Condition-1: $[M+H]^+=465.25$; Rt=1.98 min $^1$H NMR (400 MHz, DMSO-$d_6$) δ: 7.52-7.57 (m, 2H), 7.43-7.51 (m, 3H), 7.37-7.43 (m, 3H), 7.32-7.36 (m, 1H), 7.20-7.25 (m, 1H), 7.07-7.12 (m, 2H), 6.99 (dd, J=2.45, 8.80 Hz, 1H), 6.90 (dd, J=2.45, 8.80 Hz, 1H), 6.80 (d, J=7.83 Hz, 1H), 6.76 (d, J=8.31 Hz, 1H), 5.14 (s, 2H), 5.10 (s, 2H), 2.75-2.77 (m, 2H), 2.49-2.61 (m, 2H), 2.09 (s, 3H).

To 2-(4-((5-(benzyloxy)-3-fluoro-2-(o-tolyl)-1H-indol-1-yl)methyl)phenyl)ethan-1-amine 69-7 (260 mg, 0.560 mmol) in acetonitrile (4 mL) was added potassium carbonate (77.3 mg, 0.560 mmol) and 1-iodo-3-fluoro propane (105 mg, 0.560 mmol) at room temperature and stirred for 24 h. After completion of the reaction, the reaction mixture was concentrated under reduced pressure. The crude compound was purified by silica gel column chromatography eluting with 0-2% methanol in DCM to afford 140 mg (48% yield) of compound 69-8 as colorless thick oil.

LCMS-Condition-1: $[M+H]^+=525.25$; Rt=1.76 min $^1$H NMR (400 MHz, DMSO-$d_6$) δ: 7.46-7.50 (m, 2H), 7.32-7.44 (m, 6H), 7.12-7.18 (m, 1H), 7.00-7.05 (m, 2H), 6.92 (dd, J=2.20, 9.05 Hz, 1H), 6.83 (dd, J=2.45, 8.80 Hz, 1H), 6.72 (d, J=7.83 Hz, 1H), 6.68 (d, J=7.83 Hz, 1H), 6.39 (s, 1H), 5.15 (s, 1H), 5.11 (s, 1H), 4.52 (t, J=5.87 Hz, 1H), 4.40 (t, J=6.11 Hz, 1H), 2.62 (d, J=6.85 Hz, 6H), 2.07-2.12 (m, 3H), 1.75 (qd, J=6.32, 19.69 Hz, 2H), 1.22-1.26 (m, 3H).

To N-(4-((5-(benzyloxy)-3-fluoro-2-(o-tolyl)-1H-indol-1-yl)methyl)phenethyl)-3-fluoropropan-1-amine 69-8 (130 mg, 0.248 mmol) in ethyl acetate:methanol (2:1, 3 mL) was added 20% palladium hydroxide on carbon (71.5 mg, 30% w/w) at room temperature. The reaction mixture was then stirred under hydrogen atmosphere for 2 h. After completion of the reaction (monitored by TLC and LCMS), the reaction mixture was filtered through a pad of Celite™ and washed with methanol and ethyl acetate. The filtrate was concentrated under reduced pressure and the crude compound was purified by preparative HPLC to afford 20 mg (19% yield) of D-69 as light yellow solid.

LCMS-Condition-1: $[M+H]^+=435.20$; Rt=1.43 min $^1$H NMR (400 MHz, DMSO-$d_6$) δ: 9.04 (s, 1H), 7.27-7.42 (m, 5H), 7.00 (d, J=7.83 Hz, 2H), 6.84 (d, J=1.47 Hz, 1H), 6.69-6.72 (m, 1H), 6.66 (d, J=7.83 Hz, 2H), 4.99-5.12 (m, 2H), 4.50 (t, J=5.87 Hz, 1H), 4.38 (t, J=5.87 Hz, 1H), 2.53-2.65 (m, 8H), 2.06-2.11 (m, 3H), 1.65-1.78 (m, 3H).

3-Fluoro-1-(4-(2-((2-fluoroethyl)amino)ethyl)benzyl)-2-(o-tolyl)-1H-indol-5-ol (D-70)

To 2-(4-((5-(benzyloxy)-3-fluoro-2-(o-tolyl)-1H-indol-1-yl)methyl)phenyl)ethan-1-amine 69-7 (150 mg, 0.323 mmol) in THF (8 mL) was added triethylamine (0.13 mL, 0.969 mmol) and 1-fluoro-2-iodoethane (56.2 mg, 0.323 mmol) at room temperature in a seal tube. The reaction mixture was then heated to 80° C. and stirred for 18 h. After completion of the reaction (monitored by TLC), the reaction mixture was concentrated under reduced pressure and the crude residue was purified by silica gel column chromatography eluting with 0-2% methanol in DCM to afford 91 mg (55% yield) of compound 70-8 as colourless thick oil.

LCMS-Condition-1: $[M+H]^+=511.63$; Rt=1.71 min

To N-(4-((5-(benzyloxy)-3-fluoro-2-(o-tolyl)-1H-indol-1-yl)methyl)phenethyl)-2-fluoroethan-1-amine 70-8 (90 mg, 0.176 mmol) in ethyl acetate:methanol (2:1, 3 mL) was added 20% palladium hydroxide on carbon (29.6 mg, 30% w/w) at room temperature. The reaction mixture was then stirred under hydrogen atmosphere for 12 h. After completion of the reaction (monitored by TLC and LCMS), the reaction mixture was filtered through a pad of Celite™ and washed with methanol and ethyl acetate. The filtrate was concentrated under reduced pressure and the crude compound was purified by preparative HPLC to afford 15 mg (20% yield) of D-70 as light brown solid.

LCMS-Condition-1: $[M+H]^+=421.30$; Rt=1.38 min $^1$H NMR (400 MHz, DMSO-$d_6$) δ: 9.04 (s, 1H), 7.27-7.41 (m, 5H), 7.01 (d, J=7.83 Hz, 2H), 6.84 (d, J=1.96 Hz, 1H), 6.70 (dd, J=2.45, 8.80 Hz, 1H), 6.67 (d, J=7.83 Hz, 2H), 5.00-5.14 (m, 2H), 4.49 (t, J=4.89 Hz, 1H), 4.37 (t, J=4.89 Hz, 1H), 2.83 (t, J=4.89 Hz, 1H), 2.76 (t, J=4.89 Hz, 1H), 2.66-2.73 (m, 2H), 2.55-2.63 (m, 2H), 2.08 (s, 3H).

1-(4-(2-(Cyclopropylamino)propyl)benzyl)-3-fluoro-2-(o-tolyl)-1H-indol-5-ol (D-32)

To 5-(benzyloxy)-3-fluoro-2-(o-tolyl)-1H-indole 28-2 (600 mg, 1.812 mmol) in DMF (3 mL) at 0° C. was added sodium hydride (60% dispersion in oil, 27.2 mg, 1.132 mmol) portion wise and stirred at the same temperature for 30 min. To the resulting solution was added 2-(4-(bromomethyl)phenyl)acetic acid 1 (456 mg, 1.994 mmol) in DMF (1 mL) and stirred at room temperature for 18 h. After completion of the reaction, the reaction mixture was quenched with ice cold water and acidified with dilute hydrochloride solution up to pH=2. The solid precipitated was filtered and washed to afford 820 mg (94% yield) of compound 32-2 as yellow solid.

LCMS-Condition 01: $[M-18]^+=462.50$; Rt=2.29 min $^1$H NMR (400 MHz, DMSO-$d_6$) δ: 12.24 (br. s, 1H), 7.45-7.49 (m, 2H), 7.23-7.42 (m, 10H), 7.14 (d, J=1.96 Hz, 1H), 7.05 (d, J=7.82 Hz, 2H), 6.91 (dd, J=2.20, 9.05 Hz, 1H), 6.67-6.72 (m, 2H), 5.14 (s, 2H), 3.44 (s, 2H), 2.10 (s, 3H).

To 2-(4-((5-(benzyloxy)-3-fluoro-2-(o-tolyl)-1H-indol-1-yl)methyl)phenyl)acetic acid 32-2 (500 mg, 1.043 mmol) in DMF (2 mL) was added HATU (475 mg, 1.250 mmol), DIPEA (0.9 mL, 5.209 mmol) and N-methyl N-methoxylamine (191 mg, 31.27 mmol) at room temperature and stirred for 18 h. After completion of the reaction, the reaction mixture was quenched with ice cold water and extracted with ethyl acetate (2×). The combined organic layer was dried over anhydrous $Na_2SO_4$, filtered and concentrated under reduced pressure. The resulting crude compound was purified by silica gel column chromatography eluting with 0-20% ethyl acetate in n-hexane to afford 350 mg (64% yield) of compound 32-3 as yellow oil.

LCMS-Condition 01: $[M+H]^+=523.60$; Rt=2.36 min $^1$H NMR (400 MHz, DMSO-$d_6$) δ: 7.46-7.50 (m, 2H), 7.24-7.43 (m, 8H), 7.14 (d, J=2.49 Hz, 1H), 7.03 (d, J=7.98

Hz, 2H), 6.91 (dd, J=2.49, 8.98 Hz, 1H), 6.70 (d, J=8.48 Hz, 2H), 5.15 (s, 2H), 5.09-5.12 (m, 2H), 3.60-3.62 (m, 2H), 3.60 (s, 3H), 3.05 (s, 3H), 2.10 (s, 3H).

To 2-(4-((5-(benzyloxy)-3-fluoro-2-(o-tolyl)-1H-indol-1-yl)methyl)phenyl)-N-methoxy-N-methylacetamide 32-3 (300 mg, 0.574 mmol) in THF (5 mL) at 0° C. was added 3M methyl magnesium bromide solution in diethyl ether (0.38 mL, 1.140 mmol). The reaction mixture was further stirred at room temperature for 5 h. After completion of the reaction, the reaction mixture was quenched with ice cold water and extracted with ethyl acetate (2×). The combined organic layer was dried over anhydrous $Na_2SO_4$, filtered and concentrated under reduced pressure. The resulting crude compound was purified by silica gel column chromatography eluting with 0-5% methanol in DCM to afford 250 mg (91% yield) of compound 32-4 as colourless oil.

LCMS-Condition 01: [M-18]$^+$=460.55; Rt=2.39 min $^1$H NMR (400 MHz, DMSO-$d_6$) δ: 7.46-7.50 (m, 2H), 7.27-7.45 (m, 8H), 7.14 (d, J=2.45 Hz, 1H), 6.98 (d, J=8.31 Hz, 2H), 6.92 (dd, J=2.45, 9.29 Hz, 1H), 6.69 (d, J=8.31 Hz, 2H), 5.11-5.15 (m, 4H), 3.64 (s, 2H), 2.10 (s, 3H), 2.05 (s, 3H).

To 1-(4-((5-(benzyloxy)-3-fluoro-2-(o-tolyl)-1H-indol-1-yl)methyl)phenyl)propan-2-one 32-4 (250 mg, 0.524 mmol) in EDC (6 mL) at 0° C. was added sodium triacetoxy borohydride (555 mg, 2.617 mmol) portion wise, followed by cyclopropanamine (89 mg, 1.558 mmol). The reaction mixture was stirred at room temperature for 18 h. After completion of the reaction, the reaction mixture was quenched with ice cold water and extracted with ethyl acetate (2×). The combined organic layer was dried over anhydrous $Na_2SO_4$, filtered and concentrated under reduced pressure. The resulting crude compound was purified by silica gel column chromatography eluting with 0-20% ethyl acetate in n-hexane to afford 158 mg (58% yield) of compound 32-5 as colourless oil.

LCMS-Condition-1: [M+H]$^+$=519.60; Rt=1.78 min $^1$H NMR (400 MHz, DMSO-$d_6$) δ: 7.80-7.87 (m, 1H), 7.42-7.47 (m, 3H), 7.25-7.40 (m, 7H), 7.08-7.14 (m, 1H), 6.93 (d, J=7.83 Hz, 2H), 6.87-6.91 (m, 1H), 6.61 (d, J=7.83 Hz, 2H), 5.12 (s, 2H), 5.08 (d, J=4.89 Hz, 2H), 2.74-2.85 (m, 1H), 2.61-2.70 (m, 2H), 2.50-2.58 (m, 1H), 2.23-2.31 (m, 2H), 2.00 (s, 3H), 0.82 (d, J=6.36 Hz, 3H), 0.50-0.57 (m, 2H).

To N-(1-(4-((5-(benzyloxy)-3-fluoro-2-(o-tolyl)-1H-indol-1-yl)methyl)phenyl)propan-2-yl)cyclopropanamine 32-5 (150 mg, 0.289 mmol) in ethyl acetate:methanol (1:1 mL) was added 20% palladium hydroxide on carbon (50 mg, 50% moisture on carbon) at room temperature. The reaction mixture was then stirred under hydrogen atmosphere for 18 h. After completion of the reaction, the reaction mixture was filtered through a pad of Celite™ and washed with ethyl acetate. The filtrate was concentrated under reduced pressure and the crude compound was purified by preparative HPLC to afford 40 mg (32% yield) of D-32 as colourless oil.

LCMS-Condition-1: [M+H]$^+$=429.50; Rt=1.42 min $^1$H NMR (400 MHz, DMSO-$d_6$) δ: 9.04 (s, 1H), 7.28-7.40 (m, 6H), 6.95 (d, J=7.82 Hz, 2H), 6.84 (d, J=1.96 Hz, 1H), 6.71 (dd, J=2.45, 8.80 Hz, 1H), 6.64 (d, J=8.31 Hz, 2H), 5.07 (s, 2H), 2.75-2.83 (m, 1H), 2.67 (ddd, J=2.69, 5.75, 13.08 Hz, 2H), 2.53-2.60 (m, 1H), 2.25-2.34 (m, 2H), 2.03 (s, 3H), 0.85 (d, J=6.36 Hz, 3H), 0.50-0.57 (m, 2H).

1-(4-(2-((Cyclopropylmethyl)amino)ethyl)benzyl)-3-fluoro-2-(2-(trifluoromethyl)phenyl)-1H-indol-5-ol
(D-40)

To 5-(benzyloxy)-3-fluoro-2-(2-(trifluoromethyl)phenyl)-1H-indole 40-1 (1 g, 2.597 mmol) in DMF (10 mL) at 0° C. was added 60% dispersion sodium hydride in oil (370 mg, 7.791 mmol) portionwise. The reaction mixture was further stirred at 0° C. for 30 min. To the resulting solution was added (4-(bromomethyl)phenethoxy)(tert-butyl)dimethylsilane (1.1 g, 3.376 mmol). The reaction mixture was stirred at room temperature for 18 h. After completion of the reaction, the reaction mixture was quenched with ice cold water and extracted with ethyl acetate (thrice). The combined organic layer dried over anhydrous $Na_2SO_4$, filtered and concentrated under reduced pressure. The resulting crude compound was purified by silica gel column chromatography eluting with 0-10% ethyl acetate in n-hexane to afford 747 mg (45% yield) of compound 40-2 as brown thick oil.

LCMS-Condition 01: [M+H]$^+$=634.25; Rt=2.83 min $^1$H NMR (400 MHz, CDCl$_3$) δ: 7.82 (d, J=7.34 Hz, 1H), 7.52-7.60 (m, 1H), 7.49 (d, J=7.34 Hz, 2H), 7.41 (t, J=7.34 Hz, 1H), 7.33 (dd, J=7.34, 11.74 Hz, 2H), 7.19 (d, J=1.96 Hz, 1H), 7.09-7.12 (m, 3H), 7.03-7.08 (m, 2H), 6.92 (dd, J=2.45, 9.29 Hz, 1H), 6.81 (d, J=7.82 Hz, 2H), 5.14 (br. s, 1H), 5.13 (s, 1H), 5.10 (br. s, 1H), 4.79 (d, J=17.12 Hz, 1H), 3.75-3.80 (m, 2H), 2.77-2.81 (m, 2H), 0.89 (s, 6H), 0.88 (s, 3H), 0.01 (s, 3H), 0.00 (s, 3H).

To 5-(benzyloxy)-1-(4-(2-((tert-butyldimethylsilyl)oxy)ethyl)benzyl)-3-fluoro-2-(2-(trifluoromethyl)phenyl)-1H-indole 40-2 (800 mg, 1.263 mmol) in THF (8 mL) at 0° C. was added 2M solution of TBAF in THF (495 mg, 1.896 mmol). The reaction mixture was further stirred at room temperature for 2 h. After completion of the reaction, the reaction mixture was quenched with ice cold water and extracted with ethyl acetate (thrice). The combined organic layer dried was washed with water (20 mL) and brine (20 mL) dried over anhydrous $Na_2SO_4$, filtered and concentrated under reduced pressure. The resulting crude compound was purified by silica gel column chromatography eluting with 0-50% ethyl acetate in n-hexane to afford 550 mg (84% yield) of compound 40-3 as thick colorless syrup.

LCMS-Condition 01: [M+H]$^+$=520.18; Rt=2.36 min $^1$H NMR (400 MHz, CDCl$_3$) δ: 7.81 (d, J=7.34 Hz, 1H), 7.51-7.59 (m, 2H), 7.48 (d, J=7.34 Hz, 2H), 7.40 (t, J=7.34 Hz, 2H), 7.33 (dd, J=7.58, 10.03 Hz, 2H), 7.18 (d, J=1.96 Hz, 1H), 7.05-7.09 (m, 3H), 6.93 (dd, J=2.45, 8.80 Hz, 1H), 6.83 (d, J=8.31 Hz, 2H), 5.12 (s, 2H), 5.09 (s, 1H), 4.81 (d, J=16.63 Hz, 1H), 4.09-4.15 (m, 1H), 3.83-3.88 (m, 2H), 2.83-2.87 (m, 2H).

To 2-(4-((5-(benzyloxy)-3-fluoro-2-(2-(trifluoromethyl) phenyl)-1H-indol-1-yl)methyl)phenyl)ethan-1-ol 40-3 (560 mg, 1.117 mmol) in CH$_2$Cl$_2$ (10 mL) at 0° C. was added triethylamine (0.46 mL, 1.564 mmol) followed by Tosyl chloride (299 mg, 1.564 mmol). The reaction mixture was stirred at room temperature for 3 h. After completion of the reaction, the reaction mixture was diluted with CH$_2$Cl$_2$ (50 mL) and washed with water (20 mL) and brine (10 mL). The combined organic layer dried over anhydrous $Na_2SO_4$, filtered and concentrated under reduced pressure. The resulting crude compound was purified by silica gel column chromatography eluting with 0-25% ethyl acetate in n-hexane to afford 630 mg (86% yield) of compound 40-4 as thick colorless syrup.

LCMS-Condition 01: [M+H]$^+$=674.05; Rt=2.46 min $^1$H NMR (400 MHz, CDCl$_3$) δ: 7.81 (d, J=7.34 Hz, 1H), 7.69 (dd, J=8.31, 10.76 Hz, 2H), 7.46-7.59 (m, 3H), 7.40 (t, J=7.58 Hz, 1H), 7.34 (d, J=6.85 Hz, 1H), 7.28 (d, J=8.80 Hz, 2H), 7.25 (br. s, 1H), 7.21-7.24 (m, 2H), 7.18 (d, J=2.45 Hz, 1H), 7.01-7.09 (m, 3H), 6.94-6.98 (m, 2H), 6.77 (d, J=7.83 Hz, 1H), 5.12 (s, 2H), 4.12-4.22 (m, 2H), 2.86-2.96 (m, 2H), 2.85 (s, 1H), 2.43 (s, 2H), 2.40 (s, 1H), 2.00 (s, 1H).

To 4-((5-(benzyloxy)-3-fluoro-2-(2-(trifluoromethyl)phenyl)-1H-indol-1-yl)methyl)phenethyl 4-methylbenzenesulfonate 40-4 (225 mg, 0.334 mmol) in acetonitrile (4 mL) was added Cyclopropylmethylamine (0.200 g, 3.324 mmol) and DIPEA (0.57 mL, 3.380 mmol) in a seal tube. The reaction mixture was further stirred at room temperature for 72 h. After completion of the reaction, the reaction mixture was concentrated under reduced pressure, washed with ethyl acetate (2×10 mL). The combined organic layer dried over anhydrous $Na_2SO_4$, filtered and concentrated under reduced pressure to afford 210 mg (crude) of compound 40-5 as colorless residue.

LCMS-Condition 01: $[M+H]^+$=573.20; Rt=1.79 min $^1$H NMR (400 MHz, DMSO-$d_6$) δ: 7.91-7.95 (m, 1H), 7.73-7.77 (m, 1H), 7.46-7.49 (m, 3H), 7.40 (t, J=7.34 Hz, 1H), 7.16-7.35 (m, 4H), 7.07-7.15 (m, 4H), 6.93 (dd, J=2.45, 8.80 Hz, 1H), 6.82 (d, J=7.83 Hz, 1H), 5.23 (d, J=16.63 Hz, 1H), 5.16 (s, 1H), 4.87 (d, J=17.12 Hz, 1H), 3.02 (dd, J=9.29, 19.07 Hz, 2H), 2.79-2.86 (m, 2H), 2.72-2.78 (m, 2H), 2.29 (s, 2H), 0.94-1.01 (m, 1H), 0.54 (dt, J=1.96, 6.11 Hz, 2H), 0.29 (dd, J=4.89, 11.25 Hz, 2H).

To 2-(4-((5-(benzyloxy)-3-fluoro-2-(2-(trifluoromethyl)phenyl)-1H-indol-1-yl)methyl)phenyl)-N-(cyclopropylmethyl)ethan-1-amine 40-5 (210 mg, 0.367 mmol) in ethyl acetate:methanol (2:2 mL) was added 20% palladium hydroxide on carbon (51 mg) at room temperature. The reaction mixture was further stirred under hydrogen atmosphere for 2 h. After completion of the reaction, the reaction mixture was filtered through pad of a Celite™ and washed with ethyl acetate. The filtrate was concentrated under reduced pressure and the crude compound was purified by preparative HPLC to afford 22 mg (13% yield) of D-40 as off white solid.

LCMS-Condition-1: $[M+H]^+$=483.15; Rt=1.46 min $^1$H NMR (400 MHz, DMSO-$d_6$) δ: 8.25 (s, 1H), 7.83-7.87 (m, 1H), 7.65-7.69 (m, 2H), 7.41-7.46 (m, 1H), 7.13 (d, J=8.80 Hz, 1H), 7.00 (d, J=8.31 Hz, 2H), 6.79 (d, J=1.96 Hz, 1H), 6.72 (d, J=7.83 Hz, 2H), 6.66 (dd, J=1.96, 8.80 Hz, 1H), 5.11 (d, J=16.63 Hz, 1H), 4.74 (d, J=16.63 Hz, 1H), 2.79-2.86 (m, 2H), 2.64-2.71 (m, 2H), 2.54 (d, J=6.85 Hz, 2H), 0.81-0.91 (m, 1H), 0.37-0.43 (m, 2H), 0.10-0.16 (m, 2H).

1-(4-(2-(Cyclopropylamino)ethyl)benzyl)-3-fluoro-2-(2-(trifluoromethyl)phenyl)-1H-indol-5-ol (D-33)

To 4-((5-(benzyloxy)-3-fluoro-2-(2-(trifluoromethyl)phenyl)-1H-indol-1-yl)methyl)phenethyl 4-methylbenzenesulfonate D-40-4 (0.225 g, 0.334 mmol) in acetonitrile (4 mL) was added cyclopropyl amine (0.200 g, 3.324 mmol) and DIPEA (0.57 mL, 3.380 mmol) in a sealed tube. The reaction mixture was stirred at room temperature for 72 h. After completion of the reaction, the reaction mixture was concentrated under reduced pressure and extracted with ethyl acetate (3×). The combined organic layer washed with water and Brine, dried over anhydrous $Na_2SO_4$, filtered and concentrated under reduced pressure to afford 220 mg (crude) of compound 33-3 as colourless oil.

LCMS-Condition 01: $[M+H]^+$=559.20; Rt=1.75 min $^1$H NMR (400 MHz, DMSO-$d_6$) δ: 7.91-7.95 (m, 1H), 7.73-7.77 (m, 1H), 7.50-7.54 (m, 1H), 7.45-7.50 (m, 4H), 7.40 (t, J=7.34 Hz, 2H), 7.29-7.36 (m, 2H), 7.10 (dd, J=3.67, 8.07 Hz, 3H), 6.93 (dd, J=2.20, 9.05 Hz, 1H), 6.81 (d, J=7.82 Hz, 1H), 5.21 (d, J=16.8 Hz, 1H), 5.15 (s, 2H), 4.48 (d, J=16.8 Hz, 1H), 3.05-3.11 (m, 2H), 2.75-2.80 (m, 2H), 2.28 (s, 2H), 1.25 (d, J=6.85 Hz, 4H).

To N-(4-((5-(benzyloxy)-3-fluoro-2-(2-(trifluoromethyl)phenyl)-1H-indol-1-yl)methyl)phenethyl)cyclopropan-amine 33-3 (0.230 g, 0.413) in ethyl acetate:methanol (2:2 mL) was added 20% palladium hydroxide on carbon (70 mg) at room temperature. The reaction mixture was then stirred under hydrogen atmosphere for 2 h. After completion of the reaction, the reaction mixture was filtered through a pad of Celite™ and washed with ethyl acetate. The filtrate was concentrated under reduced pressure and the crude compound was purified by preparative HPLC to afford 18 mg (10% yield) of D-33 as off white solid.

LCMS-Condition-1: $[M+H]^+$=469.10; Rt=1.45 min $^1$H NMR (400 MHz, DMSO-$d_6$) δ: 9.08 (s, 1H), 8.16 (s, 1H), 7.88-7.93 (m, 1H), 7.70-7.76 (m, 2H), 7.47-7.50 (m, 1H), 7.21 (dd, J=1.83, 8.93 Hz, 1H), 7.04 (d, J=8.07 Hz, 2H), 6.85 (d, J=2.08 Hz, 1H), 6.75 (d, J=7.95 Hz, 2H), 6.72 (dd, J=2.32, 8.93 Hz, 1H), 5.16 (d, J=16.75 Hz, 1H), 4.80 (d, J=16.75 Hz, 1H), 2.73-2.78 (m, 2H), 2.59-2.65 (m, 2H), 2.10-2.14 (m, 1H), 0.33-0.38 (m, 2H), 0.19-0.24 (m, 2H).

1-(4-(2-(Ethylamino)ethyl)benzyl)-3-fluoro-2-(2-(trifluoromethyl)phenyl)-1H-indol-5-ol (D-34)

To 4-((5-(benzyloxy)-3-fluoro-2-(2-(trifluoromethyl)phenyl)-1H-indol-1-yl)methyl)phenethyl 4-methylbenzenesulfonate 33-2 (0.225 g, 0.334 mmol) in acetonitrile (5 mL) was added 2M ethyl amine in THF (150 mg, 1.66 mL, 3.324 mmol) and DIPEA (0.57 mL, 3.380 mmol) in a sealed tube. The reaction mixture was then stirred at room temperature for 72 h. After completion of the reaction, the reaction mixture was concentrated under reduced pressure and extracted with ethyl acetate (3×). The combined organic layer washed with water (20 mL), brine (20 mL) and dried over anhydrous $Na_2SO_4$, filtered and concentrated under reduced pressure to afford 195 mg (crude) of compound 34-1 as colourless thick oil.

LCMS-Condition 01: $[M+H]^+$=547.26; Rt=1.77 min $^1$H NMR (400 MHz, DMSO-$d_6$) δ: 8.24-8.33 (m, 1H), 7.90-7.96 (m, 1H), 7.75 (d, J=3.91 Hz, 1H), 7.52 (br. s, 1H), 7.47 (d, J=6.85 Hz, 3H), 7.37-7.43 (m, 2H), 7.26-7.37 (m, 2H), 7.10 (d, J=7.83 Hz, 3H), 6.93 (d, J=8.80 Hz, 1H), 6.83 (d, J=7.83 Hz, 2H), 5.24 (d, J=16.63 Hz, 1H), 5.15 (br. s, 2H), 4.81-4.90 (m, 1H), 3.02-3.10 (m, 2H), 2.91-3.00 (m, 2H), 2.75-2.83 (m, 2H), 1.12-1.17 (m, 3H).

To 2-(4-((5-(benzyloxy)-3-fluoro-2-(2-(trifluoromethyl)phenyl)-1H-indol-1-yl)methyl)phenyl)-N-ethylethan-1-amine 34-1 (0.195 g, 0.357 mmol) in ethyl acetate:methanol (1:1, 4 mL) was added 20% palladium hydroxide on carbon (60 mg) at room temperature. The reaction mixture was stirred under hydrogen atmosphere for 18 h. After completion of the reaction, the reaction mixture was filtered through a pad of Celite™ and washed with ethyl acetate. The filtrate was concentrated under reduced pressure and the crude compound was purified by preparative HPLC to afford 40 mg (21% yield) of D-34 as off white solid.

LCMS-Condition-1: $[M+H]^+$=457.10; Rt=1.42 min $^1$H NMR (400 MHz, DMSO-$d_6$) δ: 9.08 (s, 1H), 7.88-7.93 (m, 1H), 7.71-7.75 (m, 2H), 7.46-7.51 (m, 1H), 7.21 (dd, J=1.90, 8.86 Hz, 1H), 7.03 (d, J=7.95 Hz, 2H), 6.85 (d, J=2.08 Hz, 1H), 6.73-6.77 (m, 2H), 6.69-6.72 (m, 1H), 5.15 (d, J=16.63 Hz, 1H), 4.80 (d, J=16.75 Hz, 1H), 2.52-2.69 (m, 6H), 0.95 (t, J=7.09 Hz, 3H).

2-(2-Chlorophenyl)-1-(4-(2-(cyclopropylamino)ethyl)benzyl)-3-fluoro-1H-indol-5-ol (D-37)

To a solution of 4-(benzyloxy)-2-(2,2-dibromovinyl)aniline D-13-3 (2.5 g, 6.52 mmol) in toluene-ethanol (9:1, 50 mL) was added 2-Cl-phenyl boronic acid (1.32 g, 8.48 mmol) and a solution of Na$_2$CO$_3$ (2.07 g, 19.58 mmol) in water (1.5 mL) simultaneously at room temperature under argon atmosphere and degassed for 30 min. To the resulting solution was added Pd(PPh$_3$)$_4$ (376 mg, 0.326 mmol) and degassing was continued for another 10 min at room temperature. The reaction mixture was then heated at 90° C. for 18 h. After completion of the reaction (monitored by TLC and LCMS), the reaction mixture was diluted with water and extracted with ethyl acetate (3×50 mL). The combined organic layer was dried over anhydrous Na$_2$SO$_4$, filtered and concentrated under reduced pressure. The crude compound was purified by silica gel column chromatography eluting with 0-15% ethyl acetate in n-hexane to afford 650 g (30% yield) of compound 37-1 as thick yellow liquid.

LCMS-Condition 01: [M+H]$^+$=334.35; Rt=2.39 min $^1$H NMR (400 MHz, DMSO-d$_6$) δ: 8.70 (br. s, 1H), 7.67 (dd, J=1.6, 7.6 Hz, 1H), 7.48-7.51 (m, 3H), 7.39-7.43 (m, 2H), 7.30-7.37 (m, 4H), 7.20 (d, J=2.00 Hz, 1H), 6.98 (dd, J=2.40, 8.80 Hz, 1H), 6.80 (s, 1H), 5.14 (s, 2H).

To a solution of 5-(benzyloxy)-2-(2-chlorophenyl)-1H-indole 37-1 (650 mg, 1.94 mmol) in dry Acetonitrile-DMSO (1:1, 12 mL) at −10° C. was added selectfluor (690 mg, 1.94 mmol) under argon atmosphere. The reaction mixture was further stirred at 0° C. for 2 h. After completion of the reaction (Monitored by TLC), the reaction mixture was concentrated under reduced pressure, the residue was dissolved in ethyl acetate (100 mL) and washed with water (40 mL) followed by brine (30 mL). The separated organic layer was dried over anhydrous Na$_2$SO$_4$, filtered and concentrated under reduced pressure. The crude compound was purified by silica gel column chromatography eluting with 0-10% ethyl acetate in n-hexane followed by preparative TLC to afford 300 mg (44% yield) of compound 37-2 as light brown solid.

LCMS-Condition 01: [M+18]$^+$=360.90; Rt=2.38 min $^1$H NMR (400 MHz, CDCl$_3$) δ: 7.87 (d, J=7.6 Hz, 1H), 7.56 (dd, J=1.6, 7.6 Hz, 1H), 7.49-7.54 (m, 2H), 7.36-7.44 (m, 6H), 7.22 (d, J=2.0 Hz, 1H), 7.06 (dd, J=2.0, 8.4 Hz, 1H).

To 5-(benzyloxy)-2-(2-chlorophenyl)-3-fluoro-1H-indole 37-2 (300 g, 0.852 mmol) in DMF (10 mL) at 0° C. was added sodium hydride (60% dispersion in oil, 102 mg, 2.558 mmol) portion wise and stirred at 0° C. for 30 min. To the resulting solution was added (4-(bromomethyl)phenethoxy)(tert-butyl)dimethylsilane (365 mg, 1.108 mmol). The reaction mixture was stirred at room temperature for 18 h. After completion of the reaction (monitored by TLC and LCMS), the reaction mixture was quenched with ice cold water and extracted with ethyl acetate (3×15 mL). The combined organic layer was dried over anhydrous Na$_2$SO$_4$, filtered and concentrated under reduced pressure. The crude compound was purified by silica gel column chromatography eluting with 0-10% ethyl acetate in n-hexane to afford 280 mg (55% yield) of compound 37-3 as yellowish oil.

LCMS-Condition 01: [M+H]$^+$=600.35; Rt=2.83 min $^1$H NMR (400 MHz, CDCl$_3$) δ: 7.46-7.53 (m, 2H), 7.28-7.42 (m, 5H), 7.17-7.21 (m, 3H), 7.10 (dd, J=2.08, 8.68 Hz, 1H), 7.02 (d, J=8.07 Hz, 2H), 6.92 (dd, J=2.45, 8.93 Hz, 1H), 6.79 (d, J=8.07 Hz, 2H), 5.16 (d, J=16.40 Hz, 1H), 5.12 (s, 2H), 4.98 (d, J=16.87 Hz, 1H), 3.79 (t, J=7.09 Hz, 2H), 2.82 (d, J=7.2 Hz, 2H), 0.87 (s, 9H), −0.055 (s, 6H).

To 5-(benzyloxy)-1-(4-(2-((tert-butyldimethylsilyl)oxy)ethyl)benzyl)-2-(2-chlorophenyl)-3-fluoro-1H-indole 37-3 (280 mg, 0.466 mmol) in THF (6 mL) at 0° C. was added TBAF (183 mg, 0.699 mmol) portion wise. The reaction mixture was further stirred at room temperature for 1 h. After completion of the reaction, the reaction mixture was quenched with ice cold water and extracted with ethyl acetate (thrice). The combined organic layer dried over anhydrous Na$_2$SO$_4$, filtered and concentrated under reduced pressure. The resulting crude compound was purified by silica gel column chromatography eluting with 0-50% ethyl acetate in n-hexane to afford 200 mg (88% yield) of compound 37-4 as light brown thick liquid.

LCMS-Condition 01: [M+H]$^+$=486.04; Rt=2.39 min $^1$H NMR (400 MHz, CDCl$_3$) δ: 7.50 (dd, J=7.34, 12.23 Hz, 2H), 7.30-7.42 (m, 5H), 7.22 (d, J=8.31 Hz, 2H), 7.18 (d, J=2.45 Hz, 1H), 7.13 (dd, J=1.96, 9.29 Hz, 1H), 7.04 (d, J=7.83 Hz, 2H), 6.94 (dd, J=2.20, 9.05 Hz, 1H), 6.81 (d, J=8.31 Hz, 2H), 5.15-5.20 (m, 1H), 5.12 (s, 2H), 4.99-5.04 (m, 1H), 3.75-3.89 (m, 2H), 2.76-2.87 (m, 2H).

To 2-(4-((5-(benzyloxy)-2-(2-chlorophenyl)-3-fluoro-1H-indol-1-yl)methyl)phenyl)ethan-1-ol 37-4 (250 mg, 0.514 mmol) in CH$_2$Cl$_2$ (mL) at 0° C. was added triethylamine (0.21 mL, 1.543 mmol) followed by TsCl (127 mg, 0.668 mmol). The reaction mixture was stirred at room temperature for 2 h. After completion of the reaction (monitored by TLC and LCMS), the reaction mixture was quenched with sodium bicarbonate solution and extracted with ethyl acetate (3×20 mL). The combined organic layer was dried over anhydrous Na$_2$SO$_4$, filtered and concentrated under reduced pressure. The crude compound was purified by silica gel column chromatography eluting with 0-20% ethyl acetate in n-hexane to afford 300 mg (91% yield) of compound 37-5 as off white solid.

LCMS-Condition 01: [M+H]$^+$=640.20; Rt=2.47 min $^1$H NMR (400 MHz, CDCl$_3$) δ: 7.45-7.54 (m, 3H), 7.29-7.42 (m, 6H), 7.17-7.24 (m, 4H), 7.08-7.12 (m, 2H), 6.90-6.95 (m, 3H), 6.76 (d, J=8.31 Hz, 2H), 5.16 (d, J=16.63 Hz, 1H), 5.12 (s, 2H), 4.98 (d, J=16.63 Hz, 1H), 2.95 (t, J=7.09 Hz, 2H), 2.86 (t, J=7.09 Hz, 2H), 2.39 (s, 3H).

To a solution of 4-((5-(benzyloxy)-2-(2-chlorophenyl)-3-fluoro-1H-indol-1-yl)methyl)phenethyl 4-methylbenzenesulfonate 37-5 (200 mg, 0.312 mmol) in acetonitrile (3 mL) was added cyclopropanamine (178 mg, 3.124 mmol) and DIPEA (0.54 mL, 3.124 mmol) in a sealed tube. Then the reaction mixture was stirred at room temperature for 72 h. After completion of the reaction (monitored by TLC and LCMS), the reaction mixture was diluted with water and extracted with ethyl acetate (3×100 mL). The combined organic layer was dried over anhydrous Na$_2$SO$_4$, filtered and concentrated under reduced pressure. The crude compound was purified by silica gel column chromatography eluting with 0-50% ethyl acetate in n-hexane to afford 90 mg (55% yield) of compound 37-6 as off white sticky solid.

LCMS-Condition 01: [M+H]$^+$=525.15; Rt=1.83 min $^1$H NMR (400 MHz, CDCl$_3$) δ: 7.47-7.53 (m, 2H), 7.30-7.42 (m, 5H), 7.29 (d, J=2.45 Hz, 1H), 7.17-7.22 (m, 2H), 7.14 (dd, J=1.96, 8.80 Hz, 1H), 7.02 (d, J=7.83 Hz, 2H), 6.94 (dd, J=2.45, 8.80 Hz, 1H), 6.79 (d, J=7.83 Hz, 2H), 5.14-5.20 (m, 1H), 5.12 (s, 2H), 4.98-5.04 (m, 1H), 2.93-2.99 (m, 1H), 2.86-2.91 (m, 1H), 2.78-2.84 (m, 1H), 2.68-2.74 (m, 1H), 2.10-2.14 (m, 1H), 0.33-0.45 (m, 4H).

To a solution of N-(4-((5-(benzyloxy)-2-(2-chlorophenyl)-3-fluoro-1H-indol-1-yl)methyl)phenethyl)cyclopropanamine 37-6 (90 mg, 0.171 mmol) in ethyl acetate-methanol (2:1, 3 mL) was added 20% palladium hydroxide on carbon (30 mg) at room temperature. Then the reaction mixture was stirred under hydrogen atmosphere for 18 h. After completion of the reaction (monitored by TLC and LCMS), the reaction mixture was filtered through a pad of Celite™ and washed with ethyl acetate. The filtrate was concentrated under reduced pressure and the crude compound was purified by preparative HPLC to afford 14 mg (19% yield) of D-37 as white solid.

LCMS-Condition 01: [M+H]$^+$=435.10; Rt=1.51 min $^1$H NMR (400 MHz, CDCl$_3$) δ: 7.51 (dd, J=1.00, 8.03 Hz, 1H), 7.29-7.39 (m, 3H), 7.00-7.12 (m, 4H), 6.74-6.82 (m, 3H), 5.12-5.18 (m, 1H), 4.95-5.03 (m, 1H), 2.86-2.92 (m, 2H), 2.68-2.76 (m, 2H), 2.08-2.13 (m, 1H), 0.81-0.91 (m, 2H), 0.40-0.47 (m, 2H).

N-Ethyl-2-(4-((8-fluoro-7-(o-tolyl)pyrrolo[3,2-e]indazol-6(3H)-yl)methyl)phenyl)ethan-1-amine (D-85)

To 5-nitro-1H-indazole 85-1 (10 g, 61.29 mmol) in THF (100 mL) was added sodium hydroxide (6.1 g, 153.2 mmol) followed by n-tetrabutyl ammonium sulfate (312 mg, 0.917 mmol) and stirred for 1 h at room temperature. To the resulting solution was added benzene sulfonyl chloride (12 g, 67.79 mmol) drop wise and stirred for another 1 h. After completion of the reaction (monitored by TLC and LCMS), the reaction mixture was quenched with water and extracted with ethyl acetate (3×100 mL). The combined organic layer was dried over anhydrous Na$_2$SO$_4$, filtered and concentrated under reduced pressure. The resulting crude compound was purified by trituration in diethyl ether to afford 17.3 g (93% yield) of compound 85-2 as white solid.

LCMS: [M+H]$^+$=303.95; Rt=1.85 min $^1$H NMR (400 MHz, CDCl$_3$) δ: 8.66 (d, J=1.96 Hz, 1H), 8.44-8.47 (m, 1H), 8.34-8.38 (m, 2H), 8.02-8.06 (m, 2H), 7.62-7.67 (m, 1H), 7.50-7.55 (m, 2H).

To a solution of 5-nitro-1-(phenylsulfonyl)-1H-indazole 85-2 (17.3 g, 57.09 mmol) in methanol (200 mL) was added hydrazine hydrate (10 g, 199.8 mmol) and 20% palladium on carbon (2 g) at room temperature. The reaction mixture was heated at 70° C. for 3 h. After completion of the reaction (monitored by TLC and LCMS), the reaction mixture was filtered through a pad of Celite™ and the filtrate was concentrated under reduced pressure. The crude compound was purified by trituration in diethyl ether to afford 14.5 g (93% yield) of compound 85-3 as light brown solid.

LCMS: [M+H]$^+$=274.15; Rt=1.43 min $^1$H NMR (400 MHz, DMSO-d$_6$) δ: 8.27 (s, 1H), 7.76-7.84 (m, 3H), 7.64-7.71 (m, 1H), 7.52-7.59 (m, 2H), 6.96 (dd, J=1.96, 8.80 Hz, 1H), 6.77 (d, J=1.96 Hz, 1H), 5.30 (s, 2H).

To a solution of 1-(phenylsulfonyl)-1H-indazol-5-amine 85-3 (14.5 g, 53.11 mmol) in acetonitrile (300 mL) was added N-iodosuccinimide (14.3 g, 63.73 mmol) at room temperature and stirred for 2 h. After completion of the reaction (monitored by TLC and LCMS), the reaction mixture was diluted with water and extracted with ethyl acetate (3×50 mL). The combined organic layer was dried over anhydrous Na$_2$SO$_4$, filtered and concentrated under reduced pressure, crude compound was purified by silica gel column chromatography eluting with 10-15% ethyl acetate in n-hexane to afford 11 g (52% yield) of compound 85-4 as off white solid.

LCMS: [M+H]$^+$=399.90; Rt=1.97 min $^1$H NMR (400 MHz, DMSO-d$_6$) δ: 8.07-8.10 (m, 1H), 7.83-7.88 (m, 3H), 7.68-7.74 (m, 1H), 7.54-7.62 (m, 2H), 7.11 (d, J=9.29 Hz, 1H), 5.48 (s, 2H).

To 4-iodo-1-(phenylsulfonyl)-1H-indazol-5-amine 85-4 (6 g, 15.03 mmol) in CH$_2$Cl$_2$ (50 mL) at 0° C. was added triethylamine (8 mL, 57.56 mmol) and TFAA (4 mL, 28.57 mmol). The reaction mixture was then stirred at room temperature for 2 h. After completion of the reaction (monitored by TLC and LCMS), the reaction mixture was diluted with water and extracted with CH$_2$Cl$_2$ (3×50 mL). The combined organic layer was dried over anhydrous Na$_2$SO$_4$, filtered and concentrated under reduced pressure. The crude compound was purified by silica gel column chromatography eluting with 0-20% ethyl acetate in n-hexane to afford 5.5 g (71% yield) of compound 85-5 as off white solid.

LCMS: [M+H]$^+$=495.90; Rt=2.06 min $^1$H NMR (400 MHz, DMSO-d$_6$) δ: 11.43 (s, 1H), 8.45 (s, 1H), 8.20 (d, J=8.80 Hz, 1H), 7.96-8.01 (m, 2H), 7.73-7.79 (m, 1H), 7.60-7.67 (m, 3H).

To 2,2,2-trifluoro-N-(4-iodo-1-(phenylsulfonyl)-1H-indazol-5-yl)acetamide 85-5 (5.5 g, 11.11 mmol) in DMF (75 mL) was added copper iodide (212 mg, 1.115 mmol) followed by triethylamine (7.7 mL, 55.55 mmol) at room temperature and degassed with argon for 15 min. To the resulting solution was added dichlorobis(triphenylphosphine)palladium(II) (779 mg, 1.112 mmol) and 1-ethynyl-2-methylbenzene (1.54 g, 13.33 mmol) and degassing was continued for another 10 min. The reaction mixture was then heated at 130° C. for 18 h. After completion of the reaction (monitored by TLC and LCMS), the reaction mixture was filtered through a pad of Celite™ and the filtrate was diluted with water and extracted with ethyl acetate (3×50 mL). The combined organic layer was dried over anhydrous Na$_2$SO$_4$, filtered and concentrated under reduced pressure; crude compound was purified by Combiflash column chromatography eluting with 10-20% ethyl acetate in n-hexane to afford 3.5 g (81% yield) of compound 85-6 as white solid.

LCMS: [M+H]$^+$=388.30; Rt=2.08 min $^1$H NMR (400 MHz, DMSO-d$_6$) δ: 11.87 (s, 1H), 8.74 (s, 1H), 7.87-7.93 (m, 3H), 7.72 (d, J=8.80 Hz, 1H), 7.56 (t, J=7.83 Hz, 3H), 7.29-7.38 (m, 4H), 6.94 (d, J=1.47 Hz, 1H), 2.47 (s, 3H).

To 3-(phenylsulfonyl)-7-(o-tolyl)-3,6-dihydropyrrolo[3,2-e]indazole 85-6 (1 g, 2.583 mmol) in dry Acetonitrile:DMSO (4:1, 50 mL) at −10° C. was added selectfluor (1.28 g, 3.617 mmol) under argon atmosphere. The reaction mixture was further stirred at −10° C. for 2 h. After completion of the reaction (monitored by TLC and LCMS), the reaction mixture was quenched with water and extracted with ethyl acetate (3×20 mL). The combined organic layer was dried over anhydrous Na$_2$SO$_4$, filtered and concentrated under reduced pressure. The crude compound was purified by Combiflash column chromatography eluting with 0-20% ethyl acetate in n-hexane to afford 450 mg (43% yield) of compound 85-7 as light yellow solid.

LCMS: [M+H]$^+$=406.35; Rt=2.13 min $^1$H NMR (400 MHz, DMSO-d$_6$) δ: 11.80 (s, 1H), 8.68 (s, 1H), 7.98 (d, J=9.29 Hz, 1H), 7.89-7.92 (m, 2H), 7.68-7.72 (m, 2H), 7.55-7.61 (m, 2H), 7.46 (d, J=6.85 Hz, 1H), 7.33-7.39 (m, 3H), 2.36 (s, 3H).

To 8-fluoro-3-(phenylsulfonyl)-7-(o-tolyl)-3,6-dihydropyrrolo[3,2-e]indazole 85-7 (450 mg, 1.111 mmol) in DMF (10 mL) at 0° C. was added sodium hydride (60% dispersion in oil, 53 mg, 2.222 mmol) portion wise and stirred for 30 min. To the resulting solution was added (4-(bromomethyl)phenethoxy)(tert-butyl)dimethylsilane (437 mg, 1.333 mmol). The reaction mixture was stirred at room temperature for 1 h. After completion of the reaction (monitored by TLC and LCMS), the reaction mixture was quenched with water and extracted with ethyl acetate (3×20 mL). The combined organic layer dried over anhydrous Na$_2$SO$_4$, filtered and concentrated under reduced pressure. The resulting crude compound was purified by Combiflash column chromatography eluting with 0-20% ethyl acetate in n-hexane to afford 850 mg (100% yield) of compound 85-8 as light yellow solid.

LCMS: [M+H]$^+$=655.60; Rt=2.73 min

¹H NMR (400 MHz, CDCl₃) δ: 8.47-8.49 (m, 1H), 7.98-8.03 (m, 2H), 7.52-7.57 (m, 1H), 7.41-7.47 (m, 3H), 7.31 (d, J=8.31 Hz, 2H), 7.23 (d, J=3.42 Hz, 2H), 7.18 (d, J=7.83 Hz, 1H), 7.03 (d, J=8.31 Hz, 2H), 6.74 (d, J=7.82 Hz, 2H), 5.20-5.25 (m, 1H), 5.09-5.15 (m, 1H), 3.79 (t, J=6.85 Hz, 2H), 2.73 (t, J=6.85 Hz, 2H), 2.16 (s, 3H), 0.83 (s, 9H), 0.00 (s, 6H).

To a solution of 6-(4-(2-((tert-butyldimethylsilyl)oxy)ethyl)benzyl)-8-fluoro-3-(phenylsulfonyl)-7-(o-tolyl)-3,6-dihydropyrrolo[3,2-e]indazole 85-8 (850 mg, 1.301 mmol) in THF (15 mL) at 0° C. was added tetrabutylammonium fluoride solution (1M in THF, 2 mL, 1.952 mmol). The reaction mixture was stirred at room temperature for 2 h. After completion of the reaction (monitored by TLC and LCMS), the reaction mixture was quenched with water and extracted with ethyl acetate (3×30 mL). The combined organic layer was dried over anhydrous Na₂SO₄, filtered and concentrated under reduced pressure. The crude compound was purified by Combiflash column chromatography eluting with 30-40% ethyl acetate in n-hexane to afford 360 mg (51% yield) of compound 85-9 as off white solid.

LCMS: [M+H]⁺=540.65; Rt=2.17 min

¹H NMR (400 MHz, CDCl₃) δ: 8.48 (s, 1H), 7.98-8.05 (m, 3H), 7.52-7.57 (m, 1H), 7.42-7.48 (m, 3H), 7.29-7.35 (m, 2H), 7.24 (d, J=3.45 Hz, 2H), 7.06 (d, J=7.88 Hz, 2H), 6.77 (d, J=7.88 Hz, 2H), 5.13-5.27 (m, 2H), 3.77-3.84 (m, 2H), 2.79 (t, J=6.40 Hz, 2H), 2.15 (s, 3H).

To a solution of 2-(4-((8-fluoro-3-(phenylsulfonyl)-7-(o-tolyl)pyrrolo[3,2-e]indazol-6(3H)-yl)methyl)phenyl)ethan-1-ol 85-9 (350 mg, 0.649 mmol) in CH₂Cl₂ (20 mL) at 0° C. was added triethylamine (0.23 mL, 1.948 mmol) followed by tosyl chloride (148 mg, 0.779 mmol). The reaction mixture was stirred at room temperature for 18 h. After completion of the reaction (monitored by TLC and LCMS), the reaction mixture was quenched with water and extracted with ethyl acetate (2×20 mL). The combined organic layer was dried over anhydrous Na₂SO₄, filtered and concentrated under reduced pressure. The crude compound was purified by Combiflash column chromatography eluting with 0-20% ethyl acetate in n-hexane to afford 370 mg (45% yield) of compound 85-10 as light yellow solid.

LCMS: [M+H]⁺=694.30; Rt=2.39 min

¹H NMR (400 MHz, CDCl₃) δ: 8.49 (s, 1H), 8.03 (d, J=9.35 Hz, 1H), 7.98-8.01 (m, 2H), 7.65 (d, J=8.37 Hz, 2H), 7.51-7.57 (m, 1H), 7.40-7.47 (m, 4H), 7.30-7.37 (m, 2H), 7.23 (s, 1H), 7.19 (d, J=7.88 Hz, 2H), 6.95 (d, J=7.88 Hz, 2H), 6.72 (d, J=7.88 Hz, 2H), 5.19-5.26 (m, 1H), 5.07-5.15 (m, 1H), 4.13 (t, J=7.14 Hz, 2H), 2.87 (t, J=6.89 Hz, 2H), 2.37 (s, 3H), 2.15 (s, 3H).

To 4-((8-fluoro-3-(phenylsulfonyl)-7-(o-tolyl)pyrrolo[3,2-e]indazol-6(3H)-yl)methyl)phenethyl 4-methylbenzenesulfonate 85-10 (120 mg, 0.173 mmol) in acetonitrile-water (1:1, 4 mL) was added ethyl amine solution (2M in THF, 1.06 mL, 2.120 mmol) at room temperature and stirred for 72 h. After completion of the reaction (monitored by TLC and LCMS), the reaction mixture was concentrated and diluted with ethyl acetate. The organic layer was washed with brine, dried over anhydrous Na₂SO₄, filtered and concentrated under reduced pressure. The crude compound was purified by silica gel column chromatography eluting with 4-6% methanol in CH₂Cl₂ to afford 95 mg (97% yield) of compound 85-11 as white solid.

LCMS: [M+H]⁺=567.20; Rt=1.64 min

To a solution of N-ethyl-2-(4-((8-fluoro-3-(phenylsulfonyl)-7-(o-tolyl)pyrrolo[3,2-e]indazol-6(3H)-yl)methyl)phenyl)ethan-1-amine 85-11 (93 mg, 0.1643 mmol) in methanol (4 mL) was added a solution of potassium carbonate (90.6 mg, 0.657 mmol) in water (1 mL) at room temperature. The reaction mixture was heated to reflux for 2 h. After completion of the reaction (monitored by TLC and LCMS), the reaction mixture was concentrated under reduced pressure and the crude compound was purified by preparative HPLC to afford 23 mg (33% yield) of D-85 as off white solid.

LCMS: [M+H]⁺=427.25; Rt=1.39 min

¹H NMR (400 MHz, CDCl₃) δ: 8.34 (s, 1H), 7.21-7.38 (m, 6H), 7.01 (d, J=8.31 Hz, 2H), 6.75 (d, J=7.83 Hz, 2H), 5.09-5.25 (m, 2H), 2.83-2.88 (m, 2H), 2.74-2.78 (m, 2H), 2.70 (q, J=7.17 Hz, 2H), 2.19 (s, 3H), 1.11 (t, J=7.09 Hz, 3H).

N-(Cyclopropylmethyl)-2-(4-((8-fluoro-7-(o-tolyl)pyrrolo[3,2-e]indazol-6(3H)-yl)methyl)phenyl)ethan-1-amine (D-88)

To a solution of 4-((8-fluoro-3-(phenylsulfonyl)-7-(o-tolyl)pyrrolo[3,2-e]indazol-6(3H)-yl)methyl)phenethyl 4-methylbenzenesulfonate 85-10 (120 mg, 0.173 mmol) in acetonitrile (10 mL) was added cyclopropyl methyl amine (122 mg, 1.731 mmol) and DIPEA (0.3 mL, 1.731 mmol) in a sealed tube. The reaction mixture was stirred at room temperature for 72 h. After completion of the reaction (monitored by TLC and LCMS), the reaction mixture was concentrated and diluted with ethyl acetate. Organic layer was washed with brine, dried over anhydrous Na₂SO₄, filtered and concentrated under reduced pressure. The crude compound was purified by Combiflash column chromatography eluting with 0-6% methanol in CH₂Cl₂ to afford 90 mg (88% yield) of compound 88-1 as white solid.

LCMS: [M+H]⁺=593.20; Rt=1.88 min

To a solution of N-(cyclopropylmethyl)-2-(4-((8-fluoro-3-(phenylsulfonyl)-7-(o-tolyl)pyrrolo[3,2-e]indazol-6(3H)-yl)methyl)phenyl)ethan-1-amine 88-1 (90 mg, 0.152 mmol) in methanol (4 mL) was added a solution of potassium carbonate (83.7 mg, 0.607 mmol) in water (1 mL) at room temperature. The reaction mixture was heated to reflux 2 h. After completion of the reaction (monitored by TLC and LCMS), the reaction mixture was concentrated under reduced pressure and the crude compound was purified by preparative HPLC to afford 25 mg (36% yield) of D-88 as off white solid.

LCMS: [M+H]⁺=453.25; Rt=1.45 min

¹H NMR (400 MHz, CDCl₃) δ: 8.34 (s, 1H), 7.23-7.37 (m, 6H), 7.02 (d, J=7.6 Hz, 2H), 6.76 (d, J=8.31 Hz, 2H), 5.12-5.26 (m, 2H), 2.85-2.91 (m, 2H), 2.73-2.79 (m, 2H), 2.51 (d, J=6.85 Hz, 2H), 2.20 (s, 3H), 0.87-0.98 (m, 1H), 0.42-0.51 (m, 2H), 0.05-0.14 (m, 2H).

N-(4-((8-Fluoro-7-(o-tolyl)pyrrolo[3,2-e]indazol-6(3H)-yl)methyl)phenethyl)cyclobutanamine (D-89)

To a solution of 4-((8-fluoro-3-(phenylsulfonyl)-7-(o-tolyl)pyrrolo[3,2-e]indazol-6(3H)-yl)methyl)phenethyl-4-methylbenzenesulfonate 85-10 (120 mg, 0.173 mmol) in acetonitrile (10 mL) was added cyclobutanamine (124 mg, 1.7316 mmol) and DIPEA (0.3 mL, 1.7316 mmol) in a sealed tube. The reaction mixture was stirred at room temperature for 72 h. After completion of the reaction (monitored by TLC and LCMS), the reaction mixture was concentrated and diluted with ethyl acetate. The organic layer was washed with brine, dried over anhydrous Na₂SO₄, filtered and concentrated under reduced pressure. The crude compound was purified by Combiflash column chromatography eluting with 0-10% methanol in CH₂Cl₂ to afford 101 mg (99% yield) of compound 89-1 as white solid.

LCMS: [M-18]⁺=575.25; Rt=1.66 min

To a solution of N-(4-((8-fluoro-3-(phenylsulfonyl)-7-(o-tolyl)pyrrolo[3,2-e]indazol-6(3H)-yl)methyl)phenethyl)cyclobutanamine 89-1 (85 mg, 0.150 mmol) in methanol (4 mL) was added a solution of potassium carbonate (83 mg, 0.600 mmol) in water (1 mL) at room temperature. The reaction mixture was heated to reflux for 2 h. After completion of the reaction (monitored by TLC and LCMS), the reaction mixture was concentrated under reduced pressure and the crude compound was purified by preparative HPLC to afford 30 mg (44% yield) of D-89 as off white solid.

LCMS: [M+H]$^+$=453.25; Rt=1.45 min $^1$H NMR (400 MHz, CDCl$_3$) δ: 8.34 (s, 1H), 7.27-7.38 (m, 5H), 7.21-7.25 (m, 1H), 7.01 (d, J=7.83 Hz, 2H), 6.75 (d, J=7.82 Hz, 2H), 5.09-5.25 (m, 2H), 3.22-3.30 (m, 1H), 2.67-2.78 (m, 4H), 2.20 (s, 3H), 2.15-2.18 (m, 2H), 1.62-1.69 (m, 5H).

N-(4-((8-Fluoro-7-(o-tolyl)pyrrolo[3,2-e]indazol-6(3H)-yl)methyl)phenethyl)cyclopropanamine (D-90)

To a solution of 4-((8-fluoro-3-(phenylsulfonyl)-7-(o-tolyl)pyrrolo[3,2-e]indazol-6(3H)-yl)methyl)phenethyl 4-methylbenzenesulfonate 85-10 (120 mg, 0.173 mmol) in acetonitrile (10 mL) was added cyclopropanamine (98.7 mg, 1.731 mmol) and DIPEA (0.3 mL, 1.731 mmol) in a sealed tube. The reaction mixture was stirred at room temperature for 72 h. After completion of the reaction (monitored by TLC and LCMS), the reaction mixture was concentrated and diluted with ethyl acetate. The organic layer was washed with brine, dried over anhydrous Na$_2$SO$_4$, filtered and concentrated under reduced pressure. The crude compound was purified by Combiflash column chromatography eluting with 0-10% methanol in CH$_2$Cl$_2$ to afford 100 mg (99% yield) of compound 90-1 as white solid.

LCMS: [M+H]$^+$=579.20; Rt=1.65 min

To a solution of N-(4-((8-fluoro-3-(phenylsulfonyl)-7-(o-tolyl)pyrrolo[3,2-e]indazol-6(3H)-yl)methyl)phenethyl)cyclopropanamine 90-1 (105 mg, 0.181 mmol) in methanol (4 mL) was added a solution of potassium carbonate (100 mg, 0.726 mmol) in water (1 mL) at room temperature. The reaction mixture was heated to reflux for 2 h. After completion of the reaction (monitored by TLC and LCMS), the reaction mixture was concentrated under reduced pressure and the crude compound was purified by preparative HPLC to afford 32 mg (40% yield) of D-90 as off white solid.

LCMS: [M+H]$^+$=439.20; Rt=1.42 min $^1$H NMR (400 MHz, CDCl$_3$) δ: 8.35 (s, 1H), 7.27-7.37 (m, 6H), 7.22-7.25 (m, 1H), 7.02 (d, J=8.31 Hz, 2H), 6.76 (d, J=8.31 Hz, 2H), 5.10-5.26 (m, 2H), 2.86-2.92 (m, 2H), 2.69-2.74 (m, 2H), 2.20 (s, 3H), 2.07-2.12 (m, 1H), 0.39-0.45 (m, 2H), 0.29-0.35 (m, 2H).

N-(4-((8-fluoro-7-(o-tolyl)pyrrolo[3,2-e]indazol-6(3H)-yl)methyl)phenethyl)propan-1-amine (D-91)

To 4-((8-fluoro-3-(phenylsulfonyl)-7-(o-tolyl)pyrrolo[3,2-e]indazol-6(3H)-yl)methyl)phenethyl 4-methylbenzenesulfonate D-85-10 (120 mg, 0.173 mmol) in acetonitrile (10 mL) was added propan-1-amine (102 mg, 1.731 mmol) and DIPEA (0.3 mL, 1.731 mmol) in a seal tube. The reaction mixture was further stirred at room temperature for 72 h. After completion of the reaction, the reaction mixture was diluted with water and extracted with ethyl acetate (2×10 mL). The combined organic layer dried over anhydrous Na$_2$SO$_4$, filtered and concentrated under reduced pressure. The crude compound was purified by Combiflash column chromatography eluting with 0-10% methanol in CH$_2$Cl$_2$ to afford 85 mg (85% yield) of compound 91-1 as off white solid.

LCMS: [M+H]$^+$=581.25; Rt=1.86 min

To N-(4-((8-fluoro-3-(phenylsulfonyl)-7-(o-tolyl)pyrrolo[3,2-e]indazol-6(3H)-yl)methyl)phenethyl)propan-1-amine 91-1 (85 mg, 0.146 mmol) in methanol (4 mL) was added solution of potassium carbonate (81 mg, mmol) in water (1 mL) at room temperature. The reaction mixture was further heated to reflux at 70° C. and stirred for 2 h. After completion of the reaction, the reaction mixture was concentrated under reduced pressure and the crude compound was purified by preparative HPLC to afford 20 mg (31% yield) of D-91 as off white solid.

LCMS: [M+H]$^+$=441.20; Rt=1.62 min $^1$H NMR (400 MHz, CDCl$_3$) δ: 8.35 (s, 1H), 7.52 (s, 1H), 7.28-7.37 (m, 4H), 7.20-7.23 (m, 1H), 6.99-7.03 (m, 2H), 6.76 (d, J=7.82 Hz, 2H), 5.10-5.26 (m, 2H), 3.49 (s, 1H), 2.77-2.84 (m, 2H), 2.70-2.76 (m, 2H), 2.56 (t, J=7.34 Hz, 2H), 2.20 (s, 3H), 1.43-1.50 (m, 2H), 0.87 (t, J=7.34 Hz, 3H).

2-Fluoro-N-(4-((8-fluoro-7-(o-tolyl)pyrrolo[3,2-e]indazol-6(3H)-yl)methyl)phenethyl)ethan-1-amine (D-101)

To 4-((8-fluoro-3-(phenylsulfonyl)-7-(o-tolyl)pyrrolo[3,2-e]indazol-6(3H)-yl)methyl)phenethyl 4-methylbenzenesulfonate 85-10 (170 mg, 0.245 mmol) in DMF (5 mL) was added potassium pthalimide (43.2 mg, 0.294 mmol) at room temperature. The reaction mixture was further heated to 90° C. and stirred for 3 h. After completion of the reaction, the reaction mixture was cooled to room temperature, quenched with water and extracted with ethyl acetate (3×20 mL). The combined organic layer was dried over anhydrous Na$_2$SO$_4$, filtered and concentrated under reduced pressure to afford 155 mg (95% yield) of compound 101-11 as brown solid.

LCMS-Condition-1: [M+H]$^+$=669.20; Rt=2.40 min

To 2-(4-((8-fluoro-3-(phenylsulfonyl)-7-(o-tolyl)pyrrolo[3,2-e]indazol-6(3H)-yl)methyl)phenethyl)isoindoline-1,3-dione 101-11 (2 g, 2.990 mmol) in ethanol (40 mL) was added hydrazine hydrate (143 mg, 4.486 mmol) at room temperature. The reaction mixture was further heated to 80° C. and stirred for 1 h. After completion of the reaction, the reaction mixture was concentrated under reduced pressure, the DCM for 15 min and filtered. The filtrate was concentrated under reduced pressure resulting in the crude compound which was purified by silica gel column chromatography eluting with 0-5% methanol in DCM to afford 1.1 g (68% yield) of compound 101-12 as yellow solid.

LCMS-Condition-1: [M-18]$^+$=521.10; Rt=1.61 min

To 2-(4-((8-fluoro-3-(phenylsulfonyl)-7-(o-tolyl)pyrrolo[3,2-e]indazol-6(3H)-yl)methyl)phenyl)ethan-1-amine 101-12 (550 mg, 1.021 mmol) in acetonitrile (4 mL) was added DIPEA (1.77 mL, 10.21 mmol) and 1-fluoro-2-iodoethane (1.8 g, 10.21 mmol) at room temperature and stirred for 48 h. After completion of the reaction, the reaction mixture was diluted with water and extracted with DCM (3×25 mL). The combined organic layer was dried over anhydrous Na$_2$SO$_4$, filtered and concentrated under reduced pressure. The crude compound was purified by silica gel column chromatography eluting with 0-2% methanol in DCM to afford 380 mg (63% yield) of compound 101-13A as light yellow solid.

LCMS-Condition-1: [M+H]$^+$=585.15; Rt=1.71 min $^1$H NMR (400 MHz, CDCl$_3$) δ: 8.39-8.50 (m, 1H), 7.96-8.05 (m, 3H), 7.50-7.58 (m, 1H), 7.44 (t, J=8.07 Hz, 3H), 7.28-7.38 (m, 2H), 7.20-7.24 (m, 2H), 7.04 (d, J=7.82

Hz, 2H), 6.72-6.81 (m, 2H), 5.10-5.26 (m, 2H), 4.61 (t, J=4.40 Hz, 1H), 4.49 (t, J=4.40 Hz, 1H), 2.98 (t, J=4.16 Hz, 1H), 2.90 (t, J=6.85 Hz, 3H), 2.75-2.83 (m, 2H), 2.14 (s, 2H), 2.11 (s, 1H).

To 2-fluoro-N-(4-((8-fluoro-3-(phenylsulfonyl)-7-(o-tolyl)pyrrolo[3,2-e]indazol-6(3H)-yl)methyl)phenethyl) ethan-1-amine 101-13A (200 mg, 0.342 mmol) in methanol (4 mL) was added potassium carbonate (189 mg, 1.369 mmol) at room temperature. The reaction mixture was further heated to reflux at 60° C. and stirred for 3 h. After completion of the reaction, the reaction mixture was diluted with water and extracted with DCM (3×25 mL). The combined organic layer was dried over anhydrous $Na_2SO_4$, filtered and concentrated under reduced pressure resulting in the crude compound. The crude compound was purified by silica gel column chromatography eluting with 0-6% methanol in DCM to afford 10 mg (6.5% yield) of D-101 as off white solid.

LCMS-Condition-1: $[M+H]^+$=445.20; Rt=1.39 min $^1$H NMR (400 MHz, $CDCl_3$) δ: 8.32 (s, 1H), 7.30-7.36 (m, 2H), 7.26 (2H merged in solvent peak), 7.19-7.24 (m, 2H), 7.01 (d, J=7.83 Hz, 2H), 6.75 (d, J=7.83 Hz, 2H), 5.07-5.25 (m, 2H), 4.62 (t, J=4.40 Hz, 1H), 4.48-4.54 (m, 1H), 3.03-3.07 (m, 1H), 2.95-3.01 (m, 3H), 2.80 (t, J=7.09 Hz, 2H), 2.19 (s, 3H).

3-Fluoro-N-(4-((8-fluoro-7-(o-tolyl)pyrrolo[3,2-e] indazol-6(3H)-yl)methyl)phenethyl)propan-1-amine (D-102)

To a solution of 2-(4-((8-fluoro-3-(phenylsulfonyl)-7-(o-tolyl)pyrrolo[3,2-e]indazol-6(3H)-yl)methyl)phenyl)ethan-1-amine 101-12 (200 mg, 0.371 mmol) in acetonitrile (3 mL) was added DIPEA (0.16 mL, 0.742 mmol) and 1-fluoro-3-iodopropane (70 mg, 0.371 mmol) at room temperature and stirred for 48 h. After completion of the reaction (monitored by TLC and LCMS), the reaction mixture was diluted with water and extracted with DCM (3×25 mL). The combined organic layer was washed with water and brine, dried over anhydrous $Na_2SO_4$, filtered and concentrated under reduced pressure. The crude compound was purified by silica gel column chromatography eluting with 0-2% methanol in DCM to afford 90 mg (40% yield) of compound 102-13B as light yellow solid.

LCMS-Condition-1: $[M+H]^+$=599.15; Rt=1.67 min $^1$H NMR (400 MHz, $CDCl_3$) δ: 8.48 (s, 1H), 7.98-8.05 (m, 2H), 7.52-7.59 (m, 1H), 7.45 (t, J=8.07 Hz, 2H), 7.23-7.39 (m, 6H), 7.05 (d, J=7.82 Hz, 2H), 6.76 (d, J=7.34 Hz, 2H), 5.09-5.26 (m, 2H), 4.57 (t, J=5.38 Hz, 1H), 4.46 (t, J=5.38 Hz, 1H), 2.88-3.02 (m, 4H), 2.15 (s, 3H), 1.98-2.05 (m, 2H), 0.87-0.91 (m, 2H).

To a solution of 3-fluoro-N-(4-((8-fluoro-3-(phenylsulfonyl)-7-(o-tolyl)pyrrolo[3,2-e]indazol-6(3H)-yl)methyl) phenethyl)propan-1-amine 102-13B (90 mg, 0.150 mmol) in methanol (3 mL) was added potassium carbonate (72 mg, 0.526 mmol) at room temperature. The reaction mixture was heated to reflux for 20 min. After completion of the reaction (monitored by TLC and LCMS), the reaction mixture was quenched with water and extracted with ethyl acetate (3×25 mL). The combined organic layer was washed with brine, dried over anhydrous $Na_2SO_4$, filtered and concentrated under reduced pressure. The crude compound was purified by silica gel column chromatography eluting with 0-3% methanol in DCM, followed by trituration in diethyl ether and n-pentane to afford 30 mg (43% yield) of D-102 as off white solid.

LCMS-Condition-1: $[M+H]^+$=459.60; Rt=1.41 min $^1$H NMR (400 MHz, $CDCl_3$) δ: 8.35 (s, 1H), 7.27-7.36 (m, 5H), 7.21-7.24 (m, 1H), 7.02 (d, J=7.82 Hz, 2H), 6.76 (d, J=7.82 Hz, 2H), 5.09-5.26 (m, 2H), 4.53 (t, J=5.87 Hz, 1H), 4.41 (t, J=5.87 Hz, 1H), 2.78-2.84 (m, 2H), 2.69-2.75 (m, 4H), 2.20 (s, 3H), 1.76-1.90 (m, 4H).

(5R,6S)-5-(4-(2-(Ethylamino)ethyl)phenyl)-6-phenyl-5,6,7,8-tetrahydronaphthalen-2-ol (LA-18)

A mixture of 6-methoxy-3,4-dihydronaphthalen-1(2H)-one L18-1 (20 g, 120.5 mmol), benzyl bromide (22.7 g, 144.5 mmol) and cesium carbonate (117 g, 359.1 mmol) in xylene (200 mL) was degassed with argon for 15 min in a seal tube at room temperature. To the resulting solution was added $Pd(OAc)_2$ (1.34 g, 5.982 mmol) and Xanthphos (3.5 g, 6.055 mmol) and degassing was continued for another 15 min. The reaction mixture was sealed properly and heated to 130° C. for 24 h. After completion of the reaction (monitored by TLC and LCMS), the reaction mixture was diluted with water and extracted with ethyl acetate (3×). The combined organic layer was dried over anhydrous $Na_2SO_4$, filtered and concentrated under reduced pressure. The resulting crude compound was purified by silica gel column chromatography eluting with 0-10% ethyl acetate in n-hexane to afford 10 g (33% yield) of compound L18-2 as off white solid.

LCMS-Condition 01: $[M+H]^+$=253.05; Rt=1.95 min $^1$H NMR (400 MHz, DMSO-$d_6$) δ: 7.87 (d, J=9.29 Hz, 1H), 7.29-7.34 (m, 2H), 7.22-7.26 (m, 1H), 7.17 (d, J=7.34 Hz, 2H), 6.89-6.95 (m, 2H), 3.88 (d, J=4.89 Hz, 1H), 3.85 (s, 3H), 3.06-3.16 (m, 1H), 2.95 (td, J=4.04, 16.87 Hz, 1H), 2.21-2.39 (m, 2H).

To a solution of 6-methoxy-2-phenyl-3,4-dihydronaphthalen-1(2H)-one L18-2 (10 g, 36.76 mmol) in toluene (100 mL) was added $PBr_3$ (12 g, 44.42 mmol) at room temperature. The reaction mixture was heated to reflux for 16 h. After completion of the reaction (monitored by TLC and LCMS), the reaction mixture was quenched with water and extracted with ethyl acetate (3×). The combined organic layer was dried over anhydrous $Na_2SO_4$, filtered and concentrated under reduced pressure. The resulting crude compound was purified by silica gel column chromatography eluting with 0-5% ethyl acetate in n-hexane to afford 9 g (77% yield) of compound L18-3 as white solid.

LCMS-Condition 01: $[M+H]^+$=315.00; Rt=2.46 min $^1$H NMR (400 MHz, DMSO-$d_6$) δ: 7.50-7.55 (m, 1H), 7.35-7.43 (m, 4H), 7.29-7.35 (m, 1H), 6.84-6.88 (m, 2H), 3.79 (s, 3H), 2.88-2.95 (m, 2H), 2.63-2.69 (m, 2H).

To a solution of 4-bromo-7-methoxy-3-phenyl-1,2-dihydronaphthalene L18-3 (2 g, 6.349 mmol) and 2-(4-(4,4,5,5-tetramethyl-1,3,2-dioxaborolan-2-yl)phenyl)ethan-1-ol (1.57 g, 6.349 mmol) in DMF (40 mL) was added solution of cesium carbonate (6.2 g, 19.04 mmol) in water (8 mL) and degassed with argon for 20 min in a seal tube. To the resulting solution was added palladium acetate (71 mg, 0.316 mmol) followed by TPP (166 mg, 0.633 mmol) and degassing was continued for another 15 min. The reaction mixture was heated at 100° C. for 16 h. After completion of the reaction (monitored by TLC and LCMS), the reaction mixture was cooled to room temperature and quenched with ice cold water and extracted with ethyl acetate (3×). The combined organic layer dried over anhydrous $Na_2SO_4$, filtered and concentrated under reduced pressure. The resulting crude compound was purified by silica gel column chromatography eluting with 0-15% ethyl acetate in n-hexane to afford 1 g (44% yield) of compound L18-4 as yellow solid.

LCMS-Condition-1: $[M+H]^+$=357.10; Rt=2.31 min

¹H NMR (400 MHz, DMSO-d₆) δ: 7.09 (d, J=7.34 Hz, 4H), 7.04 (d, J=6.85 Hz, 1H), 6.99-7.03 (m, 2H), 6.90 (d, J=8.31 Hz, 2H), 6.85 (d, J=1.96 Hz, 1H), 6.64 (dd, J=2.45, 8.31 Hz, 1H), 6.51 (d, J=8.80 Hz, 1H), 4.63 (t, J=5.38 Hz, 1H), 3.74 (s, 3H), 3.56-3.64 (m, 2H), 2.87-2.94 (m, 2H), 2.69 (t, J=7.34 Hz, 4H).

To a solution of 2-(4-(6-methoxy-2-phenyl-3,4-dihydronaphthalen-1-yl)phenyl)ethan-1-ol L18-4 (600 mg, 1.683 mmol) in DCM (10 mL) was added triethylamine (0.9 mL, 6.734 mmol) and tosyl chloride (481 mg, 2.525 mmol) at room temperature and stirred for 18 h. After completion of the reaction (monitored by TLC and LCMS), the reaction mixture was quenched with water and extracted with ethyl acetate₂ (3×). Combined organic layer was dried over anhydrous Na₂SO₄, filtered and concentrated under reduced pressure. The crude compound was purified by silica gel column chromatography eluting with 0-15% ethyl acetate in n-hexane to afford 600 mg (70% yield) of compound L18-5 as colourless sticky solid.

LCMS-Condition-1: [M+H]⁺=511.20; Rt=2.60 min

¹H NMR (400 MHz, DMSO-d₆) δ: 7.76 (d, J=8.31 Hz, 2H), 7.48 (d, J=8.31 Hz, 2H), 7.02-7.17 (m, 7H), 6.95 (d, J=7.83 Hz, 2H), 6.90 (d, J=2.45 Hz, 1H), 6.69 (dd, J=2.69, 8.56 Hz, 1H), 6.52 (d, J=8.31 Hz, 1H), 4.26 (t, J=6.36 Hz, 2H), 3.79 (s, 3H), 2.89-2.98 (m, 4H), 2.72-2.77 (m, 2H), 2.45 (s, 3H).

To a solution of 4-(6-methoxy-2-phenyl-3,4-dihydronaphthalen-1-yl)phenethyl 4-methylbenzenesulfonate L18-5 (300 mg, 0.587 mmol) in acetonitrile (2 mL) was added ethyl amine (240 mg, 5.876 mmol) and DIPEA (1.02 mL, 5.786 mmol) in a seal tube. The reaction mixture was further stirred at room temperature for 3 days. After completion of the reaction (monitored by TLC and LCMS), the reaction mixture was diluted with water and extracted with ethyl acetate (2×). Combined organic layer dried over anhydrous Na₂SO₄, filtered and concentrated under reduced pressure. The crude compound was purified by silica gel column chromatography eluting with 0-10% methanol in CH₂Cl₂ to afford 160 mg (71% yield) of compound L18-6 as colourless semisolid.

LCMS-Condition-1: [M+H]⁺=384.20; Rt=1.81 min

To a solution of N-ethyl-2-(4-(6-methoxy-2-phenyl-3,4-dihydronaphthalen-1-yl)phenyl)ethan-1-amine L18-6 (160 mg, 0.417 mmol) in ethyl acetate (20 mL) was added 10% palladium on carbon (200 mg) at room temperature under nitrogen atmosphere. The reaction mixture was stirred under hydrogen atmosphere at room temperature for 18 h. After completion of the reaction (monitored by TLC and LCMS), the reaction mixture was filtered through a pad of Celite™ and washed with methanol. The filtrate was concentrated under reduced pressure to afford 150 mg (94% yield) of L18-7 as colourless sticky solid.

LCMS-Condition-1: [M+H]⁺=386.20; Rt=1.39/1.83 min

To N-ethyl-2-(4-((1R,2S)-6-methoxy-2-phenyl-1,2,3,4-tetrahydronaphthalen-1-yl)phenyl)ethan-1-amine L18-7 (150 mg, 0.389 mmol) in CH₂Cl₂ (15 mL) at 0° C. was added boron tribromide (0.07 mL, 0.770 mmol) drop wise. The reaction mixture was stirred at same temperature for 45 min. After completion of the reaction (monitored by TLC and LCMS), the reaction mixture was quenched with saturated NaHCO₃ solution, and extracted with CH₂Cl₂ (3×). The separated organic layer was dried over anhydrous Na₂SO₄, filtered and concentrated under reduced pressure. The crude compound was purified by preparative HPLC to afford 62 mg (43% yield) of LA-18 (TFA salt) as off white solid.

LCMS-Condition-1: [M+H]⁺=372.20; Rt=1.62 min

¹H NMR (400 MHz, DMSO-d₆) δ: 9.15 (br. s, 1H), 8.36 (br. s, 2H), 7.10-7.17 (m, 3H), 6.80-6.88 (m, 3H), 6.59-6.66 (m, 2H), 6.49 (dd, J=2.45, 8.31 Hz, 1H), 6.35 (d, J=8.31 Hz, 2H), 4.21-4.26 (m, 1H), 3.43-3.58 (m, 2H), 3.35 (dd, J=3.91, 12.23 Hz, 1H), 2.88-3.08 (m, 5H), 2.69-2.77 (m, 2H), 2.01-2.17 (m, 1H), 1.69-1.77 (m, 1H), 1.15 (t, J=7.34 Hz, 3H).

(5R,6S)-5-(4-(2-((Cyclopropylmethyl)amino)ethyl) phenyl)-6-phenyl-5,6,7,8-tetrahydronaphthalen-2-ol (LA-19)

To a solution of 4-(6-methoxy-2-phenyl-3,4-dihydronaphthalen-1-yl)phenethyl 4-methylbenzenesulfonate L18-5 (300 mg, 0.587 mmol) in acetonitrile (2 mL) was added cyclopropylmethanamine (417 mg, 5.876 mmol) and DIPEA (1.02 mL, 5.876 mmol) in a seal tube. The reaction mixture was stirred at room temperature for 3 days. After completion of the reaction (monitored by TLC and LCMS), the reaction mixture was diluted with water and extracted with ethyl acetate (2×). Combined organic layer was dried over anhydrous Na₂SO₄, filtered and concentrated under reduced pressure. The crude compound was purified by silica gel column chromatography eluting with 0-10% methanol in CH₂Cl₂ to afford 160 mg (66% yield) of compound L19-6 as colourless semisolid.

LCMS-Condition-1: [M+H]⁺=410.20; Rt=1.86 min

To a solution of N-(cyclopropylmethyl)-2-(4-(6-methoxy-2-phenyl-3,4-dihydronaphthalen-1-yl)phenyl)ethan-1-amine L19-6 (160 mg, 0.390 mmol) in ethyl acetate (20 mL) was added 10% palladium on carbon (200 mg) at room temperature under nitrogen atmosphere. The reaction mixture was further stirred at room temperature under hydrogen atmosphere for 18 h. After completion of the reaction (monitored by TLC and LCMS), the reaction mixture was filtered through a pad of Celite™ and washed with methanol. The filtrate was concentrated under reduced pressure to afford 150 mg (94% yield) of compound L19-7 as colourless sticky solid.

LCMS-Condition-1: [M+H]⁺=412.25; Rt=1.89 min

To a solution of N-(cyclopropylmethyl)-2-(4-((1R,2S)-6-methoxy-2-phenyl-1,2,3,4-tetrahydronaphthalen-1-yl)phenyl)ethan-1-amine L19-7 (150 mg, 0.364 mmol) in CH₂Cl₂ (15 mL) at 0° C. was added boron tribromide (0.07 mL, 0.729 mmol) drop wise. The reaction mixture was stirred at same temperature for 45 min. After completion of the reaction (monitored by TLC and LCMS), the reaction mixture was quenched with saturated NaHCO₃ solution, and extracted with CH₂Cl₂ (3×). The separated organic layer was dried over anhydrous Na₂SO₄, filtered and concentrated under reduced pressure. The crude compound was purified by preparative HPLC to afford 34 mg (24% yield) of LA-19 (TFA salt) as off white solid.

LCMS-Condition-1: [M+H]⁺=398.25; Rt=1.68 min

¹H NMR (400 MHz, DMSO-d₆) δ: 9.16 (br. s, 1H), 8.49 (br. s, 2H), 7.08-7.18 (m, 3H), 6.84 (dd, J=8.07, 11.49 Hz, 4H), 6.60-6.65 (m, 2H), 6.48 (dd, J=1.96, 8.31 Hz, 1H), 6.35 (d, J=7.82 Hz, 2H), 4.24 (d, J=4.89 Hz, 1H), 3.35 (dd, J=2.93, 13.20 Hz, 1H), 2.92-3.08 (m, 4H), 2.72-2.84 (m, 4H), 2.02-2.15 (m, 1H), 1.70-1.78 (m, 1H), 0.99 (ddd, J=4.65, 8.07, 12.23 Hz, 1H), 0.53-0.60 (m, 2H), 0.28-0.35 (m, 2H).

(5R,6S)-5-(4-(2-(Ethylamino)ethyl)phenyl)-6-(o-tolyl)-5,6,7,8-tetrahydronaphthalen-2-ol (LA-21)

A mixture of 6-methoxy-3,4-dihydronaphthalen-1(2H)-one L18-1 (5 g, 28.41 mmol), 2-bromo toluene (5 mL, 42.10 mmol) and cesium carbonate (32.4 g, 99.41 mmol) in xylene (125 mL) was degassed with argon for 10 min. To the resulting solution was added Pd(OAc)$_2$ (636 mg, 2.839 mmol) and Xantphos (2.5 g, 4.251 mmol) and degassing with argon was continued for another 15 min at room temperature. The reaction mixture was heated at 130° C. for 24 h. After completion of the reaction (monitored by TLC and LCMS), the reaction mixture was cooled to room temperature and filtered; the filtrate was concentrated under reduced pressure. The resulting crude material was purified by silica gel column chromatography eluting with 0-8% ethyl acetate in n-hexane to afford 3.3 g (44% yield) of compound L21-2 as yellow solid.

LCMS-Condition 01: [M+H]$^+$=267.05; Rt=2.18 min $^1$H NMR (400 MHz, CDCl$_3$) δ: 8.09 (d, J=8.80 Hz, 1H), 7.13-7.27 (m, 3H), 7.02-7.08 (m, 1H), 6.87 (dd, J=2.45, 8.80 Hz, 1H), 6.75 (d, J=2.45 Hz, 1H), 3.90-3.99 (m, 1H), 3.88 (s, 3H), 2.97-3.15 (m, 2H), 2.35-2.45 (m, 2H), 2.32-2.35 (m, 3H).

To a solution of 6-methoxy-2-(o-tolyl)-3,4-dihydronaphthalen-1(2H)-one L21-2 (8.2 g, 30.76 mmol) in toluene (150 mL) at 0° C. was added PBr$_3$ (2 mL, 21.42 mmol) drop wise. The reaction mixture was then heated to reflux for 16 h. After completion of the reaction (monitored by TLC and LCMS), the reaction mixture was washed with saturated NaHCO$_3$ solution and the separated organic layer was dried over anhydrous Na$_2$SO$_4$, filtered and concentrated under reduced pressure. The resulting crude compound was purified by silica gel column chromatography eluting with 0-8% ethyl acetate in n-hexane to afford 7 g (69% yield) of compound L21-3 as off white solid.

LCMS-Condition 01: [M+H]$^+$=329.30; Rt=2.53 min $^1$H NMR (400 MHz, CDCl$_3$) δ: 7.62 (d, J=8.80 Hz, 1H), 7.17-7.26 (m, 3H), 7.08-7.12 (m, 1H), 6.79 (dd, J=2.69, 8.56 Hz, 1H), 6.73 (d, J=2.45 Hz, 1H), 3.84 (s, 3H), 2.87-3.04 (m, 2H), 2.54-2.61 (m, 2H), 2.30 (s, 3H).

To a solution of 4-bromo-7-methoxy-3-(o-tolyl)-1,2-dihydronaphthalene L21-3 (2 g, 6.079 mmol) and 2-(4-(4,4,5,5-tetramethyl-1,3,2-dioxaborolan-2-yl)phenyl)ethan-1-ol (1.5 g, 6.079 mmol) in DMF (40 mL) was added a solution of cesium carbonate (5.9 g, 18.23 mmol) in water (8 mL) and degassed with argon for 20 min in a seal tube. To the resulting solution was added palladium acetate (68 mg, 0.304 mmol) and TPP (166 mg, 0.633 mmol) and degassing was continued for another 15 min. Then the reaction mixture was heated at 100° C. for 16 h. After completion of the reaction (monitored by TLC and LCMS), the reaction mixture was cooled to room temperature, diluted with ice cold water and extracted with ethyl acetate (3×). Combined organic layer was dried over anhydrous Na$_2$SO$_4$, filtered and concentrated under reduced pressure. The resulting crude compound was purified by silica gel column chromatography eluting with 0-15% ethyl acetate in n-hexane to afford 1 g (44% yield) of compound L21-4 as yellow solid.

LCMS-Condition-1: [M+H]$^+$=371.35; Rt=2.21 min $^1$H NMR (400 MHz, DMSO-d$_6$) δ: 7.95 (s, 1H), 6.88-7.02 (m, 6H), 6.84 (d, J=7.34 Hz, 2H), 6.79 (br. s, 1H), 6.57 (d, J=8.31 Hz, 1H), 6.45 (d, J=8.31 Hz, 1H), 3.68 (s, 3H), 3.52 (t, J=7.09 Hz, 2H), 2.77-2.84 (m, 2H), 2.59 (t, J=6.85 Hz, 2H), 2.34-2.45 (m, 2H), 2.09 (s, 3H).

To a solution of 2-(4-(6-methoxy-2-(o-tolyl)-3,4-dihydronaphthalen-1-yl)phenyl)ethan-1-ol L21-4 (800 mg, 2.162 mmol) in DCM (10 mL) was added triethylamine (1.19 mL, 8.613 mmol) and tosyl chloride (618 mg, 3.241 mmol) at room temperature and stirred for 18 h. After completion of the reaction (monitored by TLC and LCMS), the reaction mixture was quenched with water and extracted with ethyl acetate (3×). Combined organic layer was dried over anhydrous Na$_2$SO$_4$, filtered and concentrated under reduced pressure. The crude compound was purified by silica gel column chromatography eluting with 0-15% ethyl acetate in n-hexane to afford 700 mg (63% yield) of compound L21-5 as colourless sticky solid.

LCMS-Condition-1: [M+H$_2$O]$^+$=542.70; Rt=2.49 min

To a solution of 4-(6-methoxy-2-(o-tolyl)-3,4-dihydronaphthalen-1-yl)phenethyl 4-methylbenzenesulfonate L21-5 (700 mg, 1.334 mmol) in ethyl acetate (30 mL) was added 10% palladium on carbon (800 mg) at room temperature under nitrogen atmosphere. The reaction mixture was stirred under hydrogen atmosphere at room temperature for 18 h. After completion of the reaction (monitored by TLC and LCMS), the reaction mixture was filtered through a pad of Celite™ and washed with methanol. The filtrate was concentrated under reduced pressure to afford 499 mg (70% yield) of compound L21-6 as colourless sticky liquid.

LCMS-Condition-1: [M+Na]$^+$=549.20; Rt=2.46 min

To a solution of 4-(6-methoxy-2-(o-tolyl)-1,2,3,4-tetrahydronaphthalen-1-yl)phenethyl 4-methylbenzenesulfonate L21-6 (200 mg, 0.380 mmol) in acetonitrile (2 mL) was added ethyl amine (171 mg, 3.802 mmol) and DIPEA (0.66 mL, 3.802 mmol) in a seal tube. The reaction mixture was further stirred at room temperature for 3 days. After completion of the reaction (monitored by TLC and LCMS), the reaction mixture was diluted with water and extracted with ethyl acetate (3×). Combined organic layer was dried over anhydrous Na$_2$SO$_4$, filtered and concentrated under reduced pressure. The crude compound was purified by silica gel column chromatography eluting with 0-10% methanol in CH$_2$Cl$_2$ to afford 150 mg (99% yield) of compound L21-7 as colourless semisolid.

LCMS-Condition-1: [M+H]$^+$=400.25; Rt=1.86 min

To a solution of N-ethyl-2-(4-((1R,2S)-6-methoxy-2-(o-tolyl)-1,2,3,4-tetrahydronaphthalen-1-yl)phenyl)ethan-1-amine L21-7 (119 mg, 0.297 mmol) in CH$_2$Cl$_2$ (15 mL) at 0° C. was added boron tribromide (0.05 mL, 0.595 mmol) drop wise. The reaction mixture was stirred at the same temperature for 45 min. After completion of the reaction (monitored by TLC and LCMS), the reaction mixture was quenched with saturated NaHCO$_3$ solution, and extracted with CH$_2$Cl$_2$. The separated organic layer was dried over anhydrous Na$_2$SO$_4$, filtered and concentrated under reduced pressure. The crude compound was purified by preparative HPLC to afford 20 mg (16% yield) of LA-21 as off white solid.

LCMS-Condition-1: [M+H]$^+$=386.20; Rt=1.44 min $^1$H NMR (400 MHz, DMSO-d$_6$) δ: 9.14 (br. s, 1H), 7.16 (d, J=7.83 Hz, 1H), 7.00 (t, J=7.58 Hz, 1H), 6.80 (d, J=7.82 Hz, 2H), 6.74 (t, J=7.34 Hz, 1H), 6.66 (d, J=8.31 Hz, 1H), 6.62 (d, J=1.96 Hz, 1H), 6.49 (dd, J=2.45, 8.31 Hz, 1H), 6.25 (d, J=7.82 Hz, 2H), 6.09 (d, J=7.82 Hz, 1H), 4.24 (d, J=4.89 Hz, 1H), 3.46 (dd, J=4.16, 12.47 Hz, 1H), 2.93-3.02 (m, 2H), 2.63-2.71 (m, 2H), 2.56 (q, J=6.85 Hz, 4H), 2.44 (s, 3H), 2.10-2.22 (m, 2H), 1.61 (d, J=11.25 Hz, 1H), 0.99 (t, J=7.09 Hz, 3H).

(5R,6S)-5-(4-(2-((cyclopropylmethyl)amino)ethyl) phenyl)-6-(o-tolyl)-5,6,7,8-tetrahydronaphthalen-2-ol (LA-22)

To a solution of 4-(6-methoxy-2-(o-tolyl)-1,2,3,4-tetrahydronaphthalen-1-yl)phenethyl 4-methylbenzenesulfonate 21-6 (200 mg, 0.380 mmol) in acetonitrile (2 mL) was added cyclopropylmethanamine (269 mg, 3.802 mmol) and DIPEA (0.66 mL, 3.802 mmol) in a sealed tube. The reaction mixture was stirred at room temperature for 3 days. After completion of the reaction (monitored by TLC and LCMS), the reaction mixture was diluted with water and extracted with ethyl acetate (2×). Combined organic layer dried over anhydrous $Na_2SO_4$, filtered and concentrated under reduced pressure. The crude compound was purified by silica gel column chromatography eluting with 0-5% methanol in $CH_2Cl_2$ to afford 120 mg (74% yield) of compound 22-7 as colourless semisolid.

LCMS-Condition-1: [M+H]$^+$=426.25; Rt=1.90 min

To a solution of N-(cyclopropylmethyl)-2-(4-((1R,2S)-6-methoxy-2-(o-tolyl)-1,2,3,4-tetrahydronaphthalen-1-yl)phenyl)ethan-1-amine 22-7 (120 mg, 0.281 mmol) in $CH_2Cl_2$ (12 mL) at 0° C. was added boron tribromide (0.08 mL, 0.563 mmol) drop wise. Then the reaction mixture was stirred at the same temperature for 45 min. After completion of the reaction (monitored by TLC and LCMS), the reaction mixture was quenched with saturated $NaHCO_3$ solution, and extracted with $CH_2Cl_2$ (3×). The separated organic layer was dried over anhydrous $Na_2SO_4$, filtered and concentrated under reduced pressure. The crude compound was purified by preparative HPLC to afford 30 mg (24% yield) of LA-22 (TFA salt) as off white solid.

LCMS-Condition-1: [M+H]$^+$=412.20; Rt=1.71 min $^1$H NMR (400 MHz, DMSO-d$_6$) δ: 9.16 (br. s, 1H), 8.47 (br. s, 2H), 7.17 (d, J=7.34 Hz, 1H), 7.01 (t, J=7.09 Hz, 1H), 6.85 (d, J=7.82 Hz, 2H), 6.76 (t, J=7.34 Hz, 1H), 6.57-6.68 (m, 2H), 6.49 (dd, J=2.69, 8.07 Hz, 1H), 6.31 (d, J=7.82 Hz, 2H), 6.09 (d, J=7.82 Hz, 1H), 4.26 (d, J=4.89 Hz, 1H), 3.47 (m, 1H), 2.93-3.09 (m, 4H), 2.71-2.83 (m, 4H), 2.45 (s, 3H), 2.09-2.21 (m, 1H), 1.59-1.67 (m, 1H), 0.95-1.06 (m, 1H), 0.54-0.61 (m, 2H), 0.29-0.35 (m, 2H)

5-(4-(2-(Ethylamino)ethyl)phenyl)-6-(4-isopropylphenyl)-5,6,7,8-tetrahydronaphthalen-2-ol (LA-31)

To a solution of 6-methoxy-3,4-dihydronaphthalen-1(2H)-one L31-1 (5 g, 28.41 mmol) in xylene (125 mL) was added 1-bromo-4-isopropylbenzene (6.78 g, 34.07 mmol) followed by cesium carbonate (32.4 g, 99.41 mmol) and degassed with argon for 15 min in a sealed tube. To the resulting solution was added Pd(OAc)$_2$ (636 mg, 2.839 mmol) and Xanthphos (2.5 g, 4.251 mmol) and degassing was continued for another 15 min. Then the reaction mixture was sealed properly and heated to 130° C. for 24 h. After completion of the reaction (monitored by TLC and LCMS), the reaction mixture was filtered through a pad of Celite™ and the filtrate was concentrated under reduced pressure. The resulting crude compound was purified by silica gel column chromatography eluting with 0-10% ethyl acetate in n-hexane to afford 2.5 g (30% yield) of compound L31-2 as brown oil.

LCMS-Condition-1: [M+H]$^+$=295.05; Rt=2.22 min $^1$H NMR (400 MHz, DMSO-d$_6$) δ: 7.87 (d, J=8.31 Hz, 1H), 7.15-7.20 (m, 2H), 7.08 (d, J=8.31 Hz, 2H), 6.89-6.94 (m, 2H), 3.84 (s, 3H), 3.80 (dd, J=4.89, 11.25 Hz, 1H), 3.02-3.13 (m, 1H), 2.82-2.98 (m, 2H), 2.20-2.36 (m, 2H), 1.20 (d, J=6.85 Hz, 6H).

To a solution of 2-(4-isopropylphenyl)-6-methoxy-3,4-dihydronaphthalen-1(2H)-one L31-2 (2.5 g, 8.503 mmol) in toluene (50 mL) at 0° C. was added PBr$_3$ (1.2 mL, 12.74 mmol) drop wise. Then the reaction mixture was heated at 100° C. for 16 h. After completion of the reaction (monitored by TLC and LCMS), the reaction mixture was quenched with saturated $NaHCO_3$ solution and extracted with ethyl acetate (3×). Combined organic layer was dried over anhydrous $Na_2SO_4$, filtered and concentrated under reduced pressure. The resulting crude compound was purified by silica gel column chromatography eluting with 0-8% ethyl acetate in n-hexane to afford 1.3 g (43% yield) of compound L31-3 as off white solid.

LCMS-Condition-1: [M+H]$^+$=358.00; Rt=2.71 min

To a stirred solution of cesium carbonate (4.1 g, 12.60 mmol) in water (6 mL) was added solution of 4-bromo-3-(4-isopropylphenyl)-7-methoxy-1,2-dihydronaphthalene (4-isopropylphenyl)-7-methoxy-1,2-dihydronaphthalene L31-3 (1.5 g, 4.201 mmol) and 2-(4-(4,4,5,5-tetramethyl-1,3,2-dioxaborolan-2-yl)phenyl)ethan-1-ol (1.04 g, 4.201 mmol) in DMF (30 mL) and degassed with argon for 20 min in a seal tube. To the resulting solution was added TPP (0.109 g, 0.416 mmol) and palladium acetate (47 mg, 0.210 mmol) at room temperature and purged with argon for another 15 min. The reaction mixture was then heated at 100° C. for 16 h. After completion of the reaction (monitored by TLC and LCMS), the reaction mixture was concentrated under reduced pressure. The resulting crude compound was purified by silica gel column chromatography eluting with 0-15% ethyl acetate in n-hexane to afford 1.1 g (66% yield) of compound L31-4 as yellow solid.

LCMS-Condition-1: [M+H]$^+$=399.20; Rt=2.74 min

To a solution of 2-(4-(2-(4-isopropylphenyl)-6-methoxy-3,4-dihydronaphthalen-1-yl)phenyl)ethan-1-ol L31-4 (1.1 g, 2.760 mmol) in DCM (20 mL) at 0° C. was added triethylamine (1.5 mL, 11.04 mmol) followed by tosyl chloride (1.05 g, 5.520 mmol). The reaction mixture was then stirred at room temperature for 18 h. After completion of the reaction (monitored by TLC and LCMS), the reaction mixture was concentrated under reduced pressure. The crude compound was purified by silica gel column chromatography eluting with 0-15% ethyl acetate in n-hexane to afford 1.5 g (98% yield) of compound L31-5 as colourless sticky solid.

LCMS-Condition-1: [M+Na]$^+$=575.30; Rt=2.71 min

To a solution of 4-(2-(4-isopropylphenyl)-6-methoxy-3,4-dihydronaphthalen-1-yl)phenethyl 4-methylbenzenesulfonate L31-5 (300 mg, 0.542 mmol) in acetonitrile (1 mL) was added ethyl amine (146 mg, 3.256 mmol) and DIPEA (1.1 mL, 6.513 mmol) in a seal tube. The reaction mixture was then stirred at room temperature for 3 days. After completion of the reaction (monitored by TLC and LCMS), the reaction mixture was concentrated under reduced pressure. The crude compound was purified by silica gel column chromatography eluting with 0-10% methanol in $CH_2Cl_2$ to afford 200 mg (87% yield) of compound L31-6 as colourless semisolid.

LCMS-Condition-1: [M+H]$^+$=426.15; Rt=2.43 min

To a solution of N-ethyl-2-(4-(2-(4-isopropylphenyl)-6-methoxy-3,4-dihydronaphthalen-1-yl)phenyl)ethan-1-amine L31-6 (200 mg, 0.469 mmol) in ethyl acetate:methanol (4:1, 25 mL) was added 10% palladium on carbon (500 mg) at room temperature under nitrogen atmosphere. The reaction mixture was then stirred under hydrogen atmosphere at room temperature for 18 h. After completion of the reaction (monitored by TLC and LCMS), the reaction mixture was filtered through a pad of Celite™ and washed with methanol. The filtrate was concentrated under reduced pressure to afford 170 mg (85% yield) of compound L31-7 as colourless sticky solid.

LCMS-Condition-1: [M+H]$^+$=428.30; Rt=1.92 min

To a solution of N-ethyl-2-(4-(2-(4-isopropylphenyl)-6-methoxy-1,2,3,4-tetrahydronaphthalen-1-yl)phenyl)ethan-1-amine L31-7 (170 mg, 0.397 mmol) in $CH_2Cl_2$ (5 mL) at 0° C. was added 1M solution of boron tribromide in $CH_2Cl_2$ (0.8 mL, 0.795 mmol) drop wise. Then the reaction mixture was stirred at the same temperature for 45 min. After completion of the reaction (monitored by TLC and LCMS), the reaction mixture was quenched with saturated NaHCO$_3$ solution, and extracted with CH$_2$Cl$_2$ (3×). The separated organic layer was dried over anhydrous Na$_2$SO$_4$, filtered and concentrated under reduced pressure. The crude compound was purified by preparative HPLC to afford 25 mg (15% yield) of LA-31 as off white solid.

LCMS-Condition-1: [M+H]$^+$=414.40; Rt=1.59 min $^1$H NMR (400 MHz, DMSO-d$_6$) δ: 9.20 (br. s, 1H), 7.06 (d, J=8.31 Hz, 2H), 6.88 (d, J=7.83 Hz, 2H), 6.78 (d, J=8.31 Hz, 2H), 6.66-6.69 (m, 2H), 6.54 (dd, J=2.20, 8.07 Hz, 1H), 6.37 (d, J=7.83 Hz, 2H), 4.25 (d, J=4.89 Hz, 1H), 3.32-3.35 (m, 1H), 2.96-3.10 (m, 2H), 2.82-2.91 (m, 3H), 2.66-2.79 (m, 4H), 2.00-2.08 (m, 2H), 1.72-1.80 (m, 1H), 1.22 (dd, J=4.40, 6.85 Hz, 6H), 1.11 (t, J=7.09 Hz, 3H).

6-(4-Isopropylphenyl)-5-(4-(2-(propylamino)ethyl)phenyl)-5,6,7,8-tetrahydronaphthalen-2-ol (LA-32)

To a solution of 4-(2-(4-isopropylphenyl)-6-methoxy-3,4-dihydronaphthalen-1-yl)phenethyl 4-methylbenzenesulfonate L31-5 (300 mg, 0.542 mmol) in acetonitrile (1 mL) was added propyl amine (192 mg, 3.256 mmol) and DIPEA (1.1 mL, 6.513 mmol) in a seal tube. The reaction mixture was then stirred at room temperature for 3 days. After completion of the reaction (monitored by TLC and LCMS), the reaction mixture was diluted with water and extracted with ethyl acetate (2×). Combined organic layer was dried over anhydrous Na$_2$SO$_4$, filtered and concentrated under reduced pressure. The crude compound was purified by silica gel column chromatography eluting with 0-10% methanol in CH$_2$Cl$_2$ to afford 200 mg (84% yield) of compound L32-6 as colourless semisolid.

LCMS-Condition-1: [M+H]$^+$=440.55 Rt=1.66 min

To a solution of N-(4-(2-(4-isopropylphenyl)-6-methoxy-3,4-dihydronaphthalen-1-yl)phenethyl)propan-1-amine L32-6 (200 mg, 0.454 mmol) in ethyl acetate:methanol (4:1, 25 mL) was added 10% palladium on carbon (500 mg) at room temperature under nitrogen atmosphere. Then the reaction mixture was stirred under hydrogen atmosphere at room temperature for 18 h. After completion of the reaction (monitored by TLC and LCMS), the reaction mixture was filtered through a pad of Celite™ and washed with methanol. The filtrate was concentrated under reduced pressure to afford 170 mg (85% yield) of compound L32-7 as colourless sticky solid.

LCMS-Condition-1: [M+H]$^+$=442.25 Rt=1.78 min

To a solution of N-(4-(2-(4-isopropylphenyl)-6-methoxy-1,2,3,4-tetrahydronaphthalen-1-yl)phenethyl)propan-1-amine L32-7 (170 mg, 0.384 mmol) in CH$_2$Cl$_2$ (5 mL) at 0° C. was added 1M solution of boron tribromide in CH$_2$Cl$_2$ (0.77 mL, 0.769 mmol) drop wise. Then the reaction mixture was stirred at the same temperature for 45 min. After completion of the reaction (monitored by TLC and LCMS), the reaction mixture was quenched with saturated NaHCO$_3$ solution, and extracted with CH$_2$Cl$_2$ (3×). The separated organic layer was dried over anhydrous Na$_2$SO$_4$, filtered and concentrated under reduced pressure. The crude compound was purified by preparative HPLC to afford 20 mg (12% yield) of LA-32 as off white solid.

LCMS-Condition-1: [M+H]$^+$=428.40; Rt=1.65 min $^1$H NMR (400 MHz, CD$_3$OD) δ: 6.99 (d, J=7.83 Hz, 2H), 6.85 (d, J=8.31 Hz, 2H), 6.72 (d, J=7.83 Hz, 2H), 6.66-6.70 (m, 2H), 6.52 (dd, J=2.69, 8.07 Hz, 1H), 6.40 (d, J=8.31 Hz, 2H), 4.24 (d, J=4.89 Hz, 1H), 3.34-3.36 (m, 1H), 2.99-3.09 (m, 2H), 2.90-2.97 (m, 2H), 2.71-2.79 (m, 4H), 2.14-2.25 (m, 1H), 1.74-1.81 (m, 1H), 1.54-1.65 (m, 3H), 1.22 (dd, J=3.42, 6.85 Hz, 6H), 0.96 (t, J=7.34 Hz, 3H).

5-(4-(2-((Cyclopropylmethyl)amino)ethyl)phenyl)-6-(4-isopropylphenyl)-5,6,7,8-tetrahydronaphthalen-2-ol (LA-33)

To a solution of 4-(2-(4-isopropylphenyl)-6-methoxy-3,4-dihydronaphthalen-1-yl)phenethyl 4-methylbenzenesulfonate L31-5 (300 mg, 0.542 mmol) in acetonitrile (1 mL) was added cyclopropylmethanamine (231 mg, 3.256 mmol) and DIPEA (1.1 mL, 6.513 mmol) in a seal tube. Then the reaction mixture was stirred at room temperature for 3 days. After completion of the reaction (monitored by TLC and LCMS), the reaction mixture was diluted with water and extracted with ethyl acetate (2×). Combined organic layer was dried over anhydrous Na$_2$SO$_4$, filtered and concentrated under reduced pressure. The crude compound was purified by silica gel column chromatography eluting with 0-10% methanol in CH$_2$Cl$_2$ to afford 200 mg (82% yield) of compound L33-6 as colourless semisolid.

LCMS-Condition-1: [M+H]$^+$=452.35; Rt=1.98 min

To a solution of N-(cyclopropylmethyl)-2-(4-(2-(4-isopropylphenyl)-6-methoxy-3,4-dihydronaphthalen-1-yl)phenyl)ethan-1-amine L33-6 (200 mg, 0.442 mmol) in ethyl acetate:methanol (4:1, 25 mL) was added 10% palladium on carbon (500 mg) at room temperature under nitrogen atmosphere. The reaction mixture was stirred under hydrogen atmosphere at room temperature for 18 h. After completion of the reaction (monitored by TLC and LCMS), the reaction mixture was filtered through a pad of Celite™ and washed with methanol. The filtrate was concentrated under reduced pressure to afford 170 mg (85% yield) of compound L33-7 as colourless sticky solid.

LCMS-Condition-1: [M+H]$^+$=454.35; Rt=1.98 min

To a solution of N-(cyclopropylmethyl)-2-(4-(2-(4-isopropylphenyl)-6-methoxy-1,2,3,4-tetrahydronaphthalen-1-yl)phenyl)ethan-1-amine L33-7 (160 mg, 0.352 mmol) in CH$_2$Cl$_2$ (5 mL) at 0° C. was added 1M solution of boron tribromide in CH$_2$Cl$_2$ (1.2 mL, 1.237 mmol) drop wise. The reaction mixture was stirred at the same temperature for 45 min. After completion of the reaction (monitored by TLC and LCMS), the reaction mixture was quenched with saturated NaHCO$_3$ solution, and extracted with CH$_2$Cl$_2$ (3×). The separated organic layer was dried over anhydrous Na$_2$SO$_4$, filtered and concentrated under reduced pressure. The crude compound was purified by preparative HPLC to afford 50 mg (32% yield) of LA-33 as off white solid.

LCMS-Condition-1: [M+H]$^+$=440.40; Rt=1.65 min $^1$H NMR (400 MHz, DMSO-d$_6$) δ: 9.21 (s, 1H), 7.07 (d, J=7.83 Hz, 2H), 6.91 (d, J=7.83 Hz, 2H), 6.80 (d, J=8.31 Hz, 2H), 6.67-6.71 (m, 2H), 6.55 (dd, J=1.96, 8.31 Hz, 1H), 6.40 (d, J=7.83 Hz, 2H), 4.27 (d, J=4.89 Hz, 1H), 3.34-3.36 (m, 1H), 3.00-3.12 (m, 4H), 2.79-2.92 (m, 4H), 1.98-2.10 (m, 2H), 1.78 (d, J=5.38 Hz, 1H), 1.23 (dd, J=4.89, 6.85 Hz, 6H), 0.96-1.04 (m, 2H), 0.59-0.65 (m, 2H), 0.33-0.39 (m, 2H).

3-(4-(2-(Cyclopropylamino)ethyl)phenoxy)-2-(o-tolyl)benzo[b]thiophen-6-ol (BT-05)

To 3-methoxybenzenethiol T05-1 (50 g, 357.1 mmol) in acetone (1 Lit) at 0° C. was added potassium carbonate (49 g, 357.1 mmol) and 2-bromo-1,1-diethoxyethane (70 g, 357.1 mmol). The reaction mixture was allowed to attain room temperature and stirred for another 16 h. After completion of the reaction, the reaction mixture was filtered and concentrated under reduced pressure resulting in the crude residue. The crude residue was diluted with water and extracted with $CH_2Cl_2$ (500 mL x) and the separated organic layer was dried over anhydrous $Na_2SO_4$, filtered and concentrated under reduced pressure to afford 100 g (crude) of compound T05-2 as colourless oil.

$^1$H NMR (400 MHz, DMSO-$d_6$) δ: 7.28 (t, J=8.31 Hz, 1H), 6.99 (s, 1H), 6.97 (d, J=1.47 Hz, 1H), 6.80-6.84 (m, 1H), 4.67 (t, J=5.38 Hz, 1H), 3.81 (s, 3H), 3.51-3.71 (m, 4H), 3.20 (d, J=5.38 Hz, 2H), 1.16 (t, J=7.09 Hz, 6H)

To $BF_3.Et_2O$ (24 mL) in $CH_2Cl_2$ (2000 mL) at 0° C. was added a solution of (2,2-diethoxyethyl)(3-methoxyphenyl)sulfane T05-2 (25 g, 97.65 mmol) in $CH_2Cl_2$ (200 mL) drop wise. The reaction mixture was allowed to attain room temperature and stirred for 1 h. After completion of the reaction, the reaction mixture was quenched with saturated $NaHCO_3$ solution and extracted with $CH_2Cl_2$. The combined organic layer was dried over anhydrous $Na_2SO_4$, filtered and concentrated under reduced pressure. The resulting crude compound was purified by silica gel column chromatography eluting with 0-5% $CH_2Cl_2$ in n-hexane to afford 8 g (50% yield) of compound T05-4 as colourless oil.

$^1$H NMR (400 MHz, DMSO-$d_6$) δ: 7.74 (d, J=8.80 Hz, 1H), 7.55 (d, J=2.45 Hz, 1H), 7.51 (d, J=5.38 Hz, 1H), 7.32 (d, J=5.38 Hz, 1H), 6.99 (dd, J=2.45, 8.80 Hz, 1H), 3.80 (s, 3H).

To 6-methoxybenzo[b]thiophene T05-3 (1.3 g, 7.926 mmol) in DCE (30 mL) was added p-TSA (15 mg, 0.079 mmol) and stirred for 10 min at room temperature. Followed by addition of NBS (1.41 g, 7.926 mmol) at 0° C. portion wise and stirred at room temperature for 1 h. After completion of the reaction, the reaction mixture was quenched with saturated $Na_2S_2O_3/NaHCO_3$ solution and extracted with $CH_2Cl_2$. The combined organic layer was dried over anhydrous $Na_2SO_4$, filtered and concentrated under reduced pressure. The resulting crude compound was purified by silica gel column chromatography eluting with 0-6% $CH_2Cl_2$ in n-hexane to afford 1.3 g (68% yield) of compound T05-4 as white solid.

$^1$H NMR (400 MHz, DMSO-$d_6$) δ: 7.67 (d, J=8.80 Hz, 1H), 7.54 (d, J=2.45 Hz, 1H), 7.51 (s, 1H), 6.99 (dd, J=2.45, 8.80 Hz, 1H), 3.80 (s, 3H).

To 2-bromo-6-methoxybenzo[b]thiophene T05-4 (1 g, 4.149 mmol) and o-tolylboronic acid 5 (677 mg, 4.979 mmol) in ethanol:$H_2O$:Toluene (20:10:20 mL) was added $Na_2CO_3$ (1.75 g, 16.59 mmol) and purged with argon for 15 min. Followed by addition of tetrakis(triphenylphosphine)palladium(0) (230 mg, 0.207 mmol) and purged with argon for another 10 min. The reaction mixture was further heated to reflux for 16 h. After completion of the reaction, the reaction mixture was quenched with ice cold water and extracted with ethyl acetate (3×). The combined organic layer was dried over anhydrous $Na_2SO_4$, filtered and concentrated under reduced pressure. The resulting crude compound was purified by silica gel column chromatography eluting with 0-12% $CH_2Cl_2$ in n-hexane to afford 1 g (95% yield) of compound T05-6 as colourless oil.

LCMS-Condition-1: [M+H]$^+$=254.95; Rt=2.40 min $^1$H NMR (400 MHz, DMSO-$d_6$) δ: 7.75 (d, J=8.80 Hz, 1H), 7.56 (s, 1H), 7.43-7.47 (m, 1H), 7.39 (s, 1H), 7.27-7.37 (m, 3H), 7.02 (dd, J=2.45, 8.80 Hz, 1H), 3.83 (s, 3H), 2.45 (s, 3H).

To 6-methoxy-2-(o-tolyl)benzo[b]thiophene T05-6 (400 mg, 1.574 mmol) in $CHCl_3$ (40 mL) at 0° C. was added bromine (0.06 mL, 2.362 mmol) drop wise over a period of 30 min. After completion of the reaction, the reaction mixture was quenched with saturated $Na_2S_2O_3$ solution and extracted with $CH_2Cl_2$ (3×). The combined organic layer was dried over anhydrous $Na_2SO_4$, filtered and concentrated under reduced pressure. The resulting crude compound was purified by silica gel column chromatography eluting with 0-10% $CH_2Cl_2$ in n-hexane to afford 400 mg (76% yield) of compound T05-7 as off white solid.

LCMS-Condition-1: [M+H]$^+$=333.70; Rt=2.45 min $^1$H NMR (400 MHz, DMSO-$d_6$) δ: 7.58-7.62 (m, 2H), 7.22-7.37 (m, 4H), 7.08-7.13 (m, 1H), 3.80 (s, 3H), 2.15 (s, 3H)

To 3-bromo-6-methoxy-2-(o-tolyl)benzo[b]thiophene T05-7 (400 mg, 1.146 mmol) in $CH_2Cl_2$ (mL) was added TFA (mL, mmol) and 30% $H_2O_2$ (mL, mmol) at room temperature and stirred for 2 h. After completion of the reaction, the reaction mixture was quenched with saturated $NaHCO_3$ solution, and extracted with $CH_2Cl_2$. The separated organic layer was dried over anhydrous $Na_2SO_4$, filtered and concentrated under reduced pressure to afford 650 mg (crude) of the title compound T05-8 as off white solid which was used as such for the next step without further purification.

LCMS-Condition-1: [M+H]$^+$=348.80; Rt=2.00 min

To 3-bromo-6-methoxy-2-(o-tolyl)benzo[b]thiophene 1-oxide T05-8 (2.5 g, 7.143 mmol) in DMF (40 mL) was added CuI (555 mg, 2.915 mmol), cesium carbonate (950 mg, 2.915 mmol) followed by 4-(2-hydroxyethyl)phenol (2 g, 14.49 mmol) at room temperature. The reaction mixture was further heated at 100° C. for 7 h. After completion of the reaction, the reaction mixture was quenched with ice cold water and extracted with ethyl acetate. The combined organic layer was dried over anhydrous $Na_2SO_4$, filtered and concentrated under reduced pressure. The resulting crude compound was purified by silica gel column chromatography eluting with 0-80% ethyl acetate in n-hexane to afford 2.2 g (38% yield) of compound T05-9 as pale yellow oil.

LCMS-Condition 02: [M+H]$^+$=407.15; Rt=1.86 min $^1$H NMR (400 MHz, DMSO-$d_6$) δ: 7.95 (s, 1H), 7.75 (d, J=2.20 Hz, 1H), 7.28 (d, J=7.46 Hz, 1H), 7.13-7.23 (m, 4H), 7.01-7.04 (m, 2H), 6.94-6.98 (m, 2H), 4.58 (t, J=5.14 Hz, 1H), 3.88 (s, 3H), 3.43-3.49 (m, 2H), 2.89 (s, 3H), 2.58 (t, J=7.15 Hz, 2H)

To 3-(4-(2-hydroxyethyl)phenoxy)-6-methoxy-2-(o-tolyl)benzo[b]thiophene 1-oxide T05-9 (500 mg, 1.231 mmol) in DCM (10 mL) was added triethylamine (0.5 mL, 0.369 mmol) and stirred for 10 min, followed by the addition of tosyl chloride (235 mg, 1.231 mmol) in two portions at room temperature and stirred for another 16 h. After completion of the reaction, the reaction mixture was diluted with water and extracted with ethyl acetate (3×). Separated organic layer was dried over anhydrous $Na_2SO_4$, filtered and concentrated under reduced pressure. The crude compound was purified by silica gel column chromatography eluting with 0-80% ethyl acetate in n-hexane to afford 410 mg (59% yield) of compound T05-10 as pale yellow oil.

LCMS-Condition 02: [M+H]$^+$=561.20; Rt=2.17 min $^1$H NMR (400 MHz, DMSO-$d_6$) δ: 7.76 (d, J=1.96 Hz, 1H), 7.66 (d, J=8.31 Hz, 2H), 7.38 (d, J=8.80 Hz, 2H), 7.27 (d, J=6.36 Hz, 1H), 7.21-7.24 (m, 1H), 7.14-7.18 (m, 4H), 6.94-6.96 (m, 4H), 4.05-4.09 (m, 2H), 3.88 (s, 3H), 2.75 (t, J=6.36 Hz, 2H), 2.38 (s, 3H), 2.26 (s, 3H).

To 4-((6-methoxy-1-oxido-2-(o-tolyl)benzo[b]thiophen-3-yl)oxy)phenethyl 4-methylbenzenesulfonate T05-10 (350 mg, 0.624 mmol) in acetonitrile (5 mL) was added cyclopropanamine (356 mg, 6.242 mmol) and DIPEA (0.32 mL, 1.872 mmol) in a seal tube. The reaction mixture was stirred at room temperature for 48 h. After completion of the reaction, the reaction mixture was diluted with water and extracted with ethyl acetate (2×). The combined organic layer was dried over anhydrous $Na_2SO_4$, filtered and concentrated under reduced pressure. The crude compound was purified by silica gel column chromatography eluting with 0-5% methanol in $CH_2Cl_2$ to afford 100 mg (99% yield) of compound T05-11 as colourless oil.

LCMS-Condition 02: $[M+H]^+$=446.15; Rt=2.07 min $^1$H NMR (400 MHz, DMSO-$d_6$) δ: 7.75 (d, J=1.96 Hz, 1H), 7.27-7.30 (m, 1H), 7.25 (d, J=7.34 Hz, 1H), 7.11-7.20 (m, 4H), 6.98 (d, J=3.42 Hz, 4H), 4.09 (d, J=4.89 Hz, 1H), 3.89 (s, 3H), 3.17 (d, J=4.40 Hz, 1H), 2.64-2.70 (m, 2H), 2.55 (t, J=7.09 Hz, 2H), 2.26 (s, 3H), 2.05 (tt, J=3.48, 6.54 Hz, 2H), 1.88-1.92 (m, 2H).

To 3-(4-(2-(cyclopropylamino)ethyl)phenoxy)-6-methoxy-2-(o-tolyl)benzo[b]thiophene 1-oxide T05-11 (150 mg, 0.336 mmol) in THE (10 mL) at 0° C. was added LAH (64 mg, 1.684 mmol) portion wise. The reaction mixture was allowed to attain room temperature and stirred for 2 h. After completion of the reaction, the reaction mixture was quenched with saturated $Na_2SO_4$ solution, filtered through a pad of Celite™ and washed with 15% methanol in $CH_2Cl_2$. The filtrate was concentrated under reduced pressure and the crude compound was purified by silica gel column chromatography eluting with 0-5% methanol in $CH_2Cl_2$ to afford 120 mg (83% yield) of compound T05-12 as colourless oil.

LCMS-Condition 01: $[M+H]^+$=430.15; Rt=2.74 min $^1$H NMR (400 MHz, DMSO-$d_6$) δ: 7.62 (d, J=2.20 Hz, 1H), 7.36 (d, J=7.46 Hz, 1H), 7.27-7.30 (m, 2H), 7.24 (s, 1H), 7.19-7.22 (m, 1H), 7.05 (d, J=8.56 Hz, 2H), 6.99 (dd, J=2.26, 8.74 Hz, 1H), 6.77 (d, J=8.56 Hz, 2H), 3.84 (s, 3H), 2.70 (d, J=7.70 Hz, 2H), 2.55-2.61 (m, 2H), 2.33 (s, 3H), 2.04 (tt, J=3.52, 6.63 Hz, 2H), 0.30-0.36 (m, 2H), 0.14-0.19 (m, 2H).

To N-(4-((6-methoxy-2-(o-tolyl)benzo[b]thiophen-3-yl)oxy)phenethyl)cyclopropanamine T05-12 (120 mg, 0.279 mmol) in $CH_2Cl_2$ (2 mL) at 0° C. was added solution of boron tribromide (0.13 mL, 1.389 mmol) in $CH_2Cl_2$ (1 mL) drop wise. The reaction mixture was allowed to attain room temperature and stirred for 3 h. After completion of the reaction, the reaction mixture was quenched with saturated $NaHCO_3$ solution, and extracted with $CH_2Cl_2$. The separated organic layer was dried over anhydrous $Na_2SO_4$, filtered and concentrated under reduced pressure. The crude compound was purified by silica gel column chromatography eluting with 0-5% methanol in $CH_2Cl_2$ to afford 33 mg (29% yield) of BT-05 as off white solid.

LCMS-Condition-1: $[M+H]^+$=416.10; Rt=1.52 min $^1$H NMR (400 MHz, DMSO-$d_6$) δ: 9.80 (s, 1H), 7.29-7.36 (m, 2H), 7.25-7.28 (m, 2H), 7.14-7.19 (m, 2H), 7.04 (d, J=8.44 Hz, 2H), 6.84 (dd, J=1.96, 8.68 Hz, 1H), 6.76 (d, J=8.44 Hz, 2H), 2.71-2.77 (m, 2H), 2.57-2.62 (m, 2H), 2.31 (s, 3H), 2.08-2.11 (m, 1H), 0.35 (d, J=4.52 Hz, 2H), 0.19-0.24 (m, 2H).

3-(4-(2-((Cyclopropylmethyl)amino)ethyl)phenoxy)-2-(o-tolyl)benzo[b]thiophen-6-ol (BT-12)

To a solution of 4-((6-methoxy-1-oxido-2-(o-tolyl)benzo[b]thiophen-3-yl)oxy)phenethyl 4-methylbenzenesulfonate T05-10 (400 mg, 0.713 mmol) in acetonitrile (20 mL) was added cyclopropylmethanamine (506 mg, 7.114 mmol) and DIPEA (0.62 mL, 3.565 mmol). The reaction mixture was stirred at room temperature for 48 h in sealed tube. After completion of the reaction (monitored by TLC and LCMS), the reaction mixture was diluted with water and extracted with ethyl acetate (2×). The combined organic layer was dried over anhydrous $Na_2SO_4$, filtered and concentrated under reduced pressure. The crude compound was purified by silica gel column chromatography eluting with 0-5% methanol in $CH_2Cl_2$ to afford 210 mg (64% yield) of compound T12-11 as colourless oil.

LCMS-Condition 02: $[M+H]^+$=460.20; Rt=2.23 min

To a solution of 3-(4-(2-((cyclopropylmethyl)amino)ethyl)phenoxy)-6-methoxy-2-(o-tolyl)benzo[b]thiophene 1-oxide T12-11 (200 mg, 0.435 mmol) in THF (3 mL) at 0° C. was added LAH (50 mg, 1.316 mmol) portion wise. The reaction mixture was allowed to attain room temperature and stirred for another 16 h. After completion of the reaction (monitored by TLC and LCMS), the reaction mixture was cooled to 0° C. and quenched with saturated $Na_2SO_4$ solution (2 mL). The resulting solution was filtered through a pad of Celite™ and washed with 15% methanol in $CH_2Cl_2$. The filtrate was dried over anhydrous $Na_2SO_4$ and concentrated under reduced pressure to afford 150 mg (78% yield) of compound T12-12 as pale yellow oil.

LCMS-Condition 01: $[M+H]^+$=444.11; Rt=1.75 min

To a solution of N-(cyclopropylmethyl)-2-(4-((6-methoxy-2-(o-tolyl)benzo[b]thiophen-3-yl)oxy)phenyl)ethan-1-amine T12-12 (150 mg, 0.338 mmol) in $CH_2Cl_2$ (5 mL) at 0° C. was added boron tribromide (0.09 mL, 1.012 mmol) drop wise. The reaction mixture was allowed to attain room temperature and stirred for 4 h. After completion of the reaction (monitored by TLC and LCMS), the reaction mixture was quenched with saturated $NaHCO_3$ solution, and extracted with 15% methanol in $CH_2Cl_2$. The separated organic layer was dried over anhydrous $Na_2SO_4$, filtered and concentrated under reduced pressure. The crude compound was purified by silica gel column chromatography eluting with 0-8% methanol in $CH_2Cl_2$ to afford 23 mg (17% yield) of BT-12 as off white solid.

LCMS-Condition-1: $[M+H]^+$=430.10; Rt=1.53 min $^1$H NMR (400 MHz, DMSO-$d_6$) δ: 9.84 (s, 1H), 8.54-8.60 (m, 1H), 7.31-7.36 (m, 2H), 7.25-7.29 (m, 2H), 7.18-7.22 (m, 1H), 7.15 (d, J=8.80 Hz, 1H), 7.11 (d, J=8.31 Hz, 2H), 6.80-6.86 (m, 3H), 3.03-3.09 (m, 2H), 2.76-2.85 (m, 4H), 2.32 (s, 3H), 0.97-1.04 (m, 1H), 0.53-0.59 (m, 2H), 0.29-0.34 (m, 2H)

3-(4-((1-Propylazetidin-3-ylidene)methyl)phenoxy)-2-(o-tolyl)benzo[b]thiophen-6-ol (BT-17)

To a mixture of 3-bromo-6-methoxy-2-(o-tolyl)benzo[b]thiophene 1-oxide T17-1 (5.77 g, 16.53 mmol) and 4-hydroxybenzaldehyde (4 g, 32.78 mmol) in DMF (40 mL) was added cesium carbonate (32.1 g, 98.46 mmol) at room temperature in a sealed tube. The reaction mixture was heated at 100° C. for 3 h. After completion of the reaction, the reaction mixture was quenched with ice cold water and extracted with ethyl acetate. The combined organic layer was dried over anhydrous $Na_2SO_4$, filtered and concentrated under reduced pressure. The resulting crude compound was purified by silica gel column chromatography eluting with 0-40% ethyl acetate in n-hexane to afford 5.3 g (82% yield) of compound T17-2 as light yellow solid.

LCMS-Condition 01: $[M+H]^+$=391.30; Rt=1.89 min

To 4-((6-methoxy-1-oxido-2-(o-tolyl)benzo[b]thiophen-3-yl)oxy)benzaldehyde T17-2 (2 g, 5.122 mmol) in THE (40 mL) at 0° C. was added lithium aluminium hydride (583 mg, 15.36 mmol) portion wise. The reaction mixture was stirred at room temperature for 2 h. After completion of the reaction, the reaction mixture was quenched with saturated $Na_2SO_4$ solution, and extracted with ethyl acetate. The separated organic layer was dried over anhydrous $Na_2SO_4$, filtered and concentrated under reduced pressure. The crude compound was purified by silica gel column chromatography eluting with 0-15% methanol in $CH_2Cl_2$ to afford 1.9 g (98% yield) of compound T17-3 as pale yellow oil.

LCMS-Condition 01: $[M+18]^+$=393.10; Rt=2.24 min $^1$H NMR (400 MHz, DMSO-$d_6$) δ: 7.62 (d, J=1.96 Hz, 1H), 7.36 (d, J=7.82 Hz, 1H), 7.26-7.30 (m, 2H), 7.22 (d, J=8.80 Hz, 2H), 7.16 (d, J=8.80 Hz, 2H), 6.99 (d, J=1.96 Hz, 1H), 6.81 (d, J=8.31 Hz, 2H), 5.04 (t, J=5.62 Hz, 1H), 4.36 (d, J=5.87 Hz, 2H), 3.83 (s, 3H), 2.33 (s, 3H).

To a solution of (4-((6-methoxy-2-(o-tolyl)benzo[b]thiophen-3-yl)oxy)phenyl)methanol T17-3 (1.9 g, 5.046 mmol) in $CH_2Cl_2$ (20 mL) was added $PBr_3$ (1.36 g, 5.024 mmol) at 0° C. drop wise and stirred at room temperature for 2 h. After completion of the reaction, the reaction mixture was quenched with saturated $NaHCO_3$ solution and extracted with $CH_2Cl_2$. The combined organic layer was dried over anhydrous $Na_2SO_4$, filtered and concentrated under reduced pressure to afford 2.1 g (95% yield) of compound T17-4 as pale yellow oil.

LCMS-Condition 01: $[M+H]^+$=440.05; Rt=2.47 min $^1$H NMR (400 MHz, DMSO-$d_6$) δ: 7.63 (d, J=1.96 Hz, 1H), 7.35 (d, J=7.34 Hz, 1H), 7.26-7.32 (m, 4H), 7.24 (d, J=8.80 Hz, 2H), 7.00 (dd, J=1.96, 8.80 Hz, 1H), 6.83 (d, J=8.80 Hz, 2H), 4.63 (s, 2H), 3.84 (s, 3H), 2.32 (s, 3H).

To 3-(4-(bromomethyl)phenoxy)-6-methoxy-2-(o-tolyl)benzo[b]thiophene T17-4 (2 g, 4.558 mmol) in benzene (30 mL) was added triphenyl phosphine (1.8 g, 6.824 mmol) and tert-butyl 3-oxoazetidine-1-carboxylate (1.17 g, 6.842 mmol) at room temperature and stirred for 4 h. The reaction mixture was concentrated under reduced pressure and the crude intermediate was washed with n-hexane and dried. The crude intermediate was dissolved in $CH_2Cl_2$ (20 mL) and potassium tert-butoxide (1.53 g, 13.66 mmol) and solution of tert-butyl 3-oxoazetidine-1-carboxylate (1.17 g, 6.842 mmol) in $CH_2Cl_2$ (10 mL) at room temperature and stirred for 16 h. After completion of the reaction, the reaction mixture was concentrated under reduced pressure, diluted with water and extracted with $CH_2Cl_2$ (3×). The combined organic layer was dried over anhydrous $Na_2SO_4$, filtered and concentrated under reduced pressure. The resulting crude compound was purified by silica gel column chromatography eluting with 0-20% ethyl acetate in n-hexane to afford 900 mg (39% yield) of compound T17-5 as off white solid.

LCMS-Condition-1: $[M-^tBu]^+$=458.40; Rt=2.57 min $^1$H NMR (400 MHz, DMSO-$d_6$) δ: 7.63 (d, J=2.45 Hz, 1H), 7.35 (d, J=7.34 Hz, 1H), 7.26-7.31 (m, 2H), 7.24 (d, J=8.80 Hz, 1H), 7.17-7.22 (m, 1H), 7.03 (d, J=8.80 Hz, 2H), 6.99 (dd, J=1.96, 8.80 Hz, 1H), 6.83 (d, J=8.80 Hz, 2H), 6.22 (br. s, 1H), 4.69 (br. s, 2H), 4.52 (br. s, 2H), 3.84 (s, 3H), 2.32 (s, 3H), 1.39 (s, 9H).

A solution of tert-butyl 3-(4-((6-methoxy-2-(o-tolyl)benzo[b]thiophen-3-yl)oxy)benzylidene)azetidine-1-carboxylate T17-5 (832 mg, 1.619 mmol) in 4M HCl in dioxane (3 mL) was stirred at room temperature for 2 h. After completion of the reaction, the reaction mixture was quenched with saturated $NaHCO_3$ solution and extracted with 10% methanol in $CH_2Cl_2$. The combined organic layer was dried over anhydrous $Na_2SO_4$, filtered and concentrated under reduced pressure to afford 810 mg (crude) of compound T17-6 as pale yellow oil which was used in the next step without further purification.

LCMS-Condition 01: $[M+H]^+$=414.15; Rt=1.61 min $^1$H NMR (400 MHz, DMSO-$d_6$) δ: 9.28 (br. s, 1H), 7.61-7.66 (m, 1H), 7.35 (d, J=7.34 Hz, 1H), 7.28-7.30 (m, 2H), 7.18-7.26 (m, 2H), 7.06 (d, J=8.80 Hz, 2H), 7.00 (dd, J=1.96, 8.80 Hz, 1H), 6.85 (d, J=8.31 Hz, 2H), 3.84 (s, 3H), 3.34 (s, 4H), 2.33 (s, 3H).

To 3-(4-((6-methoxy-2-(o-tolyl)benzo[b]thiophen-3-yl)oxy)benzylidene)-1-propylazetidine T17-7 (200 mg, 0.438 mmol) in DMF (4 mL) was added sodium methane thiolate (61.5 mg, 0.878 mmol) at room temperature in a microwave vial. The vial was sealed properly and irradiated in microwave at 150° C. for 1 h. After completion of the reaction, the reaction mixture was quenched with saturated $NaHCO_3$ solution, and extracted with 15% methanol in $CH_2Cl_2$. The separated organic layer was dried over anhydrous $Na_2SO_4$, filtered and concentrated under reduced pressure. The crude compound was purified by silica gel column chromatography eluting with 0-5% methanol in $CH_2Cl_2$ to afford 35 mg (18% yield) of BT-17 as white solid.

LCMS-Condition-1: $[M+H]^+$=442.15; Rt=1.55 min $^1$H NMR (400 MHz, DMSO-$d_6$) δ: 9.81 (br. s, 1H), 7.29-7.35 (m, 2H), 7.22-7.28 (m, 2H), 7.17-7.20 (m, 1H), 7.15 (d, J=8.53 Hz, 1H), 6.97 (d, J=8.78 Hz, 2H), 6.84 (dd, J=2.13, 8.66 Hz, 1H), 6.80 (d, J=8.78 Hz, 2H), 6.08-6.13 (m, 1H), 4.17 (br. s, 2H), 4.01 (br. s, 2H), 2.58 (t, J=6.90 Hz, 2H), 2.31 (s, 3H), 1.33-1.37 (m, 2H), 0.85 (t, J=7.40 Hz, 3H).

5-(4-(2-(Cyclopropylamino)ethyl)benzyl)-4-(o-tolyl)-2,3-dihydrobenzo[b]oxepin-8-ol (BX-06)

To a mixture of 3-methoxyphenol (10 g, 80.64 mmol) and ethyl 4-bromobutanoate (23.6 g, 120.96 mmol) in acetone (400 mL) was added potassium carbonate (33.4 g, 241.93 mmol) at room temperature. Then the reaction mixture was heated to reflux for 18 h. After completion of the reaction (monitored by TLC), the reaction mixture was filtered and washed with acetone. The filtrate was concentrated under reduced pressure to afford 18 g (94% yield) of compound X6-2 as colourless oil.

LCMS-Condition-01: $[M+1]^+$=239.07; Rt=1.96 min $^1$H NMR (400 MHz, $CDCl_3$) δ: 7.17 (t, J=8.31 Hz, 1H), 6.44-6.53 (m, 3H), 4.15 (q, J=7.17 Hz, 2H), 3.99 (t, J=6.11 Hz, 2H), 3.78 (s, 3H), 2.46-2.54 (m, 2H), 2.04-2.15 (m, 2H), 1.21-1.30 (m, 3H).

To a solution of ethyl 4-(3-methoxyphenoxy)butanoate X6-2 (18 g, 75.63 mmol) in THF-MeOH (7:10, 170 mL) was added a solution of lithium hydroxide (6.3 g, 151.26 mmol) in water (70 mL) at room temperature and stirred for 1 h. After completion of the reaction, the reaction mixture was concentrated, acidified with 1N HCl solution upto pH=2 and extracted with ethyl acetate (3×50 mL). The combined organic layer was dried over anhydrous $Na_2SO_4$, filtered and concentrated under reduced pressure to afford 13 g (82% yield) of compound X6-3 as colourless oil.

LCMS-Condition-01: $[M+1]^+$=210.97; Rt=1.64 min $^1$H NMR (400 MHz, DMSO-$d_6$) δ: 12.09 (br. s, 1H), 7.14 (t, J=8.07 Hz, 1H), 6.49 (d, J=2.45 Hz, 1H), 6.45-6.48 (m, 2H), 3.94 (t, J=6.36 Hz, 2H), 3.71 (s, 3H), 2.36 (t, J=7.34 Hz, 2H), 1.85-1.95 (m, 2H).

A solution of 4-(3-methoxyphenoxy)butanoic acid X6-3 (13 g, 61.90 mmol) in Eaton's reagent (75 mL) in a sealed tube was heated at 80° C. for 30 min. After completion of the reaction, the reaction mixture was quenched with ice cold water and extracted with ethyl acetate (3×50 mL). The combined organic layer was dried over anhydrous $Na_2SO_4$, filtered and concentrated under reduced pressure. The crude compound was purified by silica gel column chromatography eluting with 0-20% ethyl acetate in n-hexane to afford 6 g (50% yield) of compound X6-4 as off white solid.

LCMS-Condition-1: $[M+1]^+$=193.00; Rt=1.64 min $^1$H NMR (400 MHz, DMSO-$d_6$) δ: 7.61 (d, J=8.80 Hz, 1H), 6.72 (dd, J=2.45, 8.80 Hz, 1H), 6.64 (d, J=2.45

1H), 4.20 (t, J=6.60 Hz, 2H), 3.80 (s, 3H), 2.73 (t, J=6.85 Hz, 2H), 2.10 (quin, J=6.72 Hz, 2H).

To a solution of 8-methoxy-3,4-dihydrobenzo[b]oxepin-5(2H)-one X6-4 (6 g, 31.21 mmol) in xylene (100 mL) was added cesium carbonate (30 g, 93.64 mmol) and degassed with argon for 15 min in a sealed tube. To the resulting solution was added 2-bromo toluene (8 g, 46.82 mmol), Pd(OAc)$_2$ (348 mg, 15.60 mmol) and X-phos (1.4 g, 31.21 mmol) and degassing was continued for another 5 min at room temperature. Then the reaction mixture was sealed properly and heated at 130° C. for 24 h. After completion of the reaction, the reaction mixture was filtered through a pad of Celite and the filtrate was diluted with ice water and extracted with ethyl acetate (3×30 mL). The combined organic layer dried over anhydrous Na$_2$SO$_4$, filtered and concentrated under reduced pressure. The resulting crude compound was purified by silica gel column chromatography eluting with 0-15% ethyl acetate in n-hexane to afford 2.5 g (32% yield) of compound X6-5 as yellow solid.

LCMS-Condition-1: [M+H]$^+$=283.08; Rt=2.12 min $^1$H NMR (400 MHz, DMSO-d$_6$) δ: 7.56 (d, J=8.80 Hz, 1H), 7.29 (d, J=7.34 Hz, 1H), 7.17-7.21 (m, 1H), 7.16 (d, J=3.91 Hz, 2H), 6.73 (dd, J=2.20, 8.56 Hz, 1H), 6.70 (d, J=2.45 Hz, 1H), 4.62-4.67 (m, 1H), 4.43 (dd, J=6.85, 11.25 Hz, 1H), 3.97-4.08 (m, 1H), 3.83 (s, 3H), 2.39-2.48 (m, 2H), 2.05 (s, 3H).

To 150 mL two neck round bottomed flask was added freshly activated magnesium turnings (2.7 g, 113.47 mmol) and catalytic amount of iodine. To that (4-(bromomethyl)phenethoxy)(tert-butyl)dimethylsilane C (9.3 g, 28.36 mmol) in THF (40 mL) was added and heated at 70° C. for 15 min. After de-colorization of iodine, the reaction mixture was cooled to room temperature to 0° C. and a solution of 8-methoxy-4-(o-tolyl)-3,4-dihydrobenzo[b]oxepin-5(2H)-one X6-5 (4 g, 14.18 mmol) in THF (3 mL) was added and stirred for 3 h at room temperature. After completion of the reaction, the reaction mixture was quenched with saturated ammonium chloride solution and extracted with ethyl acetate (3×100 mL). The combined organic layer was dried over anhydrous Na$_2$SO$_4$, filtered and concentrated under reduced pressure. The resulting crude compound was purified by silica gel column chromatography eluting with 0-15% ethyl acetate in n-hexane to afford 1 g (13% yield) of compound X6-6 as colorless liquid.

LCMS-Condition-1: [M+Na]$^+$=555.18; Rt=2.85 min $^1$H NMR (400 MHz, DMSO-d$_6$) δ: 7.10 (d, J=8.44 Hz, 2H), 6.96 (d, J=7.46 Hz, 2H), 6.85 (d, J=7.95 Hz, 2H), 6.79 (d, J=6.85 Hz, 2H), 6.70 (d, J=7.70 Hz, 1H), 6.59 (d, J=2.57 Hz, 1H), 6.51-6.57 (m, 1H), 4.57 (s, 1H), 4.20-4.27 (m, 1H), 3.76 (s, 3H), 3.70-3.74 (m, 4H), 3.59-3.65 (m, 1H), 3.47 (d, J=13.45 Hz, 1H), 3.11 (d, J=13.33 Hz, 1H), 2.66 (t, J=6.72 Hz, 2H), 2.23 (s, 3H), 1.55-1.59 (m, 1H), 0.84 (s, 9H), −0.05 (s, 6H).

To a boiling solution of 5-(4-(2-((tert-butyldimethylsilyl)oxy)ethyl)benzyl)-8-methoxy-4-(o-tolyl)-2,3,4,5-tetrahydrobenzo[b]oxepin-5-ol X6-6 (700 mg, 1.313 mmol) in ACN (14 mL) was added conc. HCl (0.5 mL) in ACN (1 mL) dropwise and continued stirring for 40 min. After completion of the reaction, the reaction mixture was concentrated under reduced pressure. The crude residue was dissolved in ethyl acetate and washed with saturated NaHCO$_3$ solution. The separated organic layer was dried over anhydrous Na$_2$SO$_4$, filtered and concentrated under reduced pressure. The resulting crude compound was purified by silica gel column chromatography eluting with 0-60% ethyl acetate in n-hexane to afford 350 mg (80% yield) of the title compound X6-7 as white solid.

LCMS-Condition-1: [M+H]$^+$=401.05; Rt=2.23 min $^1$H NMR (400 MHz, CDCl$_3$) δ: 7.16-7.23 (m, 3H), 7.11-7.15 (m, 1H), 7.00 (d, J=1.96 Hz, 4H), 6.87-6.96 (m, 1H), 6.63-6.65 (m, 1H), 6.60-6.63 (m, 1H), 4.66 (td, J=5.14, 10.27 Hz, 1H), 4.58 (ddd, J=4.40, 5.62, 10.03 Hz, 1H), 3.79-3.81 (m, 2H), 3.78 (s, 3H), 3.56-3.71 (m, 2H), 2.75 (t, J=6.60 Hz, 2H), 2.68 (dt, J=5.14, 9.66 Hz, 1H), 2.29 (t, J=4.40 Hz, 1H), 2.25 (s, 3H).

To a solution of 2-(4-((8-methoxy-4-(o-tolyl)-2,3-dihydrobenzo[b]oxepin-5-yl)methyl)phenyl)ethan-1-ol X6-7 (400 mg, 0.998 mmol) in CH$_2$Cl$_2$ (10 mL) at 0° C. was added triethyl amine (0.34 mL, 2.496 mmol) followed by tosyl chloride (285 mg, 1.498 mmol). Then the reaction mixture was stirred at room temperature for 18 h. After completion of the reaction, the reaction mixture was quenched with ice water and extracted with CH$_2$Cl$_2$ (3×30 mL). The combined organic layer was dried over anhydrous Na$_2$SO$_4$, filtered and concentrated under reduced pressure. The crude compound was purified by silica gel column chromatography eluting with 0-20% ethyl acetate in n-hexane to afford 380 mg (68% yield) of compound X6-8 as colorless liquid.

LCMS-Condition-1: [M+H]$^+$=555.10; Rt=2.47 min $^1$H NMR (400 MHz, DMSO-d$_6$) δ: 7.60 (d, J=7.82 Hz, 2H), 7.25-7.34 (m, 4H), 7.15-7.22 (m, 3H), 6.87-6.96 (m, 4H), 6.60-6.65 (m, 2H), 4.62 (dt, J=4.65, 10.64 Hz, 2H), 4.52 (dd, J=4.65, 9.54 Hz, 2H), 4.10-4.16 (m, 2H), 3.71 (s, 3H), 3.37-3.44 (m, 2H), 2.74 (t, J=6.60 Hz, 2H), 2.36 (s, 3H), 2.22 (s, 3H).

To a solution of 4-((8-methoxy-4-(o-tolyl)-2,3-dihydrobenzo[b]oxepin-5-yl)methyl)phenethyl-4-methylbenzenesulfonate X6-8 (350 mg, 0.630 mmol) in acetonitrile (2 mL) was added DIPEA (0.85 mL, 6.300 mmol) and cyclopropyl amine (359 mg, 6.300 mmol) at room temperature in a sealed tube. Then the reaction mixture was stirred at room temperature for 3 days. After completion of the reaction, the reaction mixture was concentrated under reduced pressure, diluted with water and extracted with ethyl acetate (2×15 mL). The combined organic layer was dried over anhydrous Na$_2$SO$_4$, filtered and concentrated under reduced pressure. The crude compound was purified by silica gel column chromatography eluting with 0-2% methanol in CH$_2$Cl$_2$ to afford 150 mg (54% yield) of compound X6-9 as colorless liquid.

LCMS-Condition-1: [M+H]$^+$=440.20; Rt=1.64 min $^1$H NMR (400 MHz, DMSO-d$_6$) δ: 7.21 (d, J=8.31 Hz, 1H), 7.17 (d, J=8.31 Hz, 1H), 7.07-7.14 (m, 3H), 6.85-6.88 (m, 4H), 6.55 (dd, J=2.69, 8.56 Hz, 1H), 6.52 (d, J=2.45 Hz, 1H), 4.48-4.67 (m, 2H), 3.71 (s, 3H), 3.68 (d, J=16.00 Hz, 1H), 3.38 (d, J=16.00 Hz, 1H), 2.61-2.69 (m, 2H), 2.52-2.58 (m, 3H), 2.13 (s, 3H), 1.93 (td, J=3.06, 6.60 Hz, 2H), 0.72-0.81 (m, 2H), 0.19-0.24 (m, 2H).

To a solution of N-(4-((8-methoxy-4-(o-tolyl)-2,3-dihydrobenzo[b]oxepin-5-yl)methyl)phenethyl)cyclopropanamine X6-9 (100 mg, 0.227 mmol) in CH$_2$Cl$_2$ (10 mL) at 0° C. was added boron tribromide (0.02 mL, 0.227 mmol) dropwise. Then the reaction mixture was stirred at the same temperature for 20 min. After completion of the reaction, the reaction mixture was quenched with saturated NaHCO$_3$ solution, and extracted with CH$_2$Cl$_2$. The separated organic layer was dried over anhydrous Na$_2$SO$_4$, filtered and concentrated under reduced pressure. The crude compound was purified by silica gel column chromatography eluting with 0-5% methanol in CH$_2$Cl$_2$ to afford 25 mg (21% yield) of BX-06 as off white solid.

LCMS-Condition-1: [M+H]$^+$=426.20; Rt=1.59 min $^1$H NMR (400 MHz, DMSO-d$_6$) δ: 9.50 (s, 1H), 7.25-7.30 (m, 1H), 7.15-7.22 (m, 4H), 6.95-7.01 (m, 4H), 6.48 (dd, J=2.45, 8.31 Hz, 1H), 6.44 (d, J=2.45 Hz, 1H), 4.51-4.57 (m, 1H), 4.40-4.48 (m, 1H), 3.62 (d, J=16 Hz, 1H), 3.34 (d, J=16 Hz, 1H), 2.63-2.70 (m, 3H), 2.51-2.58 (m, 3H), 2.19 (s, 3H), 2.19 (t, J=3.91 Hz, 1H), 2.07 (tt, J=3.48, 6.54 Hz, 1H), 0.31-0.38 (m, 2H), 0.16-0.23 (m, 2H).

5-(4-(2-(Ethylamino)ethyl)benzyl)-4-(o-tolyl)-2,3-dihydrobenzo[b]oxepin-8-ol (BX-07)

To a solution of 4-((8-methoxy-4-(o-tolyl)-2,3-dihydrobenzo[b]oxepin-5-yl)methyl)phenethyl 4-methylbenzenesulfonate X6-8 (300 mg, 0.542 mmol) in acetonitrile (2 mL) was added DIPEA (0.75 mL, 4.32 mmol) and cyclopropyl amine (2M in MeOH, 2.7 mL, 5.42 mmol) at room temperature. Then the reaction mixture was stirred at room temperature for 72 h. After completion of the reaction, the reaction mixture was concentrated under reduced pressure, and diluted with water, extracted with ethyl acetate (2×15 mL). The combined organic layer was dried over anhydrous $Na_2SO_4$, filtered and concentrated under reduced pressure. The crude compound was purified by silica gel column chromatography eluting with 0-10% methanol in $CH_2Cl_2$ to afford 150 mg (65% yield) of compound X7-9 as sticky solid.

LCMS-Condition-1: $[M+H]^+$=428.55; Rt=1.62 min $^1$H NMR (400 MHz, DMSO-$d_6$) δ: 7.46 (d, J=9.2 Hz, 2H), 7.17-7.31 (m, 5H), 7.09 (d, J=7.6 Hz, 2H), 6.61-6.63 (m, 2H), 4.49-4.62 (m, 2H), 3.73 (d, J=15.65 Hz, 1H), 3.71 (s, 3H), 3.39 (d, J=16.14 Hz, 1H), 2.95-3.00 (m, 2H), 2.82-2.88 (m, 3H), 2.71 (t, J=8.4 Hz, 2H), 2.40-2.42 (m, 1H), 2.28 (s, 3H), 2.18 (br. s, 1H), 1.11 (t, J=7.2 Hz, 3H).

To N-ethyl-2-(4-((8-methoxy-4-(o-tolyl)-2,3-dihydrobenzo[b]oxepin-5-yl)methyl)phenyl)ethan-1-amine X7-9 (150 mg, 0.351 mmol) in $CH_2Cl_2$ (10 mL) at 0° C. was added boron tribromide (0.06 mL, 0.702 mmol) dropwise. Then the reaction mixture was stirred at same the temperature for 30 min. After completion of the reaction, the reaction mixture was quenched with saturated $NaHCO_3$ solution, and extracted with $CH_2Cl_2$. The separated organic layer was dried over anhydrous $Na_2SO_4$, filtered and concentrated under reduced pressure. The crude compound was purified by preparative HPLC to afford 10 mg (7% yield) of BX-07 as off white solid.

LCMS-Condition-1: $[M+H]^+$=414.50; Rt=1.49 min $^1$H NMR (400 MHz, DMSO-$d_6$) δ: 9.57 (br. s, 1H), 7.26 (d, J=6.36 Hz, 1H), 7.12-7.21 (m, 4H), 6.94-7.07 (m, 4H), 6.46 (d, J=8.31 Hz, 1H), 6.42 (s, 1H), 4.52-4.61 (m, 1H), 4.42-4.49 (m, 1H), 3.69 (d, J=15.65 Hz, 1H), 3.39 (d, J=16.14 Hz, 1H), 2.94-3.01 (m, 2H), 2.80-2.90 (m, 2H), 2.68-2.76 (m, 2H), 2.53-2.62 (m, 1H), 2.21 (s, 3H), 2.16 (br. s, 1H), 1.23 (br. s, 1H), 1.11 (t, J=7.09 Hz, 3H).

Activity Discussion and Biological Data

In order to demonstrate the utility of the compounds of this invention, an estrogen receptor binding assay was performed wherein many of the compounds of this invention were shown to demonstrate significant affinity for the estrogen receptor. Selected compound examples were assessed for their ability to inhibit estradiol (E2)-induced proliferation and signaling and for their ability to degrade the estrogen receptor (ER) in breast cancer cells. Furthermore, the ability of selected compounds to inhibit E2-induced increase in uterine weight in immature rats was assessed by oral dosing. Selected compounds could be evaluated in an MCF-7 in vivo xenograft model of breast cancer.

Proliferation Assay in MCF-7 and T47D Cells

MCF-7 and T47D cells were stripped for 3 days in phenol red-free RPMI1640 media containing 10% charcoal-stripped fetal bovine serum (CS-FBS) and 1% Penicillin/streptomycin (P/S). Cells (volume of 90p/well) were seeded in 96 well plates at a density of 2500 cells/well for MCF-7 cells and 1500 cells/well for T47D cells. On the following day, plates were treated with the test compounds (OX concentration in media, volume of 10p/well added) both in the absence and in the presence of two doses of E2 (10 pM and 1 nM). The cells were incubated with test compounds for 7 days. The viability of the cells was assessed using CellTiterGlo (Promega, Cat #G7573) according to the manufacturer's instructions. Growth inhibition curves and $IC_{50}$ values were calculated using the GraphPadPrism 6.0 software. Data values shown in Table 1 were obtained using the 10 pM dose of E2.

Quantitative PCR (qPCR) to Assess ER Signaling in MCF-7 Cells

MCF-7 cells were stripped for 3 days in phenol red-free RPMI1640 media containing 10% charcoal-stripped fetal bovine serum (CS-FBS) and 1% Penicillin/streptomycin (P/S). Cells (volume of 90p/well) were seeded in 96 well plates at a density of 20000 cells/well. On the following day, plates were treated with the test compounds (10× concentration in media, volume of 10 μl/well added) both in the absence and in the presence of E2 (1 nM). The cells were incubated with test compounds for 24 h. Cell lysates were prepared using the Cells-to-CT kit (ThermoFisherScientific, Cat #A25603) according to the manufacturer's instructions. A PCR mix containing master mix, primers for progesterone receptor (PR) and glyceraldehyde-3-phosphate dehydrogenase (GAPDH) endogenous control (ThermoFisherScientific, PR: Cat #Hs01556702_ml and GAPDH: 4326317E), RNase free water (ThermoFisherScientific, Cat #AM9938) was prepared and 8l of this mix was added to each well of a MicroAmp Optical 384-well plate. Cell lysates (2 μl) were then added to the respective wells and samples were analyzed using the QuantStudio6 machine using the fast cycling conditions provided in the kit. Inhibition of PR induction was analyzed and IC50 values were calculated using the GraphPadPrism 6.0 software. In general, the activity in this assay tracked similarly to the MCF-7 inhibition data shown in Table 1. Many of the compounds of the invention potently suppressed PR induction when stimulated by 1 nM E2.

ER Degradation Assay in MCF-7 Cells

MCF-7 cells were stripped for 3 days in phenol red-free RPMI1640 media containing 10% charcoal-stripped fetal bovine serum (CS-FBS) and 1% Penicillin/streptomycin (P/S). Cells were seeded in 6 well plates at a density of 4×10^5 cells/well (volume of 2 ml/well). On the following day, plates were treated with the test compounds (3× concentration in media, volume of 1 ml/well added). The cells were incubated with test compounds for 48 h. Cells were washed and lysed using 70 μl/well of CelLyticM (Sigma, Cat #C2978) lysis buffer containing protease and phosphatase inhibitors at room temperature for 15 minutes. The lysates were centrifuged at 15000 rpm for 15 mins and the supernatant was collected and concentration were analyzed using the Bicinchoninic acid assay (BCA). Proteins (25 μg) were loaded and separated on a 4-15% polyacrylamide gel. Proteins were then transferred to a PVDF membrane and the membranes were then incubated with the ERα primary antibody (Cell Signaling, Cat #13258; 1:1000) and the vinculin primary antibody (Sigma, Cat #V9131, 1:1000). Membranes were incubated with the respective secondary antibodies, probed with chemiluminescent substrates (ThermoFisherScientific, Dura (ERα): Cat #34075 and Pico (Vinculin): Cat #34080), and images were captured using the Azure Biosystems c600 machine. Images were analyzed using the AzureSpot software. Several tested compounds disclosed herein decreased expression of the ER.

Immature Rat Uterine Assay

Sprague-Dawley rat pups were weaned at 19 days of age, randomized into groups (n=6), and administered vehicle (aqueous 20% HPBCD, 10% PEG400 in $H_2O$), E2 (0.01 mg/kg), test compounds (0.1 mg/kg-3 mg/kg) in combination with E2 (0.01 mg/kg), either by subcutaneous injection or by oral gavage, once daily for three consecutive days. Twenty-four hours after the final dose, all animals were killed by carbon dioxide inhalation. Body weights and wet uterine weights were recorded for each animal. GraphPad-Prism 6.0 software was used to analyze data. For example, compound D-102 suppressed wet uterine weight to baseline with an oral dose of 3 mg/kg.

MCF-7 Xenograft Models

Female athymic nude mice [Crl:NU(NCr)-Foxn1nu] are used for tumor xenograft studies. Three days before tumor cell implantation, estrogen pellets (0.36 mg E2, 60-day release; Innovative Research of America, Sarasota, Fla., USA) are implanted subcutaneously between the scapulae of test animals with a sterilized trochar. MCF-7 human breast adenocarcinoma cells are cultured to midlog phase in RPMI-1640 medium containing 10% fetal bovine serum, 100 U/ml penicillin G, 100 µg/ml streptomycin sulfate, 2 mmol/l glutamine, 10 mmol/l HEPES, 0.075% sodium bicarbonate, and 25 µg/ml gentamicin. On the day of tumor cell implantation, the cells are trypsinized, pelleted, and resuspended in PBS at a concentration of 5×107 cells/ml. Each test mouse receives 1×10$^7$ MCF-7 cells implanted subcutaneously in the right flank, and tumor growth is monitored. Volume is calculated using the following formula: tumor volume $(mm^3)$=l×w2/2, where w=width and l=length in mm of an MCF-7 tumor. When necessary, tumor weight is estimated on the basis of the assumption that 1 $mm^3$ of tumor volume is equivalent to 1 mg tumor wet weight. Fourteen days after tumor cell implantation (designated as day 1 of the study), mice are 9 weeks of age, with body weights ranging from 21.4 to 32.5 g, individual tumor volumes ranging from 75 to 144 $mm^3$, and a group mean tumor volume (MTV) of 108 $mm^3$. The mice are randomized into groups of 9-15 animals each and treated with vehicle, control SERM such as tamoxifen (1 mg/animal every other day), and test compound (0.3, 1, 3, 10, 30, 60, 90, and 120 mg/kg daily). Tumor volumes are evaluated twice per week. The tumor endpoint is defined as an MTV of 1500 $mm^3$ in the control group. Animals are also monitored for partial regression (PR) and complete regression responses. Treatment tolerability is assessed by body weight measurements and frequent observation for clinical signs of treatment-related adverse effects. Animals with weight loss exceeding 30% for one measurement, or exceeding 25% for three measurements, are humanely sacrificed and their deaths are classified as treatment-related deaths. Acceptable toxicity is defined as a group mean body weight loss of less than 20% during the study and not more than one treatment-related death among 10 treated animals, or 10%. At the end of the study, the animals are sacrificed by terminal cardiac puncture under isoflurane anesthesia.

TABLE 1

MCF-7 Proliferation Inhibition Assay

| Compound | $IC_{50}$ |
| --- | --- |
| D-01 | ++ |
| D-02 | ++ |
| D-03 | ++ |
| D-08 | ++ |
| D-12 | + |
| D-13 | ++ |
| D-15 | +++ |
| D-16 | +++ |
| D-28 | +++ |
| D-29 | +++ |
| D-32 | +++ |
| D-33 | +++ |
| D-34 | +++ |
| D-36 | +++ |
| D-37 | +++ |
| D-39 | +++ |
| D-40 | +++ |
| D-46 | +++ |
| D-50 | +++ |
| D-52 | +++ |
| D-66 | +++ |
| D-67 | +++ |
| D-68 | +++ |
| D-69 | +++ |
| D-70 | +++ |
| D-78 | +++ |
| D-85 | +++ |
| D-87 | +++ |
| D-88 | +++ |
| D-89 | +++ |
| D-90 | +++ |
| D-91 | +++ |
| D-96 | +++ |
| D-101 | +++ |
| D-102 | +++ |
| D-103 | +++ |
| D-104 | +++ |
| LA-18 | +++ |
| LA-19 | +++ |
| LA-21 | +++ |
| LA-22 | +++ |
| LA-31 | +++ |
| LA-32 | +++ |
| LA-33 | +++ |
| Bx-06 | +++ |
| Bx-07 | +++ |
| BT-05 | +++ |
| BT-12 | +++ |
| BT-17 | +++ |

+++ $IC_{50}$ < 1 nM;
++ $IC_{50}$ > 1 nM < 10 nM;
+ $IC_{50}$ > 10 nM;
na = data not available

What is claimed is:

1. A compound according to formula II'
wherein:

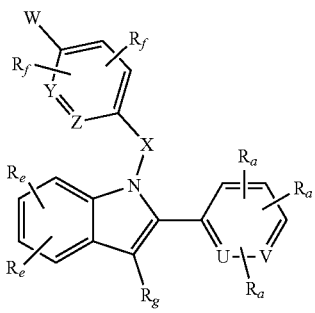

II' each $R_a$ is independently selected from H, $C_1$-$C_3$ alkyl, phenyl (optionally substituted with 1-3 groups selected from fluorine, chlorine, $C_1$-$C_3$ alkyl, CN, $OC_1$-$C_3$ alkyl, OH), OH, $OC_{1-3}$alkyl, CN, fluorine, chlorine, O(CO)R, O(CO)$NR_1R_2$, $OPO_3$, $OSO_3$,O($SO_2$)$NR_1R_2$, or two adjacent $R_a$ together form:

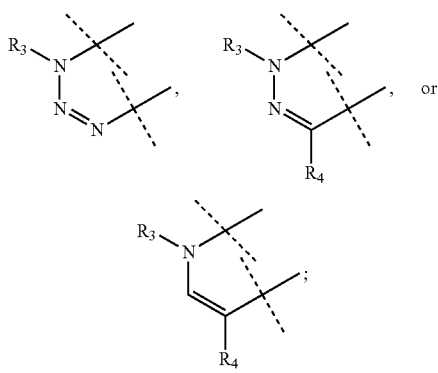

R is $C_1$-$C_6$ alkyl or aryl;

$R_1$ and $R_2$ are each independently hydrogen or $C_1$-$C_6$ alkyl;

each $R_3$ is independently hydrogen; $C_1$-$C_{12}$ acyl or $C_1$-$C_{12}$ acyloxy;

each $R_4$ is independently hydrogen, $C_1$-$C_3$ alkyl, fluorine or chlorine;

each $R_e$ is independently selected from hydrogen, halogen, OH, O(CO)R, O(CO)$NR_1R_2$, $OPO_3$, $OSO_3$,O($SO_2$)$NR_1R_2$, or wherein two adjacent $R_e$ together form:

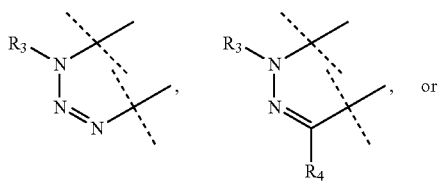

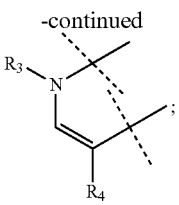

each $R_f$ is independently H, $C_1$-$C_3$ alkyl, $OC_1$-$C_3$ alkyl, fluorine or chlorine;

$R_g$ is hydrogen, $C_1$-$C_3$ alkyl, $C_1$-$C_3$ fluoroalkyl, CN, fluorine, chlorine or bromine;

X is $CH_2$ or a bond;

Y and Z are each independently selected from $CR_f$;

U and V are each independently selected from $CR_a$; and

W is CHR'—CHR'—NH—$C_1$-$C_4$alkyl, —CHR'—CHR'—NH—$C_1$-$C_4$fluoroalkyl, —CHR'—CHR'—NH—$C_3$-$C_6$cycloalkyl, —CHR'—CHR'—NH—$C_1$-$C_4$alkyl-$C_3$-$C_6$cycloalkyl,

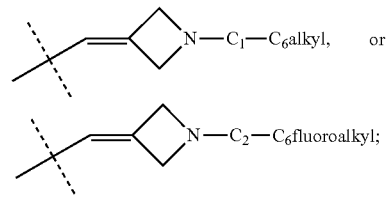

wherein each R' is independently H or $C_1$-$C_3$alkyl;

or a pharmaceutically acceptable salt thereof.

2. The compound of claim 1, wherein: X is $CH_2$; Y and Z are each $CR_f$; U and V are each $CR_a$; $R_g$ is F, Cl or $CH_3$; each $R_a$ is independently selected from H, OH, $CH_3$ and Cl; each $R_f$ is H; and W is —$CH_2$—$CH_2$—NH—$CH_2$—$CH_2$—$CH_3$, —$CH_2$—$CH_2$—NH—$CH_2$—$CH_2$—$CH_2$F,

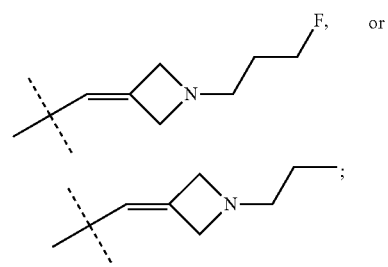

or a pharmaceutically acceptable salt thereof.

3. The compound of claim 2, wherein each $R_e$ is independently selected from hydrogen or OH, or wherein two adjacent $R_e$ together form

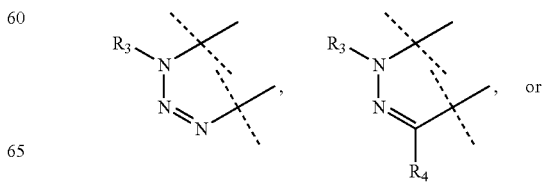

-continued

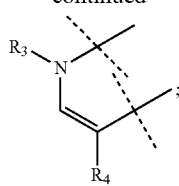

and wherein $R_3$ is H and $R_4$ is H.

4. The compound of claim 1, having a structure according to formula III':

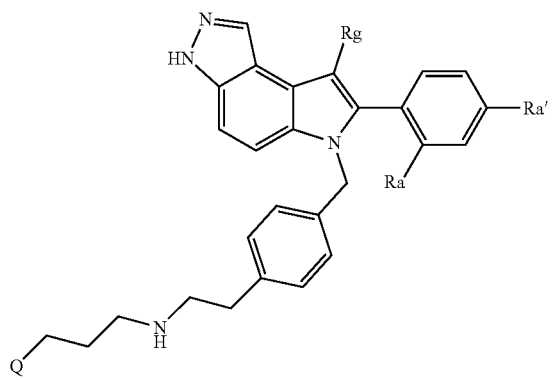

III' wherein: Q is H or F; Rg is F, Cl, or $CH_3$; Ra is $CH_3$, Cl or OMe; and Ra' is H, F or OH; or a pharmaceutically acceptable salt thereof.

5. The compound of claim 4, wherein Rg is F.

6. The compound of claim 5, wherein Ra is $CH_3$ and Ra' is H.

7. The compound of claim 1, having a structure according to formula IV':

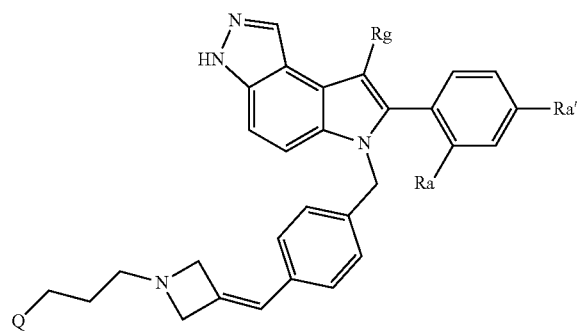

IV' wherein: Q is H or F; Rg is F, Cl, or $CH_3$; Ra is $CH_3$, Cl or OMe; and Ra' is H, F or OH; or a pharmaceutically acceptable salt thereof.

8. The compound of claim 7, wherein Rg is F.

9. The compound of claim 8, wherein Ra is $CH_3$ and Ra' is H.

10. The compound of claim 1, having a structure according to formula V':

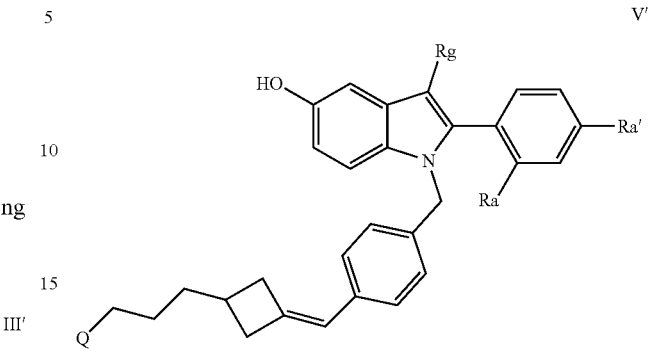

V' wherein: Q is H or F; Rg is F, Cl, or $CH_3$; Ra is $CH_3$, Cl or OMe; and Ra' is H, F or OH; or a pharmaceutically acceptable salt thereof.

11. The compound of claim 10, wherein Rg is F.

12. The compound of claim 11, wherein Ra is $CH_3$ and Ra' is H.

13. The compound of claim 1, having a structure according to formula VI':

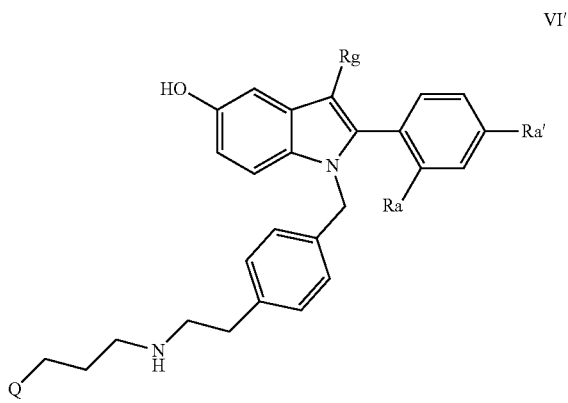

VI' wherein: Q is H or F; Rg is F, Cl, or $CH_3$; Ra is $CH_3$, Cl or OMe; and Ra' is H, F or OH; or a pharmaceutically acceptable salt thereof.

14. The compound of claim 13, wherein Rg is F.

15. The compound of claim 14, wherein Ra is $CH_3$ and Ra' is H.

16. The compound of claim 1, wherein the compound selected from:
1-(4-(2-(Ethyl amino)ethyl)benzyl)-2-(4-methoxyphenyl)-3-methyl-1H-indol-5-ol;
1-(4-(2-(Cyclopropylamino)ethyl)benzyl)-2-(4-methoxyphenyl)-3-methyl-1H-indol-5-ol;
1-(4-(2-(Isopropyl amino)ethyl)benzyl)-2-(4-methoxyphenyl)-3-methyl-1H-indol-5-ol;
1-(4-(2-(Cyclohexylamino)ethyl)benzyl)-2-(4-methoxyphenyl)-3-methyl-1H-indol-5-ol;
2-(4-Methoxyphenyl)-3-methyl-1-(4-(2-((2,2,2-trifluoroethyl)amino)ethyl)benzyl)-1 H-indol-5-ol;
1-(4-(2-(Cyclopropylamino)ethyl)benzyl)-3-fluoro-2-(4-methoxyphenyl)-1H-indol-5-ol;
1-(4-(2-(Ethyl amino)ethyl)benzyl)-3-fluoro-2-(4-methoxyphenyl)-1H-indol-5-ol;

3-Chloro-1-(4-(2-(ethyl amino)ethyl)benzyl)-2-(4-methoxyphenyl)-1H-indol-5-ol;
1-(4-(2-(Cyclopropylamino)ethyl)benzyl)-3-fluoro-2-(o-tolyl)-1H-indol-5-ol;
3-Fluoro-2-(2-methoxyphenyl)-1-(4-(2-(propylamino)ethyl)benzyl)-1H-indol-5-ol;
1-(4-(2-(Cyclobutylamino)ethyl)benzyl)-2-(2,6-dimethylphenyl)-3-fluoro-1H-indol-5-ol;
2-(2,6-Dimethylphenyl)-1-(4-(2-(ethylamino)ethyl)benzyl)-3-fluoro-1H-indol-5-ol;
1-(4-(2-(Cyclopropylamino)ethyl)benzyl)-3-fluoro-2-(4-hydroxy-2-methylphenyl)-1H-indol-5-ol;
3-Fluoro-1-(4-(2-((2-fluoroethyl)amino)ethyl)benzyl)-2-(4-methoxy-2-methylphenyl)-1H-indol-5-ol;
3-Fluoro-1-(4-(2-((3-fluoropropyl)amino)ethyl)benzyl)-2-(4-methoxy-2-methylphenyl)-1H-indol-5-ol;
1-(4-(2-(Cyclopropylamino)ethyl)benzyl)-3-fluoro-2-(4-fluoro-2-methylphenyl)-1H-indol-5-ol;
3-Fluoro-2-(4-methoxy-2-methylphenyl)-1-(4-(2-(propylamino)ethyl)benzyl)-1H-indol-5-ol; 2-([1,1'-Biphenyl]-2-yl)-3-fluoro-1-(4-(2-(propylamino)ethyl)benzyl)-1H-indol-5-ol;
1-(4-(2-(Ethylamino)ethyl)benzyl)-3-fluoro-2-(o-tolyl)-1H-indol-5-ol;
1-(4-(2-(Cyclobutylamino)ethyl)benzyl)-3-fluoro-2-(o-tolyl)-1H-indol-5-ol;
3-Fluoro-1-(4-(2-(propyl amino)ethyl)benzyl)-2-(o-tolyl)-1H-indol-5-ol;
1-(4-(2-(Butyl amino)ethyl)benzyl)-3-fluoro-2-(o-tolyl)-1H-indol-5-ol;
3-Fluoro-1-(4-(2-((3-fluoropropyl)amino)ethyl)benzyl)-2-(o-tolyl)-1H-indol-5-ol;
3-Fluoro-1-(4-(2-((2-fluoroethyl)amino)ethyl)benzyl)-2-(o-tolyl)-1H-indol-5-ol;
1-(4-(2-(Cyclopropylamino)propyl)benzyl)-3-fluoro-2-(o-tolyl)-1H-indol-5-ol;
1-(4-(2-(((Cyclopropylmethyl)amino)ethyl)benzyl)-3-fluoro-2-(2-(trifluoromethyl)phenyl)-1H-indol-5-ol;
1-(4-(2-(Cyclopropylamino)ethyl)benzyl)-3-fluoro-2-(2-(trifluoromethyl)phenyl)-1H-indol-5-ol;
1-(4-(2-(Ethyl amino)ethyl)benzyl)-3-fluoro-2-(2-(trifluoromethyl)phenyl)-1H-indol-5-ol; 2-(2-Chlorophenyl)-1-(4-(2-(cyclopropylamino)ethyl)benzyl)-3-fluoro-1H-indol-5-ol;
N-Ethyl-2-(4-((8-fluoro-7-(o-tolyl)pyrrolo[3,2-e]indazol-6(3H)-yl)methyl)phenyl)ethan-1-amine;
N-(Cyclopropylmethyl)-2-(4(2((8-fluoro-7-(o-tolyl)pyrrolo[3,2-e]indazol-6(3H)-yl)methyl)phenyl)ethan-1-amine;
N-(4((8-Fluoro-7-(o-tolyl)pyrrolo[3,2-e]indazol-6(3H)-yl)methyl)phenethyl)cyclobutanamine;
N-(4((8-Fluoro-7-(o-tolyl)pyrrolo[3,2-e]indazol-6(3H)-yl)methyl)phenethyl)cyclopropanamine;
N-(4((8-fluoro-7-(o-tolyl)pyrrol o [3,2-e]indazol-6(3H)-yl)methyl)phenethyl)propan-1-amine;
3-Fluoro-N-(4-O-fluoro-7-(o-tolyl)pyrrol o [3,2-e]indazol-6(3H)-yl)methyl)phenethyl)propan-1-amine; and
3-Fluoro-N-(4-((8-fluoro-7-(o-tolyl)pyrrolo[3,2-e]indazol-6(3H)-yl)methyl)phenethyl)propan-1-amine.

17. A pharmaceutical composition comprising a compound of claim 1 and a pharmaceutically acceptable excipient.

18. A method of treating a disease, syndrome, illness, or symptom associated with insufficient or overabundant estrogen levels in a mammal in need thereof, comprising administering to said mammal an effective amount of a compound of claim 1 or a pharmaceutically acceptable salt thereof.

19. A method of treating a cancer selected from the group consisting of prostate cancer, breast cancer, endometrial cancer, lung cancer, hepatocellular cancer, lymphoma, multiple endocrine neoplasia, vaginal cancer, renal cancer, thyroid cancer, testicular cancer, leukemia, and ovarian cancer in a mammal in need thereof, comprising administering to said mammal an effective amount of a compound of claim 1 or a pharmaceutically acceptable salt thereof.

* * * * *